United States Patent
Li et al.

(10) Patent No.: US 10,113,195 B2
(45) Date of Patent: Oct. 30, 2018

(54) NUCLEIC ACID AMPLIFICATION

(71) Applicant: LIFE TECHNOLOGIES CORPORATION, Carlsbad, CA (US)

(72) Inventors: Chieh-Yuan Li, El Cerrito, CA (US); David Ruff, San Francisco, CA (US); Jennifer O'Neil, Wakefield, MA (US); Rachel Kasinskas, Amesbury, MA (US); Shiaw-Min Chen, Fremont, CA (US); Jonathan Rothberg, Guilford, CT (US); Bin Li, Palo Alto, CA (US); Kai Qin Lao, Pleasanton, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 263 days.

(21) Appl. No.: 14/789,922

(22) Filed: Jul. 1, 2015

(65) Prior Publication Data
US 2016/0032375 A1 Feb. 4, 2016

Related U.S. Application Data

(63) Continuation of application No. 14/085,718, filed on Nov. 20, 2013, now abandoned, which is a
(Continued)

(51) Int. Cl.
*C12Q 1/68* (2018.01)
*C12Q 1/6844* (2018.01)
*C12Q 1/6874* (2018.01)

(52) U.S. Cl.
CPC ......... *C12Q 1/6846* (2013.01); *C12Q 1/6844* (2013.01); *C12Q 1/6874* (2013.01)

(58) Field of Classification Search
None
See application file for complete search history.

(56) References Cited

U.S. PATENT DOCUMENTS

| 5,223,414 A | 6/1993 | Zarling et al. |
| 5,616,478 A | 4/1997 | Chetverin et al. |

(Continued)

FOREIGN PATENT DOCUMENTS

| CN | 1489632 | 4/2004 |
| CN | 101413034 | 2/2011 |

(Continued)

OTHER PUBLICATIONS

Piepenburg and Armes, Rapid ultra-sensitive isothermal DNA detection using RPA technology and a BMG Labtech microplate reader, BMG Labtech, Application Notes AN176, Aug. 2008.*
(Continued)

*Primary Examiner* — Aaron A Priest
(74) *Attorney, Agent, or Firm* — Life Technologies Corporation; Karen Zachow

(57) ABSTRACT

In some embodiments, the present teachings provide methods for nucleic acid amplification, comprising forming a reaction mixture, and subjecting the reaction mixture to conditions suitable for nucleic acid amplification. In some embodiments, methods for nucleic acid amplification include subjecting the nucleic acid to be amplified to partially denaturing conditions. In some embodiments, methods for nucleic acid amplification include amplifying without fully denaturing the nucleic acid that is amplified. In some embodiments, the methods for nucleic acid amplification employ an enzyme that catalyzes homologous recombination and a polymerase. In some embodiments, methods for nucleic acid amplification can be conducted in a single reaction vessel. In some embodiments, methods for nucleic acid amplification can be conducted in a single continuous liquid phase of a reaction mixture, without need for compartmentalization of the reaction mixture or immobilization of reaction components. In some embodiments, methods for
(Continued)

nucleic acid amplification comprise a amplifying at least one polynucleotide onto a surface under isothermal amplification conditions, optionally in the presence of a polymer. The polymer can include a sieving agent and/or a diffusion-reducing agent.

9 Claims, 20 Drawing Sheets

Specification includes a Sequence Listing.

Related U.S. Application Data continuation of application No. 13/923,232, filed on Jun. 20, 2013, now Pat. No. 9,371,557, which is a continuation of application No. 13/842,296, filed on Mar. 15, 2013, now Pat. No. 9,309,557, application No. 14/789,922, filed on Jul. 1, 2015, which is a continuation-in-part of application No. 13/328,844, filed on Dec. 16, 2011, now abandoned, application No. 14/789,922, filed on Jul. 1, 2015, which is a continuation-in-part of application No. 13/828,049, filed on Mar. 14, 2013, now Pat. No. 9,309,566, and a continuation-in-part of application No. 13/328,844, filed on Dec. 16, 2011, now abandoned, and a continuation-in-part of application No. PCT/US2011/065535, filed on Dec. 16, 2011.

(60) Provisional application No. 61/767,766, filed on Feb. 21, 2013, provisional application No. 61/781,016, filed on Mar. 14, 2013, provisional application No. 61/635,584, filed on Apr. 19, 2012, provisional application No. 61/692,830, filed on Aug. 24, 2012, provisional application No. 61/699,810, filed on Sep. 11, 2012, provisional application No. 61/792,247, filed on Mar. 15, 2013, provisional application No. 61/424,599, filed on Dec. 17, 2010, provisional application No. 61/445,324, filed on Feb. 22, 2011, provisional application No. 61/451,919, filed on Mar. 11, 2011, provisional application No. 61/526,478, filed on Aug. 23, 2011, provisional application No. 61/552,660, filed on Oct. 28, 2011.

(56) References Cited

U.S. PATENT DOCUMENTS

| | | | |
|---|---|---|---|
| 5,670,325 A | 9/1997 | Lapidus et al. | |
| 5,928,870 A | 7/1999 | Lapidus et al. | |
| 5,958,698 A | 9/1999 | Chetverin et al. | |
| 6,001,568 A | 12/1999 | Chetverin et al. | |
| 6,033,881 A | 3/2000 | Himmler et al. | |
| 6,074,853 A | 6/2000 | Pati et al. | |
| 6,306,590 B1 | 10/2001 | Mehta et al. | |
| 6,432,360 B1 | 8/2002 | Church | |
| 6,440,706 B1 | 8/2002 | Vogelstein et al. | |
| 6,511,803 B1* | 1/2003 | Church | C07K 1/047 435/287.2 |
| 6,929,915 B2 | 8/2005 | Benkovic et al. | |
| 7,270,981 B2 | 9/2007 | Armes et al. | |
| 7,282,337 B1 | 10/2007 | Harris | |
| 7,399,590 B2* | 7/2008 | Piepenburg | C12Q 1/6844 435/6.14 |
| 7,432,055 B2 | 10/2008 | Pemov et al. | |
| 7,435,561 B2 | 10/2008 | Piepenburg et al. | |
| 7,485,428 B2 | 2/2009 | Armes et al. | |
| 7,604,940 B1 | 10/2009 | Voss | |
| 7,666,598 B2 | 2/2010 | Piepenburg et al. | |
| 7,723,031 B2 | 5/2010 | Benkovic et al. | |
| 7,763,427 B2 | 7/2010 | Piepenburg et al. | |
| 7,785,790 B1 | 8/2010 | Church et al. | |
| 7,824,889 B2 | 11/2010 | Vogelstein et al. | |
| 7,906,279 B2 | 3/2011 | Benkovic et al. | |
| 7,915,015 B2 | 3/2011 | Vogelstein et al. | |
| 7,985,565 B2 | 7/2011 | Mayer et al. | |
| 8,017,339 B2 | 9/2011 | Piepenburg et al. | |
| 8,030,000 B2 | 10/2011 | Piepenburg et al. | |
| 8,062,850 B2 | 11/2011 | Piepenburg et al. | |
| 8,071,308 B2 | 12/2011 | Piepenburg et al. | |
| 8,124,342 B2 | 2/2012 | Benkovic et al. | |
| 8,129,116 B2 | 3/2012 | Benkovic et al. | |
| 8,137,913 B2 | 3/2012 | Benkovic et al. | |
| 8,143,008 B2 | 3/2012 | Kawashima et al. | |
| 8,241,851 B2 | 8/2012 | Benkovic et al. | |
| 8,361,718 B2 | 1/2013 | Benkovic et al. | |
| 8,389,216 B2 | 3/2013 | Benkovic et al. | |
| 8,426,134 B2 | 4/2013 | Piepenburg et al. | |
| 8,460,875 B2 | 6/2013 | Armes et al. | |
| 8,476,022 B2 | 7/2013 | Ronaghi et al. | |
| 8,652,810 B2 | 2/2014 | Adessi et al. | |
| 8,673,561 B2 | 3/2014 | Benkovic et al. | |
| 8,759,000 B2 | 6/2014 | Benkovic et al. | |
| 8,765,374 B2 | 7/2014 | Benkovic et al. | |
| 8,895,249 B2 | 11/2014 | Shen et al. | |
| 9,309,557 B2 | 4/2016 | Li et al. | |
| 2003/0003609 A1 | 1/2003 | Sauer et al. | |
| 2003/0143525 A1 | 7/2003 | Benkovic et al. | |
| 2003/0219792 A1 | 11/2003 | Armes et al. | |
| 2004/0171060 A1 | 9/2004 | Benkovic et al. | |
| 2004/0259082 A1 | 12/2004 | Williams | |
| 2005/0100900 A1 | 5/2005 | Kawashima et al. | |
| 2005/0112631 A1 | 5/2005 | Piepenburg et al. | |
| 2005/0118616 A1* | 6/2005 | Kawashima | C12Q 1/682 435/6.12 |
| 2006/0269934 A1 | 11/2006 | Woudenberg et al. | |
| 2007/0054296 A1 | 3/2007 | Piepenburg et al. | |
| 2008/0009420 A1* | 1/2008 | Schroth | C12Q 1/6848 506/16 |
| 2008/0118917 A1 | 5/2008 | Hardy et al. | |
| 2008/0166727 A1 | 7/2008 | Esfandyarpour et al. | |
| 2009/0093378 A1 | 4/2009 | Bignell et al. | |
| 2009/0127589 A1 | 5/2009 | Rothberg et al. | |
| 2009/0171078 A1 | 7/2009 | Lao et al. | |
| 2009/0203531 A1* | 8/2009 | Kurn | C12Q 1/686 506/6 |
| 2009/0269813 A1* | 10/2009 | Piepenburg | C12Q 1/6816 435/91.2 |
| 2009/0286286 A1 | 11/2009 | Lim | |
| 2009/0325165 A1 | 12/2009 | Armes et al. | |
| 2010/0136544 A1 | 6/2010 | Agresti et al. | |
| 2010/0167954 A1 | 7/2010 | Earnshaw et al. | |
| 2010/0304982 A1 | 12/2010 | Hinz et al. | |
| 2010/0311127 A1 | 12/2010 | Piepenburg et al. | |
| 2011/0065106 A1 | 3/2011 | Armes et al. | |
| 2011/0123991 A1 | 5/2011 | Hoser | |
| 2012/0015367 A1 | 1/2012 | Piepenburg et al. | |
| 2012/0053063 A1 | 3/2012 | Rigatti et al. | |
| 2012/0058517 A1 | 3/2012 | Piepenburg et al. | |
| 2012/0082990 A1 | 4/2012 | Piepenburg et al. | |
| 2012/0129173 A1 | 5/2012 | Piepenburg et al. | |
| 2012/0156728 A1 | 6/2012 | Li et al. | |
| 2012/0172259 A1 | 7/2012 | Rigatti et al. | |
| 2012/0258456 A1 | 10/2012 | Armes et al. | |
| 2012/0258499 A1 | 10/2012 | Piepenburg et al. | |
| 2012/0264132 A1 | 10/2012 | Ismagilov et al. | |
| 2013/0012399 A1 | 1/2013 | Myers et al. | |
| 2013/0210008 A1 | 8/2013 | Feitsma et al. | |
| 2014/0148345 A1 | 5/2014 | Li et al. | |
| 2014/0228245 A1 | 8/2014 | Hoffmann et al. | |
| 2014/0228254 A1 | 8/2014 | Adessi et al. | |

FOREIGN PATENT DOCUMENTS

| | | |
|---|---|---|
| EP | 1275737 | 1/2003 |
| JP | 2003-510012 | 3/2003 |
| JP | 2004-524012 | 8/2004 |
| JP | 2004-535162 | 11/2004 |
| WO | 94/03624 | 2/1994 |

(56) References Cited

FOREIGN PATENT DOCUMENTS

| WO | 98/08975 | 3/1998 | | |
|---|---|---|---|---|
| WO | 98/44151 | 10/1998 | | |
| WO | 00/18957 | 4/2000 | | |
| WO | 00/47767 | 8/2000 | | |
| WO | 2000/060919 | 10/2000 | | |
| WO | 01/81908 | 11/2001 | | |
| WO | 2002/046456 | 6/2002 | | |
| WO | WO 0246456 A1 * | 6/2002 | ........... | C12Q 1/6837 |
| WO | 2002/072772 | 9/2002 | | |
| WO | 2003/072805 | 9/2003 | | |
| WO | 2005/007796 | 1/2005 | | |
| WO | WO-2005/118853 | 12/2005 | | |
| WO | 2006/099579 | 9/2006 | | |
| WO | 2007/010252 | 1/2007 | | |
| WO | 2007/107710 | 9/2007 | | |
| WO | 2008/041002 | 4/2008 | | |
| WO | 2008/107014 | 9/2008 | | |
| WO | 2009/102878 | 8/2009 | | |
| WO | 2010138187 | 12/2010 | | |
| WO | 2011/106368 | 9/2011 | | |
| WO | 2011/106460 | 9/2011 | | |
| WO | 2011/106629 | 9/2011 | | |
| WO | 2011106460 | 9/2011 | | |
| WO | 2012/036679 | 3/2012 | | |
| WO | 2012/083189 | 6/2012 | | |
| WO | 2012/106072 | 8/2012 | | |
| WO | 2013/019361 | 2/2013 | | |
| WO | 2013/045700 | 4/2013 | | |

OTHER PUBLICATIONS

Pemov (DNA analysis with multiplex microarray-enhanced PCR, Nucleic Acids Res 2005 20;33(2):e11. Epub Jan. 20, 2005).*
EP16196078.6, "EP Extended Search Report dated Feb. 21, 2017", pp. 1-7.
DNA Polymerase Selection Chart, retrieved Jul. 1, 2016, from url :http://www.neb.com/tools-and-resources/selection-chart/dna-polymerase-selection-chart, 5pgs.
EP14716714.2 EP Examination Report dated Jun. 24, 2016.
EP13771260.0 EP Examination Report dated Jul. 12, 2016.
Abrams, Ezra et al., "Bridge Amplification for DNA-based Diagnostics", Chapter 1.9, 1997, 171-189.
Adessi, C et al., "Solid Phase DNA Amplification: characterisation of primer attachment and amplification mechanisms", *Nucleic Acids Research*, vol. 28, No. 20, e87, 2000, 1-8.
Andreadis, Joanne D. et al., "Use of immobilized PCR primers to generate covalently immobilized DNAs for in vitro transcription/translation reactions", *Nucleic Acids Research*, vol. 28, No. 2, 2000, e5.
Andresen, Dennie et al., "Helicase dependent OnChip-amplification and its use in multiplex pathogen detection", *Clinica Chimica Acta*, 403, Mar. 18, 2009, 244-248.
Andresen, Dennie et al., "Helicase-dependent amplification: use in OnChip amplification and potential for point-of-care diagnostics", *Expert Rev. Mol. Diagn.*, 9(7), Oct. 2009, 645-650.
Belanger, Karyn et al., "Bacteriophage T4 Initiates Bidirectional DNA Replication through a Two-Step Process", *Molecular Cell*, vol. 2, 1998, 693-701.
Bentley, D et al., "Accurate whole human genome sequencing using reversible terminator chemistry", *Nature*, vol. 456(6), (7218), 2008, pp. 53-59.
Bing, David et al., "Bridge Amplification: A Solid Phase PCR System for the Amplification and Detection of Allelic Differences in Single Copy Genes", *Genetic Identity Conference Proceedings, Seventh International Symposium on Human Identification*, 1996.
Borer, Philip N. et al., "Stability of Ribonucleic acid Double-stranded Helices", (1974) *J. Mol. Biol.* 86, 843-853, 1974, 843-853.
Brewood, Greg P. et al., "Electrical detection of the temperature induced melting transition of a DNA hairpin covalently attached to gold interdigitated microelectrodes", *Nucleic Acids Research*, 2008, vol. 36(15):e98, Jul. 15, 2008.

Chetverin, Alexander et al., "Oligonucleotide Arrays: New Concepts and Possibilities", *Bio/Technology*, vol. 12, Nov. 12, 1994, 1093-1099.
Dubiley, Svetlana et al., "Polymorphism analysis and gene detection by minisequencing on an array of gel-immobilized primers", *Nucleic Acids Research*, vol. 27, No. 18, 1999, e19.
Formosa, Timothy et al., "DNA Synthesis Dependent on Genetic Recombination: Characterization of a Reaction Catalyzed by Purified Bacteriophage T4 Proteins", *Cell*, vol. 47, 1986, 793-806.
Fujimoto, Kenzo et al., "Site-Specific Cytosine to Uracil Transition by Using Reversible DNA Photo-crosslinking", *ChemBioChem*, 11, 2010, 1661-1664.
Glenn, Travis C., "Field Guide to Next-generation DNA Sequencers", *Molecular Ecology Resources*, vol. 11, No. 5, 2011, 759-769.
Hoser, "Oligo Calc: Oligonucleotide Properties Calculator", *Northwestern University*, http://www.basic.northwestern.edu/biotools/oligocalc.html, Dec. 4, 2014, 10 Pages.
Hoser, "Primer-BLAST", *NCBI*, http://www.ncbi.nlm.nih.gov/tools/primer-blast/primertool.cgi?ctg_time=1417731967&job_key=4PsNu7exHpUhpyWpRIcX11-qJcZMtTjD, Dec. 4, 2014, 76 Pages.
Ma, Zhaochun et al., "Isothermal amplification method for next-generation sequencing", *PNAS*, vol. 110, No. 5, Aug. 27, 2013, 14320-14323.
Mardis, E., "Next-generation DNA sequencing methods", *Annual Review of Genomics and Human Genetetics*, vol. 9, Jan. 1, 2008, 387-402.
Mercier, J et al., "Solid Phase DNA Amplification: A Brownian Dynamics Study of Crowding Effects", *Biophysical Journal*, vol. 89, Jul. 2005, 32-42.
Meunier-Prest, Rita et al., "Direct Measurement of the Melting Temperature of Supported DNA by Electrochemical Method", *Nucleic Acids Research*, vol. 31(23):e150, Dec. 1, 2003, e150.
Meuzelaar, Linda et al., "MegaPlex PCR: a strategy for multiplex amplification", *Nature Methods*, vol. 4, No. 10, Oct. 2007, 835-837.
Mitra, R et al., "Digital genotyping and haplotyping with polymerase colonies", *PNAS*, vol. 100(10), 2003, 5926-5931.
Mitra, Robi et al., "In situ localized amplification and contact replication of many individual DNA molecules", *Nuc Acids Res*, vol. 27(24), 1999, e34, pp. i-vi.
Mitterer, G. et al., "Microarray-Based Detection of Bacteria by On-Chip PCR", *Methods in Molecular Biology*, vol. 345, 2006, 37-51.
Moorthie, S. et al., "Review of massively parallel DNA sequencing technologies", *Hugo J*, vol. 5, Oct. 27, 2011, 1-2.
Morrical, Scott et al., "Amplification of Snap-back DNA Synthesis Reactions by the uvsX Recombinase of Bacteriophage T4", *The Journal of Biological Chemistry*, vol. 266, No. 21, 1991, 14031-14038.
Morrison, et al., "Nanoliter High Throughput Quantitative PCR", *Nucleic Acids Research*, vol. 34, No. 18, e123, 2006, 1-9.
Oroskar, A. et al., "Detection of immobilized amplicons by ELISA-like techniques", *Clin. Chem.*, vol. 42, No. 9, 1996, 1547-1555.
Oyola, Samuel et al., "Optimizing illumina next-generation sequencing library preparation for extremely at-biased genomes", *BMC Genomics*, 13:1, 2012, 1-12.
PCT/EP01/14369, International Search Report dated Mar. 13, 2002, 3.
PCT/US2011/065535, International Preliminary Report on Patentability dated Jun. 18, 2013, 12.
PCT/US2011/065535, International Search Report dated Jul. 4, 2012, 5.
PCT/US2013/031589, International Preliminary Report on Patentability and Written Opinion dated Mar. 5, 2015, 7 Pages.
PCT/US2013/031589, International Search Report and Written Opinion dated Jun. 25, 2013, 12.
PCT/US2013/032598, International Preliminary Report on Patentability and Written Opinion dated Oct. 21, 2014, 6 Pages
PCT/US2013/032598, International Preliminary Report on Patentability dated Oct. 30, 2014, 7 pages.
PCT/US2013/032598, International Search Report and Written Opinion dated Jun. 11, 2013.
PCT/US2013/037352, International Preliminary Report on Patentability and Written Opinion dated Oct. 21, 2014, 6 Pages.

(56) References Cited

OTHER PUBLICATIONS

PCT/US2013/059093, International Preliminary Report on Patentability and Written Opinion dated Mar. 26, 2015, 7 Pages.
PCT/US2013/059093, International Search Report and Written Opinion dated Jan. 22, 2014, 12.
PCT/US2014/026735, International Preliminary Report on Patentability, dated Sep. 15, 2015, 9 pages.
PCT/US2014/026735, International Search Report and Written Opinion dated Sep. 5, 2014, 15 Pages.
PCT/US2014/026735, Partial Search Report, dated Jun. 25, 2014, 8 pages.
Pemov, A. et al., "DNA analysis with multiplex microarray-enhanced PCR", *Nucleic Acids Research*, vol. 33, No. 2, 2005, 1-9.
Piepenburg, "Oligo Calc: Oligonucleotide Properties Calculator", *Northwestern University*, http://www.basic.northwestern.edu/biotools/oligocalc.html, Dec. 6, 2014, 20 Pages.
Piepenburg, "Primer-BLAST", *NCBI*, http://www.ncbi.nlm.nih.gov/tools/primer-blast/primertool.cgi?ctg_time=1417877793&job_key=0Ms93mzUxfD-SPpGm2jIOIBF-imTWucs, Dec. 4, 2014, 2 Pages.
Piepenburg, Olaf et al., "DNA Detection Using Recombination Proteins", *PLoS Biology*, vol. 4, issue 7 e204, Jul. 2006, 1115-1121.
Pourmand, N et al., "Direct electrical detection of DNA synthesis", *PNAS*, vol. 103(17), 2006, pp. 6466-6470.
Promega, "BioMath—Tm Calculations for Oligos", https://www.promega.com/techserv/tools/biomath/calc11.htm, Dec. 4, 2014, 5 pages.
Rehman, F. et al., "Immobilization of Acrylamide-modified Oligonucleotides by Co-polymerization", *Nucleic Acids Research*, vol. 27, No. 2, 1999, pp. 649-655.
Rothberg, J. et al., "An integrated semiconductor device enabling non-optical genome sequencing", *Nature*, vol. 475, No. 7356, Jul. 21, 2011, pp. 348-352.
Rychlik, et al., "A computer program for choosing optimal oligonucleotides for filter hybridization, sequencing and in vitro amplification of DNA", *Nucleic Acids Research*, vol. 17, No. 21, Nov. 11, 1989, 8543-8551.
Santalucia, John , "A unified view of polymer, dumbbell, and oligonucleotide DNA nearest-neighbor thermodynamics", *Biochemistry*, vol. 95, Proceedings of the National Academy of Sciences, USA, Feb. 1998, 1460-1465.
Sato, Kae et al., "Microbead-based rolling circle amplification in a microchip for sensitive DNA detection", *Lab Chip*, 10, 2010, 1262-1266.
Schadt, E. et al., "A window into third-generation sequencing", *Human Molecular Genetics*, vol. 19 (2), Sep. 21, 2010, R227-R240.
Schroth, "Oligo Calc: Oligonucleotide Properties Calculator", *Northwestern University*, http://www.basic.northwestern.edu/biotools/oligocalc.html, Dec. 4, 2014, 5 Pages.
Schroth, "Primer-BLAST", *NCBI*, http://www.ncbi.nlm.nih.gov/tools/primer-blast/primertool.cgi?ctg_time=1417745143&job_key=WkG3eUFz6Fz6FfT79fhts_In63i146-_cqL, Dec. 4, 2014, 1 page.
SG11201406717R, Written Opinion dated Nov. 24, 2015, 8 pgs.

Shapero, Michael et al., "SNP Genotyping by Multiplexed Solid-Phase Amplification and Fluorescent Minisequencing", *Genome Research*, 11, 2001, 1926-1934.
Shen, Feng et al., "Digital Isothermal Quantification of Nucleic Acids via Simultaneous Chemical Initiation of Recombinase Polymerase Amplification Reactions on SlipChip", *Anal. Chem.*, 83, 2011, 3533-3540.
Shendure, Jay et al., "Next-generation DNA sequencing", *Nature Biotechnology*, vol. 26, No. 10, Oct. 2008, 1135-1145.
Shigemori, Yasushi et al., "Multiplex PCR: use of heat-stable Thermus thermophilus RecA protein to minimize non-specific PCR products", *Nucleic Acids Research*, vol. 33, No. 14, e126, 2005, 1-9.
Sigma-Aldrich, "Oligos Melting Temperature", http://www.sigmaaldrich.com/life-science/custom-oligos/custom-dna/learning-center/oligos-melting-temp.html, Dec. 4, 2014, 2 pages.
Spink, Charles H., "Differential Scanning Calorimetry", *Methods Cell Biol.* (2008) 84:115-141, 2008, 115-141.
Vogelstein, et al., "Digital PCR", *Proc. Natl. Acad. Sci. USA*, vol. 96, Aug. 1999, 9236-9241.
Von Ahsen, N. et al., "Oligonucleotide Melthing Temperatures under PCR Conditions: Nearest-Neighbor Corrections for Mg2+, Deoxynucleotide Triphosphate, and Dimethyl Sulfoxide Concentrations with Comparison to Alternative Empirical Formulas", *Clinical Chemistry*, vol. 47 (11), 2001, 1956-1961.
Von Nickisch-Rosenegk, M. et al., "On-chip PCR amplification of very long templates using immobilized primers on glassy surfaces", *Biosensors & Bioelectronics*, vol. 20, 2005, 1491-1498.
Walker, et al., "Strand displacement amplification—an isothermal, in vitro DNA amplification technique", *Nucleic Acids Research*, vol. 20, Issue 7,, 1992, 1691-1696.
Walter, Nils et al., "Strand displacement amplification as an in vitro model for rolling-circle replication: Deletion formation and evolution during serial transfer", *Proc. Natl. Acad. Sci. USA*, vol. 91, Aug. 1994, 7937-7941.
Westin, Lorelei et al., "Anchored multiplex amplification on a microelectronic chip array", *Nature Biotechnology*, vol. 18, Feb. 2000, 119-204.
Xu, Ming Y. et al., "Dual primer emulsion PCR for next-generation DNA sequencing", *BioTechniques*, vol. 48, No. 5, 2010, 409-412.
Yershov, et al., "DNA Analysis and Diagnostics on Oligonucleotide Microchips", *Proc. Natl, Acad. Sci. USA 93*, 1996, 4913-4918.
EP16177421.1, European Search Report dated Oct. 17, 2016, 1-7.
SG11201406717R, SG Written Opinion dated Oct. 18, 2016, 1-10.
EP17178012.5 European Search Report, dated Nov. 20, 2017, 1-4.
EP17178957.1, European Search Report, dated Sep. 6, 2017, 1-8.
Xu et al., "Simultaneous amplification and screening of a whole plasmids using the T7 bacteriophage replisome", *Nucleic Acids Research*, vol. 34, No. 13, 2006, e98 (9 pages).
Patel, Smita et al., "Pre-Steady-State Kinetic Analysis of Processive DNA Replication Including Complete Characterization of an Exonuclease-Deficient Mutant", *Biochemistry*, 30, 1991, 511-525.
Ronaghi, M et al., "Real-time DNA Sequencing Using Detection of Pyrophosphate Release", *Anal Biochem*, vol. 242(1), 1996, pp. 84-89.

\* cited by examiner

| | FAM | VIC | | FAM | VIC | | FAM | VIC | | FAM | VIC |
|---|---|---|---|---|---|---|---|---|---|---|---|
| A1 | 50 | 31.96548 | C1 | 50 | | E1 | 50 | | G1 | 50 | 50 |
| A2 | 50 | 39.86279 | C2 | 50 | | E2 | 50 | | G2 | 50 | 30.95665 | 38.49394 |
| A3 | 44.3971 | 50 | C3 | 50 | | E3 | 50 | | G3 | 50 | 42.10394 | 36.18042 |
| A4 | 50 | 50 | C4 | 50 | | E4 | 45.15652 | 50 | G4 | 50 | 50 | 50 |
| A5 | 50 | 50 | C5 | 50 | | E5 | 50 | 39.25991 | G5 | 50 | 43.07935 | 50 |
| A6 | 50 | 50 | C6 | 50 | | E6 | 50 | 50 | G6 | 50 | 40.46702 | 50 |
| A7 | 50 | 50 | C7 | 50 | | E7 | 50 | 27.78382 | G7 | 50 | 50 | 50 |
| A8 | 50 | 50 | C8 | 50 | 38.08558 | E8 | 50 | 50 | G8 | 50 | 50 | 31.60849 |
| A9 | 50 | 50 | C9 | 50 | 44.47919 | E9 | 50 | 50 | G9 | 50 | 50 | 50 |
| A10 | 50 | 50 | C10 | 50 | | E10 | 50 | 50 | G10 | 50 | 50 | 50 |
| A11 | 50 | 50 | C11 | 50 | | E11 | 50 | 50 | G11 | 50 | 50 | 31.61124 |
| A12 | 50 | 50 | C12 | 50 | 32.6227 | E12 | 50 | 41.63503 | G12 | 50 | 50 | 50 |
| B1 | 50 | 39.01974 | D1 | 50 | 32.34154 | F1 | 38.27389 | 39.91924 | H1 | 50 | 50 | 50 |
| B2 | 50 | 50 | D2 | 50 | | F2 | 37.80156 | 50 | H2 | 50 | 50 | 50 |
| B3 | 50 | 50 | D3 | 50 | | F3 | 50 | 50 | H3 | 50 | 30.91996 | 38.31835 |
| B4 | 50 | 50 | D4 | 50 | 42.20201 | F4 | 50 | 50 | H4 | 50 | 50 | 50 |
| B5 | 42.93367 | 35.26348 | D5 | 50 | | F5 | 50 | 50 | H5 | 50 | 50 | 37.56089 |
| B6 | 50 | 40.18534 | D6 | 50 | | F6 | 39.90506 | 50 | H6 | 50 | 50 | 50 |
| B7 | 50 | 50 | D7 | 50 | 46.95021 | F7 | 39.65005 | 30.11287 | H7 | 36.69026 | 50 | 50 |
| B8 | 50 | 30.90235 | D8 | 50 | | F8 | 50 | 50 | H8 | 36.95259 | 50 | 50 |
| B9 | 50 | 50 | D9 | 50 | | F9 | 30.54854 | 50 | H9 | 50 | 50 | 50 |
| B10 | 50 | 50 | D10 | 50 | | F10 | 50 | 29.22241 | H10 | 50 | 50 | 50 |
| B11 | 50 | 50 | D11 | 50 | 34.98179 | F11 | 50 | 50 | H11 | 50 | 50 | 50 |
| B12 | 50 | 50 | D12 | 50 | | F12 | 50 | 50 | H12 | 50 | 50 | 50 |

FIG. 6

NUCLEIC ACID AMPLIFICATION

The present application claims the benefit of priority under 35 U.S.C. § 119 to U.S. Provisional Application No. 61/767,766, filed Feb. 21, 2013; 61/781,016, filed Mar. 14, 2013, and 61/792,247, filed Mar. 15, 2013; the present application is also a continuation of U.S. application Ser. No. 14/085,718, filed Nov. 20, 2013, which is a continuation of U.S. application Ser. No. 13/923,232, filed Jun. 20, 2013, which is a continuation of U.S. application Ser. No. 13/842,296, filed Mar. 15, 2013, which claims priority to U.S. Provisional Application Nos. 61/635,584, filed Apr. 19, 2012; 61/692,830, filed Aug. 24, 2012; 61/699,810, filed Sep. 11, 2012; 61/767,766, filed Feb. 21, 2013; 61/781,016, filed Mar. 14, 2013; and 61/792,247, filed Mar. 15, 2013. The present application is also a continuation-in-part of each of the following applications: (1) U.S. application Ser. No. 13/328,844, filed Dec. 16, 2011 and published as U.S. Patent Publ. No. 2012/0156728 on Jun. 21, 2012, which claims priority to U.S. Provisional Application Nos. 61/424,599, filed Dec. 17, 2010; 61/445,324, filed Feb. 22, 2011; 61/451,919, filed Mar. 11, 2011; 61/526,478, filed Aug. 23, 2011; and 61/552,660, filed Oct. 28, 2011; (2) U.S. application Ser. No. 13/828,049, filed Mar. 14, 2013, which claims priority to 61/692,830, filed Aug. 24, 2012; and which is a continuation-in-part of U.S. application Ser. No. 13/328,844, filed Dec. 16, 2011, which claims priority to U.S. Provisional Application Nos. 61/424,599, filed Dec. 17, 2010; 61/445,324, filed Feb. 22, 2011; 61/451,919, filed Mar. 11, 2011; 61/526,478, filed Aug. 23, 2011; and 61/552,660, filed Oct. 28, 2011; and (3) International PCT Application No. PCT/US2011/65535, filed Dec. 16, 2011, which claims priority to U.S. Provisional Application Nos. 61/424,599, filed Dec. 17, 2010; 61/445,324, filed Feb. 22, 2011; 61/451,919, filed Mar. 11, 2011; 61/526,478, filed Aug. 23, 2011; and 61/552,660, filed Oct. 28, 2011; the disclosures of all of which aforementioned applications are incorporated herein by reference in their entireties.

SEQUENCE LISTING

This application refers to a "Sequence Listing" listed below, which is provided as a text file. The text file contains a document entitled "LT00718_CON.TXT" (1,049 bytes, created Oct. 16, 2013), which is incorporated by reference in its entirety.

BACKGROUND

Nucleic acid amplification is very useful in molecular biology and has wide applicability in practically every aspect of biology, therapeutics, diagnostics, forensics and research. Generally, amplicons are generated from a starting template using one or more primers, where the amplicons are homologous or complementary to the template from which they were generated. Multiplexed amplification can also streamline processes and reduce overheads. This application relates to methods and reagents for nucleic acid amplification and/or analysis.

SUMMARY

Methods, reagents and products of nucleic acid amplification and/or analysis are provided herein. Amplification can make use of immobilized and/or soluble primers. A single set of primers can be mixed with different templates, or a single template can be contacted with multiple different primers, or multiple different templates can be contacted with multiple different primers. Amplicons generated from methods provided herein are suitable substrates for further analysis, e.g., sequence determination.

In some embodiments, the present teachings provide compositions, systems, methods, apparatuses and kits for nucleic acid amplification.

DETAILED DESCRIPTION OF THE DRAWINGS

FIG. 1 provides a schematic showing an embodiment of template walking. In an alternative embodiment, the immobilized primer comprises an adenosine-rich sequence designated as $(A)_n$, e.g., $(A)_{30}$, and the primer binding site for the immobilized primer on the template comprises a complementary T-rich sequence, e.g., (Mo.

FIG. 2 depicts an overview of amplification on beads by template walking and deposition of beads onto a planar array for sequencing.

FIG. 3 depicts some alternative embodiments using semiconductor-based detection of sequencing by synthesis. Template walking can be used to generate a population of clonal amplicons on a bead or on the base or bottom of a reaction chamber. In an alternative embodiment, the immobilized primer comprises an adenosine-rich sequence designated as $(A)_n$, e.g., $(A)_{30}$, and the primer binding site for the immobilized primer on the template comprises a complementary T-rich sequence, e.g., $(T)_{30}$.

FIG. 4 depicts some alternative embodiments of immobilization sites in the form of primer lawns on planar substrates. Arrays of separated immobilization sites can be used or else a single continuous lawn of primers can be considered to be a random array of immobilization sites. Optionally, the location of one or more immobilization sites in the continuous lawn of primers can be undetermined as yet, where the location is determined at the time of attachment of the initial template before walking or is determined by the space occupied by the amplified cluster. In an alternative embodiment, the immobilized primer comprises an adenosine-rich sequence designated as $(A)_n$, e.g., $(A)_{30}$, and the primer binding site for the immobilized primer on the template comprises a complementary T-rich sequence, e.g., (Mo.

FIG. 5 illustrates the influence of temperature on the template walking reaction. A graphical plot of the delta Ct before and after the template walking amplification was calculated and plotted against reaction temperature.

FIG. 6 provides a table of the Ct values of the 96 duplex TaqMan qPCR reactions.

FIG. 7 depicts data illustrating roughly 100,000-fold. amplification by template walking on beads. Delta Ct before and after the template walking reaction and fold of amplification before and after the template walking reaction was calculated and plotted against reaction time.

FIGS. 8A-C provides a schematic depiction of an exemplary strand-flipping and walking strategy. FIG. 8A depicts template walking, FIG. 8B depicts strand flipping to generate flipped strands, FIG. 8C depicts addition of new primer-binding sequence Pg' on final flipped strands.

Figure 13:
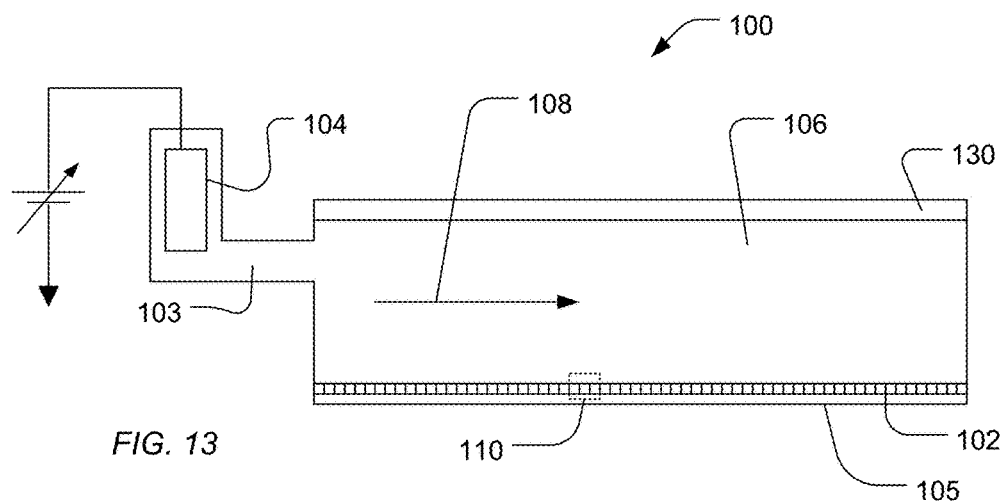

FIG. 13 includes an illustration of an exemplary measurement system.

Figure 14:
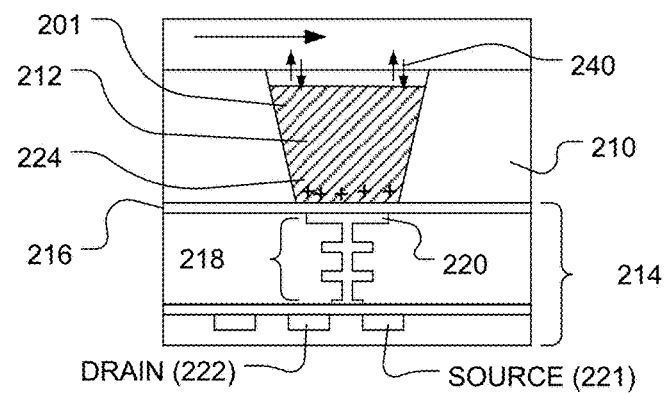

FIG. 14 includes an illustration of an exemplary measurement component.

Figure 15:
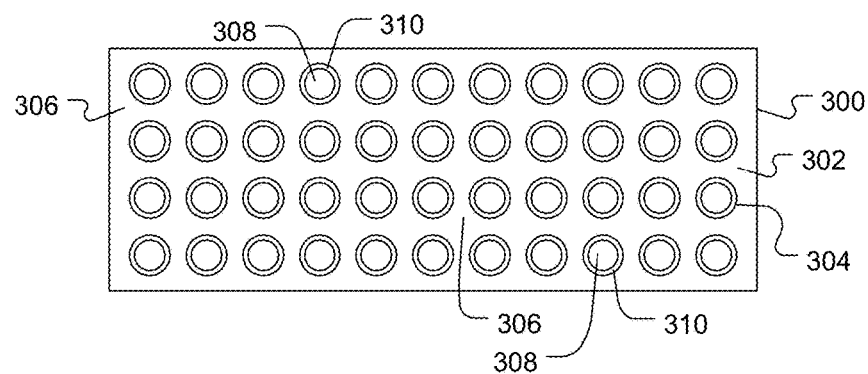

FIG. 15 includes an illustration of exemplary array of measurement components.

Figure 16:
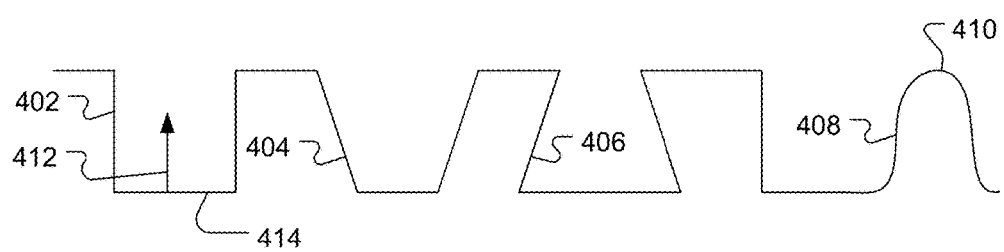

FIG. 16 includes an illustration of exemplary well configurations.

Figure 17:
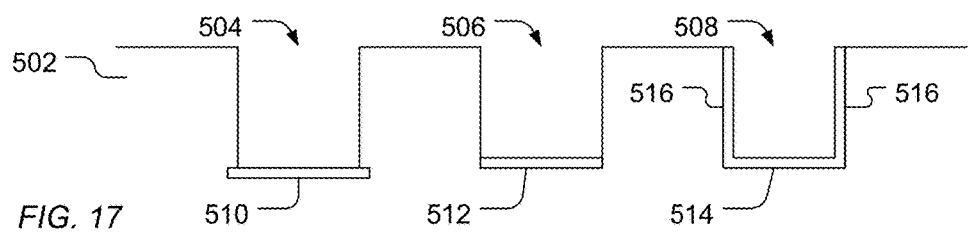

FIG. 17 includes an illustration of exemplary well and sensor configurations.

FIG. 18, FIG. 19, FIG. 20 and FIG. 21 include illustrations of workpieces during processing by an exemplary method.

Figure 22:
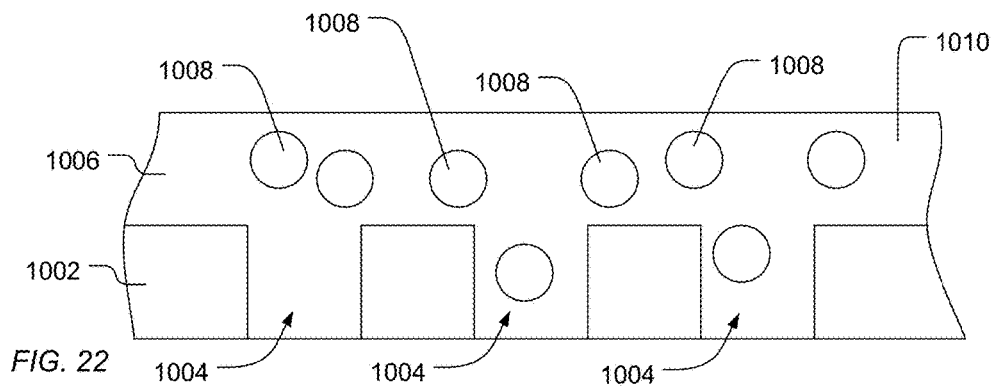
Figure 23:
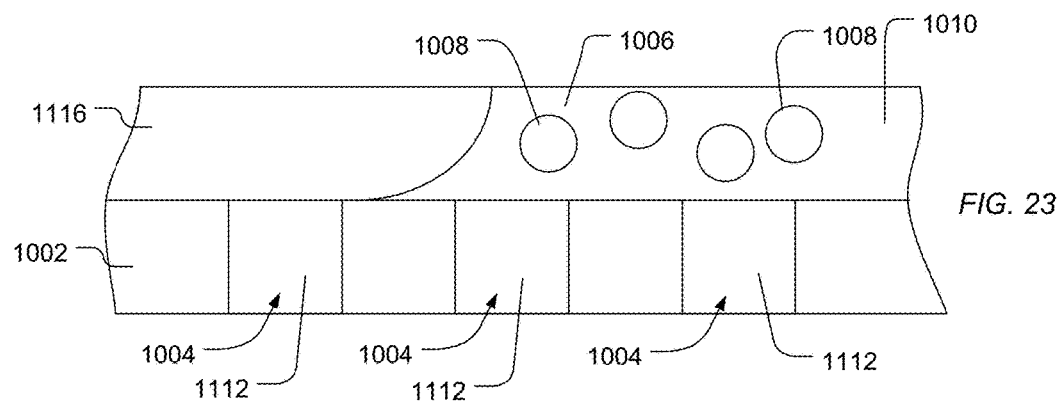
Figure 24:
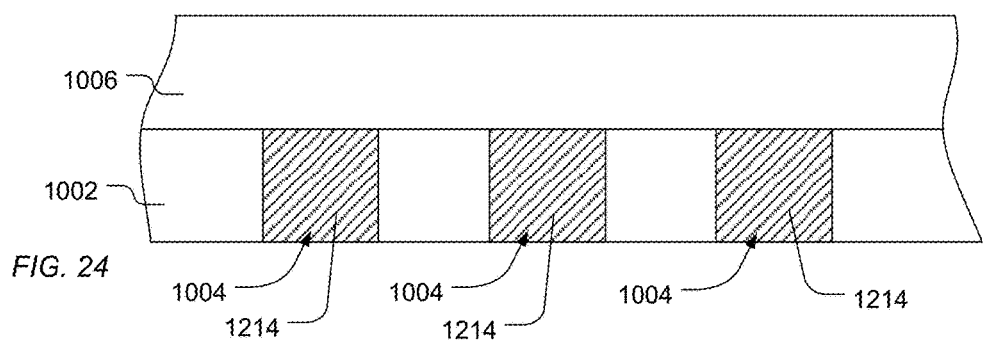

FIG. 22, FIG. 23 and FIG. 24 include illustrations of workpieces during processing by an exemplary method.

Figure 25:
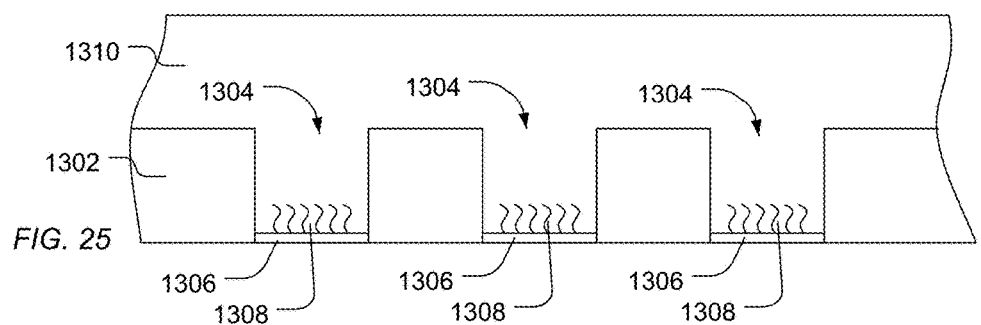
Figure 26:
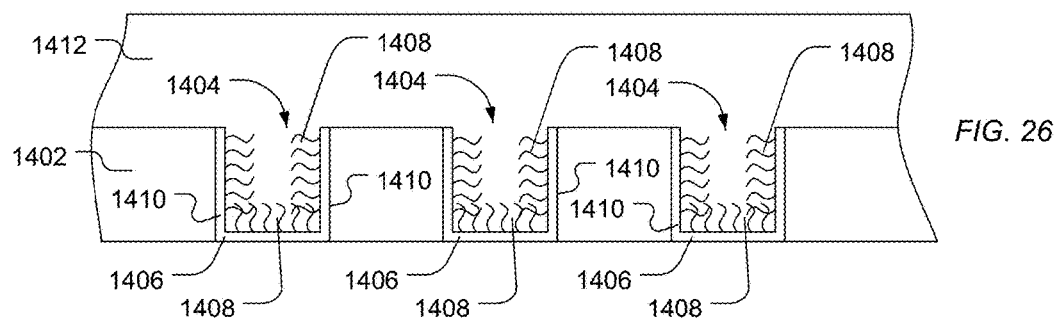
Figure 27:
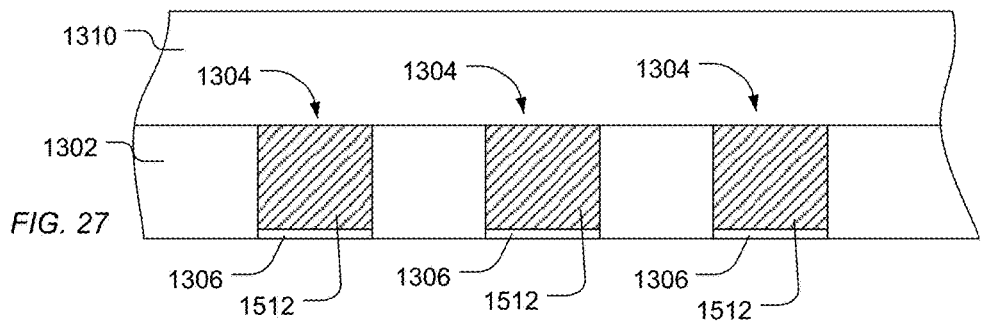

FIG. 25, FIG. 26 and FIG. 27 include illustrations of workpieces during processing by an exemplary method.

Figure 28:
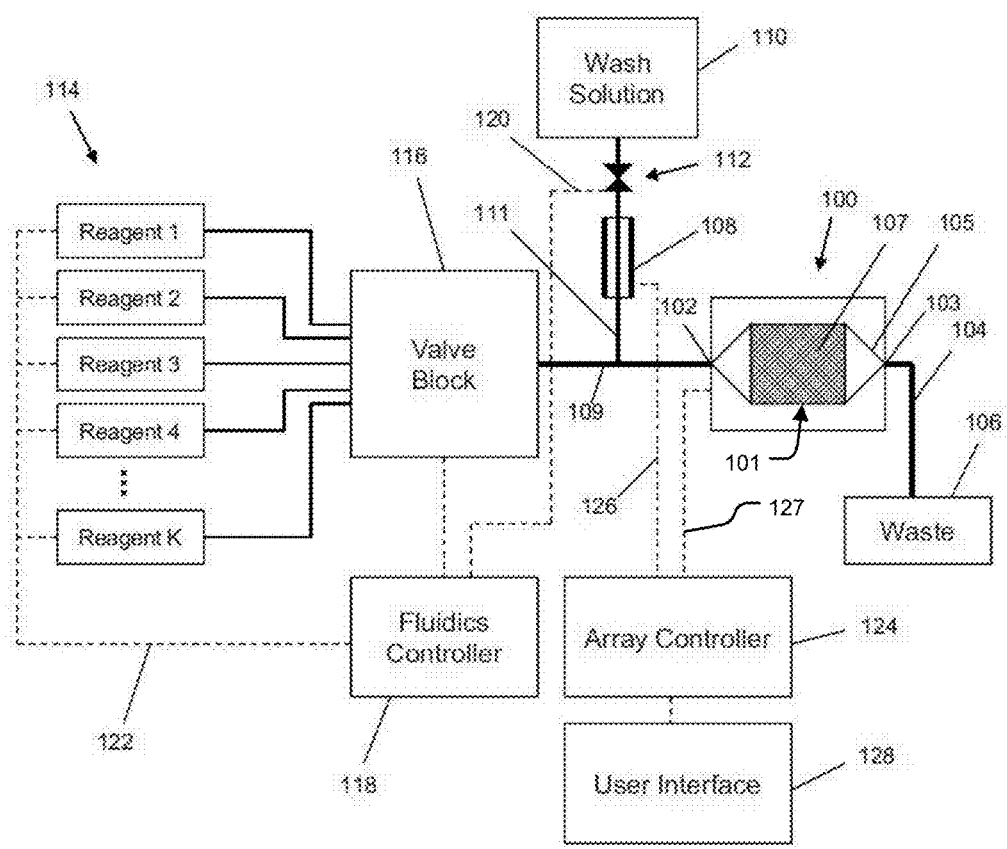

FIG. 28 illustrates an exemplary block diagram of components of a system for nucleic acid sequencing according to an exemplary embodiment.

Figure 29:
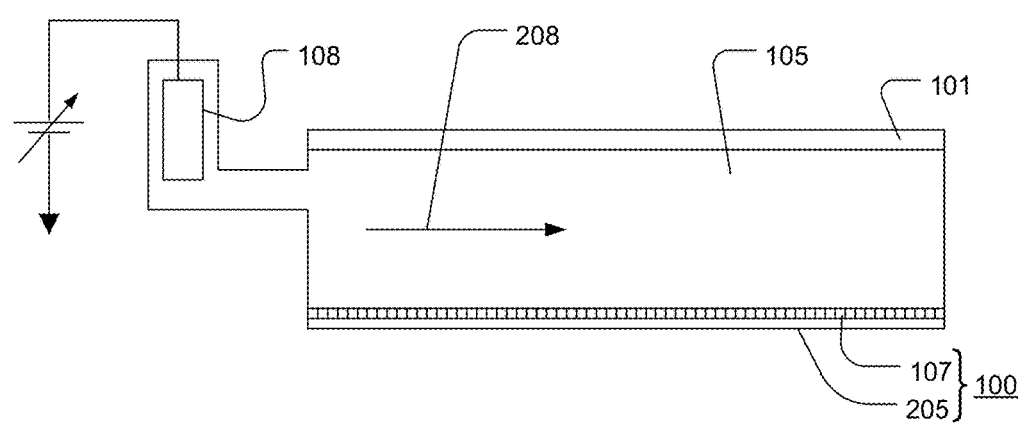

FIG. 29 illustrates an exemplary cross-sectional view of a portion of the integrated circuit device and flow cell according to an exemplary embodiment.

Figure 30:
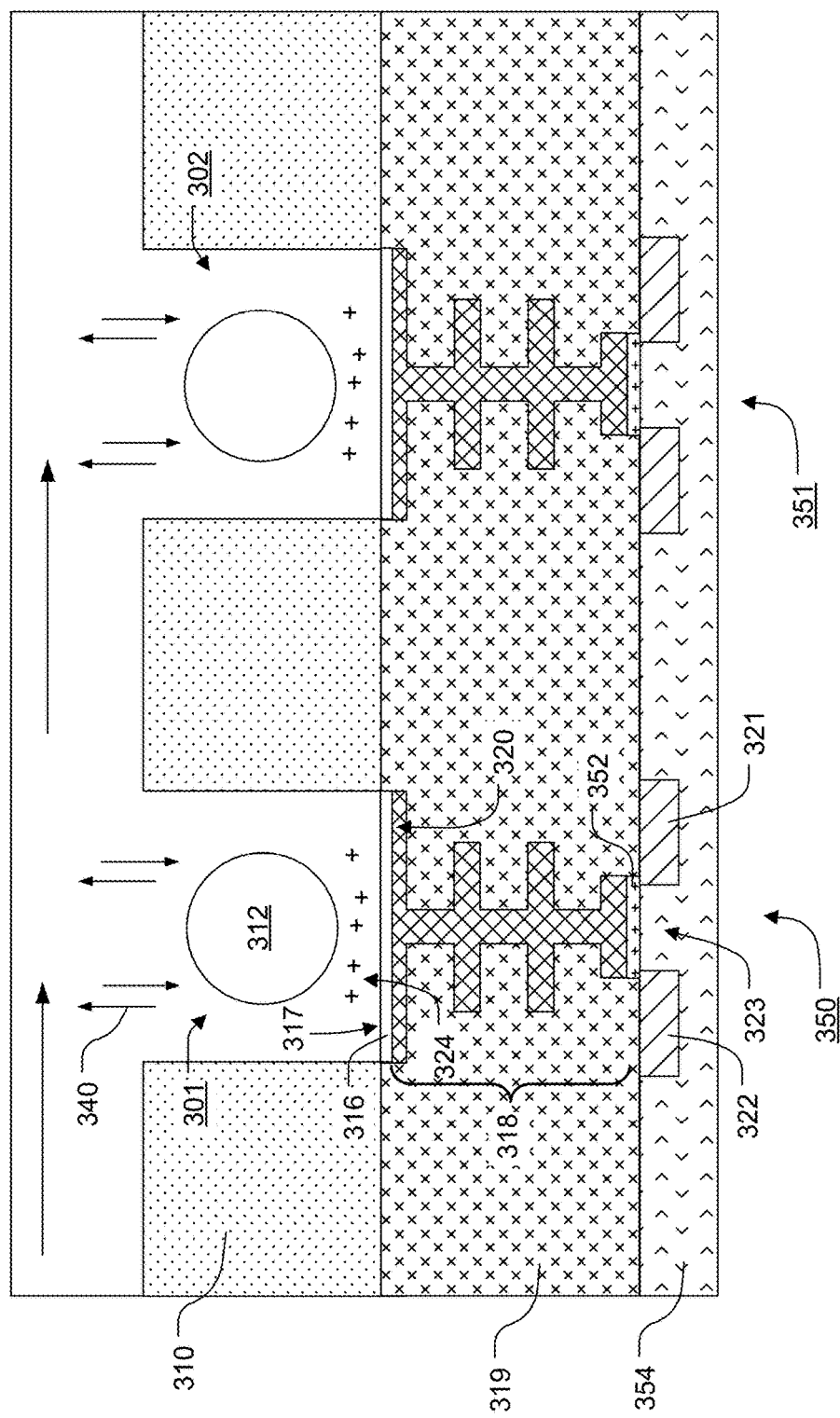

FIG. 30 illustrates an exemplary cross-sectional view of representative chemical sensors and corresponding reaction regions according to an exemplary embodiment.

DETAILED DESCRIPTION

Conventional amplification of a nucleic acid template typically involves repeated replication of the template (and/or its progeny) using appropriate synthetic systems. In such conventional methods, each instance of replication is typically preceded by denaturation of the template to be amplified using extreme denaturing conditions, thereby rendering the template substantially single stranded. Some common and widely used examples of extreme denaturing conditions used for conventional amplification including thermal denaturation using temperatures well above the melting point of the nucleic acid template to be amplified (e.g., conventional PCR involving thermocycling using denaturation temperatures of well above 90° C., typically around 94-95° C.) or exposure of the template to harsh denaturants such as NaOH, guanidium agents, and the like. Such methods typically require specialized equipment (e.g., thermocyclers), and entail additional manipulations during the amplification process (e.g., annealing step for conventional PCR; wash step to remove chemical denaturants, etc.), thereby increasing the cost, effort and time associated with such amplification, as well as constraining the yields ultimately obtainable using such methods. Moreover, such extreme denaturing conditions typically render the template to be amplified substantially single stranded, posing a challenge for the large number of applications involving multiplex clonal amplification, i.e., clonal amplification of multiple different templates within the same reaction mixture. For such multiplex applications, use of these extreme denaturing conditions can be counterproductive because it typically results in the liberation of one strand of the template from its associated location, leaving the liberated strand free to migrate within the solution and contaminate other amplicons developing in close proximity. Such cross-contamination typically results in reduced yields of monoclonal amplified populations and increased yield of polyclonal contaminants that typically not useful for many downstream applications. There exists a need for improved nucleic acid amplification methods (as well as associated compositions, systems, and kits) that eliminate the pitfalls associated with conventional amplification methods.

In some embodiments, the disclosure relates generally to methods, as well as related compositions, systems and apparatuses, for nucleic acid amplification, comprising amplifying a nucleic acid template to produce an amplicon comprised of a substantially monoclonal population of polynucleotides. Monoclonality is typically considered to be desirable in nucleic acid assays because the different characteristics of the diverse polynucleotides within a polyclonal population can complicate the interpretation of assay data. One example involves nucleic acid sequencing applications, in which the presence of polyclonal populations can complicate the interpretation of sequencing data; however, with many sequencing systems are not sensitive enough to detect nucleotide sequence data from a single polynucleotide template, thus requiring clonal amplification of templates prior to sequencing.

In some embodiments, the amplification methods of the present disclosure can be employed to clonally amplify two or more different nucleic acid templates, optionally using and within the same reaction mixture, to produce at least two substantially monoclonal nucleic acid populations. Optionally, at least one of the substantially monoclonal population is formed via amplification of a single polynucleotide template.

Optionally, the two or more different nucleic acid templates are amplified simultaneously and/or in parallel.

In some embodiments, the disclosure relates generally to methods (as well as related compositions, systems and kits) for nucleic acid synthesis, comprising: providing at least two double stranded nucleic acid templates in a reaction mixture; and forming at least two substantially monoclonal nucleic acid populations by clonally amplifying the at least two double stranded nucleic acid templates according to any of the methods described herein.

In some embodiments, clonally amplifying optionally includes forming a reaction mixture. The reaction mixture can include a continuous liquid phase. In some embodiments, the continuous liquid phase includes a single continuous aqueous phase. The liquid phase can include two or more polynucleotide templates, which can optionally have the same nucleotide sequence, or can have nucleotide sequences that are different from each other. In some embodiments, at least one of the two or more polynucleotide templates can include at least one nucleic acid sequence that is substantially non-identical, or substantially non-complementary, to at least one other polynucleotide template within the reaction mixture.

In some embodiments, the two or more different nucleic acid templates are localized, deposited or positioned at different sites prior to the amplifying.

In some embodiments, the two or more different nucleic acid templates are clonally amplified in solution, optionally within a single reaction mixture, and the resulting two or more substantially monoclonal nucleic acid populations are then localized, deposited or positioned at different sites following such clonal amplification.

The different sites are optionally members of an array of sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

Optionally, the two or more different nucleic acid templates are amplified within a continuous liquid phase, typically a continuous aqueous phase, of the same reaction mixture, thereby producing two or more different and substantially monoclonal populations of polynucleotides, each population being generated via amplification of a single polynucleotide template present in the reaction mixture.

Optionally, the continuous liquid phase is contained within a single or same phase of the reaction mixture.

In some embodiments, the disclosure relates generally to methods (as well as related compositions, systems and kits) for nucleic acid synthesis, comprising: providing a double stranded nucleic acid template; and forming a substantially monoclonal nucleic acid population by amplifying the double stranded nucleic acid template. Optionally, the amplifying includes clonally amplifying the double stranded nucleic acid template.

Optionally, the amplifying includes performing at least one round of amplification under substantially isothermal conditions.

Optionally, the amplifying includes performing at least two consecutive cycles of nucleic acid synthesis under substantially isothermal conditions.

In some embodiments, the amplifying includes recombinase polymerase amplification (RPA). For example, the amplifying can include performing at least one round of RPA.

In some embodiments, the amplifying includes template walking. For example, the amplifying can include performing at least one round of template walking.

In some embodiments, the amplifying optionally includes performing two different rounds of amplification within the sites or reaction chambers. For example, the amplifying can include performing at least one round of RPA within the sites or reaction chambers, and performing at least one round of template walking within the sites or reaction chambers, in any order or combination of rounds. In some embodiments, at least two consecutive cycles in any one or more of the rounds of amplification are performed under substantially isothermal conditions. In some embodiments, at least one of the rounds of amplification is performed under substantially isothermal conditions.

Optionally, the nucleic acid template to be amplified is double stranded, or is rendered at least partially double stranded using appropriate procedures prior to amplification. (The template to be amplified is referred to interchangeably herein as a nucleic acid template or a polynucleotide template). In some embodiments, the template is linear. Alternatively, the template can be circular, or include a combination of linear and circular regions.

Optionally, the double stranded nucleic acid template includes a forward strand. The double stranded nucleic acid template can further include a reverse strand. The forward strand optionally includes a first primer binding site. The reverse strand optionally includes a second primer binding site.

In some embodiments, the template already includes a first and/or second primer binding site. Alternatively, the template optionally does not originally include a primer binding site, and the disclosed methods optionally include attaching or introducing a primer binding site to the template prior to the amplifying. For example, the method can optionally include ligating or otherwise introducing an adaptor containing a primer binding site to, or into, the templates. The adapter can be ligated or otherwise introduced to an end of a linear template, or within the body of a linear or circular template. Optionally, the template can be circularized after the adapter is ligated or introduced. In some embodiments, a first adapter can be ligated or introduced at a first end of a linear template, and a second adaptor can be ligated or introduced at a second end of the template.

In some embodiments, the amplifying includes contacting the partially denatured template with a first primer, with a second primer, or with both a first primer and a second primer, in any order or combination.

In some embodiments, the first primer contains a first primer sequence. The first primer optionally includes an extendible end (e.g., a 3'OH containing end). The first primer can optionally be attached to a compound (e.g., a "drag tag"), or to a support (e.g., a bead or a surface of the site or reaction chamber).

In some embodiments, the second primer contains a second primer sequence. The second primer optionally includes an extendible end (e.g., a 3'OH containing end). The second primer can optionally be attached to a compound (e.g., a "drag tag"), or to a support (e.g., a bead or a surface of the site or reaction chamber).

Optionally, the first primer binds to the first primer binding site to form a first primer-template duplex. The second primer can bind to the second primer binding site to form a second primer-template duplex.

In some embodiments, amplifying includes extending the first primer to form an extended first primer. For example, amplifying can include extending the first primer of the first primer-template duplex to form an extended first primer.

In some embodiments, amplifying includes extending the first primer to form an extended first primer. For example, amplifying can include extending the first primer of the first primer-template duplex to form an extended first primer.

Optionally, the extending is performed by a polymerase. The polymerase can be a strand-displacing polymerase.

In some embodiments, the amplifying includes contacting the template to be amplified with a recombinase.

In some embodiments, the amplifying includes forming a partially denatured template. For example, the amplification can include partially denaturing the double stranded nucleic acid template.

Optionally, partially denaturing includes subjecting the double stranded nucleic acid template to partially denaturing conditions.

In some embodiments, partially denaturing conditions include temperatures that are less than the Tm of the nucleic acid template including, for example, at least 5° C., 10° C., 15° C., 20° C., 25° C. or 50° C. below the Tm of the nucleic acid template. In some embodiments, partially denaturing conditions include temperatures greater (for example, at least 5° C., 10° C., 15° C., 20° C., 25° C. or 50° C. greater) than the Tm of the first primer, the second primer, or both the first and second primer. In some embodiments, partially denaturing conditions include temperatures greater (for example, at least 5° C., 10° C., 15° C., 20° C., 25° C. or 50° C. greater) than the Tm of the first primer binding site, the second primer binding site, or both the first primer binding site and the second primer binding site. In some embodiments, the nucleic acid template can include an adaptor sequence at one or both ends, and the partially denaturing conditions can include temperatures greater than the Tm of the adaptor sequence. In some embodiments, partially denaturing conditions (particularly partially denaturing temperatures) are employed to selectively amplify nucleic acid templates in a "template walking" process, as described further herein.

In other embodiments, partially denaturing conditions include treating or contacting the nucleic acid templates to be amplified with one or more enzymes that are capable of partially denaturing the nucleic acid template, optionally in a sequence-specific or sequence-directed manner. In some embodiments, at least one enzyme catalyzes strand invasion and/or unwinding, optionally in a sequence-specific manner. Optionally, the one or more enzymes include one or more enzymes selected from the group consisting of: recombinases, topoisomerases and helicases. In some embodiments, partially denaturing the template can include contacting the template with a recombinase and forming a nucleoprotein complex including the recombinase. Optionally, the template is contacted with a recombinase in the presence of a first primer, a second primer, or both a first and second primer. Partially denaturing can include catalyzing strand exchange using the recombinase and hybridizing the first primer to the first primer binding site (or hybridizing the second primer to the second primer binding site). In some embodiments, partially denaturing includes performing strand exchange and hybridizing both the first primer to the first primer binding site and the second primer to the second primer binding site using the recombinase.

In some embodiments, the partially denatured template includes a single stranded portion and a double stranded portion. In some embodiments, the single stranded portion includes the first primer binding site. In some embodiments, the single stranded portion includes the second primer binding site. In some embodiments, the single stranded portion includes both the first primer binding site and the second primer binding site.

In some embodiments, partially denaturing the template includes contacting the template with one or more nucleoprotein complexes. At least one of the nucleoprotein complexes can include a recombinase. At least one of the nucleoprotein complexes can include a primer (e.g., a first primer or a second primer, or a primer including a sequence complementary to a corresponding primer binding sequence in the template). In some embodiments, partially denaturing the template can include contacting the template with a nucleoprotein complex including a primer. Partially denaturing can include hybridizing the primer of the nucleoprotein complex to the corresponding primer binding site in the template, thereby forming a primer-template duplex.

In some embodiments, partially denaturing the template can include contacting the template with a first nucleoprotein complex including a first primer. Partially denaturing can include hybridizing the first primer of the first nucleoprotein complex to the first primer binding site of the forward strand, thereby forming a first primer-template duplex.

In some embodiments, partially denaturing the template can include contacting the template with a second nucleoprotein complex including a second primer. Partially denaturing can include hybridizing the second primer of the second nucleoprotein complex to the second primer binding site of the reverse strand, thereby forming a second primer-template duplex.

In some embodiments, the disclosed methods (and related compositions, systems and kits) can further include one or more primer extension steps. For example, the methods can include extending a primer via nucleotide incorporation using a polymerase.

In some embodiments, the polymerase is a strand-displacing polymerase.

Optionally, extending a primer includes contacting the primer with a polymerase and one or more types of nucleotides under nucleotide incorporation conditions. In some embodiments, the one or more types of nucleotides do not include extrinsic labels, particularly optically detectable labels, for example fluorescent moieties or dyes. Optionally, the reaction mixture includes nucleotides that are naturally occurring nucleotides. Optionally, the nucleotides do not include groups that terminate nucleic acid synthesis (e.g., dideoxy groups, reversible terminators, and the like). Typically, extending a primer occurs in a template-dependent fashion.

Optionally, the disclosed methods (and related compositions, systems and kits) include extending the first primer by incorporating one or more nucleotides into the first primer of the first primer-template duplex using the polymerase, thereby forming an extended first primer.

Optionally, the disclosed methods (and related compositions, systems and kits) include binding a second primer to the second primer binding site of the first extended primer by any suitable method (e.g., ligation or hybridization).

Optionally, the disclosed methods (and related compositions, systems and kits) include extending the second primer by incorporating one or more nucleotides into the second primer of the second primer-template duplex using the polymerase, thereby forming an extended second primer.

In some embodiments, extending the first primer results in formation of a first extended primer. The first extended primer can include some or all of the sequence of the reverse strand of the template. Optionally, the first extended primer includes a second primer binding site.

In some embodiments, extending the second primer results in formation of a second extended primer. The second extended primer can include some or all of the sequence of the forward strand of the template. Optionally, the second extended primer includes a first primer binding site.

In some embodiments, the methods are performed without subjecting the double stranded nucleic acid template to extreme denaturing conditions during the amplifying. For example, the methods can be performed without subjecting the nucleic acid template(s) to temperatures equal to or greater than the Tm of the template(s) during the amplifying. In some embodiments, the methods can be performed without contacting the template(s) with chemical denaturants such as NaOH, urea, guanidium, and the like, during the amplifying. In some embodiments, the amplifying includes isothermally amplifying.

In some embodiments, the methods are performed without subjecting the nucleic acid template(s) to extreme denaturing conditions during at least two, three, four, or more than four, consecutive cycles of nucleic acid synthesis. For example, the methods can include two, three, four, or more than four, consecutive cycles of nucleic acid synthesis without contacting the nucleic acid template(s) with a chemical denaturant. In some embodiments, the methods can include performing two, three, four, or more than four, consecutive cycles of nucleic acid synthesis without subjecting the nucleic acid template(s) to temperatures that are greater than 25, 20, 15, 10, 5, 2 or 1° C. below the actual or calculated Tm of the template, or population of templates (or the actual or calculated average Tm of the template, or population of templates). The two, three, four, or more than four, consecutive cycles of nucleic acid synthesis may include intervening steps of partial denaturation and/or primer extension.

In some embodiments, the disclosed methods (and related compositions, systems and kits) can further include linking one or more extended primer strands to a support. The linking can optionally be performed during the amplifying, or alternatively after the amplification is complete. In some embodiments, the support includes multiple instances of a second primer, and the methods can include hybridizing at least one of the extended first primer strands to a second primer of the support.

In some embodiments, the disclosed methods (and related compositions, systems and kits) can further include linking one or more extended second primer strands to a support. In some embodiments, the support is attached to a first primer. For example, the support can include multiple instances of a first primer, and the methods can include hybridizing at least one of the extended second primers to a first primer of the support, thereby linking the extended second primer to the support. For example, the first primer can hybridize to a first primer binding site in the extended second primer.

In some embodiments, the support is attached to a second primer. For example, the support can include multiple instances of a second primer, and the methods can include hybridizing at least one of the extended first primers to a second primer of the support, thereby linking the extended first primer to the support. For example, the first primer can hybridize to a second primer binding site in the extended first primer.

In some embodiments, the support includes both at least one first primer and at least one second primer, and the disclosed methods (and related compositions, systems and kits) including linking both an extended first primer and an extended second primer to the support.

Optionally, the support is attached to a target-specific primer. The target-specific primer optionally hybridizes (or is capable of hybridizing) to a first subset of templates within the reaction mixture, but is unable to bind to a second subset of templates within the reaction mixture.

Optionally, the support is attached to a universal primer. The universal primer optionally hybridizes (or is capable of hybridizing) to all, or substantially all, of the templates within the reaction mixture.

Optionally, the reaction mixture includes a first support covalently attached to a first target-specific primer and a second support covalently attached to a second target-specific primer, and wherein the first and second target-specific primers are different from each other.

Optionally, the first target-specific primer is substantially complementary to a first target nucleic acid sequence and the second target-specific primer is substantially complementary to a second target nucleic acid sequence, and wherein the first and second target nucleic acid sequences are different.

In some embodiments, the disclosed methods include forming a first amplicon by amplifying a first template onto a first support, and forming a second amplicon by amplifying a second template onto a second support, optionally within the same continuous phase of a reaction mixture. The first amplicon is optionally linked or attached to the first support, and the second amplicon is optionally linked or attached to the second support.

The disclosed methods optionally comprise producing two or more monoclonal, or substantially monoclonal, amplicons by clonally amplifying two or more polynucleotide templates. The two or more polynucleotide templates are optionally clonally amplified within a continuous liquid phase of an amplification reaction mixture. The continuous liquid phase of the amplification reaction mixture can include a continuous aqueous phase. In some embodiments, the amplifying includes generating at least two substantially monoclonal populations of amplified polynucleotides, each of said populations being formed via amplification of a single polynucleotide template. Optionally, the clonally amplifying includes at least one round of RPA. Optionally, the clonally amplifying includes at least one round of template walking.

In some embodiments, the amplifying optionally includes forming an amplification reaction mixture including a continuous liquid phase. In some embodiments, the continuous liquid phase is a single continuous aqueous phase. The liquid phase can include two or more polynucleotide templates, which can optionally be different from each other. For example, the two or more polynucleotide templates can include at least one nucleic acid sequence that is substantially non-identical, or substantially non-complementary, to at least one other polynucleotide template within the amplification reaction mixture.

In some embodiments, the amplifying optionally includes forming an amplification reaction mixture including a single continuous aqueous phase having two or more polynucleotide templates. Amplifying optionally includes forming two or more substantially monoclonal nucleic acid populations by clonally amplifying the two or more polynucleotide templates within the single aqueous phase. Optionally, the clonally amplifying includes at least one round of RPA. Optionally, the clonally amplifying includes at least one round of template walking.

In some embodiments, the disclosure relates generally to methods (and related compositions, systems and kits) for amplifying one or more nucleic acid templates, optionally in parallel, using partially denaturing conditions. In some embodiments, two or more templates are amplified using such methods, optionally in array format. Optionally, the templates are amplified in bulk in solution prior to distribution into the array. Alternatively, the templates are first distributed to sites in the array and then amplified in situ at (or within) the sites of the array.

Optionally, the template is single stranded or double stranded. The template optionally includes one or more primer binding sites.

In some embodiments, the methods can include subjecting a double-stranded nucleic acid template including a primer binding site on at least one strand to at least one cycle of template-based replication using a polymerase.

Optionally, the at least one cycle of template-based replication includes a partial denaturation step, an annealing step, and an extension step.

In some embodiments, the methods include amplifying the double stranded nucleic acid template by subjecting the template to at least two consecutive cycles of template-based replication.

In some embodiments, the methods include partially denaturing the template.

Optionally, the methods include forming a partially denatured template including a single stranded region. The partially denatured template can also include a double stranded region. The single stranded region can contain the primer binding site.

Optionally, the partially denaturing includes subjecting the template to a temperature that is at least 20, 15, 10, 5, 2, or 1° C. lower than the Tm of the primer binding site.

Optionally, the partially denaturing includes subjecting the template to a temperature that is equal to or greater than the Tm of the primer binding site.

Optionally, the partially denaturing includes contacting the double stranded template with a recombinase and a primer. The recombinase and primer may form part of a nucleoprotein complex, and the partially denaturing includes contacting the template with the complex.

In some embodiments, the methods include forming a primer-template duplex by hybridizing a primer to the primer binding site of the single stranded region. In some embodiments, the primed template includes a double stranded region. Optionally, the double stranded region does not contain a primer binding site.

In some embodiments, the methods include extending the primer of the primer-template duplex. Optionally, the methods include forming an extended primer.

In some embodiments, different templates can be clonally amplified onto different discrete supports (e.g., beads or particles) without the need for compartmentalization prior to amplification. In other embodiments, the templates are partitioned or distributed into emulsions prior to amplifying. Optionally, the templates are distributed into droplets forming part of a hydrophilic phase of an emulsion having a discontinuous hydrophilic phase and a continuous hydrophobic phase. In some embodiments, the emulsion droplets of the hydrophilic phase also include one or more components necessary to practice RPA. For example, the emulsion droplets can include a recombinase. Optionally, the droplets include a strand-displacing polymerase. In some embodiments, the droplets include a support-immobilized primer and/or a solution phase primer. Optionally, the primer can bind to the template, or to an amplification product thereof.

In some embodiments, the disclosed compositions, systems, methods, apparatuses and kits for nucleic acid amplification using emulsion-based amplification comprising nucleic acid synthesis following partial denaturation of the template offer advantages over conventional amplification methods (including emulsion based PCR or emPCR involving traditional thermocycling). For example, a nucleic acid amplification reaction comprising emulsion-based RPA ("emRPA"), or emulsion-based template walking, can yield longer amplified polynucleotide templates, fewer amplification steps, reduced time for preparing amplified polynucleotide templates, and/or increased quality of sequencing data. Some suitable emulsion compositions for use with the disclosed amplification methods can be found, for example, in U.S. Pat. Nos. 7,622,280, 7,601,499 and 7,323,305, incorporated by reference herein in their entireties.

In some embodiments, the methods include providing a double stranded template including a forward strand containing a first primer binding site, a reverse strand containing a second primer binding site; partially denaturing the template and forming a partially denatured template including a single stranded region containing the first primer binding site and at least one double stranded region; forming a first primer-template duplex by hybridizing a first primer to the first primer binding site of the single stranded region; extending the first primer of the first primer-template duplex using a polymerase to form an extended first primer including a second primer binding site, wherein the extended first primer is at least partially hybridized to the forward strand of the template; partially denaturing the extended first strand from the template to form a single stranded region including a second primer binding site; hybridizing a second primer to the second primer binding site of the single stranded region and forming a second primer-template duplex, and extending the second primer of the second primer-template duplex, thereby forming an extended second primer.

In some embodiments, the disclosure relates generally to methods (and related compositions, systems and kits) for a method for nucleic acid synthesis from a nucleic acid template, comprising: providing a first nucleic acid duplex including a forward strand and a reverse strand, wherein the forward strand contains a forward primer binding site and the reverse strand contains a reverse primer binding site and wherein the first duplex has a first melting temperature ("template Tm"), the forward primer binding site has a second melting temperature ("forward primer Tm") and the reverse primer binding site has a third melting temperature ("reverse primer Tm"); partially denaturing the first duplex, wherein the partially denatured first duplex includes a single-stranded region containing the forward primer binding site and at least one double stranded region; forming a primed first duplex by hybridizing a forward primer to the forward primer binding site of the partially denatured first duplex; extending the forward primer by contacting the primed first duplex with a strand displacing polymerase and nucleotides under primer extension condition, thereby forming second duplex having a fourth melting temperature ("fourth Tm") and including one strand containing the forward primer binding site and one strand containing the reverse primer binding site; partially denaturing the second duplex, wherein the partially denatured second duplex includes a single-stranded region containing the reverse primer binding site and at least one double stranded region; forming a reverse primed second duplex by hybridizing a reverse primer to the reverse primer binding site of the partially denatured second duplex; extending the reverse primer of the reverse primed second duplex by contacting the reverse primed second duplex with a strand displacing polymerase and nucleotides under primer extension conditions.

In some embodiments, the methods (and related compositions, systems, and kits) can further include sequencing an amplified template, or sequencing an extended primer, (e.g. an extended first primer, or extended second primer). The sequencing can include any suitable method of sequencing known in the art. In some embodiments, the sequencing includes sequencing by synthesis or sequencing by electronic detection (e.g., nanopore sequencing). In some embodiments, sequence includes extending a template or amplified template, or extending a sequencing primer hybridized to a template or amplified template, via nucleotide incorporation by a polymerase. In some embodiments, sequencing includes sequence a template or amplified template that is attached to a support by contacting the template or extended primer with a sequencing primer, a polymerase, and at least one type of nucleotide. In some embodiments, the sequencing includes contacting the template, or amplified template, or extended primer, with a sequencing primer, a polymerase and with only one type of nucleotide that does not include an extrinsic label or a chain terminating group.

Optionally, the template (or amplified product) can be deposited, localized, or positioned, to a site. In some embodiments, multiple templates/amplified templates/extended first primers are deposited or positioned to different sites in an array of sites. In some embodiments, the depositing, positioning or localizing is performed prior to amplification of the template. In some embodiments, the depositing, positioning or localizing is performed after the amplifying. For example, amplified templates or extended first primers can be deposited, positioned or localized to different sites of an array.

The disclosed methods result in the production of a plurality of amplicons, at least some of which amplicons include a clonally amplified nucleic acid population. The clonally amplified populations produced by the methods of the disclosure can be useful for a variety of purposes. In some embodiments, the disclosed methods (and related compositions, systems and kits) optionally include further analysis and/or manipulation of the clonally amplified populations (amplicons). For example, in some embodiments, the numbers of amplicons exhibiting certain desired characteristics can be detected and optionally quantified.

In some embodiments, the methods can include determining which of the discrete supports (e.g., beads), include amplicons. Similarly, the methods can include determining which sites of an array that include amplicons. The presence of amplicons at supports or sites can optionally be detected determined using DNA-based detection procedures such as UV absorbance, staining with DNA-specific dyes, TAQ-MAN® assays, qPCR, hybridization to fluorescent probes, and the like. In some embodiments, the methods can include determining which bead supports (or sites of an array) have received substantially monoclonal amplicons. For example, the bead supports (or array sites) can be analyzed to determine which supports or sites can produce a detectable and coherent (i.e., analyzable) sequence-dependent signal.

In some embodiments, the amplifying is followed by sequencing the amplified product. The amplified product that is sequenced can include an amplicon comprising a substantially monoclonal nucleic acid population. In some embodiments, the disclosed methods include forming or positioning single members of a plurality of amplicons to different sites. The different sites optionally form part of an array of sites. In some embodiments, the sites in the array of sites include wells (reaction chambers) on the surface of an isFET array, as described further herein.

In some embodiments, the methods (and related compositions, systems, and kits) can further include sequencing an amplified template, or sequencing an extended primer, (e.g. an extended first primer, or extended second primer). The sequencing can include any suitable method of sequencing known in the art. In some embodiments, the sequencing includes sequencing by synthesis or sequencing by electronic detection (e.g., nanopore sequencing). In some embodiments, sequence includes extending a template or amplified template, or extending a sequencing primer hybridized to a template or amplified template, via nucleotide incorporation by a polymerase. In some embodiments, sequencing includes sequence a template or amplified template that is attached to a support by contacting the template or extended primer with a sequencing primer, a polymerase, and at least one type of nucleotide. In some embodiments, the sequencing includes contacting the template, or amplified template, or extended primer, with a sequencing primer, a polymerase and with only one type of nucleotide that does not include an extrinsic label or a chain terminating group.

In some embodiments, methods of downstream analysis include sequencing at least some of the plurality of amplicons in parallel. Optionally, the multiple templates/amplified templates/extended first primers situated at different sites of the array are sequenced in parallel.

In some embodiments, the sequencing can include binding a sequencing primer to the nucleic acids of at least two different amplicons, or at least two different substantially monoclonal populations.

In some embodiments, the sequencing can include incorporating a nucleotide into the sequencing primer using the polymerase. Optionally, the incorporating includes forming at least one nucleotide incorporation byproduct.

Optionally, the nucleic acid to be sequenced is positioned at a site. The site can include a reaction chamber or well. The site can be part of an array of similar or identical sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

In some embodiments, the site is operatively coupled to a sensor. The method can include detecting the nucleotide incorporation using the sensor. Optionally, the site and the sensor are located in an array of sites coupled to sensors.

In some embodiments, the site comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET).

In some embodiments, the methods (and related compositions, systems and kits) can include detecting the presence of one or more nucleotide incorporation byproducts at a site of the array, optionally using the FET.

In some embodiments, the methods can include detecting a pH change occurring within the at least one reaction chamber, optionally using the FET.

In some embodiments, the disclosed methods include introducing a nucleotide into the site; and detecting an output signal from the sensor resulting from incorporation of the nucleotide into the sequencing primer. The output signal is optionally based on a threshold voltage of the FET. In some embodiments, the FET includes a floating gate conductor coupled to the site.

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

In some embodiments, the amplification reaction mixture can include a recombinase. The recombinase can include any suitable agent that can promote recombination between polynucleotide molecules. The recombinase can be an enzyme that catalyzes homologous recombination. For example, the amplification reaction mixture can include a recombinase that includes, or is derived from, a bacterial, eukaryotic or viral (e.g., phage) recombinase enzyme.

In some embodiments, the amplification reaction mixture includes an enzyme that can bind a primer and a polynucleotide template to form a complex, or can catalyze strand invasion of the polynucleotide template to form a D-loop structure. In some embodiments, the amplification reaction mixture includes one or more proteins selected from the group consisting of: UvsX, RecA and Rad51.

In some embodiments, the amplification reaction mixture can include a recombinase accessory protein, for example UvsY.

In some embodiments, the amplification reaction mixture can include a single stranded binding protein (SSBP).

In some embodiments, the amplification reaction mixture can include a polymerase. The polymerase optionally has, or lacks, exonuclease activity. In some embodiments, the polymerase has 5' to 3' exonuclease activity, 3' to 5' exonuclease activity, or both. Optionally, the polymerase lacks any one or more of such exonuclease activities.

In some embodiments, the polymerase has strand displacing activity.

In some embodiments, the amplification reaction mixture can include one or more solid or semi-solid supports. At least one of the supports can include one or more instances of a first primer including a first primer sequence. In some embodiments, at least one polynucleotide template in the reaction mixture includes a first primer binding sequence. The first primer binding sequence can be substantially identical or substantially complementary to the first primer sequence. In some embodiments, at least one, some or all of the supports include a plurality of first primers that are substantially identical to each other. In some embodiments, all of the primers on the supports are substantially identical to each other, or all include a substantially identical first primer sequence.

In some embodiments, at least one of the supports includes two or more different primers attached thereto. For example, the at least one support can include at least one instance of the first primer and at least one instance of a second primer.

In some embodiments, the aqueous phase of the reaction mixture includes a plurality of supports, at least two supports of the plurality being attached to primers including a first priming sequence. In some embodiments, the reaction mixture includes two or more different polynucleotide templates having a first primer binding sequence.

In some embodiments, the amplification reaction mixture can include a diffusion limiting agent. The diffusion limiting agent can be any agent that is effective in preventing or slowing the diffusion of one or more of the polynucleotide templates and/or one or more of the amplification reaction products through the amplification reaction mixture.

In some embodiments, the amplification reaction mixture can include a sieving agent. The sieving agent can be any agent that is effective in sieving one or more polynucleotides present in the amplification reaction mixture, such as for example amplification reaction products and/or polynucleotide templates. In some embodiments, the sieving agent restricts or slows the migration of polynucleotide amplification productions through the reaction mixture.

In some embodiments, the amplification reaction mixture can include a crowding agent.

In some embodiments, the amplification reaction mixture includes both a crowding agent and a sieving agent.

In some embodiments, the disclosed methods comprise clonally amplifying at least two of the two or more polynucleotide templates by (a) forming an amplification reaction mixture including a single continuous liquid phase containing two or more polynucleotide templates, one or more surfaces or supports, and amplification components; and (b) clonally amplifying at least two of said polynucleotide templates onto one or more supports. Optionally, the clonally amplifying includes forming at least two different substantially monoclonal amplicons. In some embodiments, the clonally amplifying includes subjecting the amplification reaction mixture to amplification conditions. In some embodiments, two or more of said amplicons are each linked to a surface or support. For example, the amplification reaction mixture may include a single support or surface, such that each polynucleotide template attaches to a given region of the support or surface.

In some embodiments, methods for nucleic acid amplification can be conducted in a single reaction vessel.

In some embodiments, methods for nucleic acid amplification can be conducted in a single continuous liquid phase that does not provide compartmentalization of the multiple nucleic acid amplification reactions occurring in a single reaction vessel. In some embodiments, methods for nucleic acid amplification can be conducted in water-in-oil emulsions that provide compartmentalization (micro-reactors).

In some embodiments, the methods for nucleic acid amplification can be practiced to attach a plurality of polynucleotides to a support or surface. For example, the methods can comprise forming a reaction mixture containing at least one surface, and subjecting the reaction mixture to amplification conditions. In some embodiments, a surface includes the surface of a bead, a planar surface or an interior wall of a channel or tube.

In some embodiments, methods for nucleic acid amplification comprise: (a) forming an amplification reaction mixture including a single continuous liquid phase containing a plurality of beads, a plurality of different polynucleotides and a recombinase; (b) subjecting the amplification reaction mixture to isothermal amplification conditions, thereby generating a plurality of beads attached to substantially monoclonal nucleic acid populations attached thereto.

In some embodiments, the disclosure relates generally to methods (as well as related compositions, systems and kits) for array-based amplification of nucleic acid templates directly onto the surface of an array, resulting in the formation of any array whose individual features include amplicons containing substantially monoclonal populations of amplified product. These embodiments contrast with other embodiments described herein where the nucleic acid templates are optionally amplified in solution onto discrete supports (e.g., beads), which are then distributed into an array.

In some embodiments, methods (as well as related compositions, systems and kits) for array-based amplification are provided. In some embodiments, different polynucleotide templates are distributed into an array of sites and then amplified in situ. The resulting array of amplicons can then be analyzed using appropriate downstream procedures.

In some embodiments, methods for nucleic acid amplification comprise:
a) distributing at least two different polynucleotides into sites by introducing a single one of said polynucleotides into at least two of said sites that are in fluid communication with each other; and (b) forming at least two substantially monoclonal nucleic acid populations by amplifying the polynucleotides within said at least two sites. The sites can optionally include surfaces, wells, grooves, flowcells, reaction chambers or channels. In some embodiments, the amplifying is performed without sealing the sites from each other. For example, the at least two sites can remain in fluid communication with each other during the amplifying.

In some embodiments, methods for nucleic acid amplification comprise:
a) distributing at least two different polynucleotides into sites by introducing a single one of said polynucleotides into at least two of said sites; and (b) forming at least two substantially monoclonal nucleic acid populations by amplifying the polynucleotides within said at least two sites. The sites can optionally include surfaces, wells, grooves, flowcells, reaction chambers or channels. In some embodiments, the amplifying is performed without sealing the sites from each other. For example, the at least two sites can remain in fluid communication with each other during the amplifying.

In some embodiments, the sites comprise reaction chambers, and the methods for nucleic acid amplification comprise: (a) distributing at least two polynucleotide templates into reaction chambers by introducing a single one of said polynucleotides into at least two of said reaction chambers that are in fluid communication with each other; and (b) forming at least two substantially monoclonal nucleic acid populations by amplifying the polynucleotide templates within said at least two reaction chambers. In some embodiments, the amplifying is performed without sealing the reaction chambers from each other. For example, the at least two reaction chambers can remain in fluid communication with each other during the amplifying.

In some embodiments, the sites comprise reaction chambers, and the methods for nucleic acid amplification comprise: (a) distributing at least two different polynucleotides into reaction chambers by introducing a single one of said polynucleotides into at least two of said reaction chambers that are in fluid communication with each other; and (b) forming at least two substantially monoclonal nucleic acid populations by amplifying the polynucleotides within said at least two reaction chambers. In some embodiments, the amplifying is performed without sealing the reaction chambers from each other. For example, the at least two reaction chambers can remain in fluid communication with each other during the amplifying.

In some embodiments, the amplifying step of any and all methods of the disclosure can be performed without completely denaturing the polynucleotides during the amplifying. For example, the disclosed methods can include amplifying the at least two different polynucleotides via isothermal amplification. The amplifying can include amplifying the at least two different polynucleotides under substantially isothermal conditions. Optionally, the amplifying is performed without contacting the polynucleotides with chemical denaturants during the amplifying.

Optionally, the amplifying includes performing at least one round of amplification under substantially isothermal conditions.

Optionally, the amplifying includes performing at least two consecutive cycles of nucleic acid synthesis under substantially isothermal conditions.

In some embodiments, the amplifying includes recombinase polymerase amplification (RPA). For example, the amplifying can include performing at least one round of RPA.

In some embodiments, the amplifying includes template walking. For example, the amplifying can include performing at least one round of template walking.

In some embodiments, the amplifying optionally includes performing two different rounds of amplification within the sites or reaction chambers. For example, the amplifying can include performing at least one round of RPA within the sites or reaction chambers, and performing at least one round of template walking within the sites or reaction chambers, in any order or combination of rounds. In some embodiments, at least two consecutive cycles in any one or more of the rounds of amplification are performed under substantially isothermal conditions. In some embodiments, at least one of the rounds of amplification is performed under substantially isothermal conditions.

In some embodiments, amplifying includes contacting the polynucleotides to be amplified with a reaction mixture. The contacting can optionally be performed prior to or after the distributing; it is to be understood that the present disclosure embraces embodiments where the polynucleotides are contacted with individual components (or combinations of components) of the reaction mixture at different times and in series, as well as embodiments where are any one or some components of the reaction mixture are contacted with the at least two different polynucleotides prior to the distributing, while the remaining components of the reaction mixture are contacted with the at least two different polynucleotides after the distributing.

The at least two polynucleotides that are distributed can optionally serve as templates for nucleic acid synthesis within their respective reaction chambers. In some embodiments, the at least two polynucleotides include different sequences. In some embodiments, the polynucleotides are double stranded or as single stranded prior to distributing. In some embodiments, the polynucleotides are linear, circular, or a combination of both. In a typical embodiment, the polynucleotides are at least partially double stranded (or are distributed in single stranded form and then rendered at least partially double stranded within the sites or reaction chambers after the distributing. The polynucleotides can be rendered double stranded prior to the amplifying (especially in embodiments where the amplifying includes RPA or template walking).

In some embodiments, the at least two different polynucleotide templates to be amplified each contain a primer binding site, and the amplifying includes binding a primer to the primer binding site to form a primer-template duplex.

Optionally, the amplifying includes extending the primer of the primer-template duplex. The extending optionally occurs at or within the site or reaction chamber of the array. Optionally, extending a primer includes contacting the primer with a polymerase and one or more types of nucleotides under nucleotide incorporation conditions. In some embodiments, the one or more types of nucleotides do not include extrinsic labels, particularly optically detectable labels, for example fluorescent moieties or dyes. Optionally, the reaction mixture includes nucleotides that are naturally occurring nucleotides. Optionally, the nucleotides do not include groups that terminate nucleic acid synthesis (e.g., dideoxy groups, reversible terminators, and the like). Typically, extending a primer occurs in a template-dependent fashion.

Optionally, the at least two different polynucleotides (i.e., the templates to be amplified) individually include a first sequence (referred to as "first primer binding site") that is substantially identical, or substantially complementary, to at least some portion of the first primer.

In some embodiments, the reaction mixture includes a first primer containing a first primer sequence. The first primer optionally includes an extendible end (e.g., a 3'OH containing end). The first primer can optionally be attached to a compound (e.g., a "drag tag"), or to a support (e.g., a bead or a surface of the site or reaction chamber).

Optionally, the disclosed methods (and related compositions, systems and kits) include extending the first primer by incorporating one or more nucleotides into the first primer of the first primer-template duplex using the polymerase, thereby forming an extended first primer.

In some embodiments, the at least two different polynucleotides include a second sequence (referred to as "second primer binding site") that is substantially identical, or substantially complementary, to at least some portion of a second primer In some embodiments, extending the first primer results in formation of a first extended primer. The first extended primer can include some or all of the sequence of the reverse strand of the template. Optionally, the first extended primer includes a second primer binding site.

Optionally, the disclosed methods (and related compositions, systems and kits) include binding a second primer to the second primer binding site of the first extended primer by any suitable method (e.g., ligation or hybridization).

In some embodiments, the second primer contains a second primer sequence. The second primer optionally includes an extendible end (e.g., a 3'OH containing end). The second primer can optionally be attached to a compound (e.g., a "drag tag"), or to a support (e.g., a bead or a surface of the site or reaction chamber).

In some embodiments, the methods include extending the second primer by incorporating one or more nucleotides into the second primer of the second primer-template duplex using the polymerase, thereby forming an extended second primer.

In some embodiments, extending the second primer results in formation of a second extended primer. The second extended primer can include some or all of the sequence of the forward strand of the template. Optionally, the second extended primer includes a first primer binding site.

In some embodiments, the methods are performed without subjecting the double stranded nucleic acid template to extreme denaturing conditions during the amplifying. For example, the methods can be performed without subjecting the nucleic acid template(s) to temperatures equal to or greater than the Tm of the template(s) during the amplifying. In some embodiments, the methods can be performed without contacting the template(s) with chemical denaturants such as NaOH, urea, guanidium, and the like, during the amplifying. In some embodiments, the amplifying includes isothermally amplifying.

In some embodiments, the methods are performed without subjecting the nucleic acid template(s) to extreme denaturing conditions during at least two, three, four, or more than four, consecutive cycles of nucleic acid synthesis. For example, the methods can include two, three, four, or more than four, consecutive steps of nucleic acid synthesis without contacting the nucleic acid template(s) with a chemical denaturant. In some embodiments, the methods can include performing two, three, four, or more than four, consecutive cycles of nucleic acid synthesis without subjecting the nucleic acid template(s) to temperatures that are greater than 25, 20, 15, 10, 5, 2 or 1° C. below the actual or calculated Tm of the template, or population of templates (or the actual or calculated average Tm of the template, or population of templates). The two, three, four, or more than four, consecutive cycles of nucleic acid synthesis may include intervening steps of partial denaturation and/or primer extension.

In some embodiments, the disclosed methods (and related compositions, systems and kits) can further include linking one or more extended primer strands to a support. The linking can optionally be performed during the amplifying, or alternatively after the amplification is complete. In some embodiments, the support includes multiple instances of a second primer, and the methods can include hybridizing at least one of the extended first primer strands to a second primer of the support.

In some embodiments, the disclosed methods (and related compositions, systems and kits) can further include linking one or more extended second primer strands to a support. In some embodiments, the support is attached to a first primer. For example, the support can include multiple instances of a first primer, and the methods can include hybridizing at least one of the extended second primers to a first primer of the support, thereby linking the extended second primer to the support. For example, the first primer can hybridize to a first primer binding site in the extended second primer. The support can include, for example, the surface of any array.

In some embodiments, the support is attached to a second primer. For example, the support can include multiple instances of a second primer, and the methods can include hybridizing at least one of the extended first primers to a second primer of the support, thereby linking the extended first primer to the support. For example, the first primer can hybridize to a second primer binding site in the extended first primer.

In some embodiments, the support includes both at least one first primer and at least one second primer, and the disclosed methods (and related compositions, systems and kits) including linking both an extended first primer and an extended second primer to the support.

Optionally, the support is attached to a target-specific primer. The target-specific primer optionally hybridizes (or is capable of hybridizing) to a first subset of templates within the reaction mixture, but is unable to bind to a second subset of templates within the reaction mixture.

Optionally, the support is attached to a universal primer. The universal primer optionally hybridizes (or is capable of hybridizing) to all, or substantially all, of the templates within the reaction mixture.

Optionally, the first target-specific primer is substantially complementary to a first target nucleic acid sequence and the second target-specific primer is substantially complementary to a second target nucleic acid sequence, and wherein the first and second target nucleic acid sequences are different.

In some embodiments, the disclosed methods include forming a first amplicon by amplifying a first template onto a first support, and forming a second amplicon by amplifying a second template onto a second support, optionally within the same continuous phase of a reaction mixture and at different sites of a surface (e.g., within an array). The first amplicon is optionally linked or attached to the first support, and the second amplicon is optionally linked or attached to the second support.

The disclosed methods optionally comprise producing two or more monoclonal, or substantially monoclonal, amplicons by clonally amplifying two or more polynucleotide templates at two or more different sites of an array of sites, such that at least two sites are formed each including a substantially monoclonal nucleic acid population. The two or more polynucleotide templates are optionally deposited or positioned at the different sites and then clonally amplified within a continuous liquid phase of an amplification reaction mixture that is contacted with the array. The continuous liquid phase of the amplification reaction mixture can include a continuous aqueous phase.

In some embodiments, the amplifying includes generating at least two substantially monoclonal populations of amplified polynucleotides, each of said populations being formed via amplification of a single polynucleotide template.

Optionally, the clonally amplifying includes at least one round of RPA.

Optionally, the clonally amplifying includes at least one round of template walking.

In some embodiments, the amplifying optionally includes forming an amplification reaction mixture including a continuous liquid phase. In some embodiments, the continuous liquid phase is a single continuous aqueous phase. The liquid phase can include two or more polynucleotide templates, which can optionally be different from each other. For example, the two or more polynucleotide templates can include at least one nucleic acid sequence that is substantially non-identical, or substantially non-complementary, to at least one other polynucleotide template within the amplification reaction mixture.

In some embodiments, the amplifying optionally includes forming an amplification reaction mixture including a single continuous aqueous phase having two or more polynucleotide templates. Amplifying optionally includes forming two or more substantially monoclonal nucleic acid populations by clonally amplifying the two or more polynucleotide templates within the single aqueous phase. Optionally, the clonally amplifying includes at least one round of RPA. Optionally, the clonally amplifying includes at least one round of template walking.

In some embodiments, multiple different polynucleotide templates are deposited or positioned to different sites prior to the amplifying. For example, amplified templates or extended first primers can be deposited, positioned or localized to different sites of an array.

In some embodiments, the amplifying results in the formation of at least two substantially monoclonal nucleic acid populations (e.g., amplicons) in at least two different sites of the surface, which can then be analyzed in situ using appropriate procedures.

In some embodiments, the disclosure relates generally to methods (and related compositions, systems and kits) for preparing a surface. Optionally, the surface includes a plurality of sites, including a first site and a second site.

In some embodiments, the methods include forming a nucleic acid array on the surface, wherein the forming includes linking a first nucleic acid to the first site and linking a second nucleic acid to the second site. The linking can optionally be performed using any of the methods disclosed herein, including for example by linking the nucleic acid to a primer that is covalently attached to the surface.

In some embodiments, the methods include contacting at least the first and second nucleic acids with a single reaction mixture including reagents for nucleic acid synthesis. The reaction mixture can optionally include any one or more of the components described herein. In some embodiments, the reaction mixture includes all of the components required to perform RPA. In some embodiments, the reaction mixture includes all of the components to perform template walking.

In some embodiments, the methods include forming a first amplicon at the first site and a second amplicon at the second site by replicating the first and second nucleic acids using the reagents for nucleic acid synthesis in the reaction mixture.

The replicating can include primer extension. The replicating can include one or more cycles of RPA. The replicating can include one or more cycles of template walking.

In some embodiments, the replicating includes at least one cycle of RPA.

In some embodiments, the replicating includes at least one cycle of template walking.

In some embodiments, the replicating includes at least one cycle of RPA and at least one cycle of template walking.

In some embodiments, the replicating includes at least one round of RPA.

In some embodiments, the replicating includes at least one round of template walking.

In some embodiments, the replicating includes at least one round of RPA and at least one round of template walking.

In some embodiments, the disclosure relates generally to methods (and related compositions, systems and kits) for preparing a surface, comprising: (a) providing a surface with a plurality of sites, including a first site and a second site; (b) forming a nucleic acid array on the surface, wherein the forming includes linking a first nucleic acid to the first site and linking a second nucleic acid to the second site; (c); and (d) forming a first amplicon at the first site and a second amplicon at the second site by replicating the first and second nucleic acids using the reagents for nucleic acid synthesis in the reaction mixture.

In some embodiments, the disclosure relates generally to a method for preparing a surface, comprising: providing a surface with a plurality of sites, including a first site and a second site; forming a nucleic acid array on the surface, wherein the forming includes linking a first nucleic acid to the first site and linking a second nucleic acid to the second site; contacting at least the first and second nucleic acids with a single reaction mixture including reagents for nucleic acid synthesis; and forming a first substantially monoclonal amplicon at the first site and a second substantially monoclonal amplicon at the second site by amplifying the first and second nucleic acids using the reagents for nucleic acid synthesis in the reaction mixture. Optionally, the first and second sites remain in fluid communication during the amplifying. Optionally, the amplifying is performed without completely denaturing the polynucleotides during the amplifying. For example, the disclosed methods can include amplifying the at least two different polynucleotides via isothermal amplification. The amplifying can include amplifying the at least two different polynucleotides under substantially isothermal conditions. Optionally, the amplifying is performed without contacting the polynucleotides with chemical denaturants during the amplifying.

In some embodiments, at least one site of the plurality includes a reaction well, channel, groove or chamber.

In some embodiments, at least one site of the plurality is linked to a sensor.

In some embodiments, the sensor is capable of detecting a nucleotide incorporation occurring at or near the at least one site.

In some embodiments, the sensor includes a field effect transistor (FET)

In some embodiments, at least the first site, or the second site, or both the first and second sites, include a primer linked to the surface.

In some embodiments, at least one of the sites of the plurality of sites comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET), chemFET, bioFET, and the like.

In some embodiments, the FET is capable of detecting the presence of a nucleotide incorporation byproduct at the at least one site.

In some embodiments, the FET is capable of detecting a chemical moiety selected from the group consisting of: hydrogen ions, pyrophosphate, hydroxyl ions, and the like.

In some embodiments, the methods (and related compositions, systems and kits) can include detecting the presence of one or more nucleotide incorporation byproducts at a site of the array, optionally using the FET.

In some embodiments, the methods can include detecting a pH change occurring at the site or within the at least one reaction chamber, optionally using the FET.

In some embodiments, the disclosed methods include introducing a nucleotide into at least one of the sites in the plurality of sites; and detecting an output signal from the sensor resulting from incorporation of the nucleotide into the sequencing primer. The output signal is optionally based on a threshold voltage of the FET. In some embodiments, the FET includes a floating gate conductor coupled to the site.

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

In some embodiments, the reaction mixture includes all of the components required to perform RPA.

In some embodiments, the reaction mixture includes all of the components required to perform template walking.

In some embodiments, the reaction mixture can include one or more solid or semi-solid supports. At least one of the supports can include one or more instances of a first primer including a first primer sequence. In some embodiments, at least one of the supports includes two or more different primers attached thereto. For example, the at least one support can include at least one instance of the first primer and at least one instance of a second primer.

Alternatively, in some embodiments, the reaction mixture does not include any supports. In some embodiments, the at least two different polynucleotide templates are amplified directly onto a surface of the site or reaction chamber of the array.

In some embodiments, the reaction mixture can include a recombinase. The recombinase can include any suitable agent that can promote recombination between polynucleotide molecules. The recombinase can be an enzyme that catalyzes homologous recombination. For example, the reaction mixture can include a recombinase that includes, or is derived from, a bacterial, eukaryotic or viral (e.g., phage) recombinase enzyme.

Optionally, the reaction mixture includes nucleotides that are not extrinsically labeled. For example, the nucleotides can be naturally occurring nucleotides, or synthetic analogs that do not include fluorescent moieties, dyes, or other extrinsic optically detectable labels. Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, the reaction mixture includes nucleotides that are naturally occurring nucleotides. Optionally, the nucleotides do not include groups that terminate nucleic acid synthesis (e.g., dideoxy groups, reversible terminators, and the like).

In some embodiments, the reaction mixture includes an enzyme that can bind a primer and a polynucleotide template to form a complex, or can catalyze strand invasion of the polynucleotide template to form a D-loop structure. In some embodiments, the reaction mixture includes one or more proteins selected from the group consisting of: UvsX, RecA and Rad51.

In some embodiments, the disclosure relates generally to methods (and related compositions, systems and kits) for preparing a surface, comprising: (a) providing a surface with a plurality of sites, wherein each site is linked to a nucleic acid primer; (c) contacting the surface with a plurality of polynucleotide templates and binding at least one of templates to the surface; and amplifying at least one of the templates onto the surface, thereby forming at least one substantially monoclonal population of the amplified target polynucleotide sequence situated at a site on the surface.

In some embodiments, the disclosure relates generally to a method for nucleic acid amplification, comprising: (1) providing a surface having a first site and a second site, the first site being operatively coupled to a first sensor and including a first template; the second site being operatively coupled to a second sensor and including a second template; (2) distributing to the first and the second sites a reaction mixture; and (3) forming a first amplicon by amplifying the first template at the first site; and forming a second amplicon by amplifying the second template at the second site.

In some embodiments, the amplifying includes at least one cycle of RPA.

In some embodiments, the amplifying includes at least one cycle of template walking.

In some embodiments, the amplifying includes at least one cycle of RPA and at least one cycle of template walking.

In some embodiments, the amplifying includes at least one round of RPA.

In some embodiments, the amplifying includes at least one round of template walking.

In some embodiments, the amplifying includes at least one round of RPA and at least one round of template walking.

In some embodiments, any some or all of the methods disclosed herein can result in the production of a plurality of amplicons, at least some of which amplicons include a clonally amplified nucleic acid population. The clonally amplified populations produced by the methods of the disclosure can be useful for a variety of purposes. In some embodiments, the disclosed methods (and related compositions, systems and kits) optionally include further analysis and/or manipulation of the clonally amplified populations (amplicons).

In some embodiments, amplicons produced according to the present disclosure can be subjected to downstream analysis methods such as sequencing.

In some embodiments, the amplified nucleic acids can be further analyzed (e.g., sequencing) at the site of distribution without recovering and moving the amplified products to a different site or surface for analysis (e.g., sequencing).

In some embodiments, methods of downstream analysis include sequencing at least some of the plurality of amplicons in parallel. Optionally, the multiple templates/amplified templates/extended first primers situated at different sites of the array are sequenced in parallel.

In some embodiments, the methods (and related compositions, systems, and kits) can further include sequencing an amplified template, or sequencing an extended primer, (e.g. an extended first primer, or extended second primer). The sequencing can include any suitable method of sequencing known in the art. In some embodiments, the sequencing includes sequencing by synthesis or sequencing by electronic detection (e.g., nanopore sequencing). In some embodiments, sequence includes extending a template or amplified template, or extending a sequencing primer hybridized to a template or amplified template, via nucleotide incorporation by a polymerase. In some embodiments, sequencing includes sequence a template or amplified template that is attached to a support by contacting the template or extended primer with a sequencing primer, a polymerase, and at least one type of nucleotide. In some embodiments, the sequencing includes contacting the template, or amplified template, or extended primer, with a sequencing primer, a polymerase and with only one type of nucleotide that does not include an extrinsic label or a chain terminating group.

For example, in some embodiments, amplifying is followed by sequencing the amplified products in situ. The amplified product that is sequenced can include an amplicon comprising a substantially monoclonal nucleic acid population. Optionally, monoclonal nucleic acid populations (amplicons) situated at different sites of the array are sequenced in parallel.

In some embodiments, the sequencing can include binding a sequencing primer to the nucleic acids of at least two different amplicons, or at least two different substantially monoclonal populations.

In some embodiments, the sequencing can include incorporating a nucleotide into the sequencing primer using the polymerase. Optionally, the incorporating includes forming at least one nucleotide incorporation byproduct.

Optionally, the nucleic acid to be sequenced is positioned at a site. The site can include a reaction chamber or well. The site can be part of an array of similar or identical sites. The array can include a two-dimensional array of sites on a surface (e.g., of a flowcell, electronic device, transistor chip, reaction chamber, channel, and the like), or a three-dimensional array of sites within a matrix or other medium (e.g., solid, semi-solid, liquid, fluid, and the like).

In some embodiments, the site is operatively coupled to a sensor. The method can include detecting the nucleotide incorporation using the sensor. Optionally, the site and the sensor are located in an array of sites coupled to sensors.

In some embodiments, the site comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET).

In some embodiments, the methods (and related compositions, systems and kits) can include detecting the presence of one or more nucleotide incorporation byproducts at a site of the array, optionally using the FET.

In some embodiments, the methods can include detecting a pH change occurring at the site or within the at least one reaction chamber, optionally using the FET.

In some embodiments, the disclosed methods include introducing a nucleotide into the site; and detecting an output signal from the sensor resulting from incorporation of the nucleotide into the sequencing primer. The output signal is optionally based on a threshold voltage of the FET. In some embodiments, the FET includes a floating gate conductor coupled to the site.

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

In some embodiments, the reaction mixture includes all of the components required to perform RPA.

In some embodiments, the reaction mixture includes all of the components required to perform template walking.

In some embodiments, the reaction mixture can include one or more solid or semi-solid supports. At least one of the supports can include one or more instances of a first primer including a first primer sequence. In some embodiments, at least one of the supports includes two or more different primers attached thereto. For example, the at least one support can include at least one instance of the first primer and at least one instance of a second primer.

Alternatively, in some embodiments, the reaction mixture does not include any supports. In some embodiments, the at least two different polynucleotide templates are amplified directly onto a surface of the site or reaction chamber of the array.

In some embodiments, the reaction mixture can include a recombinase. The recombinase can include any suitable agent that can promote recombination between polynucleotide molecules. The recombinase can be an enzyme that catalyzes homologous recombination. For example, the reaction mixture can include a recombinase that includes, or is derived from, a bacterial, eukaryotic or viral (e.g., phage) recombinase enzyme.

Optionally, the reaction mixture includes nucleotides that are not extrinsically labeled. For example, the nucleotides can be naturally occurring nucleotides, or synthetic analogs that do not include fluorescent moieties, dyes, or other extrinsic optically detectable labels. Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, the reaction mixture includes nucleotides that are naturally occurring nucleotides. Optionally, the nucleotides do not include groups that terminate nucleic acid synthesis (e.g., dideoxy groups, reversible terminators, and the like).

In some embodiments, the reaction mixture includes an enzyme that can bind a primer and a polynucleotide template to form a complex, or can catalyze strand invasion of the polynucleotide template to form a D-loop structure. In some embodiments, the reaction mixture includes one or more proteins selected from the group consisting of: UvsX, RecA and Rad51.

In some embodiments, the reaction mixture can include a recombinase accessory protein, for example UvsY.

In some embodiments, the reaction mixture can include a single stranded binding protein (SSBP).

In some embodiments, the reaction mixture can include a polymerase. The polymerase optionally has, or lacks, exonuclease activity. In some embodiments, the polymerase has 5' to 3' exonuclease activity, 3' to 5' exonuclease activity, or both. Optionally, the polymerase lacks any one or more of such exonuclease activities.

In some embodiments, the polymerase has strand displacing activity.

In some embodiments, the reaction mixture can include a diffusion limiting agent. The diffusion limiting agent can be any agent that is effective in preventing or slowing the diffusion of one or more of the polynucleotide templates and/or one or more of the amplification reaction products through the reaction mixture.

In some embodiments, the reaction mixture can include a sieving agent. The sieving agent can be any agent that is effective in sieving one or more polynucleotides present in the reaction mixture, such as for example amplification reaction products and/or polynucleotide templates. In some embodiments, the sieving agent restricts or slows the migration of polynucleotide amplification productions through the reaction mixture.

In some embodiments, the reaction mixture can include a crowding agent.

In some embodiments, the reaction mixture includes both a crowding agent and a sieving agent.

In some embodiments, the disclosed methods include contacting each of the at least two polynucleotides with a recombinase, a support attached to a plurality of first oligonucleotide primers, the first oligonucleotide primers being at least partially complementary to at least some portion of the polynucleotides, a polymerase, and a plurality of nucleotides, in any order and in any combination.

In some embodiments, the at least two different polynucleotides include a forward strand containing a first primer binding site, and the amplifying within the at least two sites (or within the at least two reaction chambers) optionally includes binding a first primer to a first primer binding site to form a first primer-template duplex within the sites or reaction chambers. Optionally, the binding of the first primer to the at least two different polynucleotide templates is mediated by a recombinase. For example, the amplifying can include forming a nucleoprotein complex containing a recombinase and first primer. Optionally, the first primer is attached to a surface of the site or reaction chamber. In some embodiments, the amplifying within the sites or reaction chambers includes: forming a first nucleoprotein complex (or "first nucleoprotein filament"). The amplifying optionally further includes contacting at least one of the polynucleotides in the sites or reaction chambers with the first nucleoprotein filament, a polymerase and a plurality of nucleotides, in any order or combination.

Optionally, discrete supports (e.g., beads), each containing a plurality of first primers, are individually distributed into the reaction chambers or sites prior to the amplifying, and the amplifying includes amplifying one of the at least two different polynucleotides onto the support within the site or reaction chamber. In some embodiments, any one of the distributing and/or contacting steps can be repeated prior to the amplifying, optionally to increase yield and/or number of sites or reaction chambers yielding monoclonal product.

Optionally, the amplifying includes extending the first primer of the first primer-template duplex using a polymerase within the reaction chamber, thereby forming an extended first primer. Optionally, extending the first primer displaces the reverse strand from the forward strand. The extended first primer optionally includes a second primer binding site.

Optionally, the amplifying includes a step of reverse synthesis comprising binding a second primer to the second primer binding site of the extended first primer, and extending the second primer to form a second primer-template duplex. Optionally, the binding of the second primer to the polynucleotide templates is mediated by a recombinase. For example, the amplifying can include forming a nucleoprotein complex containing a recombinase and a second primer. Optionally, the second primer is attached to a surface of the site or reaction chamber. In some embodiments, the amplifying within the sites or reaction chambers includes: forming a second nucleoprotein complex (or "second nucleoprotein filament"). The amplifying optionally further includes contacting at least one of the polynucleotide templates, or at least one of the extended first primers in the sites or reaction chambers with the second nucleoprotein filament, a polymerase and a plurality of nucleotides, in any order or combination.

Optionally, the amplifying includes extending the first primer-template duplex, the second primer-template duplex, or both, using a polymerase. The polymerase can have strand-displacing activity.

In some embodiments, the methods (and related compositions, systems and kits) can include depositing, positioning or localizing at least one substantially monoclonal population at a site. The site can form part of an array of sites.

Optionally, at least one of the sites includes a reaction chamber, support, particle, microparticle, sphere, bead, filter, flowcell, well, groove, channel reservoir, gel or inner wall of a tube.

In some embodiments, at least one site comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET).

In some embodiments, the methods (and related compositions, systems and kits) can include detecting the presence of one or more nucleotide incorporation byproducts at a site of the array, optionally using the FET.

In some embodiments, the methods can include detecting a pH change occurring within the at least one reaction chamber, optionally using the FET.

In some embodiments, the disclosed methods include introducing a nucleotide into the site; and detecting an output signal from the sensor resulting from incorporation of the nucleotide into the sequencing primer. The output signal is optionally based on a threshold voltage of the FET. In some embodiments, the FET includes a floating gate conductor coupled to the site.

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

Optionally, the plurality of different polynucleotide templates (or amplified polynucleotides) includes at least one nucleic acid containing a selectively cleavable moiety.

Optionally, the selectively cleavable moiety includes uracil.

Optionally, methods for nucleic acid amplification further include cleaving the cleavable moiety with a cleaving agent.

Optionally, the cleaving can be performed prior to the amplifying, for example before forming the reaction mixture.

Optionally, the cleaving can be performed after the amplifying, e.g., after the nucleic acid template(s) are amplified.

Optionally, the reaction mixture includes at least one primer containing a cleavable moiety.

Optionally, methods for nucleic acid amplification further include cleaving the cleavable moiety with a cleaving agent.

Optionally, the plurality of different polynucleotides includes a plurality of amplicons.

Optionally, the plurality of different polynucleotides includes a plurality of different amplicons.

In some embodiments, amplification can be practiced using any of the methods, compositions, systems and kits disclosed in U.S. Provisional Application No. 61/792,247, filed Mar. 15, 2013, incorporated by reference herein in its entirety.

In some embodiments, amplicons produced according to the present disclosure can be subjected to downstream analysis methods such as quantification. For example, in some embodiments, the numbers of amplicons exhibiting certain desired characteristics can be detected and optionally quantified.

In some embodiments, in the disclosed methods the amplified nucleic acids can optionally be subjected to additional steps of downstream analysis.

In some embodiments involving amplification of different polynucleotide templates onto discrete and separate supports, the methods can include determining which of the discrete supports (e.g., beads), include amplicons. Similarly, in embodiments where the templates are distributed into an array prior to the amplifying, the methods can include determining which sites of the array include amplicons, and can optionally further include counting the number of sites that include amplicons. The presence of amplicons at supports or sites can optionally be detected determined using DNA-based detection procedures such as UV absorbance, staining with DNA-specific dyes, TAQMAN® assays, qPCR, hybridization to fluorescent probes, and the like. In some embodiments, the methods can include determining which bead supports (or sites of an array) have received substantially monoclonal amplicons. For example, the bead supports (or array sites) can be analyzed to determine which supports or sites can produce a detectable and coherent (i.e., analyzable) sequence-dependent signal.

In some embodiments, the disclosed methods include additional steps of downstream analysis that provide the same type of information previously obtained through conventional techniques such as digital PCR or digital RPA as described, for example, in Shen 2011 Analytical Chemistry 83:3533-3540; U.S. published applications 2012/0264132 and 2012/0329038; all of which are incorporated by reference in their entireties. Digital PCR (dPCR) is a refinement of conventional polymerase chain reaction (PCR) methods which can be used to directly quantify and clonally amplify nucleic acids (including DNA, cDNA, methylated DNA, or RNA). One difference between dPCR and traditional PCR lays in the method of measuring nucleic acids amounts. Both PCR and dPCR carry out one reaction per single sample, dPCR also carries out a single reaction within a sample, however the sample is separated into a large number of partitions and the reaction is carried out in each partition individually. This separation allows for sensitive measurement of nucleic acid amounts. dPCR has been demonstrated as useful for studying variations in gene sequences, such as copy number variation or point mutations.

In contract to the instant methods, dPCR typically requires partitioning of the sample prior to amplification; in contrast, several of the embodiments disclosed herein provide for parallel amplification of different templates within a single continuous phase of a reaction mixture without need for partitioning. In dPCR, a sample is typically partitioned so that individual nucleic acid molecules within the sample are localized and concentrated within many separate regions. The sample is fractionated by the simple process of dilution so that each fraction contains approximately one copy of DNA template or less. By isolating individual DNA templates this process effectively enriches DNA molecules that were present at very low levels in the original sample. The partitioning of the sample facilitates counting of molecules using Poisson statistics. As a result, each partition will contain "0" or "1" molecule(s), or a negative or positive reaction, respectively. While the starting copy number of a molecule is proportional to the number of amplification cycles in conventional PCR, dPCR is not typically dependent on the number of amplification cycles to determine the initial sample amount.

Conventional methods of dPCR analysis typically utilize fluorescent probes and light based detection methods to identify the products of amplification. Such approaches require sufficient amplification of the target molecules to generate enough signal to be detectable but can lead to additional error or bias.

In those embodiments of the present disclosure involving distribution of nucleic acid templates into the wells of an isFET array and subsequent amplification of templates inside the wells of the array, an optional step of downstream analysis can be performed after the amplification that quantifies the number of sites or wells that include amplification product. In some embodiments, the products of the nucleic acid amplification reactions can be detected in order to count the number of sites or wells that include an amplified template.

For example, in some embodiments the disclosure relates generally to methods of nucleic acid analysis, comprising: providing a sample including a first number of polynucleotides; and distributing single polynucleotides of the sample into different sites in an array of sites.

Optionally, the methods can further include forming substantially monoclonal nucleic acid populations by amplifying the single polynucleotides within their respective sites.

Optionally, the sites remain in fluid communication during the amplifying.

Optionally, the amplifying includes partially denaturing the template.

Optionally, the amplifying includes subjecting the template to partially denaturing temperatures. In some embodiments, the template includes a low-melt sequence including a primer binding site, which is rendered single stranded when the template is subjected to partially denaturing temperatures.

Optionally, the amplifying includes partially denaturing the template.

Optionally, the amplifying includes contacting at least two different templates at two different sites of the array with a single reaction mixture for nucleic acid amplification.

Optionally, the reaction mixture includes a recombinase.

Optionally, the reaction mixture includes at least one primer including a "drag-tag".

Optionally, the amplifying includes performing at least one amplification cycle that includes partially denaturing the template, hybridizing a primer to the template, and extending the primer in a template-dependent fashion. Optionally, the amplifying includes isothermally amplifying. In some embodiments, the amplifying is performed under substantially isothermal conditions.

In some embodiments, the percentage of sites containing one or more template molecules is greater than 50% and less than 100%.

In some embodiments, the disclosed methods can further include detecting a change in ion concentration in at least one of the sites as a result of the at least one amplification cycle.

In some embodiments, the disclosed methods can further include quantitating an initial amount of target nucleic acid.

Some examples of array-based digital PCR using ion-based sensing technology can be found, for example, in U.S. Provisional Appl. No. 61/635,584, filed Apr. 19, 2012, hereby incorporated by reference in its entirety.

In some embodiments, the disclosure relates generally to methods for detection of a target nucleic acid comprising: fractionating a sample into a plurality of sample volumes wherein more than 50% of the fractions contain no more than 1 target nucleic acid molecule per sample volumes; subjecting the plurality of sample volumes to conditions for amplification, wherein the conditions include partially denaturing conditions; detecting a change in ion concentration in a sample volume wherein a target nucleic acid is present; counting the number of fractions with an amplified target nucleic acid; and determining the quantity of target nucleic acid in the sample. The change in ion concentration may be an increase in ion concentration or may be a decrease in ion concentration. In some embodiments, the method may further include combining a sample with bead. In some embodiments, the method may include loading the sample on a substrate wherein the substrate includes at least one well.

In some embodiments, subjecting the target nucleic acids to partially denaturing conditions includes contacting the target nucleic acid molecules in their respective sample volumes with a recombinase and a polymerase under RPA conditions.

In some embodiments, subjecting the target nucleic acids to partially denaturing conditions includes subjecting the target nucleic acid molecules to partially denaturing temperatures.

In some embodiments, the disclosure relates generally to a method for performing absolute quantification of a nucleic acid comprising: diluting a sample containing an initial number of nucleic acid templates and distributing the nucleic acid templates of the sample into a plurality of sites of an array, wherein the percentage of sites containing one or more nucleic acid templates is greater than 50% and less than 100%; subjecting the plurality of sites to at least one amplification cycle, wherein the amplification cycle is performed according to any of the amplification methods disclosed herein; detecting a change in ion concentration in at least one of the plurality of sample volumes as a result of the at least one amplification cycle; and quantitating an initial amount of nucleic acid templates. The change in ion concentration may be an increase in ion concentration, a decrease in ion concentration, a change in pH, may involve the detection of a positive ion such as a hydrogen ion, a negative ion such as a pyrophosphate molecule, or both positive and negative ion.

In some embodiments, the disclosure also relates generally to methods (and related compositions, systems and kits) for linking individual members of a population of nucleic acid templates to different supports in a plurality of supports, or to different sites in a plurality of sites using recombinase-mediated strand exchange. These methods, compositions, systems and kits can be useful for generating populations of immobilized amplicons amenable to manipulation in applications requiring different amplicons to be individually accessible or distinguishable. In some embodiments, the plurality of discrete supports, or the plurality of sites in the array, each include a capture primer. Immobilization of individual templates to individual supports (or to individual sites of the array) can be achieved by contacting the templates with the supports or sites in the presence of a primer ("fusion primer"). In some embodiments, the fusion primer includes a target-specific portion that is complementary to a portion of the template, and a universal primer-binding site that is complementary to at least some portion of the capture primer of the support or site. Optionally, the contacting is performed in the presence of RPA components. The RPA components can include a recombinase. The RPA components can include a strand-displacing polymerase. In some embodiments, the fusion primer is recombined into the template via recombinase-mediated strand exchange, thereby forming a template:primer adduct including a universal primer-binding site. In some embodiments, the capture primer is then recombined into the universal primer-binding site, forming an immobilized template that is attached to the support or site.

In some embodiments of bead-based amplification, a library of fusion primers, each including a different target-specific portion and a common universal primer-binding site, is contacted with a plurality of templates and a plurality of supports in a reaction mixture including a polymerase and a strand-displacing polymerase. The template library is then attached to the plurality of supports by subjecting the mixture to RPA conditions, thereby generating a plurality of supports each attached to a different template.

In some embodiments of array-based amplification, a library of fusion primers, each including a different target-specific portion and a common universal primer-binding site, is contacted with a plurality of templates and a surface including a plurality of sites in a reaction mixture including a polymerase and a strand-displacing polymerase. At least some of the plurality of sites include a universal capture primer. The template library is then attached to the plurality of sites of the surface by subjecting the mixture to RPA conditions, thereby generating a plurality of supports each attached to a different template.

In some embodiments, the disclosure relates generally to compositions (and relate methods for making and using said compositions) comprising reagents for amplifying one or more nucleic acid templates in parallel using partially denaturing conditions.

In some embodiments, the compositions can include any of the components described herein for performing RPA.

In some embodiments, the compositions can include any of the components described herein for performing template walking.

In some embodiments, the disclosure relates generally to compositions and systems for nucleic acid amplification, comprising: a surface including a first site and a second site; and a nucleic acid amplification reaction mixture, wherein the mixture is in contact with the first and second sites.

In some embodiments, the reaction mixture includes a recombinase.

In some embodiments, the first site is operatively coupled to a first sensor, and the second site being operatively linked to a second sensor.

In some embodiments, the first and second sites are operatively linked to the same sensor.

Optionally, the first site includes a first substantially monoclonal population of nucleic acid. The second site optionally includes a second substantially monoclonal population of nucleic acids In some embodiments, the disclosed compositions comprise: a surface including a first site and a second site, wherein the first site includes a first substantially monoclonal population of nucleic acids and the second site includes a second substantially monoclonal population of nucleic acids; and a nucleic acid amplification reaction mixture, wherein the mixture is in contact with the first and second sites.

In some embodiments, the compositions include an array of sites, including a first site containing (e.g., linked to) a first capture primer, and a second site containing (e.g., linked to) a second capture primer.

In some embodiments, at least one site of the plurality includes a reaction well, channel, groove or chamber.

In some embodiments, at least one site of the plurality is linked to a sensor.

In some embodiments, the sensor is capable of detecting a nucleotide incorporation occurring at or near the at least one site.

In some embodiments, the sensor includes a field effect transistor (FET)

In some embodiments, at least the first site, or the second site, or both the first and second sites, include a capture primer linked to the surface.

In some embodiments, at least one of the sites of the plurality of sites comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET), chemFET, bioFET, and the like.

In some embodiments, the FET is capable of detecting the presence of a nucleotide incorporation byproduct at the at least one site.

In some embodiments, the FET is capable of detecting a chemical moiety selected from the group consisting of: hydrogen ions, pyrophosphate, hydroxyl ions, and the like.

In some embodiments, the methods (and related compositions, systems and kits) can include detecting the presence of one or more nucleotide incorporation byproducts at a site of the array, optionally using the FET.

In some embodiments, the methods can include detecting a pH change occurring at the site or within the at least one reaction chamber, optionally using the FET.

In some embodiments, the disclosed methods include introducing a nucleotide into at least one of the sites in the plurality of sites; and detecting an output signal from the sensor resulting from incorporation of the nucleotide into the sequencing primer. The output signal is optionally based on a threshold voltage of the FET. In some embodiments, the FET includes a floating gate conductor coupled to the site.

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

In some embodiments, the reaction mixture includes all of the components required to perform RPA.

In some embodiments, the reaction mixture includes all of the components required to perform template walking.

In some embodiments, the reaction mixture can include one or more solid or semi-solid supports. At least one of the supports can include one or more instances of a first primer including a first primer sequence. In some embodiments, at least one of the supports includes two or more different primers attached thereto. For example, the at least one support can include at least one instance of the first primer and at least one instance of a second primer.

Alternatively, in some embodiments, the reaction mixture does not include any supports. In some embodiments, the at least two different polynucleotide templates are amplified directly onto a surface of the site or reaction chamber of the array.

In some embodiments, the reaction mixture can include a recombinase. The recombinase can include any suitable agent that can promote recombination between polynucleotide molecules. The recombinase can be an enzyme that catalyzes homologous recombination. For example, the reaction mixture can include a recombinase that includes, or is derived from, a bacterial, eukaryotic or viral (e.g., phage) recombinase enzyme.

Optionally, the reaction mixture includes nucleotides that are not extrinsically labeled. For example, the nucleotides can be naturally occurring nucleotides, or synthetic analogs that do not include fluorescent moieties, dyes, or other extrinsic optically detectable labels. Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, the reaction mixture includes nucleotides that are naturally occurring nucleotides. Optionally, the nucleotides do not include groups that terminate nucleic acid synthesis (e.g., dideoxy groups, reversible terminators, and the like).

In some embodiments, the reaction mixture includes an enzyme that can bind a primer and a polynucleotide template to form a complex, or can catalyze strand invasion of the polynucleotide template to form a D-loop structure. In some embodiments, the reaction mixture includes one or more proteins selected from the group consisting of: UvsX, RecA and Rad51.

In some embodiments, methods of amplifying can include performing "template walking" as described in U.S. Patent Publ. No. 2012/0156728, published Jun. 21, 2012, incorporated by reference herein in its entirety. For example, in some embodiments, the disclosure relates generally to methods, compositions, systems, apparatuses and kits for clonally amplifying one or more nucleic acid templates to form clonally amplified populations of nucleic acid templates. Any amplification method described herein optionally comprises repeated cycles of nucleic acid amplification. A cycle of amplification optionally comprises (a) hybridization of primer to a template strand, (b) primer extension to form a first extended strand, (c) partial or incomplete denaturation of the extended strand from the template strand. The primer that hybridizes to the template strand (designated "forward" primer for convenience) is optionally immobilized on or to a support. The support is for example solid or semi-solid. Optionally, the denatured portion of the template strand from step (c) is free to hybridize with a different forward primer in the next amplification cycle. In an embodiment, primer extension in a subsequent amplification cycle involves displacement of the first extended strand from the template strand. A second "reverse" primer can for example be included which hybridizes to the 3' end of the first extended strand. The reverse primer is optionally not immobilized.

In an embodiment, the templates are amplified using primers immobilized on/to one or more solid or semi-solid supports. Optionally the support comprises immobilized primers that are complementary to a first portion of a template strand. Optionally, the support does not significantly comprise an immobilized primer that is homologous to a second non-overlapping portion of the same template strand. The two portions are non-overlapping if they do not contain any subportions that hybridize to each other or to a complement thereof. In another example, the support optionally does not significantly comprise an immobilized primer that can hybridize to the complement of the template strand).

Optionally, a plurality of nucleic acid templates are amplified simultaneously in a single continuous liquid phase in the presence of one or more supports, where each support comprises one or more immobilization sites. In an embodiment, each template is amplified to generate a clonal population of amplicons, where individual clonal populations are immobilized within or on a different support or immobilization site from other amplified populations. Optionally, the amplified populations remain substantially clonal after amplification.

A template is for example amplified to generate clonal populations which comprise template-homologous strands (called "template strands" or "reverse strands" herein) and/or template-complementary strands (called "primer strands" or "forward strands" herein). In an embodiment clonality is maintained in the resulting amplified nucleic acid populations by maintaining association between template strands and its primer strands, thereby effectively associating or "tethering" associated clonal progeny together and reducing the probability of cross-contamination between different clonal populations. Optionally, one or more amplified nucleic acids in the clonal population is attached to a support. A clonal population of substantially identical nucleic acids can optionally have a spatially localized or discrete macroscopic appearance. In an embodiment a clonal population can resemble a distinct spot or colony (e.g., when distributed in a support, optionally on the outer surface of the support).

In some embodiments, the disclosure relates generally to novel methods of generating a localized clonal population of clonal amplicons, optionally immobilized in/to/on one or more supports. The support can for example be solid or semisolid (such as a gel or hydrogel). The amplified clonal population is optionally attached to the support's external surface or can also be within the internal surfaces of a support (e.g., where the support has a porous or matrix structure).

In some embodiments, amplification is achieved by multiple cycles of primer extension along a template strand of interest (also called a "reverse" strand). For convenience, a primer that hybridizes to the template strand of interest is termed a "forward" primer, and is optionally extended in template-dependent fashion to form a "forward" strand that is complementary to the template strand of interest. In some methods, the forward strand is itself hybridized by a second primer termed the "reverse" primer, which is extended to form a new template strand (also called a reverse strand). Optionally, at least a portion of the new template strand is homologous to the original template ("reverse") strand of interest.

As mentioned, one or more primers can be immobilized in/on/to one or more supports. Optionally, one primer is immobilized by attachment to a support. A second primer can be present and is optionally not immobilized or attached to a support. Different templates can for example be amplified onto different supports or immobilization sites simultaneously in a single continuous liquid phase to form clonal nucleic acid populations. A liquid phase can be considered continuous if any portion of the liquid phase is in fluid contact or communication with any other portion of the liquid body. In another example, a liquid phase can be considered continuous if no portion is entirely subdivided or compartmentalized or otherwise entirely physically separated from the rest of the liquid body. Optionally, the liquid phase is flowable. Optionally, the continuous liquid phase is not within a gel or matrix. In other embodiments, the continuous liquid phase is within a gel or matrix. For example the continuous liquid phase occupies pores, spaces or other interstices of a solid or semisolid support.

Where the liquid phase is within a gel or matrix, one or more primers are optionally immobilized on a support. Optionally the support is the gel or matrix itself. Alternatively the support is not the gel or matrix itself. In an example one primer is immobilized on a solid support contained within a gel and is not immobilized to gel molecules. The support is for example in the form of a planar surface or one or more microparticles. Optionally the planar surface or plurality of microparticles comprises forward primers having substantially identical sequence. In an embodiment, the support does not contain significant amounts of a second different primer. Optionally, a second non-immobilized primer is in solution within the gel. The second non-immobilized primer for example binds to a template strand (i.e., reverse strand), whereas the immobilized primer binds to a forward strand.

An embodiment of template walking includes a method of primer extension, comprising: (a) a primer-hybridization step, (b) an extension step, and (c) a walking step. Optionally, the primer-hybridization step comprises hybridizing a first primer molecule ("first forward primer") to a complementary forward-primer-binding sequence ("forward PBS") on a nucleic acid strand ("reverse strand"). Optionally the extension step comprises generating an extended first forward strand that is a full-length complement of the reverse strand and is hybridized thereto. The extended first forward strand is for example generated by extending the first forward primer molecule in template-dependent fashion using the reverse strand as template. Optionally the walking step comprises hybridizing a second primer ("second forward primer") to the forward PBS where the reverse strand is also hybridized to the first forward strand. For example, the walking step comprises denaturing at least a portion of the forward PBS from the forward strand ("free portion"), where another portion of the reverse strand remains hybridized to the forward strand.

In an embodiment, the primer extension method is an amplification method that includes template walking, in which any one or more steps of primer-hybridization, extension and/or walking are repeated at least once. For example, the method can comprise amplifying the forward strand by one or more amplification cycles. An amplification cycle optionally comprises extension and walking. An exemplary amplification cycle comprises or consists essentially of extension followed by walking Optionally, the second forward primer of a first amplification cycle acts as the first forward primer of a subsequent amplification cycle. For example, the second forward primer of a walking step in a first amplification cycle acts as the first forward primer of an extension step of a subsequent amplification cycle.

Optionally, the method of primer extension or amplification further comprises extending or amplifying the reverse strand by (a) hybridizing a first reverse primer molecule to a complementary reverse-primer-binding sequence ("reverse PBS") on an extended forward strand; (b) generating an extended first reverse strand that is a full-length complement of the forward strand and hybridized thereto, by extending the first reverse primer molecule in template-dependent fashion using the forward strand as template; and (c) hybridizing a second primer ("second reverse primer") to the reverse PBS where the forward strand is also hybridized to the first reverse strand. One or more repetitions of steps (b)-(c) are optionally performed, wherein the second reverse primer of step (c) is the first reverse primer of repeated step (b); and wherein a substantial proportion of forward strands are hybridized to reverse strands at all times during or between said one or more repetitions. In embodiments, the substantial proportion is optionally at least 30%, 40%, 50%, 60%, 65%, 70%, 75%, 80%, 85%, 90%, 95% or 99%.

Optionally, during amplification the reverse strand and/or forward strand is not exposed to totally-denaturing conditions that would result in complete separation of a significant fraction (e.g., more than 10%, 20%, 30%, 40% or 50%) of a large plurality of strands from their extended and/or full-length complements.

In an embodiment a substantial proportion of forward and/or reverse strands are optionally hybridized to extended and/or full-length complements at all times during or between one or more amplification cycles (e.g., 1, 5, 10, 20, or all amplification cycles performed). In embodiments, the substantial proportion of strands is optionally at least 60%, 65%, 70%, 75%, 80%, 85%, 90%, 95% or 99% of strands. In an embodiment this is achieved by maintaining the amplification reaction at a temperature higher than the $T_m$ of unextended primers, but lower than the $T_m$ of the primer-complementary strands. For example, amplification conditions are kept within a temperature that is higher than the $T_m$ of unextended forward primers, but lower than the $T_m$ of extended or full-length reverse strands. Also for example, amplification conditions are kept within a temperature that is higher than the $T_m$ of unextended reverse primers, but lower than the $T_m$ of extended or full-length forward strands.

Optionally, one or more forward primers, and/or one or more reverse primers are breathable, e.g., have a low $T_m$. In an example at least 60%, 65%, 70%, 75%, 80%, 85%, 90%, 95% or 99% of nucleotide bases of a breathable primer are adenine, thymine or uracil or are complementary to adenine, thymine or uracil.

In some embodiments, the disclosure relates generally to methods, compositions, systems, apparatuses and kits for clonally amplifying a nucleic acid template onto a support in an amplification reaction solution. Optionally, the nucleic acid template is contacted with a support in a solution comprising a continuous liquid phase. The support can include a population of primers, including at least a first primer and a second primer. The population of primers can be immobilized on the support, for example by covalent attachment to the support. In some embodiments, the nucleic acid template includes a primer binding sequence adjacent to a target sequence. The primer binding sequence can by complementary to a sequence of the first primer and optionally a sequence of the second primer. The target sequence can be noncomplementary to the primers in the population. In some embodiments, the primer binding sequence of the nucleic acid template is hybridized to the first primer. The first primer can be extended along the template using a polymerase, thereby forming an extended first primer. At least a portion of the primer binding sequence of the template can be separated (e.g., denatured or melted) from the extended first primer. The separating is optionally performed while maintaining hybridization between a portion of the template and the extended first primer. The separated portion of the primer binding sequence can be subsequently hybridized to the second primer. Optionally, such hybridization is performed while maintaining hybridization between the other portion of the template and the extended first primer. The second primer can be extended along the template using a polymerase, thereby forming a support including an extended first primer and an extended second primer. The extended portion of the extended first primer and/or the extended second primer can include sequence complementary to the target sequence.

In some embodiments, the disclosure relates generally to methods for clonally amplifying a nucleic acid template onto a support in an amplification reaction solution, comprising: contacting a nucleic acid template with a support in a liquid solution, wherein the support includes a population of immobilized primers including at least a first primer and a second primer, and wherein the nucleic acid template includes a primer binding sequence adjacent to a target sequence, where the primer binding sequence is complementary to a sequence of the first primer and a sequence of the second primer, and the target sequence is noncomplementary to the primers in the population; hybridizing the primer binding sequence of the nucleic acid template to the first primer; extending the first primer along the template using a polymerase, thereby forming an extended first primer; denaturing at least a portion of the primer binding sequence of the template from the extended first primer while maintaining hybridization between another portion of the template and the extended first primer; hybridizing the denatured portion of the primer binding sequence to the second primer while maintaining hybridization between the other portion of the template and the extended first primer; and extending the second primer along the template using a polymerase, thereby forming a support including an extended first primer and an extended second primer, where the extended first primer and the extended second primer each include sequence complementary to the target sequence. The population of primers can be comprised of substantially identical primers that differ in sequence by no more than one, two, three, four or five nucleotides. In some embodiments, the primer population is comprised of different primers, at least some of which include a sequence that is complementary to the primer binding sequence of the template. In some embodiments, the primers of population are noncomplementary to the sequence of the 5' terminal half of the template. In some embodiments, the primers of the population are noncomplementary to the sequence of the 3' terminal half of any of the extended primers of the support. In some embodiments, the primers of the population are noncomplementary to any sequence of the template other than the primer binding sequence.

In some embodiments, the disclosure relates generally to methods for clonally amplifying a population of nucleic acid templates onto a population of supports in an amplification reaction solution, comprising: clonally amplifying a first template onto a first nucleic acid template onto a first support according to any of the methods disclosed herein, and clonally amplifying a second nucleic acid template onto a second support according to the same method, wherein both supports are included within a single continuous liquid phase during the amplifying.

Among other things, a method is provided of generating a localized clonal population of immobilized clonal amplicons of a single-stranded template sequence, comprising: (a) attaching the single-stranded template sequence ("template 1") to an immobilization site ("IS1"), wherein IS1 comprises multiple copies of an immobilized primer ("IS1 primer") which can hybridize substantially to template 1, and template 1 is attached to IS1 by hybridization to an IS1 primer, and (b) amplifying template 1 using IS1 primer and a non-immobilized primer ("SP1 primer") in solution, wherein amplified strands that are complementary to the single-stranded template 1 cannot hybridize substantially when single-stranded to primers on IS1, wherein amplification generates a localized clonal population of immobilized clonal amplicons around the point of initial hybridization of template 1 to IS1.

Also provided is a method of generating separated and immobilized clonal populations of a first template sequence ("template 1") and a second template sequence ("template 2"), comprising amplifying the first and second template sequence to generate a population of clonal amplicons of template 1 substantially attached to first immobilization site ("IS1") and not to a second immobilization site ("IS2"), or a population of clonal amplicons of template 2 substantially attached to IS2 and not to IS1, wherein: (a) both templates and all amplicons are contained within the same continuous liquid phase, where the continuous liquid phase is in contact with a first and second immobilization site (respectively, "IS1" and "IS2"), and where IS1 and IS2 are spatially separated, (b) template 1 when in single-stranded form comprises a first subsequence ("T1-FOR") at one end, and a second subsequence ("T1-REV") at its opposite end, (c) template 2 when in single-stranded form comprises a first subsequence ("T2-FOR") at one end, and a second subsequence ("T2-REV") at its opposite end, (d) IS1 comprises multiple copies of an immobilized nucleic acid primer ("IS1 primer") that can hybridize substantially to T1-FOR and T2-FOR when T1 and T2 are single-stranded, (e) IS2 comprises multiple copies of an immobilized primer ("IS2 primer") that can hybridize substantially to both T1-FOR and T2-FOR when T1 and T2 are single-stranded, (f) the reverse complement of T1-REV when single-stranded cannot hybridize substantially to primers on IS1, but can hybridize substantially to a non-immobilized primer ("SP1") in the continuous liquid phase; and (g) the reverse complement of T2-REV when single-stranded cannot hybridize substantially to primers on IS2, but can hybridize substantially to a non-immobilized primer ("SP2") in the continuous liquid phase.

Optionally, in any method described herein, any nucleic acid that has dissociated from one immobilization site is capable of substantially hybridizing to both immobilization sites and any movement (e.g., movement by diffusion, convection) of said dissociated nucleic acid to another immobilization site is not substantially retarded in the continuous liquid phase.

Optionally, in any method described herein, the continuous liquid phase is in simultaneous contact with IS1 and IS2.

Optionally, in any method described herein, a first portion of a template that is bound by an immobilized primer does not overlap with a second portion of the template whose complement is bound by a non-immobilized primer.

Optionally, in any method described herein, at least one template to be amplified is generated from an input nucleic acid after the nucleic acid is placed in contact with at least one immobilization site.

Optionally, any method described herein comprising the steps of: (a) contacting a support comprising immobilized primers with a single-stranded nucleic acid template, wherein: hybridizing a first immobilized primer to a primer-binding sequence (PBS) on the template (b) extending the hybridized first primer in template-dependent extension to form an extended strand that is complementary to the template and at least partially hybridized to the template; (c) partially denaturing the template from the extended complementary strand such that at least a portion of the PBS is in single-stranded form ("free portion"); (d) hybridizing the free portion to a non-extended, immobilized second primer (e) extending the second primer in template-dependent extension to form an extended strand that is complementary to the template (f) optionally, separating the annealed extended immobilized nucleic acid strands from one another.

Optionally, in any method described herein (a) during amplification, nucleic acid duplexes are formed comprising a starting template and/or amplified strands; which duplexes are not subjected during amplification to conditions that would cause complete denaturation of a substantial number of duplexes.

Optionally, in any method described herein, the single-stranded templates are produced by taking a plurality of input double-stranded or single-stranded nucleic acid sequences to be amplified (which sequence may be known or unknown) and appending or creating a first universal adaptor sequence and a second universal adaptor sequence onto the ends of at least one input nucleic acid; wherein said first universal adaptor sequence hybridizes to IS1 primer and/or IS2 primer, and the reverse complement of said second universal adaptor sequence hybridizes to at least one non-immobilized primer. The adaptors can be double-stranded or single-stranded.

Optionally, in any method described herein, first and second nucleic acid adaptor sequences are provided at first and second ends of said single-stranded template sequence.

Optionally, in any method described herein, a tag is also added to one or more nucleic acid sequences (e.g., a template or a primer or an amplicons), said tag enabling identification of a nucleic acid containing the tag.

Optionally, in any method described herein, all primers on at least one immobilization site or support have the same sequence. Optionally, an immobilization site or support comprises a plurality of primers having at least two different sequences. In some embodiments, an immobilization site or support includes at least one target-specific primer.

Optionally, in any method described herein, the continuous medium is flowable. Optionally, intermixing of non-immobilized nucleic acid molecules is substantially unretarded in the continuous liquid phase during at least a portion of the amplification process, e.g., during any one or more steps or cycles described herein.

Optionally, in any method described herein, intermixing is substantially unretarded for a period of time during amplification. For example, intermixing is substantially unretarded during the entire duration of amplification.

In an embodiment, amplification is achieved using RPA, i.e., recombinase-polymerase amplification (see, e.g., WO2003072805, incorporated by reference herein). RPA optionally is carried out without substantial variations in temperature or reagent conditions. In an embodiment herein, partial denaturation and/or amplification, including any one or more steps or methods described herein, can be achieved using a recombinase and/or single-stranded binding protein. Suitable recombinases include RecA and its prokaryotic or eukaryotic homologues, or functional fragments or variants thereof, optionally in combination with single-strand binding proteins (SSBs). In an embodiment, the recombinase agent optionally coats single-stranded DNA (ssDNA) such as an amplification primer to form a nucleoprotein filament strand which invades a double-stranded region of homology on a template. This optionally creates a short hybrid and a displaced strand bubble known as a D-loop. In an embodiment, the free 3'-end of the filament strand in the D-loop is extended by DNA polymerases to synthesize a new complementary strand. The complementary strand displaces the originally-paired partner strand of the template as it elongates. In an embodiment, one or more of a pair of amplification primers are contacted with one or more recombinase agents before be contacted with a template which is optionally double-stranded.

In any method described herein, amplification of a template (target sequence) comprises contacting a recombinase agent with one or more of at least one pair of amplification primers, thereby forming one or more "forward" and/or "reverse" RPA primers. Any recombinase agent that has not associated with the one or more primers is optionally removed. Optionally, one or more forward RPA primers are then contacted with a template strand, which optionally has a region of complementarity to at least one RPA primer. The template strand can be hybridized to a Contacting of a RPA primer with a complementary template optionally results hybridization between said primer and the template. Optionally, the 3' end of the primer is extended along the template with one or more polymerases (e.g., in the presence of dNTPs) to generate a double stranded nucleic acid and a displaced template strand. The amplification reaction can comprise repeated cycles of such contacting and extending until a desired degree of amplification is achievable. Optionally the displaced strand of nucleic acid is amplified by a concurrent RPA reaction. Optionally, the displaced strand of nucleic acid is amplified by contacting it in turn with one or more complementary primers; and (b) extending the complementary primer by any strategy described herein.

In an embodiment the one or more primers comprise a "forward" primer and a "reverse" primer. Placing both primers and the template in contact optionally results in a first double stranded structure at a first portion of said first strand and a double stranded structure at a second portion of said second strand. Optionally, the 3' end of the forward and/or reverse primer is extended with one or more polymerases to generate a first and second double stranded nucleic acid and a first and second displaced strand of nucleic acid. Optionally the second displaced strand is at least partially complementary to each other and can hybridize to form a daughter double stranded nucleic acid which can serve as double stranded template nucleic acid in a subsequent amplification cycles.

Optionally said first and said second displaced strands is at least partially complementary to said first or said second primer and can hybridize to said first or said second primer.

In an alternative embodiment of any method or step or composition or array described herein, the support optionally comprises immobilized primers of more than one sequence. After a template nucleic acid strand hybridizes to first complementary immobilized primer, the first primer can then be extended and the template and the primer can be separated partially or completely from one another. The extended primer can then be annealed to a second immobilised primer that has different sequence from the first, and the second primer can be extended. Both extended primers can then be separated (e.g., fully or partially denatured from one another) and can be used in turn as templates for extension of additional immobilized primers. The process can be repeated to provide amplified, immobilised nucleic acid molecules. In an embodiment, this amplification results in immobilized primer extension products of two different sequences that are complementary to each other, where all primer extension products are immobilized at the 5' end to the support In some embodiments, the disclosed methods include amplifying, wherein the amplifying includes strand flipping. In a "flipping" embodiment described below, two or more primers are extended to form two or more corresponding extended strands. Optionally, the two or more primers that are extended comprise or consist essentially of substantially identical sequence, and the extended portions of corresponding extended strand are at least partly non-identical and/or complementary to each other.

One exemplary embodiment of flipping is as follows. A starting template is amplified, e.g., by template walking, to generate a plurality of primer-extended strands (which for convenience will be designated as "forward" strands). Optionally, the forward strands are complementary to the starting template. Optionally, the forward strands are immobilized on the support. Optionally, the forward strands comprise substantially identical sequence, e.g., the forward strands are substantially identical to each other. In an embodiment the forward strands are formed by extension of one or more primers immobilized on a support ("forward" primers). The forward primers and/or the forward strands are optionally attached to the support at or near their 5' ends. Optionally, one or more of the primer-extended forward strands comprises a 3' sequence (called a self-hybridizing sequence) that is absent in the unextended primer and can hybridize under the conditions of choice to a 5' sequence (this process will be termed "self-hybridization"). The 5' sequence is optionally part of the unextended forward primer. In an example, the forward extension product forms a "stem-loop" structure upon such hybridization. Optionally, the unextended forward primer comprises a "cleavable" nucleotide at or near its 3' terminus that is susceptible to cleavage. In an embodiment, the cleavable nucleotide is linked to at least one other nucleotide by a "scissile" internucleoside linkage that can be cleaved under conditions that will not substantially cleave phosphodiester bonds.

After extension, the forward-primer extension product (i.e., the forward strand) is optionally allowed to self-hybridize. In a further embodiment, after allowing for self-hybridization the forward strand is cleaved at a scissile linkage of a cleavable nucleotide (for example a nucleotide which forms a scissile linkage with a neighboring nucleotide). The cleavage results in two fragments of the primer-extension product (i.e., the extended forward strand). In an embodiment, a first fragment comprises at least a portion of the original unextended forward primer. Optionally, the first fragment does not comprise any extended sequence. Optionally, the first fragment is immobilized (e.g., because the unextended forward primer was already immobilized). In an embodiment, a second fragment comprises extended sequence. Optionally the second fragment comprises any 3' portion of the unextended primer beyond the cleavable nucleotide or does not comprise any portion of the unextended primer. Optionally, the second fragment is hybridized to the first portion through its self-hybridizing sequence.

In an example, the cleavable nucleotide is one that is removed by one or more enzymes. The enzyme can for instance be a glycosylase. The glycosylase optionally has N-glycosylase activity which releases the cleavable nucleotide from double stranded DNA. Optionally, the removal of the cleavable nucleotide generates an abasic, apurinic or apyrimidinic site. The abasic site can optionally be further modified, for example by another enzymatic activity. Optionally, the abasic site is modified by a lyase to generate a base gap. The lyase for example cleaves 3' and/or 5' to the abasic site. Cleavage optionally occurs at both the 5' and 3' end by the lyase, resulting in removing the abasic site and leaving a base gap. Exemplary cleavable nucleotides such as 5-hydroxy-uracil, 7,8-dihydro-8-oxoguanine (8-oxoguanine), 8-oxoadenine, fapy-guanine, methy-fapy-guanine, fapy-adenine, aflatoxin B1-fapy-guanine, 5-hydroxy-cytosine can be recognized and removed by various glycosylases to form an apurinic site. One suitable enzyme is formamidopyrimidine [fapy]-DNA glycosylase, also known as 8-oxoguanine DNA glycosylase or FPG. FPG acts both as a N-glycosylase and an AP-lyase. The N-glycosylase activity optionally releases damaged purines from double stranded DNA, generating an apurinic (AP site), where the phosphodiester backbone is optionally intact. The AP-lyase activity cleaves both 3' and 5' to the AP site thereby removing the AP site and leaving a one-base gap. In an example the cleavable nucleotide is 8-oxoadenine, which is converted to a one-base gap by FPG with both glycosylase and lyase activities.

In another embodiment the cleavable nucleotide is uridine. Optionally, the uridine is cleaved by "USER" reagent, which includes Uracil DNA glycosylase (UDG) and the DNA glycosylase-lyase Endonuclease VIII, where UDG catalyses the excision of a uracil base, forming an abasic (apyrimidinic) site while leaving the phosphodiester backbone intact, and where the lyase activity of Endonuclease VIII breaks the phosphodiester backbone at the 3' and 5' sides of the abasic site so that base-free deoxyribose is released, after which kinase is optionally used to convert the phosphate group on the 3' end of cleaved product to an —OH group).

At least one cleaved fragment is optionally contacted with a polymerase. Optionally the first immobilized fragment can be extended by the polymerase. If so desired the second hybridized fragment can act as template for extension of the first fragment. In an embodiment a "flipped" double-stranded extension product is formed. This flipped product can optionally be subjected to template walking in any manner described herein. When both flipped and unflipped are subjected to template walking, a cluster of two different extension products is formed, where both extension products have an identical portion (corresponding to the unextended primers) and portion complementary to each other, corresponding to the extended portions of the extension products.

In an embodiment, a sequence of interest, such as a self-hybridizing sequence or a new primer-binding site, can be optionally added at the 3' ends of extended forward strands by contacting the extended forward strands with a single-stranded "splice" adaptor sequence in the presence of extension reagents (e.g., a polymerase and dNTPs). This splice sequence optionally comprises a 3' portion that is substantially complementary to a 3' end portion of the extended forward strand, and a 5' portion that is substantially complementary to the sequence of interest to be added. After hybridizing the splice adaptor to the 3' end of the extended forward strand, the forward strand is subjected to template-dependent polymerase extension using the splice adaptor as template. Such extension results in the addition of the sequence of interest to the 3' end of the extended forward strand.

Thus, any method of primer extension and/or amplification described herein can include any one or more of the following steps: (a) extension of immobilized forward primers by template walking to generate a plurality of extended forward strands which are optionally identical; (b) optionally hybridizing a splice adaptor to a 3' end of the extended forward strands and subjecting the forward strands to template-dependent extension using the splice adaptor as a template, thereby adding a further 3' sequence to the further-extended forward strands, wherein a portion of the added 3' sequence is complementary to a portion of the unextended forward primer and hybridizes thereto to form a stem-loop structure; (c) cleaving the forward strands at a scissile linkage of a cleavable nucleotide located at or near the junction of unextended forward primer sequence and extended forward strand sequence; and optionally removing the cleavable nucleotide, thereby generating two cleaved fragments, the first fragment comprising a portion of an unextended forward primer hybridized to a 3' primer-complementary sequence on the second fragment; (d) optionally subjecting the first fragment to polymerase extension using the second fragment as template to generate a flipped forward strand; (e) optionally hybridizing a second splice adaptor to a 3' end of the flipped forward strand, and subjecting the forward strands to template-dependent extension using the splice adaptor as a template, thereby adding a further 3' sequence to the flipped forward strands, wherein a portion of the added 3' sequence is a new primer-binding sequence that is absent in the flipped strands; (f) selectively extending or amplifying the flipped strands which comprise the new primer-binding sequence by contacting with the new primer and extending or amplifying by any method, e.g., as described herein. The new primer will not bind to unflipped strands or to flipped strands that were not further extended in step (e).

Figure 8A:
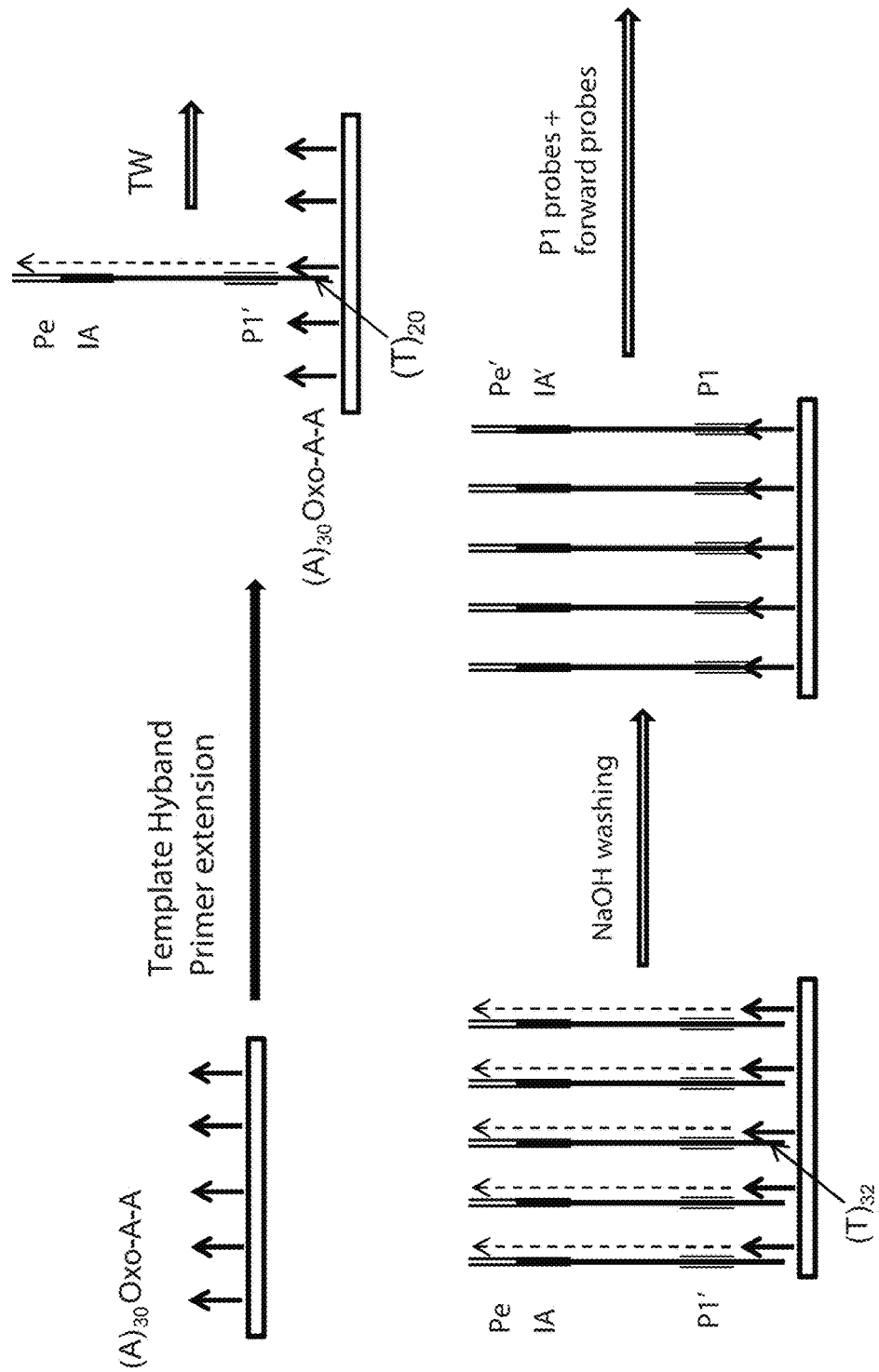
Figure 8B:
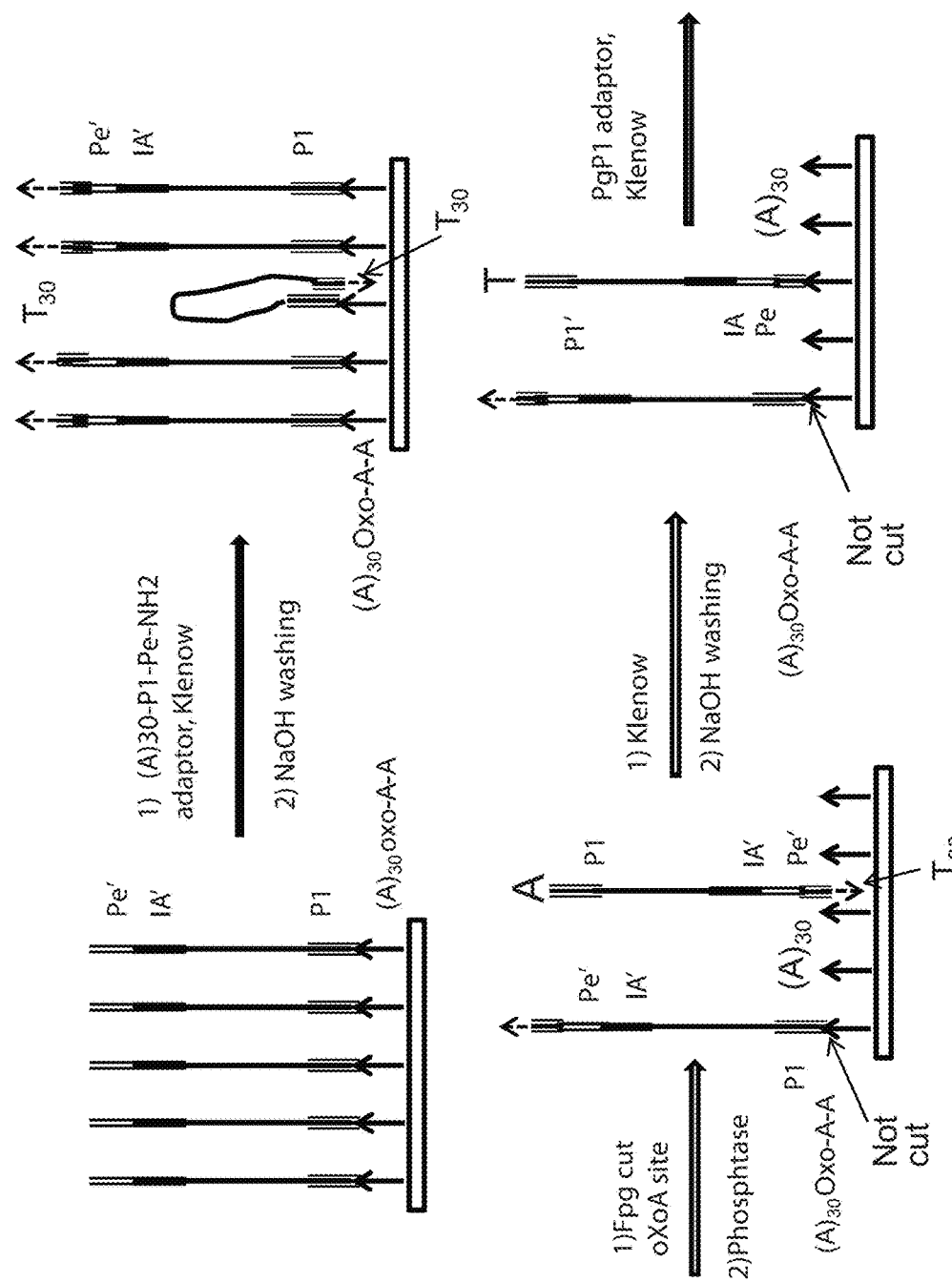
Figure 8C:
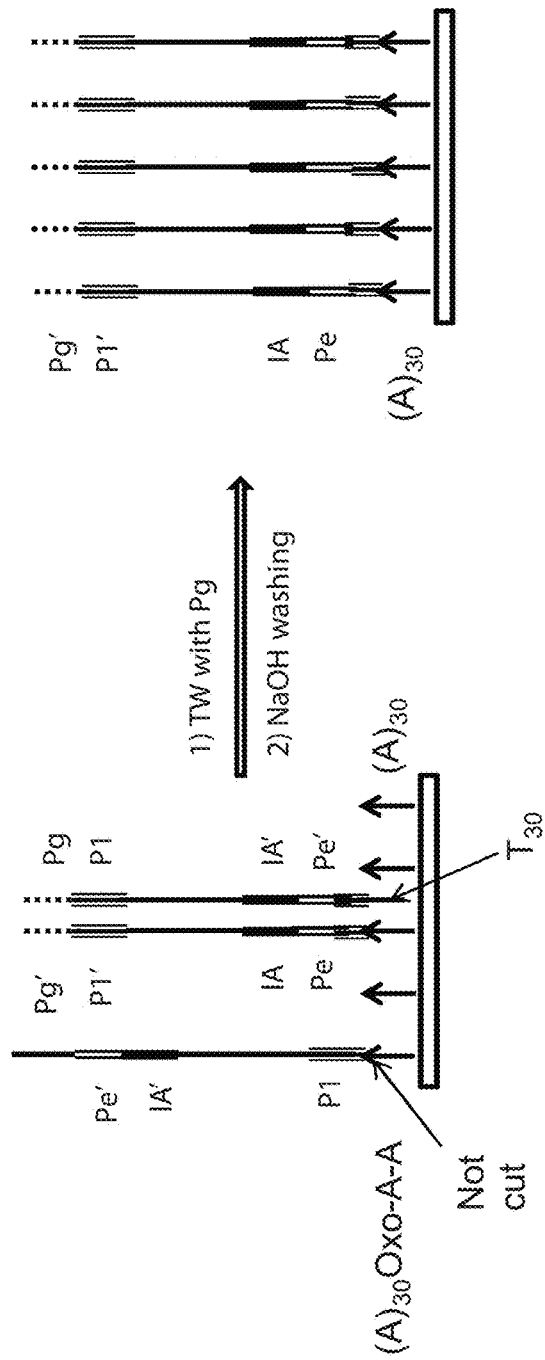

FIGS. 8 A-C shows a schematic depiction of an exemplary strand-flipping and walking strategy. FIG. 8A template walking, FIG. 8B strand flipping to generate flipped strands, FIG. 8C addition of new primer-binding sequence Pg' on final flipped strands.

Optionally, a single support is used in any of the amplification methods herein, where the single support has a plurality of primers that can hybridize to the templates. In such an embodiment, the concentration of the template collection is adjusted before it is contacted with a solid support so that individual template molecules in the collection get attached or associated (e.g., by hybridization to primers immobilized on the solid support) at a density of at least $10^2$, $10^3$, $10^4$, $10^5$, $4\times10^5$, $5\times10^5$, $6\times10^5$, $8\times10^5$, $10^6$, $5\times10^6$ or $10^7$ molecules per $mm^2$.

Optionally, individual template molecules are amplified in-situ on the support, giving rise to clonal populations that are spatially-centered around the point of hybridization of the initial template. Optionally, the amplification generates no more than about $10^2$, $10^3$, $10^4$, $10^5$, $10^6$, $10^7$, $10^8$, $10^9$, $10^{10}$, $10^{11}$, $10^{12}$, $10^{15}$, or $10^{20}$ amplicons from a single amplified template. Optionally, the colonies of clonal amplicons are situated on the solid support at a density of at least $10^2$, $10^3$, $10^4$, $10^5$, $4\times10^5$, $5\times10^5$, $6\times10^5$, $8\times10^5$, $10^6$, $5\times10^6$ or $10^7$ molecules per $mm^2$.

In some embodiments, the nucleic acid collection can be contacted with one or more supports under conditions where multiple nucleic acids bind to the same support. Such contacting can be particularly useful in methods that involve parallel clonal amplification of nucleic acids in different regions of the same support. The ratio of the number of nucleic acids to the surface area of the support can be adjusted to facilitate mono-clone formation by, e.g., ensuring that the nucleic acids are appropriately spaced in the support to favor formation of monoclonal populations of amplified nucleic acids without substantial cross-contamination between different clonal populations. For example where a single support us used, the collection of nucleic acids to be amplified is adjusted to such a dilution that the resulting amplified clonal populations generated from individual nucleic acids are generally discrete or distinct, e.g., without overlap. For example, individual nucleic acids within 50%, 70%, 80% or 90% or more of the amplified clonal populations are not interspersed with substantially non-identical nucleic acids. Optionally, different amplified populations are not in contact or completely overlapping with other amplified populations, or are distinguishable from each other using a detection method of choice.

In some embodiments, the nucleic acids are attached to the surface of a support. In some embodiments, the nucleic acids can be attached within the support. For example, for supports comprised of hydrogel or other porous matrices, the nucleic acids can be attached throughout the volume of the support including on the surface and within the support.

In some embodiments, the support (or at least one support in a population of supports) can be attached to at least one primer, optionally to a population of primers. For example, the support (or at least one support) can include a population of primers. The primers of the population can be substantially identical each other, or may include a substantially identical sequence. One, some or all of the primers can include a sequence that is complementary to a sequence within one or more nucleic acid templates. In some embodiments, the population of primers can include at least two noncomplementary primers.

The primers can be attached to the support through their 5' end, and have free 3' ends. The support can be the surface of a slide or the surface of a bead. The primers have low melting temperature, such as oligo $(dT)_{20}$, and can hybridize to the low $T_m$ region of the collection adaptor. The distances between the primers need to be shorter than the adapter length to allow templates waking, or alternatively, a long primer with 5' end long linker will increase the chance of walking.

In some embodiments, the support is attached to and/or contacted with a primer and a template (or reverse strand) under conditions where the primer and template hybridize to each other to form a nucleic acid duplex. The duplex can include a double stranded portion that comprises complementary sequences of the template and primer, where at least one nucleotide residue of the complementary sequences are base paired with each other. In some embodiments, the duplex can also include a single stranded portion. The duplex can also include a single stranded portion. The single stranded portion can include any sequence within the template (or primer) that is not complementary to any other sequence in the primer (or template).

A non-limiting exemplary method of clonal nucleic acid amplification on a support is as follows. A nucleic acid (which shall be designated for convenience as the reverse strand) is clonally amplified onto a support on which multiple copies of a complementary forward primer are attached. An exemplary nucleic acid is one of a plurality of DNA collection molecules, that for example the plurality of nucleic acid members have one or more common ("adaptor") sequences at or near their 5' and/or 3' ends and variable sequences in between, such as gDNA or cDNA. In an embodiment, the 3' common portion, e.g., adaptor, has a breathable (e.g., low $T_m$) region, and the 5' common sequence (e.g., adaptor) optionally has a less breathable (e.g., higher $T_m$) region, or vice versa. In another embodiment, both the 5' and 3' common sequences are breathable. The breathable (e.g., low $T_m$) region is for example a region that is rich in A, T and/or U, such as an AT (or U)-rich sequence, such as polyT, polyA, polyU and any combinations of A, T and U bases, or bases complementary to such bases. Exemplary methods are described herein.

Figure 1:
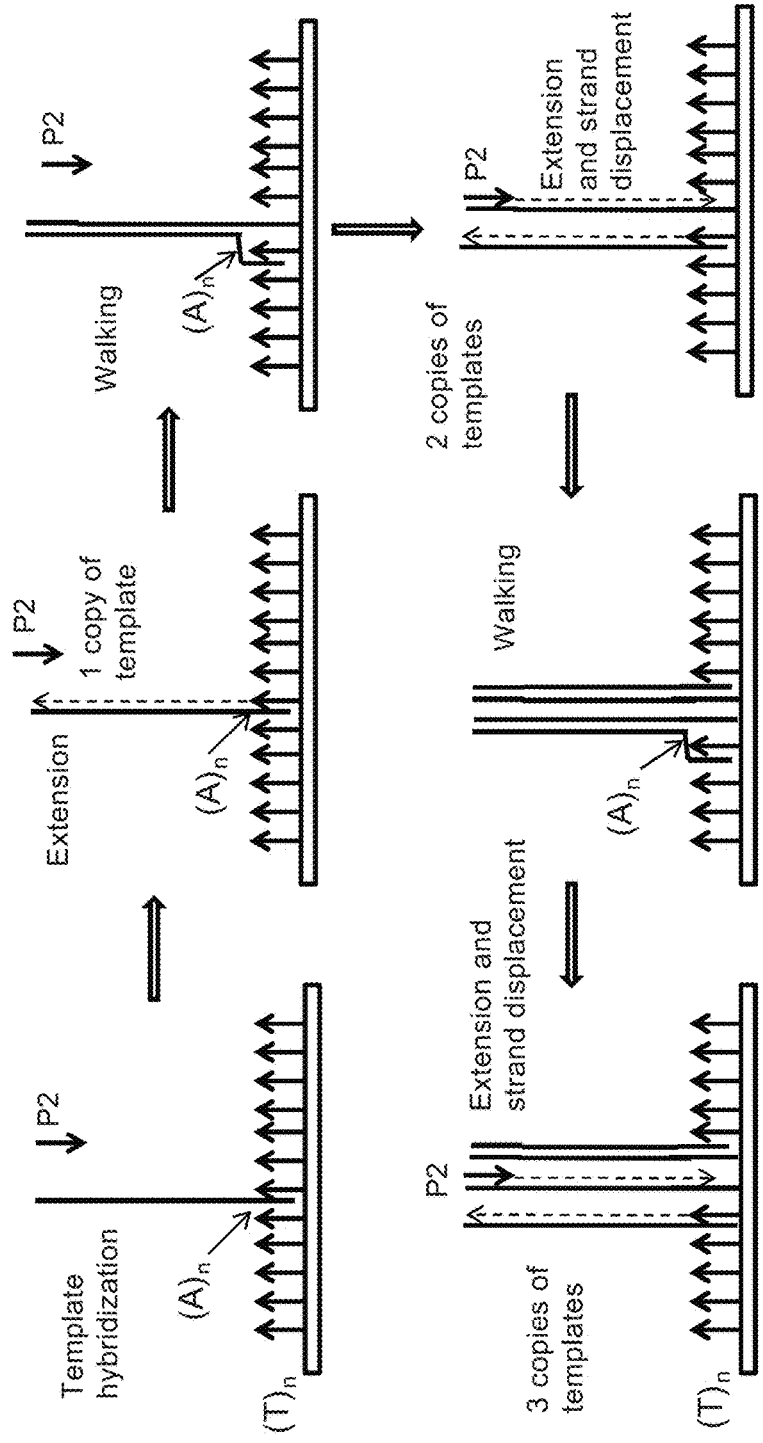
Figure 2:
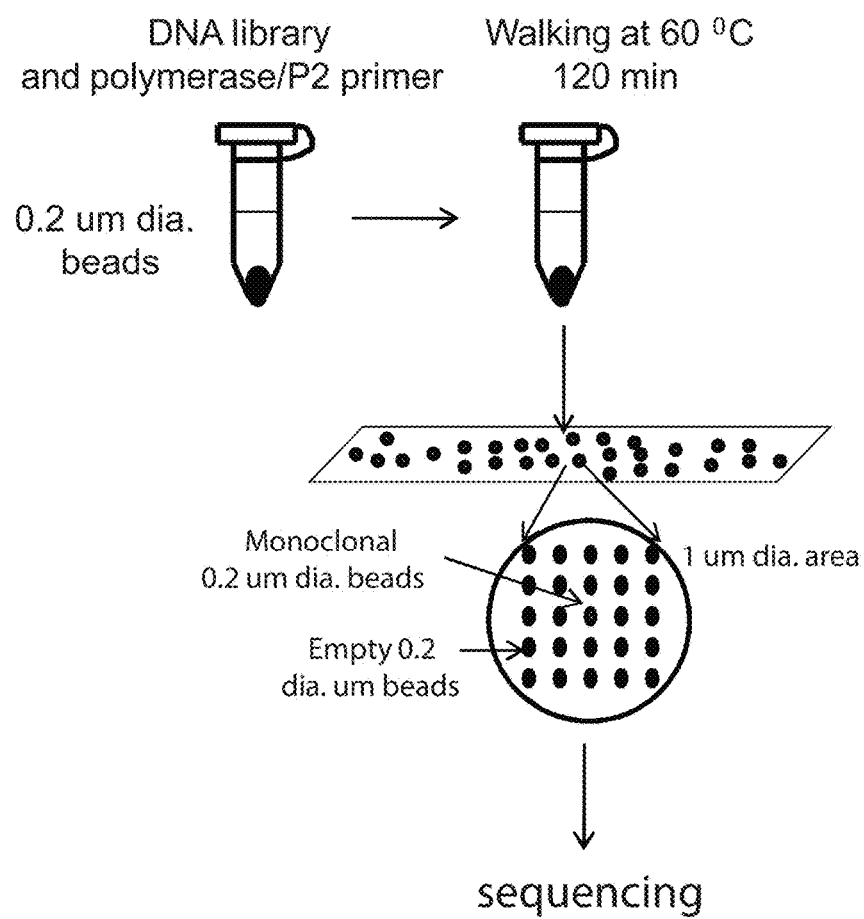
Figure 3:
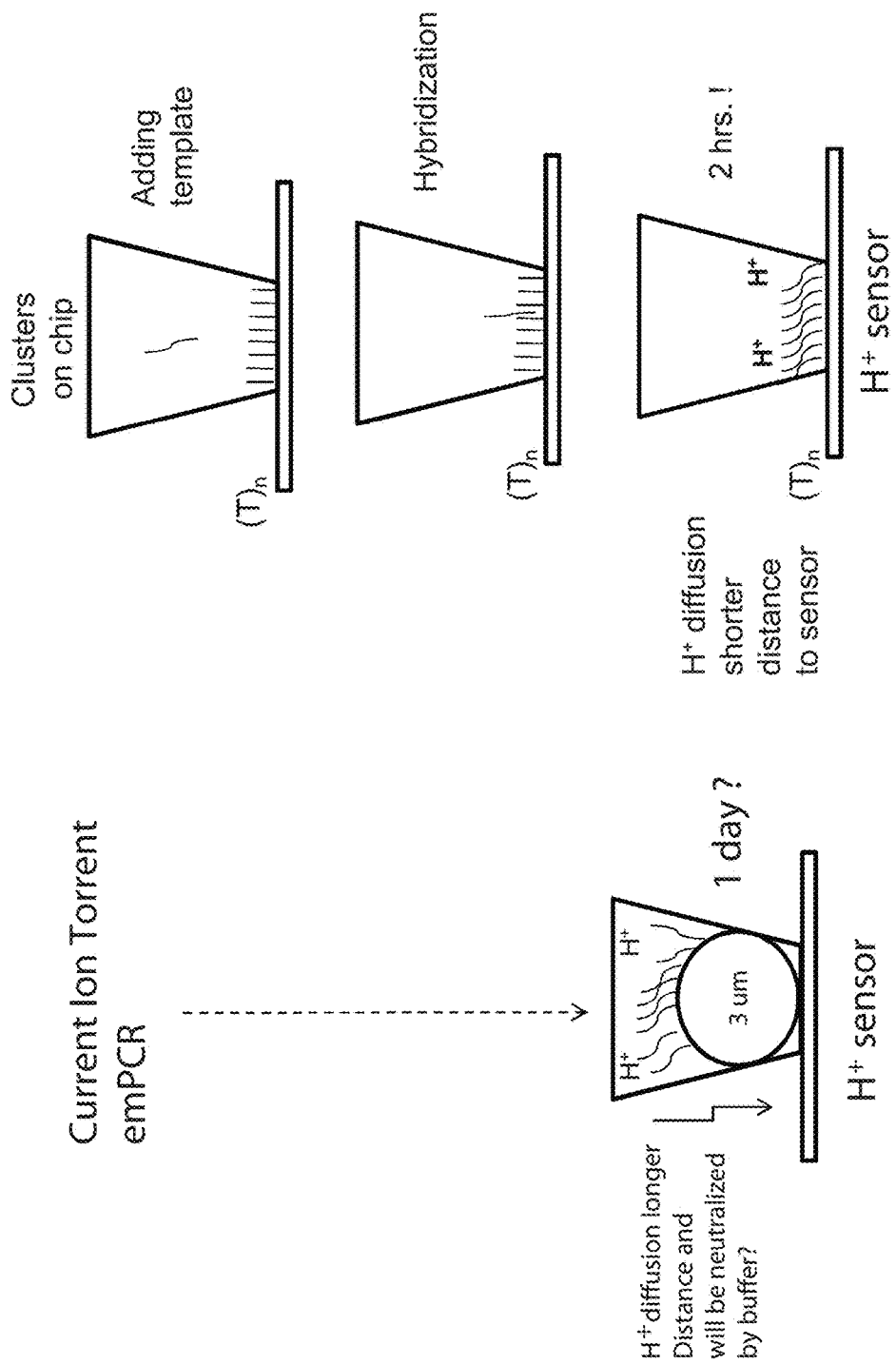
Figure 4:
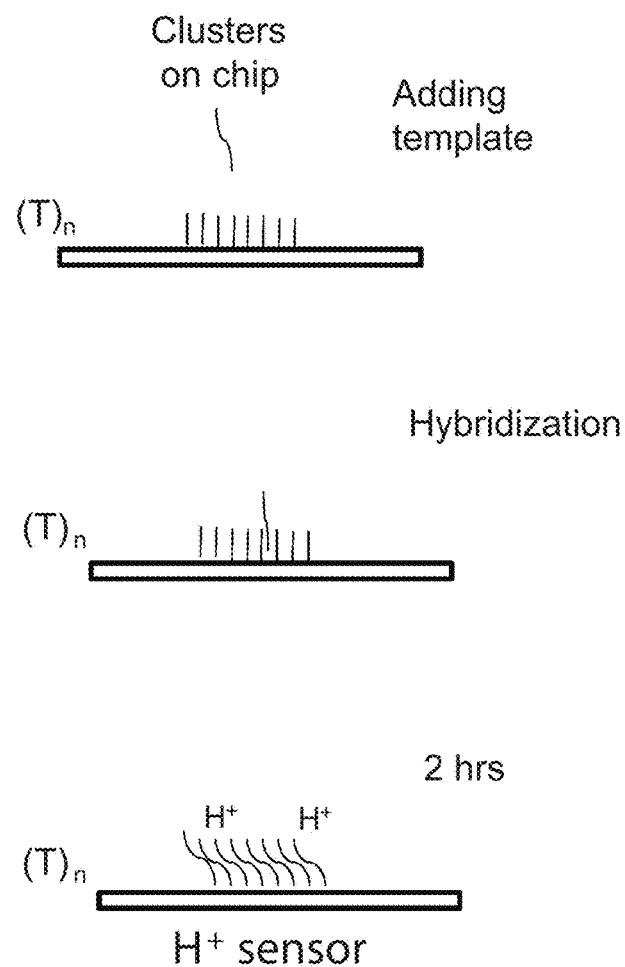
Figure 5:
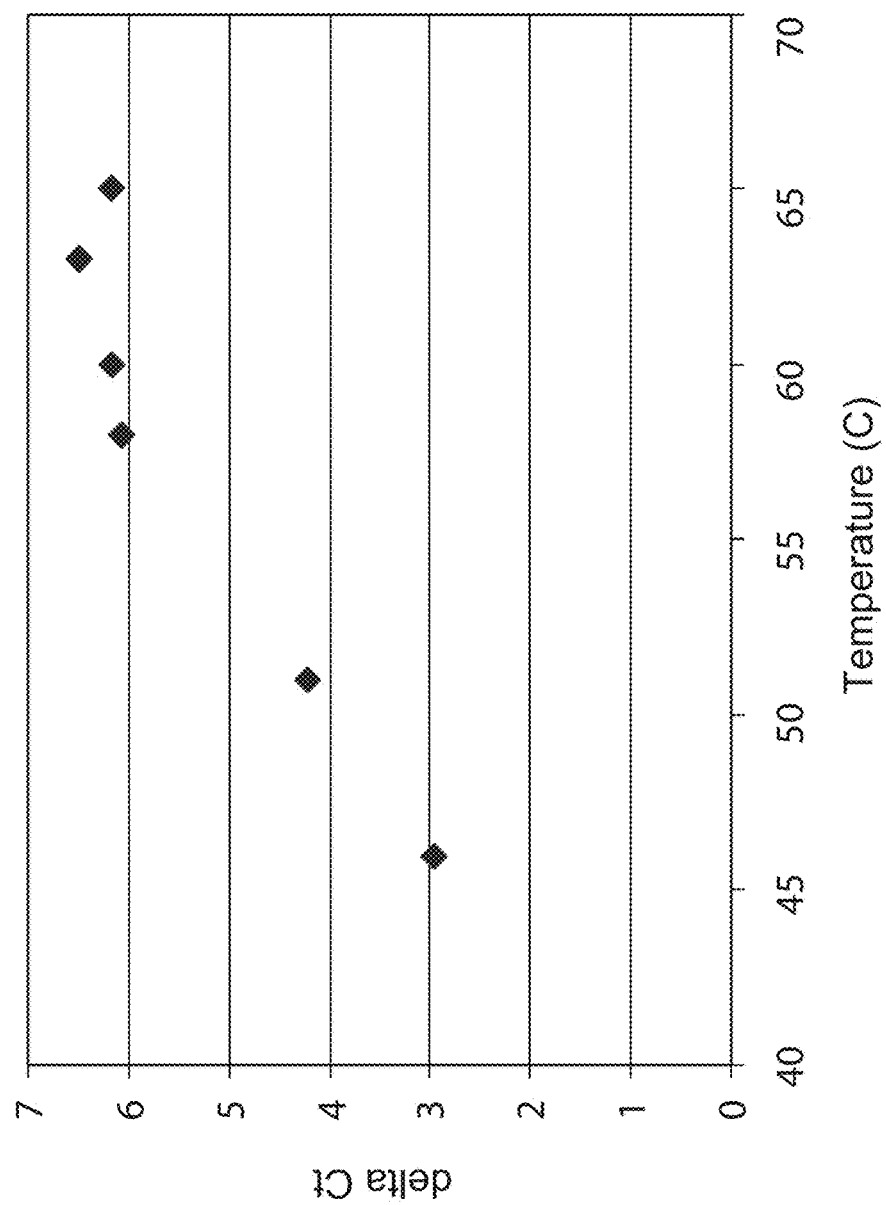
Figure 7:
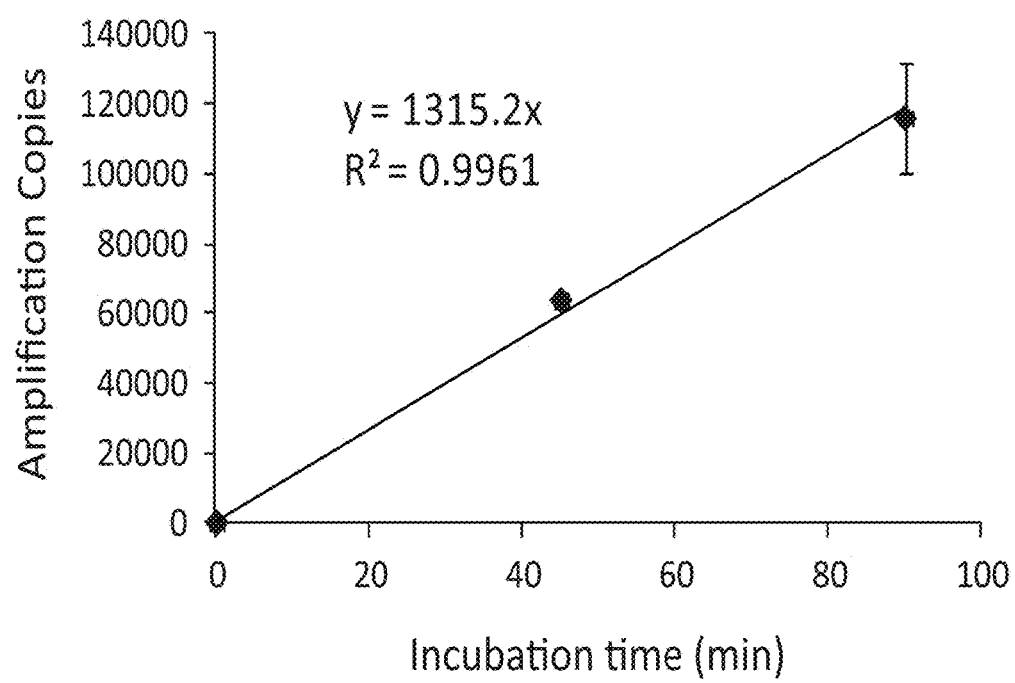

One non-limiting exemplary method of clonal nucleic acid amplification on a support via "template walking" is shown in FIG. 1. A non-limiting description of an exemplary method of template walking is as follows.

A double stranded DNA library molecule is denatured and the single stranded DNA is attached to the support through hybridization to the primers on the surface. The ratio of number of DNA molecules to support area or number of beads is set to facilitate mono-clone formation.

Primers are attached on a support through their 5' and have free 3'. The support can be the surface of a slide or the surface of a bead. The primers have low melting temperature, such as oligo $(dT)_{20}$ or oligo $(dA)_{30}$ and can hybridize to the low Tm region of the library adaptor. The distances between the primers can be shorter than the adapter length to allow templates waking, or alternatively, a long primer with 5' end long linker will increase the chance of walking.

A nucleic acid is clonally amplified onto a support on which multiple copies of a primer are attached. An exemplary nucleic acid is one of a plurality of DNA library molecules, which for example have one or more common (e.g., "adaptor") sequences at their 5' and/or 3' ends and variable sequences in between, such as gDNA or cDNA. In an embodiment, the 3' adaptor has a low Tm region, and the 5' adaptor optionally has a higher Tm region, or vice versa. The low Tm region is for example a pyrimidine-rich region, such as an AT (or U)-rich sequence, such as polyT, polyA, polyU and any combinations of A, T and U bases or bases complementary to such bases. Exemplary methods are described herein.

One or more primers, whether in soluble form or attached to a support, is incubated with a DNA polymerization or extension reaction mix, which optionally comprises any one or more of reagents such as enzyme, dNTPs and buffers. The primer (e.g., a forward primer) is extended. Optionally, the extension is a template-dependent extension of a primer along a template comprising the successive incorporation of nucleotides that are individually complementary to successive nucleotides on the template, such that the extended or nonextended forward primer is complementary to the reverse strand (also termed antiparallel or complementary). Optionally, the extension is achieved by an enzyme with polymerase activity or other extension activity, such as a polymerase. The enzyme can optionally have other activities including 3'-5' exonuclease activity (proofreading activity) and/or 5'-3' exonuclease activity. Alternatively, in some embodiments the enzyme can lack one or more of these activities. In an embodiment the polymerase has strand-displacing activity. Examples of useful strand-displacing polymerases include Bacteriophage Φ29 DNA polymerase and Bst DNA polymerase. Optionally, the enzyme is active at elevated temperatures, e.g., at or above 45° C., above 50° C., 60° C., 65° C., 70° C., 75° C., or 85° C.

An exemplary polymerase is Bst DNA Polymerase (Exonuclease Minus), is a 67 kDa *Bacillus stearothermophilus* DNA Polymerase protein (large fragment), exemplified in accession number 2BDP_A, which has 5'-3' polymerase activity and strand displacement activity but lacks 3'-5' exonuclease activity. Other polymerases include Taq DNA polymerase I from *Thermus aquaticus* (exemplified by accession number 1TAQ), Eco DNA polymerase I from *Escherichia coli* (accession number P00582), Aea DNA polymerase I from *Aquifex aeolicus* (accession number 067779), or functional fragments or variants thereof, e.g., with at least 80%, 85%, 90%, 95% or 99% sequence identity at the nucleotide level.

Generally, the extension step produces a nucleic acid, which comprises a double-stranded duplex portion in which two complementary strands are hybridized to each other. In one embodiment, walking involves subjecting the nucleic acid to partially-denaturing conditions that denature a portion of the nucleic acid strand but are insufficient to fully denature the nucleic acid across its entire length. In an embodiment, the nucleic acid is not subjected to fully-denaturing conditions during a portion or the entire duration of the walking procedure.

In an embodiment, the sequence of the negative and/or positive strand designed such that a primer-binding sequence or a portion thereof is breathable, i.e., is susceptible to denaturation under the conditions of choice (e.g., amplification conditions). The breathable portion is optionally more susceptible than a majority of nucleic acids of similar length with randomized sequence, or more susceptible than at least another portion of the strand comprising the breathable sequence. Optionally, the breathable sequence shows a significant amount of denaturation (e.g., at least 10%, 20%, 30%, 50%, 70%, 80%, 90% or 95% of molecules are completely denatured across the breathable sequence) at the amplification conditions of choice. For example the breathable sequence is designed to be fully-denatured in 50% of strand molecules at 30, 35, 40, 42, 45, 50, 55, 60, 65 or 70° C. under the conditions of choice (e.g., amplification conditions).

Where partial denaturation is achieved by heating or elevated temperatures, an exemplary breathable PBS may be pyrimidine-rich (e.g., with a high content of As and/or Ts and/or Us). The PBS comprises for example a poly-A, poly-T or poly-U sequence, or a polypyrimidine tract. One or more amplification or other primers (e.g., an immobilized primer) are optionally designed to be correspondingly complementary to these primer-binding sequences. An exemplary PBS of a nucleic acid strand comprises a poly-T sequence, e.g., a stretch of at least 10, 15, 20, 25 or 30 thymidine nucleotides, while the corresponding primer has a complementary sequence to the PBS, e.g., a stretch of at least 10, 15, 20, 25 or 30 adenosine nucleotides. Exemplary low-melt primers optionally have a high proportion (e.g., at least 50%, 60%, 65%, 70%, 75%, 80%, 85% 90% 95% or 100%) of nucleobases that generally (e.g., under amplification conditions of choice) form no more than two hydrogen bonds with a complementary base when the primer is hybridized to a complementary template. Examples of such nucleobases include A (adenine), T (thymine) and U (uracil). Exemplary low-melt primers optionally have a high proportion of any one or more of A (adenine), T (thymine) and/or U (uracil) nucleotides or derivatives thereof. In an embodiment, the derivatives comprise nucleobases that are complementary to A (adenine), T (thymine) and/or U (uracil). The portion of the primer that hybridizes to the PBS optionally has at least 50%, 60%, 65%, 70%, 75%, 80%, 85%, 90% 95% or 100% of A (adenine), T (thymine) or U (uracil) nucleotides, or any combination thereof. In another example, the portion of the primer that hybridizes to the PBS comprises a polyA sequence (e.g., at least 5, 10, 15, 20, 25 or 30 nucleotides long). Other exemplary primers comprise $(NA_x)_n$ repeats. Optionally, n (in lower case) is from 2 to 30, e.g., from 3 to 10, for example 4 to 8. "N" (in upper case) is any nucleotide—and optionally, N is C or G. "A" is the shorthand convention for adenine, and "x" denotes the number of adenine residues in the repeat, for example 2, 3, 4, 5, 6, 10 or more. Exemplary primers comprise multiple repeats of $(CAA)_n$, $CA)_n$, $(CAAA)_n$ or even $(GAA)_n$.

Optionally only one strand (e.g., the forward or the reverse strand) has a breathable PBS. In another embodiment, both the forward and reverse strands have a breathable PBS. The breathable PBS is optionally complementary to a primer that is either immobilized to a support or is not immobilized (e.g., in soluble form). Optionally the strand comprising the breathable PBS is either immobilized to a support or is not immobilized (e.g., in soluble form). Optionally both primers are immobilized, or both strands are immobilized. Optionally neither primer is immobilized, or neither strand is immobilized.

An amplification cycle optionally comprises breathing, annealing and extension. The nucleic acid to be amplified is optionally subjected to conditions which are suitable for or optimized for at least one of these steps. In an embodiment, the nucleic acid is subjected to conditions which are suitable for more than one of these steps, (e.g., annealing and extension, or breathing and extension). In some instances, all three of these steps can take place simultaneously under the same conditions.

In an exemplary method the nucleic acid can be subjected to conditions which permit or facilitate breathing. In an embodiment, "breathing" is said to occur when the two strands of a double-stranded duplex are substantially hybridized to each other, but are denatured across a local portion of interest (e.g., the terminal ends or primer-binding sites). One or more breathable sequences (e.g., a forward and/or reverse PBS having a low Tm portion) of the nucleic acid gets locally denatured ("breathes") from a first complementary strand (e.g., a forward or reverse strand) which it is hybridized to, and is thus made available to hybridize to another second strand. An exemplary first strand is a primer extension product from a first primer. An exemplary second strand is for example a second unextended primer (e.g., a PBS-complementary oligonucleotide comprising, e.g., a dT or dA sequence). Optionally, the first and second strands are immobilized on a support, and can be closely situated (e.g., in close enough proximity to allow walking) The conditions for breathing are optionally partially-denaturing conditions under which the PBS is generally denatured but another portion of nucleic acid remains in a hybridized or double-stranded state. Optionally, DNA helicase can be included in the reaction mix to facilitate the partial denaturing.

Optionally, the nucleic acid is then subjected to conditions which facilitate annealing, e.g., the temperature is decreased, to enable hybridization between the breathable PBS and the second strand. In an embodiment, the same conditions are used to facilitate both breathing and extension. In another embodiment, annealing conditions are different from breathing conditions—for example, the annealing conditions are nondenaturing conditions or conditions that favor denaturation less than the breathing conditions. In an example, annealing conditions involve a lower temperature (such as 37° C.) than breathing conditions, in which a higher temperature (e.g., 60-65° C.) is used. Optionally, fully denaturing conditions are avoided during one or more cycles of amplification (e.g., the majority of amplification cycles or substantially all amplification cycles).

Optionally, one or more of the PBS-breathing and primer extension steps are repeated multiple times to amplify an initial nucleic acid. Where one or more nucleic acid reagents (e.g., primers) are immobilized to a support, the primer-extension products remain substantially attached to the support, e.g., by virtue of attachment of an unextended extended primer to the support prior to amplification, or by hybridization to such a primer).

Optionally, a sample is prepared of a population of one or more nucleic acids to be amplified. The population of nucleic acids can be in single-stranded or double-stranded form; optionally one or more nucleic acids individually comprises a nucleic acid strand with a known 3' end sequence and a known 5' end sequence which are substantially identical or complementary to the one or more primers used in the amplification. A 3' portion of the nucleic acid strand can for example be complementary to an immobilized primer, whereas a 5' portion can be identical to a soluble primer. The 5' and/or 3' portions can be common ("universal") or invariant between individual nucleic acids within the population. Optionally, the nucleic acids within the population individually comprise variant (e.g., unknown) sequence between the common portions, such as genomic DNA, cDNAs, mRNAs, mate-pair fragments, exomes. etc. The collection can for example have enough members to ensure over 50%, 70%, or 90% coverage of the corresponding genetic source (e.g., the genome or the exome).

In some embodiments, the disclosure relates generally to compositions, as well as related systems, apparatuses, kits and methods, for nucleic acid amplification, comprising a reaction mixture for nucleic acid amplification.

In some embodiments, the disclosure relates generally to compositions, as well as related systems, apparatuses, kits and methods, for nucleic acid amplification, comprising a reaction mixture including a continuous liquid phase, the continuous liquid phase containing (i) a polymerase and (ii) a plurality of supports, at least one of the supports being attached to a substantially monoclonal population of nucleic acids.

In some embodiments, the disclosure relates generally to compositions, as well as related systems, apparatuses, kits and methods, for nucleic acid amplification, comprising a reaction mixture including a continuous liquid phase, the continuous liquid phase containing (i) a recombinase and (ii) a plurality of supports including a first support and a second support.

In some embodiments, the disclosure relates generally to compositions (as well as related systems, apparatuses, kits and methods) for nucleic acid amplification, comprising: a reaction mixture including a continuous liquid phase, the continuous liquid phase containing (i) a plurality of supports including a first support and a second support, (ii) a plurality of different polynucleotides including a first polynucleotide and a second polynucleotide and (iii) reagents for isothermal nucleic acid amplification. In some embodiments, the reagents for nucleic acid amplification include a polymerase and one or more types of nucleotide (e.g., a plurality of nucleotides). Optionally, the reagents for isothermal nucleic acid amplification include a recombinase.

Optionally, the first and second polynucleotides have different sequences.

Optionally, at least one end of at least one of the plurality of different polynucleotides is joined to at least one oligonucleotide adaptor.

Optionally, at least one end of at least some of the plurality of different polynucleotides includes a common sequence.

Optionally, at least two of the different polynucleotides in the reaction mixture include a common sequence.

Optionally, the first and second polynucleotides are different.

In some embodiments, the liquid phase includes one or more supports of the plurality include a primer.

In some embodiments, the disclosure relates generally to compositions, as well as related systems, apparatuses, kits and methods, for nucleic acid amplification, comprising a reaction mixture for nucleic acid amplification.

Optionally, the reaction mixture includes a continuous liquid phase.

Optionally, the reaction mixture can be used to conduct isothermal or thermocycling nucleic acid amplification.

Optionally, the continuous liquid phase includes any one or any combination of (i) one or more polymerases and/or (ii) at least one support.

Optionally, the continuous liquid phase includes a plurality of supports.

Optionally, the continuous liquid phase includes a first support.

Optionally, the continuous liquid phase includes a second support.

Optionally, at least one of the supports in the plurality can be attached to a substantially monoclonal population of nucleic acids.

Optionally, the first support can be attached to a first substantially monoclonal population of nucleic acids.

Optionally, the second support can be attached to a second substantially monoclonal population of nucleic acids.

Optionally, the first and the second substantially monoclonal population of nucleic acids comprise different sequences or essentially identical sequences.

Optionally, the first and second substantially monoclonal populations of nucleic acids do or do not hybridize with each other under stringent hybridization conditions.

Optionally, the first and second substantially monoclonal populations of nucleic acids are non-identical.

Optionally, the first and second substantially monoclonal populations of nucleic acids are non-complementary.

Optionally, the reaction mixture includes nucleotides that are not extrinsically labeled. For example, the nucleotides can be naturally occurring nucleotides, or synthetic analogs that do not include fluorescent moieties, dyes, or other extrinsic optically detectable labels.

Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, the reaction mixture is contained in a single reaction vessel.

Optionally, the reaction mixture comprises an isothermal or a thermocycling reaction mixture.

Optionally, the plurality of supports comprises beads, particles, microparticles, spheres, gels, filters or inner walls of a tube.

Optionally, at least one of the support in the plurality can be attached to a plurality of nucleic acids.

Optionally, at least one of the support in the plurality can be attached to one or more primers. The primers may be the same (or include a common sequence), or different.

Optionally, at least one of the supports can be attached to a plurality of a first primer.

Optionally, at least one of the supports is attached to a plurality of a first primer and to a plurality of a second primer.

Optionally, the plurality of the first primer comprises essentially identical sequences.

Optionally, the plurality of the first primer includes at least one first primer containing a sequence that is identical, or complementary, to at least a portion of a polynucleotide of the plurality of different polynucleotides.

Optionally, the plurality of the second primer includes at least one second primer containing a sequence that is identical, or complementary, to at least a portion of a polynucleotide of the plurality of different polynucleotides.

In some embodiments, at least one polynucleotide of the plurality of different polynucleotides includes a first sequence that is substantially identical or substantially complementary to a sequence within the first primer. In some embodiments, the at least one polynucleotide also includes a second sequence that is substantially identical or substantially complementary to a sequence within the second primer. In some embodiments, substantially all of the polynucleotides in the plurality of different polynucleotides including the first sequence and the second sequence.

Optionally, at least one of the supports in the plurality is attached to a plurality of 2-10 different primers.

Optionally, the plurality of the 2-10 different primers comprises different sequences.

Optionally, the plurality of the 2-10 different primers comprises at least one sequence that hybridizes with at least a portion of the different polynucleotides.

Optionally, the plurality of the 2-10 different primers comprise at least one sequence that hybridizes with at least a portion of a common sequence in the different polynucleotides.

Optionally, at least one of the supports is attached to at least one uniquely identifying barcode sequence.

Optionally, the first and second substantially monoclonal population of nucleic acids have sequences that are essentially the same or are different.

Optionally, the reaction mixture includes at least one recombinase.

Optionally, the recombinase can catalyze homologous recombination, strand invasion and/or D-loop formation.

Optionally, the recombinase is part of a nucleoprotein filament that includes the recombinase bound to a primer attached to a support in the reaction mixture. The primer bound by the recombinase can be attached to a support or in solution.

Optionally, the reaction mixture includes a nucleoprotein complex, or a plurality of nucleoprotein complexes.

Optionally, the reaction mixture includes a first nucleoprotein complex.

Optionally, the reaction mixture includes a second nucleoprotein complex.

Optionally, at least one nucleoprotein complex of the plurality includes at least one recombinase bound to a primer.

Optionally, the reaction mixture includes a first nucleoprotein complex which includes at least one recombinase bound to a first primer.

Optionally, the reaction mixture includes a second nucleoprotein complex which includes at least one recombinase bound to a second primer.

Optionally, the recombinase comprises a phage recombinase from T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2.

Optionally, the recombinase comprises a uvsX recombinase from T4 bacteriophage or a recA recombinase from *E. coli*.

Optionally, the reaction mixture further includes a polymerase.

Optionally, the polymerase lacks a 5' to 3' exonuclease activity.

Optionally, the polymerase includes a strand displacing activity.

Optionally, the polymerase comprises a thermostable or thermo-sensitive polymerase.

Optionally, the polymerase comprises a DNA polymerase or an RNA polymerase.

Optionally, the reaction mixture further includes at least one type of nucleotide.

Optionally, the reaction mixture includes nucleotides that are not extrinsically labeled. For example, the nucleotides can be naturally occurring nucleotides, or synthetic analogs that do not include fluorescent moieties, dyes, or other extrinsic optically detectable labels.

Optionally, the reaction mixture includes nucleotides that are naturally occurring nucleotides. Optionally, the nucleotides do not include groups that terminate nucleic acid synthesis (e.g., dideoxy groups, reversible terminators, and the like).

Optionally, at least one support of the plurality includes at least one primer.

Optionally, the first support is attached to a first substantially monoclonal nucleic acid population and the second support is attached to a second substantially monoclonal nucleic acid population.

Optionally, the first and second substantially monoclonal nucleic acid populations have different nucleic acid sequences.

Optionally, the first and second substantially monoclonal nucleic acid populations do not hybridize with each other under stringent hybridization conditions.

Optionally, the first and second nucleic acid substantially monoclonal nucleic acid populations are non-identical and non-complementary.

Optionally, the reaction mixture includes (i) at least two polynucleotide templates to be amplified and/or (ii) at least one nucleoprotein filament complex.

Optionally, the reaction mixture includes at least one polynucleotide, primer, template, or amplification product that is attached to a drag compound. The term "drag compound" and its variants, as used herein, describe any chemical compositions that can be attached to nucleic acids and retard their diffusion through a reaction mixture, but still permit nucleic acid synthesis to proceed using such polynucleotide, primer, template or amplification product in a nucleic acid synthesis reaction. Attachment of such drag compounds to nucleic acids within a synthesis reaction typically reduces the mobility of such nucleic acids in the reaction mixture and can be useful in preventing cross-contamination of amplification products or templates between different synthetic reactions occurring with the same reaction mixture. In some embodiments, the attachment of drag components to one or more nucleic acid components can increase the number or proportion of monoclonal products.

In some embodiments, the present teachings provide methods for nucleic acid amplification comprising at least one mobility-altered nucleic acid (e.g., a primer). In some embodiments, a mobility-altered nucleic acid exhibits increased or decreased mobility through an aqueous medium. In some embodiments, a modified nucleic acid comprises a nucleic acid (e.g., a primer) attached at any location along the nucleic acid length to one or more compounds (e.g., drag compound) that alter the mobility of a nucleic acid through an aqueous medium. In some embodiments, a drag compound that alters the mobility of a nucleic acid can be attached to any primer in a nucleic acid amplification reaction, including a first, second, third, fourth, or any other primer. For example, one or more drag compounds can be attached to a nucleic acid at any one or any combination of the 5' end, the 3' end, and/or an internal location. In some embodiments, a modified nucleic acid can be attached covalently or non-covalently to a drag compound that changes the mobility of the nucleic acid through an aqueous medium. For example, a drag compound can provide hydro hydrodynamic drag when attached to a nucleic acid by altering the overall size, length, radius, shape or electrical charge of the modified nucleic acid compared to the nucleic acid lacking the attached compound. In some embodiments, a drag compound attached to a nucleic acid can alter interaction between the nucleic acid and an aqueous medium compared to the interaction between the aqueous medium and a nucleic acid lacking the attached compound. In some embodiments, the drag compound can be synthetic, recombinant or naturally-occurring. In some embodiments, the drag compound can be charged, uncharged, polar or hydrophobic. In some embodiments, the drag compound can be linear, branched or have a dendrimeric structure. In some embodiments, the drag compound can comprise a single moiety or polymers of nucleosides, saccharides, lipids, or amino acids.

Optionally, a drag compound comprises a saccharide moiety, a polysaccharide, a protein, a glycoprotein or polypeptide. Optionally, a drag compound comprises BSA, lysozyme, beta-actin, myosin, lactalbumin, ovalbumin, beta-galactosidase, lactate dehydrogenase or immunoglobulin (e.g., IgG).

Optionally, a drag compound that alters the mobility of the nucleic acid through an aqueous medium comprises one or more polyethylene oxide (PEO) or polypropylene oxide (PPO) moieties, including polymers of polyethylene oxide (PEO) or polypropylene oxide (PPO). Non-limiting examples of such polymers include triblock copolymers (e.g., PEO-PPO-PEO), Pluronics™-type polymers, and hydrophobically-modified PEO polymers. Optionally, the drag compound comprises one or more amino acid moieties, polypeptides and polypeptoids. Optionally, the drag compound comprises a saccharide moiety, polysaccharides, hydrophobically-modified polysaccharides, cellulose derivatives, sodium carboxymethylcellulose, hydroxymethylcellulose, hydroxyethylcellulose, hydroxypropylcellulose, or hydroxypropylmethyl cellulose. Optionally, the drag compound comprises a hydrophobically-modified alkali-soluble associative (HASE) polymers, hydrophobically modified polyacrylamides, thermally responsive polymers, or N-isopropylacrylamide (NTPAAm), Optionally, the drag compound comprises a poly(ethylene glycol))methylether acrylate (PEGMEA), tetraethylene glycol diacrylate (TEGDA), poly(ethylene glycol)dimethacrylate (EGDMA), or N,N'-methylene-bis-acrylamide, (NMBA).

Optionally, a drag compound comprises a protein or polypeptide, including BSA, lysozyme, beta-actin, myosin, lactalbumin, ovalbumin, beta-galactosidase, or lactate dehydrogenase. In some embodiments, a drag compound can be attached to a nucleic acid by an amine or thiol linkage.

In some embodiments, a mobility-altered nucleic acid comprises a nucleic acid attached to a binding partner, such as an affinity moiety for interaction with a receptor moiety. In some embodiments, a receptor moiety can serve as a drag compound. In some embodiments, an affinity moiety can be attached to a nucleic acid, and the affinity moiety (which serves as the drag compound) interacts with a receptor moiety. For example, a nucleic acid can be attached to a biotin moiety which can bind an avidin-like moiety. An avidin-like moiety can serve as a drag compound. An avidin-like moiety includes avidin and any derivatives, analogs and other non-native forms of avidin that can bind to biotin moieties. Other examples of binding partners include epitopes (e.g., protein A) and their respective antibodies (e.g., anti-FLAG antibodies), and fluorescein and anti-fluorescein antibodies. One skilled in the art will readily recognize other binding partner combinations for attaching a drag compound to a nucleic acid.

Optionally, the drag compound can be attached to the primer by attaching the drag compound and the primer to each of two members of a pair of binding partner.

Optionally, at least one primer in the reaction mixture includes biotin.

Optionally, the drag compound includes avidin or streptavidin.

Optionally, the drag compound comprises a saccharide moiety, a polysaccharide, a protein, a glycoprotein or polypeptide.

Optionally, the drag compound comprises BSA, lysozyme, beta-actin, myosin, lactalbumin, ovalbumin, beta-galactosidase, lactate dehydrogenase or immunoglobulin (e.g., IgG).

Optionally, the reaction mixture further includes an accessory protein.

Optionally, the accessory protein comprises a helicase, a single-stranded binding protein, or a recombinase loading factor.

Optionally, the helicase comprises a uvsW from T4 phage.

Optionally, the single stranded binding protein comprises Sso SSB from *Sulfolobus solfataricus*, MjA SSB from *Methanococcus jannaschii*, or *E. coli* SSB protein.

Optionally, the single stranded binding protein comprises gp32 protein from T4 phage or a modified gp32 protein from T4 phage.

Optionally, the recombinase loading protein comprises uvsY from T4 phage.

Optionally, the reaction mixture further includes ATP.

Optionally, the reaction mixture further includes an ATP regeneration system.

Optionally, the ATP regeneration system includes phosphocreatine.

Optionally, the ATP regeneration system includes creatine kinase.

Optionally, the reaction mixture further includes an additive compound for enhancing the efficiency of, or yield of, a nucleic acid amplification reaction.

Optionally, the additive compound comprises betaine, DMSO, proline, trehalose, MMNO (4-methylmorpholine N-oxide) or a PEG-like compound.

Optionally, at least one polynucleotide template in the reaction mixture includes both a first sequence that is complementary or identical to at least some portion of the first primer, and a second sequence that is complementary or identical to at least some portion of the second primer. Optionally, the reaction mixture includes a plurality of double stranded polynucleotides containing both a first sequence that is complementary or identical to at least some portion of the first primer, and a second sequence that is complementary or identical to at least some portion of the second primer. Optionally, the first sequence is located at or near an end of at least one double stranded polynucleotide of the plurality, and the second sequence is located at or near another end of at least one double stranded polynucleotide of the plurality.

Optionally, the reaction mixture further includes a diffusion-limiting agent.

Optionally, the diffusion-limiting agent reduces the rate of diffusion of the polynucleotide away from the support.

Optionally, the diffusion-limiting agent reduces the level of polyclonal nucleic acid populations attached to the support.

Optionally, the diffusion-limiting agent comprises a polymer compound.

Optionally, the diffusion-limiting agent comprises a saccharide polymer.

Optionally, the diffusion-limiting agent comprises a cellulose-based compound.

Optionally, the diffusion-limiting agent comprises a glucose or galactose polymer.

Optionally, the saccharide polymer comprises cellulose, dextran, starch, glycogen, agar or agarose.

Optionally, the diffusion-limiting agent comprises a block copolymer compound.

Optionally, the diffusion-limiting agent comprises a central chain of poly(propylethylene oxide) flanked by two hydrophilic chains of poly(ethylene oxide).

Optionally, the diffusion-limiting agent forms a micelle.

Optionally, the diffusion-limiting agent forms a micellar liquid crystal.

Optionally, the diffusion-limiting agent comprises a Pluronics™ compound.

Optionally, the reaction mixture further includes a diffusion-reducing agent at a concentration of about 0.025-0.8% w/v, or about 0.05-0.7% w/v, or about 0.075-0.6% w/v, or about 0.1-0.5% w/v, or about 0.2-0.4% w/v.

Optionally, the compositions, as well as related systems, apparatuses, kits and methods, for nucleic acid amplification further include a surface, matrix or medium including a plurality of sites, at least one of the sites being operatively coupled to one or more sensors.

Optionally, the plurality of sites comprise reaction chambers, supports, particles, microparticles, spheres, beads, filters, flowcells, wells, grooves, channel reservoirs, gels or inner wall of a tube.

Optionally, the plurality of sites can be arranged in a random or organized array.

Optionally, the plurality of sites can be in fluid communication with each other.

Optionally, at least one of the plurality of sites includes a three-dimensional chemical matrix.

Optionally, at least one of the plurality of sites can be covalently attached to a three-dimensional chemical matrix.

Optionally, at least one of the plurality of sites includes an acrylamide layer. Optionally, at least one of the plurality of sites includes a nucleic acid that is covalently attached to an acrylamide layer.

In some embodiments, the site comprises a hydrophilic polymer matrix conformally disposed within a well operatively coupled to the sensor.

Optionally, the hydrophilic polymer matrix includes a hydrogel polymer matrix.

Optionally, the hydrophilic polymer matrix is a cured-in-place polymer matrix.

Optionally, the hydrophilic polymer matrix includes polyacrylamide, copolymers thereof, derivatives thereof, or combinations thereof.

Optionally, the polyacrylamide is conjugated with an oligonucleotide primer.

Optionally, the well has a characteristic diameter in a range of 0.1 micrometers to 2 micrometers.

Optionally, the well has a depth in a range of 0.01 micrometers to 10 micrometers.

In some embodiments, the sensor includes a field effect transistor (FET). The FET can include an ion sensitive FET (ISFET), chemical-sensitive field-effect transistor (chemFET), or biologically active field-effect transistor (bioFET).

Optionally, the one or more sensors are configured to detect a byproduct of a nucleotide incorporation.

Optionally, the one or more sensors can be configured to detect the presence of a chemical moiety at one or more of the plurality of sites.

Optionally, the one or more sensors comprise field-effect transistors (FET), ion-sensitive field-effect transistors (ISFET), chemical-sensitive field-effect transistors (chemFET), or biologically active field-effect transistors (bioFET).

In some embodiments, the FET includes a floating gate structure comprising a plurality of conductors electrically coupled to one another and separated by dielectric layers, and the floating gate conductor is an uppermost conductor in the plurality of conductors.

In some embodiments, the floating gate conductor includes an upper surface defining a bottom surface of the site.

In some embodiments, the floating gate conductor comprises an electrically conductive material, and the upper surface of the floating gate conductor includes an oxide of the electrically conductive material.

In some embodiments, the floating gate conductor is coupled to the at least one reaction chamber via a sensing material.

In some embodiments, the sensing material comprises a metal-oxide.

In some embodiments, the sensing material is sensitive to hydrogen ions.

Optionally, the byproduct from a nucleotide incorporation reaction comprises pyrophosphate, hydrogen ions, or protons.

Also provided herein are compositions comprising any one or any subset or all of the following: at least one reverse nucleic acid strand, a plurality of forward primers immobilized on at least one support, a plurality of reverse primers in solution, and a polymerase. The forward and/or reverse primers are optionally low-melt or rich is adenine, thymine or uracil as described herein. An exemplary composition comprises a solid support comprising a plurality of spatially-separated clonal populations each comprising a low-melt primer-binding sequence at the 3' end and a low-melt primer sequence on the 5' end. Optionally, the composition further comprises a recombinase. Alternatively, the composition is optionally free of another enzyme that is not a polymerase, e.g., a recombinase or reverse transcriptase or helicase or nicking enzyme. Another exemplary composition comprises any one or more of: (1) a reverse nucleic acid strand, (2) a plurality of low-melt forward primers immobilized on a support, (3) a plurality of low-melt reverse primers in solution, and (4) a polymerase. Optionally, the forward primers are hybridizable (e.g., complementary) to a 3' portion or end of the reverse strand. Optionally, the reverse primers are substantially identical to a 5' portion or end of the reverse strand. The composition can contain any one or more reagents described herein, and/or be subjected to any one or more procedures or conditions described herein.

In some embodiments, the disclosure relates generally to compositions comprising amplified nucleic acids produced by any of the methods of the disclosure. In some embodiments, a localized clonal population of clonal amplicons is formed around a discrete site on the support. An exemplary discrete site is a point of attachment of an initial nucleic acid strand to the support, and from which other nucleic acids within the clonal population are directly or indirectly generated by primer extension, using the initial nucleic acid or its copies as a template.

Optionally the composition comprises a collection of nucleic acids producible by any one or more methods described herein. For example, the collection can comprise immobilized nucleic acids which occupy one or more distinct areas on a surface. In some embodiments, each area comprises a plurality of identical nucleic acid strands and optionally, a plurality of identical complementary strands hybridized thereto, where the complementary strands have no attachment or linkage or association with the solid support except by virtue of hybridization to the immobilized nucleic acid. Optionally, an individual nucleic acid strand within such an area is located so that another nucleic acid strand is located on the surface within a distance of the length of that strand. Optionally there is at least one distinct area present per $mm^2$ of surface on which the nucleic acids are immobilized. For example the number of distinct areas/$mm^2$ of surface on which the nucleic acids are immobilized is greater than $10^2$, greater than $10^3$, greater than $10^4$, greater than $10^5$, greater than $10^6$, greater than $10^7$, or greater than $10^8$.

The collections of amplified clonal populations can form arrays, which can be one-dimensional (e.g., a queue of generally monoclonal microbeads) or two-dimensional (e.g., the amplified clonal populations are situated on a planar support), or three-dimensional. The individual clonal populations of an array are optionally but not necessarily situated or arranged such that they are addressed or addressable. Optionally, different clonal populations are spaced at an appropriate distance from one another, which distance is generally sufficient to permit different clonal populations to be distinguished from each other. In an embodiment, localized clonal populations are scattered in an ordered or disordered, e.g., random, pattern over a planar substrate.

The features of an exemplary array are individual distinguishable clonal populations of nucleic acids, where optionally the features are distributed over one or more supports. In an exemplary microbead embodiment, an array comprises a plurality of microbeads, where an individual microbead generally comprises a monoclonal population of nucleic acids, and different microbeads generally comprise different clonal populations (e.g., which differ in sequence). Optionally, the microbeads are distributed or packed in a monolayer over a planar substrate. In other embodiments, the array comprises a single (e.g., planar) support, the single support comprising a plurality of spatially discrete clonal populations of nucleic acids, where different clonal populations optionally differ in sequence.

Optionally, one or more nucleic acids within individual clonal populations can be attached to the planar substrate directly. In another example, the nucleic acids of individual clonal populations are attached to microbeads, for example as discussed herein. The clonal microbeads are optionally packed closely together over a planar substrate, in random or ordered fashion. Optionally, more than 20%, 30%, 50%, 70%, 80%, 90%, 95% or 99% of the microbeads are in contact with at least one, two, four or six other microbeads. Optionally, less than 10%, 20%, 30%, 50%, 70%, 80%, 90%, 95% or 99% of the microbeads are in contact with one, two, four or six other microbeads.

In some embodiments, the disclosure relates generally to methods, as well as related compositions, systems, kits and apparatuses, for nucleic acid amplification, comprising conducting a multiplex nucleic acid amplification using any of the amplification methods, compositions or systems disclosed herein.

In some embodiments, the methods include performing multiplex amplification using a recombinase (e.g., a recombinase-mediated multiplex nucleic acid amplification reaction).

In some embodiments, the methods can further include re-amplifying the amplicons from the multiplex nucleic acid amplification using a nucleic acid amplification reaction, Optionally, a multiplex nucleic acid amplification can be conducted in a single reaction mixture.

Optionally, a multiplex nucleic acid amplification can be conducted on a sample containing a plurality of different nucleic acid target sequences.

Optionally, a plurality of different nucleic acid target sequences can be amplified in a single reaction mixture.

Optionally, at least dozens, or at least hundreds, or at least thousands (or more) of nucleic acid target sequences can be amplified in the single reaction mixture.

Optionally, at least fifty, or at least one hundred nucleic acid target sequences can be amplified in the single reaction mixture.

Optionally, the multiplex amplifying can include contacting at least a portion of the sample with any one or any combination of a recombinase, a polymerase and/or at least one primer.

Optionally, the multiplex amplifying can be conducted under isothermal or thermocycling conditions.

In some embodiments, the disclosure relates generally to methods, as well as related compositions, systems, kits and apparatuses, for nucleic acid amplification, comprising multiplex nucleic acid amplification, which includes amplifying within a single reaction mixture at least fifty different nucleic acid target sequences (or more) from a sample containing a plurality of different nucleic acid target sequences, the amplifying including contacting at least a portion of the sample with a recombinase and a plurality of primers under isothermal amplification conditions.

In some embodiments, the disclosure relates generally to methods, as well as related compositions, systems, kits and apparatuses, for nucleic acid amplification, comprising multiplex nucleic acid amplification, which includes amplifying within a single reaction mixture different nucleic acid target sequences from a sample containing a plurality of different nucleic acid target sequences, the amplifying including generating a plurality of at least fifty different amplified target sequences (or more) by contacting at least a portion of the sample with a polymerase and a plurality of primers under isothermal amplification conditions.

In some embodiments, the disclosure relates generally to methods, as well as related compositions, systems, kits and apparatuses, for nucleic acid amplification, comprising generating substantially monoclonal nucleic acid populations by re-amplifying the amplicons from the multiplex nucleic acid amplification using a nucleic acid amplification reaction (e.g., a recombinase).

Optionally, methods for multiplex nucleic acid amplification can further include a recombinase-mediated nucleic acid amplification method which includes re-amplifying at least some of the at least fifty different amplified target sequences by: (a) forming a reaction mixture including a single continuous liquid phase containing (i) a plurality of supports, (ii) at least one of the fifty different amplified target sequences and (iii) a recombinase; and (b) subjecting the reaction mixture to amplification conditions, thereby generating a plurality of supports attached to substantially monoclonal nucleic acid populations attached thereto.

Optionally, in methods for multiplex nucleic acid amplification, the different nucleic acid target sequences from the sample can be amplified under conditions that are substantially non-exhaustive.

Optionally, in methods for multiplex nucleic acid amplification, the different nucleic acid target sequences from the sample can be amplified under conditions that are substantially exhaustive.

Optionally, in methods for multiplex nucleic acid amplification, the single reaction mixture comprises an isothermal or a thermocycling reaction mixture.

In some embodiments, two or more of the template or targets can be amplified within separate chambers, wells, cavities or sites of an array that are in fluid communication with each other, or that are occupied by the same single continuous liquid phase of an amplification reaction mixture. Such embodiments include embodiments for array-based nucleic acid amplification.

For example, in some embodiments the disclosure relates to methods for nucleic acid amplification, comprising: distributing a target polynucleotide into a reaction chamber or site in an array of reaction chambers or sites, and amplifying the single target polynucleotide within the reaction chamber or site. Optionally, two or more target polynucleotides are distributed into two or more reaction chambers or sites of the array, and two or more of the distributed target polynucleotides are amplified in parallel within their respective reaction chambers or sites. Optionally, at least two of the reaction chambers or sites each receive a single target polynucleotide during the distributing (one or more of the reaction chambers or sites can optionally receive zero or more than one target polynucleotide during the distributing). At least two target polynucleotides can be clonally amplified within their respective reaction chambers. At least one of the reaction chambers including a target polynucleotide can be in fluid communication with at least one other reaction chamber including a target polynucleotide during the amplifying.

In some embodiments, the disclosure relates generally to methods (as well as related compositions, systems, apparatuses and kits) for nucleic acid amplification, comprising: (a) distributing at least two different polynucleotides into an array of reaction chambers by introducing a single one of said polynucleotides into at least two of said reaction chambers that are in fluid communication with each other; and (b) forming at least two substantially monoclonal nucleic acid populations by amplifying the polynucleotides within said at least two reaction chambers. Typically, the at least two reaction chambers remain in fluid communication with each other during the amplifying.

In some embodiments, the disclosure relates generally to methods (as well as related compositions, systems, apparatuses and kits) for nucleic acid amplification, comprising (a) in an array of reaction chambers including a first and a second reaction chamber, distributing a first template polynucleotide into the first reaction chamber and a second template polynucleotide into the second reaction chamber, and (b) forming at least two substantially monoclonal nucleic acid population by clonally amplifying the first and second template polynucleotides within their respective reactions chamber, where the single polynucleotide is distributed from a nucleic acid sample having multiple different polynucleotides. Optionally, the first and second reaction chambers include different portions of a single continuous liquid phase during the amplifying. For example, the first and second reaction chambers of the array can be in fluid communication during the amplifying.

In some embodiments, the disclosure relates generally to methods for nucleic acid amplification, comprising (a) distributing a different single polynucleotide into each of a plurality of reaction chambers, and (b) forming a monoclonal nucleic acid population in each of the reaction chambers by amplifying the different single polynucleotides within the plurality of reaction chambers, where the single different polynucleotides are distributed from a nucleic acid sample having multiple different polynucleotides.

In some embodiments, the disclosure relates generally to methods for nucleic acid amplification, comprising (a) distributing at least two different polynucleotides into an array of reaction chambers by introducing a single one of said polynucleotides into at least two of said reaction chambers that are in fluid communication with each other; and (b) forming at least two substantially monoclonal nucleic acid populations by amplifying the polynucleotides within said at least two reaction chambers.

In some embodiments, the methods can further include introducing one or more supports (e.g., beads or particles and the like) into at least one reaction chamber or site of the array. The one or more supports can be introduced into the at least one reaction chamber or site prior to, during or after the polynucleotides are distributed into the array. In some embodiments, at least one reaction chamber or site of the array receives a single support. In some embodiments, the majority of reaction chambers or sites receive a single support. In some embodiments, the supports can be mixed with the polynucleotides prior to the distributing, and distributed into the array together with the polynucleotides. At least one support can optionally be linked to a nucleic acid molecule comprising a primer sequence that is substantially complementary or substantially identical to a portion of a polynucleotide present in the reaction chamber or site during the amplifying. In some embodiments, the at least one support includes a nucleic acid molecule comprising a primer sequence that is substantially complementary or substantially identical to a portion of a target polynucleotide or template in the reaction chamber or well. In some embodiments, the at least one support includes a nucleic acid molecule comprising a primer sequence that is substantially complementary or substantially identical to at least a portion of another primer present in the reaction chamber or site during the amplifying.

In some embodiments, the amplifying can include introducing a reaction mixture into at least one reaction chamber or site in the array. The reaction mixture is optionally introduced into the reaction chamber or site prior to, during or after the distributing of the polynucleotides into the array, or the introducing of the supports into the array. The reaction mixture, supports and polynucleotides can be introduced or distributed into the array in any order or any combination. In some embodiments, at least one reaction chamber or site of the array receives a single support, a single polynucleotide and sufficient reaction mixture to support amplification of the polynucleotide within the reaction chamber or site.

In some embodiments, the method can include hybridizing at least a portion of the polynucleotide to the support by contacting the support with the polynucleotide under hybridization conditions. The hybridizing can occur before, during or after introduction of the supports and/or polynucleotides into the reaction chambers or sites of the array. In some embodiments, at least one support linked to a first priming sequence is introduced into at least one reaction chamber or site of the array, and then a polynucleotide is introduced into the reaction chamber or site, and the polynucleotide is hybridized to the support within the reaction chamber or site. Alternatively, the support can hybridize to an amplification product generated via amplification of the polynucleotide within the reaction chamber or site.

The reaction mixture can include any of the reaction mixtures and components described herein. In some embodiments, the reaction mixture includes any one or more of the following components: Isothermal amplification reagents (e.g., one or more recombinases, helicases and related accessory factors, polymerases and the like), sieving agents, nucleotides, and the like.

In some embodiments, the disclosure relates generally to methods (and related compositions, kits, systems and apparatuses) for nucleic acid amplification, comprising: (a) introducing, in any order or combination, a first polynucleotide template and a first support into a first reaction chamber or site of an array of reaction chambers or sites, and a second polynucleotide template and a second support into a second reaction chamber or site of the array; and (b) clonally amplifying the first polynucleotide template onto the first support within the first reaction chamber or site, and the second polynucleotide template onto the second support within the second reaction chamber or site, while the first reaction chamber or site is in fluid communication with the second reaction chamber or site during the amplifying. The clonally amplifying can include generating a first support attached to a first amplicon derived from the first polynucleotide template, and a second support attached to a second amplicon derived from the second polynucleotide template. Optionally, both the first and second sites (or reaction chambers) include the same continuous liquid phase of the same reaction mixture during the amplifying. For example, the reaction mixture can include a single continuous liquid phase that includes both the first and second polynucleotide templates and the first and second supports. The reaction mixture can be introduced into the reaction chambers or sites of the array before, during or after introduction of the polynucleotide template and/or the support. In some embodiments, the disclosed method further includes introducing the reaction mixture into the first and second reaction chambers or sites after introducing the first and second polynucleotides templates and the first and second supports. In some embodiments, the reaction mixture includes a recombinase or a helicase or both a recombinase and helicase. The recombinase can be derived from a myoviral (e.g., uvsX), bacterial, yeast or human recombinase, or analog thereof from another species. In some embodiments, the reaction mixture includes a polymerase. In some embodiments, the reaction mixture includes a sieving agent, for example polyacrylamide, agarose or a cellulose polymer (e.g., HEC, CMC or MC, or derivatives thereof). In some embodiments, the reaction mixture includes a diffusion-limiting agent.

In some embodiments, the amplifying includes linking a polynucleotide template to a support or surface (e.g., a particle or bead) having a first primer containing a first primer sequence, by hybridizing the first primer binding sequence of said polynucleotide template to a first primer sequence in the first primer of the support.

In some embodiments, methods for nucleic acid amplification can be conducted in a single continuous liquid phase that does not provide compartmentalization of the multiple nucleic acid amplification reactions occurring in a single reaction vessel. In some embodiments, methods for nucleic acid amplification can be conducted in water-in-oil emulsions that provide compartmentalization (micro-reactors).

In embodiments where the amplifying is performed within the reaction chambers or sites of an array, as well as embodiments where the amplifying is performed within a single reaction vessel, the surface or support optionally includes at least a first primer including a first primer sequence. In some embodiments, one or more of the polynucleotide templates include a first primer binding sequence. The first primer binding sequence can be identical, or substantially identical, to the first primer sequence. Alternatively, the first primer binding sequence can be complementary, or substantially complementary, to the first primer sequence. In some embodiments, the first primer sequence and the first primer binding sequence do not exhibit significant identity or complementarity, but instead are substantially identical to, or substantially complementary to, another nucleotide sequence present in the reaction mixture. In such embodiments, amplification can include formation of an amplification reaction intermediate that includes nucleotide sequences having significant identity, or complementarity to, the first primer sequence, the first primer binding sequence, or both.

In some embodiments, at least two different polynucleotide templates are present in the reaction mixture, and the amplification results in the formation of at least two different substantially monoclonal populations, each derived from amplification of a single one of said polynucleotide templates. In some embodiments, two or more of the at least two substantially monoclonal populations are attached to the same support or surface. Each of the two or more substantially monoclonal populations can be attached to a different unique location on the same support or surface. Alternatively, each of the two or more substantially monoclonal populations can each be attached to a different support or surface. Segregation of different monoclonal populations to different supports or surfaces can be advantageous in applications requiring segregation of the populations prior to analysis. In some embodiments, the support or surface is part of a bead or particle, which can be spheroid or spherical in shape. In some embodiments, the support or surface forms part of a two-dimensional or three-dimensional array.

In some embodiments, the disclosed methods for nucleic acid amplification can be performed while including a sieving agent or a diffusion-reducing agent within the reaction mixture. These agents can increase the total number and/or proportion (e.g., percentage) of monoclonal populations formed during the amplification. In some embodiments, the methods include use of reaction mixtures providing for increased yields of monoclonal or substantially monoclonal amplicons relative to conventional reaction mixtures.

In some embodiments, the methods include amplifying by partially denaturing the templates. For example, the amplifying can include template walking. For example, the templates to be amplified can include an adapter sequence containing a primer binding site that has a relatively low Tm compared to the template as a whole. In some embodiments, amplification is performed at temperatures that are substantially higher than the Tm of adapter sequence but are substantially lower than the Tm of the template, as described in more detail herein. In some embodiments, amplification is performed at temperatures that are at least 5° C., 10° C., 15° C., 20° C., 25° C. or 50° C. below the Tm of the nucleic acid template. In some embodiments, amplification is performed at temperatures greater (for example, at least 5° C., 10° C., 15° C., 20° C., 25° C. or 50° C. greater) than the Tm of the first primer, the second primer, or both the first and second primer.

In some embodiments, the reaction mixtures can optionally include any one or more of the following: (a) one or more supports, optionally including at least a first primer sequence; (2) a recombinase; (3) a polymerase; (4) a diffusion limiting agent; (5) a sieving agent; (6) a crowding agent; (7) an ATP regeneration system; (8) a single stranded binding protein (SSBP); and (8) a recombinase accessory factor, for example a recombinase loading protein. In some embodiments, the yield of monoclonal, or substantially monoclonal, populations is increased by amplifying the polynucleotide templates onto a surface (for example, by attaching one of the amplification primers to the surface) in the presence of a diffusion-limiting and/or a sieving agent. The diffusion limiting agent, or the sieving agent, can provide for increased yields of monoclonal populations by reducing diffusion or migration of amplified product polynucleotides away from the surface during the amplification.

In some embodiments, the reaction mixture includes one or more isothermal amplification reagents. Such reagents can include, for example, recombinases or helicases.

In some embodiments, methods for nucleic acid amplification can be conducted with an enzyme that catalyzes homologous recombination, for example an enzyme that can bind a first primer to form a complex or can catalyze strand invasion or can form a D-loop structure. In some embodiments, an enzyme that catalyzes homologous recombination comprises a recombinase.

In some embodiments, amplification conditions include isothermal conditions or thermocycling conditions.

In some embodiments, methods for nucleic acid amplification comprise: (a) forming a reaction mixture including a single continuous liquid phase containing (i) an enzyme that catalyzes homologous recombination, (ii) one or a plurality of surfaces, and (iii) a plurality of different polynucleotides; and (b) subjecting the reaction mixture to a condition suitable for nucleic acid amplification.

In some embodiments, methods for nucleic acid amplification comprise: (a) forming a reaction mixture including a single continuous liquid phase containing (i) an enzyme that catalyzes homologous recombination, (ii) one or a plurality of beads each attached to a plurality of a first primers, and (iii) a plurality of different polynucleotides; (b) forming two or more substantially monoclonal amplified nucleic acid populations by subjecting the reaction mixture to amplification conditions. The amplification conditions can include isothermal or thermocyling conditions. In some embodiments, the first primers can hybridize to at least a portion of the polynucleotides.

In some embodiments, the disclosure relates generally to a method for nucleic acid amplification, comprising: (a) forming a reaction mixture including a single continuous liquid phase containing one or more supports (or surfaces), a plurality of polynucleotides and a recombinase; (b) clonally amplifying at least two of said plurality of different polynucleotides onto at least one support (or surface) by subjecting the reaction mixture to amplification conditions. In some embodiments, the amplification conditions can include isothermal or thermocyclic amplification conditions. The reaction mixture can optionally include a recombinase. In some embodiments, the reaction mixture includes a polymerase. In some embodiments, the reaction mixture includes a primer, which can be in solution. Optionally, at least one of the supports or surfaces can include a primer.

In some embodiments, the disclosure relates generally to a method for nucleic acid amplification comprising: (a) forming a reaction mixture including a single continuous liquid phase containing (i) a recombinase, (ii) a plurality of beads attached or one or more first primers including a first primer sequence, and (iii) a plurality of different polynucleotide templates; (b) hybridizing at least one of said first primers to at least one of the plurality of different polynucleotide templates; (c) subjecting the reaction mixture to a nucleic acid amplification conditions and generating at least one substantially monoclonal polynucleotide population by amplifying at least one of the polynucleotide templates to form at least a first amplified population. In some embodiments, at least 30%, 90% of the polynucleotides in the at least one substantially monoclonal population are substantially identical (or substantially complementary) to at least one of the polynucleotide templates originally present in the reaction mixture. In some embodiments, at least a portion of the first amplified population is attached to one bead of the plurality of beads.

In some embodiments, forming a reaction mixture in step (a) comprises: forming a nucleoprotein complex by contacting the recombinase with at least one of the plurality of the first primers which are attached to the plurality of beads.

In some embodiments, the subjecting the reaction mixture to a nucleic acid amplification conditions in step (b) comprises conducting a nucleotide polymerization reaction. For example, a nucleotide polymerization reaction can include incorporating a nucleotide into a first primer sequence, optionally when the first primer sequence is hybridized to one of the polynucleotide templates in the reaction mixture.

In some embodiments, subjecting the reaction mixture to a nucleic acid amplification conditions includes contacting the first primer with a polynucleotide template, a recombinase, a polymerase and nucleotides, in any order or in any combinations.

In some embodiments, the nucleic acid amplification conditions include repeating cycles of: forming a nucleoprotein complex including a recombinase, at least a portion of the a first primer, and at least a portion of a first polynucleotide template, and contacting the nucleoprotein complex with a polymerase that catalyzes the incorporation of one or more nucleotides into the first primer.

In some embodiments, recurring nucleic acid amplification reactions can be conducted to generate a plurality of beads each attached with a substantially monoclonal population of polynucleotides.

In some embodiments, methods for nucleic acid amplification can be conducted under isothermal conditions or thermocycling conditions.

In some embodiments, the plurality of different polynucleotides can be single- or double-stranded polynucleotides. In some embodiments, heat or chemical denaturation of double-stranded polynucleotides is not necessary because the recombinase can generate localized strand denaturation by catalyzing strand invasion.

In some embodiments, methods for nucleic acid amplification can be conducted in a single reaction vessel. In some embodiments, a nucleic acid amplification reaction can be conducted in a single reaction vessel comprising a single continuous liquid phase. For example, the single continuous liquid phase can include an amplification mixture comprising a plurality of beads each attached with a plurality of a first primer, a plurality of different polynucleotides, and a plurality of recombinases. In some embodiments, an amplification mixture can further include a polymerase and a plurality of nucleotides. In some embodiments, an amplification mixture can further include ATP, nucleotides and co-factors. Non-limiting examples of a single reaction vessel include a tube, well or similar structures.

In some embodiments, polynucleotides and reagents can be deposited into a reaction vessel in any order, including sequentially or substantially simultaneously or a combination of both. In some embodiments, reagents include a beads attached with multiple first primers, recombinases, polymerases, nucleotides, ATP, divalent cations, and co-factors.

In some embodiments, methods for nucleic acid amplification can be conducted in a single continuous liquid phase. The single continuous liquid phase can include any liquid phase wherein any given portion or region of the single liquid continuous phase is in fluid communication with any other portion or region of the same single liquid continuous phase. Typically, components that are dissolved or suspended in the single continuous liquid phase can freely diffuse or migrate to any other point in the liquid phase. In some embodiments, however, the single continuous liquid phase can include diffusion limiting agents that slow down the rate of diffusion within the single continuous liquid phase. One exemplary embodiment of a single continuous liquid phase is a single aqueous droplet in a water-in-oil emulsion; in such an emulsion, each droplet will form a separate phase; two droplets may coalesce to form a single phase.

In some embodiments, a single continuous liquid phase consists essentially of a single aqueous phase. In some embodiments, the single continuous liquid phase lacks a non-aqueous phase; for example, the continuous liquid phase does not include oil or organic solvents. In some embodiments, multiple nucleic acid amplification reactions occur in an aqueous phase in a single reaction vessel. In some embodiments, a single continuous liquid phase does not compartmentalize the multiple nucleic acid amplification reactions occurring in a single reaction vessel.

In some embodiments, methods for nucleic acid amplification can be conducted in water-in-oil emulsions that provide compartmentalization.

When conducting a nucleic acid amplification using a plurality of polynucleotide templates, clonal amplification using traditional amplification methods typically relies on techniques such as compartmentalization of the reaction mixture into segregated portions or components that are not in fluid communication with each other in order to maintain clonality and prevent cross-contamination of different amplified populations and to maintain adequate yields of monoclonal amplified product. Using such conventional amplification methods, it is typically not feasible to clonally amplify polynucleotide templates within the same reaction mixture without resorting to compartmentalization or distribution of the reaction mixture into separate compartments or vessels, because any polynucleotides within the reaction mixture (including templates and/or amplified products) will tend to migrate randomly through the mixture due to diffusion and/or Brownian motion during such amplification. Such diffusion or migration typically increases the incidence of polyclonal amplification and thus very few, if any, monoclonal populations will be produced.

One suitable technique to reduce the production of polyclonal populations in conventional amplification methods uses physical barriers to separate individual amplification reactions into discrete compartments. For example, emulsion PCR uses water-in-oil microreactors, where an oil phase includes many separate, i.e., discontinuous, aqueous reaction compartments. Each compartment serves as an independent amplification reactor, thus the entire emulsion is capable of supporting many separate amplification reactions in separate (discontinuous) liquid phases in a single reaction vessel (e.g., an Eppendorf tube or a well). Similarly, an amplification "master mix" can be prepared and distributed into separate reaction chambers (e.g., an array of wells), creating a set of discrete and separate phases, each of which defines a separate amplification reaction. Such separate phases can be further sealed off from each other prior to amplification. Such sealing can be useful in preventing cross-contamination between parallel and separate reactions. Exemplary forms of sealing can include use of lids or phase barriers (e.g., mineral oil layer on top of an aqueous reaction) to compartmentalize the PCR reactions into individual and discrete compartments, between which transfer of reaction components does not occur.

Other techniques to prevent cross-contamination and reduce polyclonality rely on immobilization of one or more reaction components (for example, one or more templates and/or primers) during amplification to prevent cross contamination of amplification reaction products and consequent reduction in monoclonality. One such example includes bridge PCR, where all of the primers required for amplification (e.g., forward and reverse primer) are attached to the surface of a matrix support. In addition to such immobilization, additional immobilization components can be included in the reaction mixture. For example, the polynucleotide template and/or amplification primers cam be suspended in gels or other matrices during the amplification so as to prevent migration of amplification reaction products from the site of synthesis. Such gels and matrices typically require to be removed subsequently, requiring the use of appropriate "melting" or other recovery steps and consequent loss of yield.

In some embodiments, the disclosure provides methods for performing substantially clonal amplification of multiple polynucleotide templates in parallel in a single continuous liquid phase of a reaction mixture, without need for compartmentalization or immobilization of multiple reaction components (e.g., both primers) during amplification. Instead, mixtures of polynucleotide templates in solution can be directly contacted with amplification reaction components and a suitable surface or support having a first primer attached thereto, Other components required for amplification can be provided in the same continuous liquid phase, including a polymerase, one or more types of nucleotide and optionally a second primer. In some embodiments, the reaction mixture also includes a recombinase. Optionally, the reaction mixture further includes at least one agent selected from the group consisting of: a diffusion limiting agent, a sieving agent, and a crowding agent. Examples of amplification mixtures suitable for achieving monoclonal amplification of templates contained in a single continuous liquid phase are described further herein. Optionally, different templates can be amplified onto different locations on a single surface or support, or different templates can be amplified onto different surfaces or different supports within the same reaction mixture.

In some embodiments, the reaction mixture can include one or more sieving agents. The sieving agent optionally includes any compound that can provide a physical barrier to migration of polynucleotide templates or their corresponding amplified products. (Migration can include any movement of template or amplified product within the reaction mixture; diffusion includes forms of migration involving movement along a concentration gradient). In some embodiments, a sieving agent comprises any compound that can provide a matrix having a plurality of pores that are small enough to reduce the movement of any one or more specific components of a nucleic acid synthesis reaction mixture, or a nucleic acid reaction mixture.

In some embodiments, a sieving agent provides a molecular sieve. For example, a sieving agent can reduce the movement of a polynucleotide (or a polynucleotide associated with a surface or bead) through a reaction mixture containing the sieving agent. The sieving agent can optionally have pores.

Inclusion of a sieving agent may be advantageous when clonally amplifying two or more template polynucleotides within a single continuous liquid phase of a reaction mixture. For example, the sieving agent can prevent or slow diffusion of templates, or amplified polynucleotides produced via replication of at least some portion of a template, within the reaction mixture, thus preventing the formation of polyclonal contaminants without requiring compartmentalization of the reaction mixture by physical means or encapsulation means (e.g., emulsions) during the amplification. Such methods of clonally amplifying templates within a single continuous liquid phase of a single reaction mixture without need for compartmentalization greatly reduces the cost, time and effort associated with generation of libraries amenable for high-throughput methods such as digital PCR, next generation sequencing, and the like.

In some embodiments, the average pore size of the sieving agent is such that movement of a target component within the reaction mixture (e.g., a polynucleotide) is selectively retarded or prevented. In one example, the sieving agent comprises any compound that can provide a matrix having a plurality of pores that are small enough to slow or retard the movement of a polynucleotide through a reaction mixture containing the sieving agent. Thus, a sieving agent can reduce Brownian motion of a polynucleotide.

In some embodiments, the sieving agent acts selectively to retard migration of molecules having an average molecular size or weight above a particular threshold value or range, without retarding the migration of other molecules having an average molecular size or weight below the threshold value or range.

In some embodiments, the sieving agent acts selectively to retard migration of molecules having an average molecular size or weight below a particular threshold value or range, without retarding the migration of other molecules having an average molecular size or weight above the threshold value or range.

In some embodiments, a sieving agent can be selected to selectively retard, slow down, reduce or prevent movement of a polynucleotide through a reaction mixture, but large enough to permit movement of smaller components (for example, cations, nucleotides, ATP and co-factors) through the reaction mixture. In some embodiments, the sieving agent has an average pore size or average pore size range that can be modulated by increasing or decreasing the concentration of the sieving agent. For example, the molecular weight, intrinsic viscosity and concentration of a sieving agent (or a combination of sieving agents) can be selected to prepare a nucleic acid reaction mixture in a particular solvent (e.g., water) to produce a matrix having a desired capacity to prevent migration of target polynucleotides of a particular size or length; or a desired average pore size or viscosity. In some embodiments, a sieving agent can reduce bulk flow by increasing the viscosity of a nucleic acid reaction mixture. In some embodiments, a sieving agent can be water soluble. In some embodiments, a matrix having a plurality of pores can be prepared by mixing a sieving agent with a solvent (e.g., an aqueous solvent, such as water). In some embodiments, a sieving agent does not interfere with formation of a recombinase nucleoprotein complex or with nucleotide polymerization.

In some embodiments, the disclosure relates generally to methods for conducting a nucleic acid amplification reaction, comprising generating two or more substantially monoclonal populations by amplifying a target polynucleotide onto a surface or support in the presence of one or more sieving agents, optionally in the presence of a recombinase, a polymerase, or any other suitable agent capable of catalyzing or promoting nucleic acid amplification.

In some embodiments, inclusion of a sieving agent in a reaction mixture can reduce the movement of a polynucleotide away from a given support or surface (e.g., reduce polynucleotide shedding) and can increase the likelihood that the polynucleotide will hybridize to the support or surface and provide an initiation site for nucleotide polymerization, thereby increasing the proportion of substantially monoclonal amplicons generated during the amplification reaction.

In some embodiments, the amplification includes amplifying a plurality of different polynucleotide templates onto a plurality of different bead supports in the presence of a sieving agent, and recovering a percentage of substantially monoclonal bead supports, each such substantially monoclonal bead support include a bead support attached to a substantially monoclonal polynucleotide population. In some embodiments, the percentage of substantially monoclonal bead supports recovered is substantially greater than 5%, 10%, 15%, 20%, 25%, 30%, 35%, 40%, 50%, 55%, 60%, 65%, 70%, 75%, 89%, 90%, or 95% of total amplified bead supports (i.e., total bead supports including either polyclonal or monoclonal populations) recovered from the reaction mixture. In some embodiments, the percentage of substantially monoclonal bead supports recovered is substantially greater than the percentage of substantially monoclonal bead supports recovered following amplification in the absence of the sieving agent but under otherwise essentially similar or same amplification conditions.

In some embodiments, a sieving agent comprises a polymer compound. In some embodiments, a sieving agent comprises a cross-linked or a non-cross linked polymer compounds. By way of non-limiting examples, the sieving agent can include polysaccharides, polypeptides, organic polymers, etc.

In some embodiments, a sieving agent comprises linear or branched polymers. In some embodiments, a sieving agent comprises charged or neutral polymers.

In some embodiments, the sieving agent can include a blend of one or more polymers, each having an average molecular weight and viscosity.

In some embodiments, the sieving agent comprises a polymer having an average molecular weight of about 10,000-2,000,000, or about 12,000-95,000, or about 13,000-95,000.

In some embodiments, a sieving agent can exhibit an average viscosity range of about 5 centipoise to about 15,000 centipoise when dissolved in water at 2 weight percent measured at about 25° C., or about 10 centipoise to about 10,000 centipoise as a 2% aqueous solutions measured at about 25° C., or about 15 centipoise to about 5,000 centipoise as a 2% aqueous solution measured at about 25° C.

In some embodiments, a sieving agent comprises a viscosity average molecular weight ($M_v$) of about 25 to about 1,5000 $kM_v$, or about 75-1,000 $kM_v$, or about 85-800 $kM_v$. In some embodiments, the reaction mixture comprises a sieving agent at about 0.1 to about 20% weight per volume, or about 1-10% w/v, or about 2-5% w/v.

In some embodiments, a sieving agent comprises an acrylamide polymer, for example polyacrylamide.

In some embodiments, a sieving agent comprises a polymer of one or amino acids. For example, the sieving agent can include polylysine, poly-glutamic acid, actin, myosin, keratin, tropmyosin, and the like. In some embodiments, the sieving agent can include a derivative of any of these polypeptides.

In some embodiments, a sieving agent comprises a polysaccharide polymer. In some embodiments, a sieving agent comprises a polymer of glucose or galactose. In some embodiments, a sieving agent comprises one or more polymers selected from the group consisting of: cellulose, dextran, starch, glycogen, agar, chitin, pectin or agarose. In some embodiments, the sieving agent comprises a glucopyranose polymer.

In some embodiments, the sieving agent comprises a polymer having one or more groups that are polar or charged under amplification reaction conditions. For example, the polymer can include one or more cationic groups, one or more anionic groups, or both. In some embodiments, the sieving agent is a polysaccharide including one or more charged groups. In some embodiments, the sieving agent is a polysaccharide including one or more carboxy groups that are, or tend to be, negatively charged under amplification reaction conditions. For example, the sieving agent can include carboxy-methyl cellulose (CMC) polymers. In some embodiments, the sieving agent can include spermine and/or spermidine. In some embodiments, the sieving agent includes polylysine and/or polyarginine. For example, the sieving agent can include poly-L-lysine, poly-D-lysine, poly-D-glutamic acid, and the like. In some embodiments, the sieving agent includes one or more histone proteins or histone-nucleic acid complexes or derivatives thereof. The histones are highly alkaline proteins that are capable of binding to nucleic acid and include the proteins H1, H2A, H2B, H3 and H4. In some embodiments, the histone protein is modified, for example via methylation, acetylation, phosphorylation, ubiquitination, SUMOylation, citrullination, ribosylation (including ADP-ribosylation), and the like.

In some embodiments, the sieving agent includes a polymer that includes chemically substituted polymers. The polymers can include reactive groups (for example, which can be reacted with suitable substituents to produce substituted polymers. In some embodiments, the polymer includes a fluoro-, carboxy-, amino-, or alkoxy-substituted polymer. In some embodiments, the polymer is modified via methylation, acetylation, phosphorylation, ubiquitination, carboxylation, and the like. The substituent can include a charged group, for example an anionic or cationic group, and substitution of this group into the polymer chain can result in generation of a charged polymer. The degree of substitution can vary from between about 0.2 and about 1.0 derivatives per monomer unit, typically between about 0.4 and about 1.0, even more typically between about 0.6 and 0.95.

In some embodiments, the sieving agent includes a cellulose derivative, such as sodium carboxymethyl cellulose, sodium carboxymethyl 2-hydroxyethyl cellulose, methyl cellulose, hydroxyl ethyl cellulose, 2-hydroxypropyl cellulose, carboxy methyl cellulose, hydroxyl propyl cellulose, hydroxyethyl methyl cellulose, hydroxybutyl methyl cellulose, (hydroxypropyl)methyl cellulose or hydroxyethyl ethyl cellulose, or a mixture including any one or more of such polymers.

In some embodiments, a nucleic acid reaction mixture comprises a mixture of different sieving agents, for example, a mixture of different cellulose derivatives, starch, polyacrylamide, and the like.

In some embodiments, the sieving agent includes one or more composite polymers comprised of subportions of any two different polymers, including any of the polymers described herein. For example, the composite polymer can include polysaccharide polymer linked to a polynucleotide polymer, such as a polysaccharide linked to DNA or RNA. In some embodiments, the sieving agent can include a polymer comprising both a cellulose portion and a nucleic acid portion, for example DNA-cellulose. In other embodiments, the composite polymer can include a polyacrylamide linked to a polynucleotide, and/or to a polypeptide. Inclusion of such composite polymers in the reaction mixture can be useful in further retarding the movement of target polynucleotides through the reaction mixture.

In some embodiments, the sieving agent can include polymers that have first been contacted or reacted with appropriate crosslinking agents. For example, the sieving agent can include acrylamide that has been reacted with bis-acrylamide and/or Bis(acryloyl)cystamine.

In some embodiments, the reaction mixture includes at least one diffusion-reducing agent. In some embodiments, a diffusion-reducing agent comprises any compound that reduces migration of polynucleotides from a region of higher concentration to one having a lower concentration. In some embodiments, a diffusion reducing agent comprises any compound that reduces migration of any component of a nucleic acid amplification reaction irrespective of size. In some embodiments, components of a nucleic acid amplification reaction include beads/primers, polynucleotides, recombinase, polymerase, nucleotides, ATP and/or co-factors.

It should be noted that the concepts of a sieving agent and a diffusion-reducing agent are not necessarily mutually exclusive; a sieving agent can frequently be effective in reducing diffusion of target compounds through a reaction mixture, whereas a diffusion reducing agent can frequently have a sieving effect on reaction components. In some embodiments, the same compound or reaction mixture additive can act both as a sieving agent and/or a diffusion reducing agent. Any of the sieving agents disclosed herein can in some embodiments be capable of acting as a diffusion reducing agent and vice versa.

In some embodiments, the diffusion reducing agent and/or sieving agent includes polyacrylamide, agar, agarose or a cellulose polymer such as hydroxyethylcellulose (HEC), methyl-cellulose (MC) or carboxymethylcellulose (CMC).

In some embodiments, the sieving agent and/or the diffusion reducing agent is included in the reaction mixture at concentrations of at least 1%, 2%, 5%, 10%, 15%, 20%, 25%, 30%, 40%, 50%, 74%, 90%, or 95% w/v (weight of agent per unit volume of reaction mixture).

In some embodiments, the reaction mixture includes at least one crowding agent. For example, a crowding agent can increase the concentration of one or more components in a nucleic acid amplification reaction by generating a crowded reaction environment. In some embodiments, the reaction mixture includes both a sieving agent and a crowding agent.

In some embodiments, methods for nucleic acid amplification comprise one or more surfaces. In some embodiments, a surface can be attached with a plurality of first primers, the first primers of the plurality sharing a common first primer sequence.

In some embodiments, a surface can be an outer or top-most layer or boundary of an object. In some embodiments, a surface can be interior to the boundary of an object.

In some embodiments, the reaction mixture includes multiple different surfaces, for example, the reaction mixture can include a plurality of beads (such as particles, nanoparticles, microparticles, and the like) and at least two different polynucleotide templates can be clonally amplified onto different surfaces, thereby forming at least two different surfaces, each of which is attached to an amplicon. In some embodiments, the reaction mixture includes a signal surface (for example, the surface of a slide or array of reaction chambers) and at least two different polynucleotide templates are amplified onto two different regions or locations on the surface, thereby forming a single surface attached to two or more amplicons.

In some embodiments, a surface can be porous, semi-porous or non-porous. In some embodiments, a surface can be a planar surface, as well as concave, convex, or any combination thereof. In some embodiments, a surface can be a bead, particle, microparticle, sphere, filter, flowcell, well, groove, channel reservoir, gel or inner wall of a capillary. In some embodiments, a surface includes the inner walls of a capillary, a channel, a well, groove, channel, reservoir. In some embodiments, a surface can include texture (e.g., etched, cavitated, pores, three-dimensional scaffolds or bumps).

In some embodiments, particles can have a shape that is spherical, hemispherical, cylindrical, barrel-shaped, toroidal, rod-like, disc-like, conical, triangular, cubical, polygonal, tubular, wire-like or irregular.

In some embodiments, a surface can be made from any material, including glass, borosilicate glass, silica, quartz, fused quartz, mica, polyacrylamide, plastic polystyrene, polycarbonate, polymethacrylate (PMA), polymethyl methacrylate (PMMA), polydimethylsiloxane (PDMS), silicon, germanium, graphite, ceramics, silicon, semiconductor, high refractive index dielectrics, crystals, gels, polymers, or films (e.g., films of gold, silver, aluminum, or diamond).

In some embodiments, a surface can be magnetic or paramagnetic bead (e.g., magnetic or paramagnetic nanoparticles or microparticles). In some embodiments, paramagnetic microparticles can be paramagnetic beads attached with streptavidin (e.g., Dynabeads™ M-270 from Invitrogen, Carlsbad, Calif.). Particles can have an iron core, or comprise a hydrogel or agarose (e.g., Sepharose™).

In some embodiments, the surface can be attached with a plurality of a first primer. A surface can be coated with an acrylamide, carboxylic or amine compound for attaching a nucleic acid (e.g., a first primer). In some embodiments, an amino-modified nucleic acid (e.g., primer) can be attached to a surface that is coated with a carboxylic acid. In some embodiments, an amino-modified nucleic acid can be reacted with EDC (or EDAC) for attachment to a carboxylic acid coated surface (with or without NHS). A first primer can be immobilized to an acrylamide compound coating on a surface. Particles can be coated with an avidin-like compound (e.g., streptavidin) for binding biotinylated nucleic acids.

In some embodiments, the surface comprises the surface of a bead. In some embodiments, a bead comprises a polymer material. For example, a bead comprises a gel, hydrogel or acrylamide polymers. A bead can be porous. Particles can have cavitation or pores, or can include three-dimensional scaffolds. In some embodiments, particles can be Ion Sphere™ particles.

In some embodiments, the disclosed methods (as well as related compositions, systems and kits) include immobilizing one or more nucleic acid templates onto one or more supports. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube. means any solid phase material upon which a oligomer is synthesized, attached, ligated or otherwise immobilized. A support can optionally comprise a "resin", "phase", "surface" and "support". A support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support is optionally addressable (e.g., for robotic delivery of reagents), or by detection means including scanning by laser illumination and confocal or deflective light gathering. An amplification support (e.g., a bead) can be placed within or on another support (e.g., within a well of a second support).

In an embodiment the solid support is a "microparticle," "bead" "microbead", etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). Microparticles (e.g., Dynabeads from Dynal, Oslo, Norway) may be made of a variety of inorganic or organic materials including, but not limited to, glass (e.g., controlled pore glass), silica, zirconia, cross-linked polystyrene, polyacrylate, polymehtymethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments of the invention a population of microparticles having different shapes sizes and/or colors can be used. The microparticles can optionally be encoded, e.g., with quantum dots such that each microparticle can be individually or uniquely identified.

In some embodiments, a bead surface can be functionalized for attaching a plurality of a first primer. In some embodiments, a bead can be any size that can fit into a reaction chamber. For example, one bead can fit in a reaction chamber. In some embodiments more than one bead can fit in a reaction chamber. In some embodiments, the smallest cross-sectional length of a bead (e.g., diameter) can be about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In some embodiments, a bead can be attached with a plurality of one or more different primer sequences. In some embodiments, a bead can be attached with a plurality of one primer sequence, or can be attached a plurality of two or more different primer sequences. In some embodiments, a bead can be attached with a plurality of at least 1,000 primers, or about 1,000-10,000 primers, or about, 10,000-50,000 primers, or about 50,000-75,000 primers, or about 75,000-100,000 primers, or more.

In some embodiments, the reaction mixture comprises a recombinase. The recombinase can include any agent that is capable of inducing, or increasing the frequency of occurrence, of a recombination event. A recombination event includes any event whereby two different polynucleotides strands are recombined with each other. Recombination can include homologous recombination. The recombinase can be an enzyme, or a genetically engineered derivative thereof. The recombinase optionally can associate with (e.g., bind) a single-strand oligonucleotide (e.g., a first primer). In some embodiments, an enzyme that catalyzes homologous recombination can form a nucleoprotein complex by binding a single-stranded oligonucleotide. In some embodiments, a homologous recombination enzyme, as part of a nucleoprotein complex, can bind a homologous portion of a double-stranded polynucleotide. In some embodiments, the homologous portion of the polynucleotide can hybridize to at least a portion of the first primer. In some embodiment, the homologous portion of the polynucleotide can be partially or completely complementary to at least a portion of the first primer.

In some embodiments, a homologous recombination enzyme can catalyze strand invasion by forming a nucleoprotein complex and binding to a homologous portion of a double-stranded polynucleotide to form a recombination intermediate having a triple-strand structure (D-loop formation) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308). In some embodiments, a homologous recombination enzyme comprises wild-type, mutant, recombinant, fusion, or fragments thereof. In some embodiments, a homologous recombination enzyme comprises an enzyme from any organism, including myoviridae (e.g., uvsX from bacteriophage T4, RB69, and the like) *Escherichia coli* (e.g., recA), or human (e.g., RAD51).

In some embodiments, methods for nucleic acid amplification comprise one or more accessory proteins. For example, an accessory protein can improve the activity of a recombinase enzyme (U.S. Pat. No. 8,071,308 granted to Piepenburg, et al.). In some embodiments, an accessory protein can bind single strands of nucleic acids, or can load a recombinase onto a nucleic acid. In some embodiments, an accessory protein comprises wild-type, mutant, recombinant, fusion, or fragments thereof. In some embodiments, accessory proteins can originate from any combination of the same or different species as the recombinase enzyme that are used to conduct a nucleic acid amplification reaction. Accessory proteins can originate from any bacteriophage including a myoviral phage. Examples of a myoviral phage include T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Accessory proteins can originate from any bacterial species, including *Escherichia coli, Sulfolobus* (e.g., *S. solfataricus*) or *Methanococcus* (e.g., *M. jannaschii*).

In some embodiments, methods for nucleic acid amplification can include single-stranded binding proteins. Single-stranded binding proteins include myoviral gp32 (e.g., T4 or RB69), Sso SSB from *Sulfolobus solfataricus*, MjA SSB from *Methanococcus jannaschii*, or *E. coli* SSB protein.

In some embodiments, methods for nucleic acid amplification can include proteins that can improve recombinase loading onto a nucleic acid. For example, a recombinase loading protein comprises a UsvY protein (U.S. Pat. No. 8,071,308 granted to Piepenburg).

In some embodiments, methods for nucleic acid amplification can include at least one proteins that bind nucleic acids, including proteins that unwind duplex nucleic acids (e.g., helicase).

In some embodiments, methods for nucleic acid amplification can include at least one co-factor for recombinase or polymerase activity. In some embodiments, a co-factor comprises one or more divalent cation. Examples of divalent cations include magnesium, manganese and calcium.

In some embodiments, a nucleic acid amplification reaction can be pre-incubated under conditions that inhibit premature reaction initiation. For example, one or more components of a nucleic acid amplification reaction can be withheld from a reaction vessel to prevent premature reaction initiation. To start the reaction, a divalent cation can be added (e.g., magnesium or manganese). In another example, a nucleic acid amplification reaction can be pre-incubated at a temperature that inhibits enzyme activity. The reaction can be pre-incubated at about 0-15° C., or about 15-25° C. to inhibit premature reaction initiation. The reaction can then be incubated at a higher temperature to induce enzymatic activity.

In some embodiments, methods for nucleic acid amplification can include at least one co-factor for recombinase assembly on nucleic acids or for homologous nucleic acid pairing. In some embodiments, a co-factor comprises any form of ATP including ATP and ATPγS.

In some embodiments, methods for nucleic acid amplification can include at least one co-factor that regenerates ATP. For example, a co-factor comprises an enzyme system that converts ADP to ATP. In some embodiments, a co-factor comprises phosphocreatine and creatine kinase.

In some embodiments, any of the nucleic acid amplification methods disclosed herein can be conducted, or can include steps that are conducted, under isothermal or substantially isothermal amplification conditions. In some embodiments isothermal amplification conditions comprise a nucleic acid amplification reaction subjected to a temperature variation which is constrained within a limited range during at least some portion of the amplification (or the entire amplification process), including for example a temperature variation is equal or less than about 20° C., or about 10° C., or about 5° C., or about 1-5° C., or about 0.1-1° C., or less than about 0.1° C.

In some embodiments, an isothermal nucleic acid amplification reaction can be conducted for about 2, 5, 10, 15, 20, 30, 40, 50, 60 or 120 minutes.

In some embodiments, an isothermal nucleic acid amplification reaction can be conducted at about 15-25° C., or about 25-35° C., or about 35-40° C., or about 40-45° C., or about 45-50° C., or about 50-55° C., or about 55-60° C.

In some embodiments, methods for nucleic acid amplification comprise a plurality of different polynucleotides. In some embodiments, a plurality of different polynucleotides comprises single-stranded or double-stranded polynucleotides, or a mixture of both. In some embodiments, a plurality of different polynucleotides comprises polynucleotides having the same or different sequences. In some embodiments, a plurality of different polynucleotides comprises polynucleotides having the same or different lengths. In some embodiments, a plurality of different polynucleotides comprises about 2-10, or about 10-50, or about 50-100, or about 100-500, or about 500-1,000, or about 1,000-5,000, or about $10^3$-$10^6$, or about $10^6$-$10^{10}$ or more different polynucleotides. In some embodiments, a plurality of different polynucleotides comprises polymers of deoxyribonucleotides, ribonucleotides, and/or analogs thereof. In some embodiments, a plurality of different polynucleotides comprises naturally-occurring, synthetic, recombinant, cloned, amplified, unamplified or archived (e.g., preserved) forms. In some embodiments, a plurality of different polynucleotides comprises DNA, cDNA RNA or chimeric RNA/DNA, and nucleic acid analogs.

In some embodiments, a plurality of different polynucleotide templates can comprise a double-stranded polynucleotide library construct having one or both ends joined with a nucleic acid adaptor sequence. For example, a polynucleotide library construct can comprise a first and second end, where the first end is joined to a first nucleic acid adaptor. A polynucleotide library construct can also include a second end joined to a second nucleic acid adaptor. The first and second adaptors can have the same or different sequence. In some embodiments, at least a portion of the first or second nucleic acid adaptor (i.e., as part of the polynucleotide library construct) can hybridize to the first primer. In some embodiments, a homologous recombination enzyme, as part of a nucleoprotein complex, can bind to a polynucleotide library construct having a first or second nucleic acid adaptor sequence.

In some embodiments, polynucleotide library constructs can be compatible for use in any type of sequencing platform including chemical degradation, chain-termination, sequence-by-synthesis, pyrophosphate, massively parallel, ion-sensitive, and single molecule platforms.

In some embodiments, methods for nucleic acid amplification include diluting the amount of polynucleotides that are reacted with beads (e.g., beads attached with a plurality of a first primer) to reduce the percentage of beads that react with more than one polynucleotide. In some embodiments, nucleic acid amplification reactions can be conducted with a polynucleotide-to-bead ratio that is selected to optimize the percentage of beads having a monoclonal population of polynucleotides attached thereto. For example, a nucleic acid amplification reaction can be conducted at anyone of polynucleotide-to-bead ratios in a range of about 1:2 to 1:500. In some embodiments, a polynucleotide-to-bead ratio includes about 1:2, or about 1:5, or about 1:10, or about 1:25, or about 1:50, or about 1:75, or about 1:100, or about 1:125, or about 1:150, or about 1:175, or about 1:200, or about 1:225, or about 1:225, or about 1:250. In some embodiments, a nucleic acid amplification reaction can produce beads having zero types of polynucleotides attached thereto, other beads having one type of polynucleotide attached thereto, and other beads having more than one type of polynucleotides attached thereto.

In some embodiments, the reaction mixture comprises one or more primers. For example, the reaction mixture can include at least a first oligonucleotide primer. In some embodiments, a first primer can include a forward amplification primer which hybridizes to at least a portion of one strand of a polynucleotide. In some embodiments, a first primer comprises an extendible 3' end for nucleotide polymerization.

In some embodiments, methods for nucleic acid amplification comprise hybridization to the template of additional primers. For example, a second primer can be a reverse amplification primer which hybridizes to at least a portion of one strand of a polynucleotide. In some embodiments, a second primer comprises an extendible 3' end. In some embodiment, a second primer is not attached to a surface.

In some embodiments, a third primer can be a forward amplification primer which hybridizes to at least a portion of one strand of a polynucleotide. In some embodiments, a third primer comprises an extendible 3' end. In some embodiment, a third primer is not attached to a surface. In some embodiments, a third primer comprises an binding partner or affinity moiety (e.g., biotin) for enriching the amplified nucleic acids.

In some embodiments, primers (e.g., first, second and third primers) comprise single-stranded oligonucleotides.

In some embodiments, at least a portion of a primer can hybridize with a portion of at least one strand of a polynucleotide in the reaction mixture. For example, at least a portion of a primer can hybridize with a nucleic acid adaptor that is joined to one or both ends of the polynucleotide. In some embodiments, at least a portion of a primer can be partially or fully complementary to a portion of the polynucleotide or to the nucleic acid adaptor. In some embodiments, a primer can be compatible for use in any type of sequencing platform including chemical degradation, chain-termination, sequence-by-synthesis, pyrophosphate, massively parallel, ion-sensitive, and single molecule platforms.

In some embodiments, a primer (e.g., first, second or third primer) can have a 5' or 3' overhang tail (tailed primer) that does not hybridize with a portion of at least one strand of a polynucleotide in the reaction mixture. In some embodiments, a tailed primer can be any length, including 1-50 or more nucleotides in length.

In some embodiments, primers comprise polymers of deoxyribonucleotides, ribonucleotides, and/or analogs thereof. In some embodiments, primers comprise naturally-occurring, synthetic, recombinant, cloned, amplified, or unamplified forms. In some embodiments, primers comprise DNA, cDNA RNA, chimeric RNA/DNA, or nucleic acid analogs.

In some embodiments, primers can be any length, including about 5-10 nucleotides, or about 10-25 nucleotides, or about 25-40 nucleotides, or about 40-55 nucleotides, or longer.

In some embodiments, methods for nucleic acid amplification can include one or more different polymerases. In some embodiments, a polymerase includes any enzyme, or fragment or subunit of thereof, that can catalyze polymerization of nucleotides and/or nucleotide analogs. In some embodiments, a polymerase requires an extendible 3' end. For example, a polymerase requires a terminal 3' OH of a nucleic acid primer to initiate nucleotide polymerization.

A polymerase comprises any enzyme that can catalyze the polymerization of nucleotides (including analogs thereof) into a nucleic acid strand. Typically but not necessarily such nucleotide polymerization can occur in a template-dependent fashion. In some embodiments, a polymerase can be a high fidelity polymerase. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide, such as, for example, a reporter enzyme or a processivity-enhancing domain. Typically, the polymerase comprises one or more active sites at which nucleotide binding and/or catalysis of nucleotide polymerization can occur. In some embodiments, a polymerase includes or lacks other enzymatic activities, such as for example, 3' to 5' exonuclease activity or 5' to 3' exonuclease activity. In some embodiments, a polymerase can be isolated from a cell, or generated using recombinant DNA technology or chemical synthesis methods. In some embodiments, a polymerase can be expressed in prokaryote, eukaryote, viral, or phage organisms. In some embodiments, a polymerase can be post-translationally modified proteins or fragments thereof.

In some embodiments, the polymerase can include any one or more polymerases, or biologically active fragment of a polymerase, which is described in U.S. Patent Publ. No. 2011/0262903 to Davidson et al., published Oct. 27, 2011, and/or International PCT Publ. No. WO 2013/023176 to Vander Horn et al., published Feb. 14, 2013.

In some embodiments, a polymerase can be a DNA polymerase and include without limitation bacterial DNA polymerases, eukaryotic DNA polymerases, archaeal DNA polymerases, viral DNA polymerases and phage DNA polymerases.

In some embodiments, a polymerase can be a replicase, DNA-dependent polymerase, primases, RNA-dependent polymerase (including RNA-dependent DNA polymerases such as, for example, reverse transcriptases), a thermo-labile polymerase, or a thermo-stable polymerase. In some embodiments, a polymerase can be any Family A or B type polymerase. Many types of Family A (e.g., *E. coli* Pol I), B (e.g., *E. coli* Pol II), C (e.g., *E. coli* Pol III), D (e.g., Euryarchaeotic Pol II), X (e.g., human Pol beta), and Y (e.g., *E. coli* UmuC/DinB and eukaryotic RAD30/xeroderma pigmentosum variants) polymerases are described in Rothwell and Watsman 2005 Advances in Protein Chemistry 71:401-

440. In some embodiments, a polymerase can be a T3, T5, T7, or SP6 RNA polymerase.

In some embodiments, nucleic acid amplification reactions can be conducted with one type or a mixture of polymerases, recombinases and/or ligases. In some embodiments, nucleic acid amplification reactions can be conducted with a low fidelity or high fidelity polymerase.

In some embodiments, nucleic acid amplification reactions can be catalyzed by heat-stable or heat-labile polymerases.

In some embodiment, a polymerase can lack 5'-3' exonuclease activity. In some embodiments, a polymerase can have strand-displacement activity.

In some embodiments, an archaeal DNA polymerase can be, without limitation, a thermostable or thermophilic DNA polymerase such as, for example: a *Bacillus subtilis* (Bsu) DNA polymerase I large fragment; a *Thermus aquaticus* (Taq) DNA polymerase; a *Thermus filiformis* (Tfi) DNA polymerase; a Phi29 DNA polymerase; a *Bacillus stearothermophilus* (Bst) DNA polymerase; a *Thermococcus* sp. 9° N-7 DNA polymerase; a *Bacillus smithii* (Bsm) DNA polymerase large fragment; a *Thermococcus litoralis* (Tli) DNA polymerase or Vent™ (exo-) DNA polymerase (from New England Biolabs); or "Deep Vent" (exo-) DNA polymerase (New England Biolabs).

In some embodiments, methods for nucleic acid amplification can include one or more types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

In some embodiments, the nucleotide is unlabeled. In some embodiments, the nucleotide comprises a label and referred to herein as a "labeled nucleotide". In some embodiments, the label can be in the form of a fluorescent dye attached to any portion of a nucleotide including a base, sugar or any intervening phosphate group or a terminal phosphate group, i.e., the phosphate group most distal from the sugar.

In some embodiments, a nucleotide (or analog thereof) can be attached to a label. In some embodiments, the label comprises an optically detectable moiety. In some embodiments, the label comprises a moiety not typically present in naturally occurring nucleotides. For example, the label can include fluorescent, luminescent or radioactive moieties.

In some embodiments, methods for nucleic acid amplification can further comprise an enrichment step. In some embodiments, methods for nucleic acid amplification can produce at least one bead attached with a plurality of polynucleotides (e.g., amplified nucleic acids) having a sequence that is complementary to a template polynucleotide. At least one of the polynucleotides attached to the bead can be hybridized to a polynucleotide having a biotinylated moiety (e.g., a reverse amplification product with the third primer). In some embodiments, an enrichment step comprises forming a purification complex by binding the polynucleotide having a biotinylated moiety with a purification bead (e.g., paramagnetic bead) that is attached to a streptavidin moiety (e.g., (MyOne™ Bead from Dynabeads). In some embodiments, the purification complex can be separated/removed from the reaction mixture by attraction with a magnet.

In some embodiments, amplicons including substantially monoclonal nucleic acid populations are individually deposited, distributed or positioned to different sites in an array of sites.

In some embodiments, the disclosed methods include distributing, depositing or otherwise positioning a single template molecule (e.g., a single target polynucleotide of a sample) into a reaction chamber or site (e.g., within an array). A single polynucleotide can be distributed from a sample into a reaction chamber by flowing a fluid having the sample of polynucleotides over the reaction chamber. A single polynucleotide distributed into a reaction chamber can be single-stranded or double-stranded. In some embodiments, the nucleic acid is amplified in the reaction chamber or site after the distributing.

In some embodiments, different single target polynucleotides can be distributed from a sample into each of different reaction chambers arranged in an array. Different single polynucleotides can be distributed from a sample into each of different reaction chambers by flowing a fluid having the sample of polynucleotides over the reaction chambers. Different single polynucleotides distributed into each of different reaction chambers can be single-stranded or double-stranded.

In some embodiments, the methods include distributing a single polynucleotide into a reaction chamber, and amplifying the single polynucleotide within the reaction chamber, thereby producing a monoclonal nucleic acid population in the reaction chamber.

In some embodiments, methods for distributing a single target polynucleotide into the reaction chamber and amplifying the single target polynucleotide comprise a nucleic acid sample. In some embodiments, a single polynucleotide, or different single polynucleotides, can be distributed from a nucleic acid sample having a plurality of polynucleotides. For example, a nucleic acid sample can include about 2-10, or about 10-50, or about 50-100, or about 100-500, or about 500-1,000, or about 1,000-5,000, or about $10^3$-$10^6$, or more different polynucleotides. Different polynucleotides can have the same or different sequences. Different polynucleotides can have the same or different lengths. A sample can include single-stranded or double-stranded polynucleotides or a mixture of both.

In some embodiments, methods for distributing a single target polynucleotide into the reaction chamber and amplifying the single target polynucleotide comprise distributing single polynucleotides. In some embodiments, single polynucleotides can include single-stranded and double-stranded nucleic acid molecules. In some embodiments, nucleic acids can include polymers of deoxyribonucleotides, ribonucleotides, and/or analogs thereof. In some embodiments, nucleic acids can include naturally-occurring, synthetic, recombinant, cloned, amplified, unamplified or archived (e.g., preserved) forms. In some embodiments, nucleic acids can include DNA, cDNA RNA or chimeric RNA/DNA, and nucleic acid analogs. In some embodiments, single polynucleotides can include nucleic acid library constructs comprising a nucleic acid joined at one or both ends to an oligonucleotide adaptor. In some embodiments, nucleic acid library constructs can be compatible for use in any type of sequencing platform including chemical degradation, chain-termination, sequence-by-synthesis, pyrophosphate, massively parallel, ion-sensitive, and single molecule platforms.

In some embodiments, the sites of an array can include one or more reaction chambers can be a well on a solid surface. A reaction chamber can have walls that define width and depth. The dimensions of a reaction chamber can be sufficient to permit deposition of reagents or for conducting reactions. A reaction chamber can have any shape including cylindrical, polygonal or a combination of different shapes. Any wall of a reaction chamber can have a smooth or irregular surface. A reaction chamber can have a bottom with a planar, concave or convex surface. The bottom and side walls of a reaction chamber can comprise the same or different material and/or can be coated with a chemical group that can react with a biomolecule such as nucleic acids, proteins or enzymes.

In some embodiments, the reaction chamber can be one of multiple reaction chambers arranged in a grid or array. An array can include two or more reaction chambers. Multiple reaction chambers can be arranged randomly or in an ordered array. An ordered array can include reaction chambers arranged in a row, or in a two-dimensional grid with rows and columns.

An array can include any number of reaction chambers for depositing reagents and conducting numerous individual reactions. For example, an array can include at least 256 reaction chambers, or at least 256,000, or at least 1-3 million, or at least 3-5 million, or at least 5-7 million, or at least 7-9 million, at least 9-11 million, at least 11-13 million reaction chambers, or even high density including 13-700 million reaction chambers or more. Reaction chambers arranged in a grid can have a center-to-center distance between adjacent reaction chambers (e.g., pitch) of less than about 10 microns, or less than about 5 microns, or less than about 1 microns, or less than about 0.5 microns.

An array can include reaction chambers having any width and depth dimensions. For example, a reaction chamber can have dimensions to accommodate a single microparticle (e.g., microbead) or multiple microparticles. A reaction chamber can hold 0.001-100 picoliters of aqueous volume.

In some embodiments, at least one reaction chamber can be coupled to one or more sensors or can be fabricated above one or more sensors. A reaction chamber that is coupled to a sensor can provide confinement of reagents deposited therein so that products from a reaction can be detected by the sensor. A sensor can detect changes in products from any type of reaction, including any nucleic acid reaction such as primer extension, amplification or nucleotide incorporation reactions. A sensor can detect changes in ions (e.g., hydrogen ions), protons, phosphate groups such as pyrophosphate groups. In some embodiments, at least one reaction chamber can be coupled to one or more ion sensitive field effect transistor (ISFET). Examples of an array of reaction chambers coupled to ISFET sensors can be found at U.S. Pat. No. 7,948,015, and U.S. Ser. No. 12/002,781.

In some embodiments, the amplification methods (as well as relating compositions, systems and apparatuses) described herein can be practiced in an array of reaction chambers, where the reaction chambers of the array form part of a single fluidic system. In some embodiments, an array of multiple reaction chambers can include a fluidic interface which flows fluids (e.g., liquid or gas) across the reaction chambers in a controlled laminar flow. In some embodiments, an array of reaction chambers can include a fluid head space above the reaction chambers for laminar flow. In some embodiments, an array of reaction chambers can be part of a flow cell or flow chamber, where the reaction chambers are in fluid communication with each other. For example, a fluid can flow onto an array to at least partially or fully fill one or multiple reaction chambers of the array. In some embodiments, a fluid can completely fill multiple reaction chambers and the excess fluid can flood the top of the reaction chambers to form a fluid layer on top of the reaction chambers. The fluid layer on top of the reaction chambers can provide fluid communication with multiple reaction chambers in the array. In some embodiments, a fluid communication among multiple reaction chambers in an array can be used to conduct separate parallel reactions in the multiple reaction chambers. For example, fluid communication can be used to deliver polynucleotides and/or reagents to multiple reaction chambers for conducting parallel nucleic acid amplification reactions.

In some embodiments, sample having a plurality of different polynucleotides can be applied to a flow chamber to distribute single polynucleotides to individual reaction chambers in the array. In some embodiments, additional reagents can be applied to the flow chamber for distribution into individual reaction chambers in the array. For example, additional reaction reagents can include microparticles, one or more enzymes, enzyme co-factors, primers and/or nucleoside triphosphates. In some embodiments, polynucleotides and reagents can be delivered to an array of reaction chambers in any order, including sequentially or substantially simultaneously or a combination of both. For example, in some embodiments, polynucleotides can be distributed to an array of reaction chambers first followed by reagents, or the reverse order can be used, or polynucleotides and reagents can be distributed essentially simultaneously.

In some embodiments, any means (including flow chamber) can be used to deliver polynucleotides and/or reagents to a percentage of reaction chambers in an array. For example, the percentage of reaction chambers in an array that are loaded includes about 1-25%, or about 25%, or about 30%, or about 40%, or about 50%, or about 60%, or about 70%, or higher percentages. In some embodiments, the percentage of reaction chambers loaded with polynucleotides and/or reagents can be increased by conducting two or more rounds of loading steps. For example, (a) in a first round polynucleotides and/or reagents can be distributed to multiple reaction chambers in an array, and (b) in a second round polynucleotides and/or reagents can be distributed to the same array. Additional loading rounds (e.g., third, fourth or more round) can be conducted. In some embodiments, any type of reaction can be conducted between any of the loading rounds and/or any type of reaction can be conducted after multiple loading rounds are completed. For example, a nucleic acid amplification reaction can be conducted between any of the loading rounds or a nucleic acid amplification reaction can be conducted after multiple loading rounds are completed. In some embodiments, after each loading round, a compound can be layered on the array to prevent migration of the polynucleotides and beads out of the reaction chambers. For example, after each loading round, a solution containing at least one sieving agent can be layered on the array. In some embodiments, the sieving agent comprises a cellulose derivative. Alternatively, an oil layer can be layered on top of the reaction mixture within wells or chambers of the array.

In some embodiments, the disclosed methods (and related compositions, systems and kits) further include attaching the nucleic acid template to a site of the array prior to amplification of the template. Optionally, the site includes a primer, and the attaching includes hybridizing the primer to the primer binding site of the template. For example, the site within the array can include at least one immobilized primer that includes a sequence complementary to at least a portion of the primer binding site of the template that is distributed or deposited at the site. The primer facilitates attachment of the template to the array. In some embodiments, a substantial portion of the sites in the array include at least one primer. The primers of different sites can be identical to each other. Alternatively, the primers of different sites can be different from each other. In one exemplary embodiment, at least two sites each include a different target-specific primer.

The primer may be attached to the site of the array using any suitable means. In order to attach primers to the surface of a nanoarray of reaction chambers (for example, an ISFET array of the type using in ion-based sequencing), it can be useful to first synthesize or fabricate a three-dimensional matrix within at least some reaction chambers of the array. In an embodiment, polymer matrix precursors can be applied to an array of wells associated with one or more sensors. The polymer matrix precursors can be polymerized to form an array of polymer matrices. These polymer matrices can be conjugated to oligonucleotides and can be useful in various analytical techniques including genetic sequencing techniques.

In some embodiments, hydrophilic polymer matrices are distributed in wells associated with sensors, such as sensors of a sensor array. In an example, the hydrophilic matrices are as hydrogel matrices. The hydrophilic matrices can correspond with sensors of the sensor array in a one-to-one configuration. In a further example, the sensors of the sensor array can include field effect transistor (FET) sensors, such as ion sensitive field effect transistors (ISFET). In particular, the matrix material is cured-in-place and conforms to the configuration of individual wells of a sensing device. The interstitial areas between the wells can be substantially free of the polymer matrix. In an example, the matrix material can be bonded, such as covalently bonded, to a surface of the wells. In an example, the wells have a depth or thickness in a range of 100 nm to 10 micrometers. In another example, the wells can have a characteristic diameter in a range of 0.1 micrometers to 2 micrometers.

In an exemplary method, the polymer matrix array can be formed by applying an aqueous solution including polymer precursors into wells of a well array. Volumes of the aqueous material defined by the well array can be isolated using an immiscible fluid disposed over the well array. The isolated volumes of the solution can be initiated to facilitate polymerization of the matrix precursors, resulting in a matrix array distributed within the wells. In an example, an aqueous solution including matrix precursors is distributed to the wells of the sensing device by flowing the aqueous precursor over the wells. In another example, the aqueous solution is included as a dispersed phase within an emulsion. The dispersed phase can settle or be motivated into wells of the well array. The polymerization of the matrix precursors can be initiated using initiators disposed within the aqueous phase or within the immiscible fluid. In another example, the polymerization can be initiated thermally.

In another exemplary method, a matrix array can be formed within wells of a sensing device by anchoring initiator molecules to a surface within wells of the well array. The solution including matrix precursors can be provided over the wells of the well array. An initiator can initiated polymerization of the matrix precursors, resulting in the formation of the polymer matrix within wells of the well array. In a further example, aspects of the above methods can be combined to further enhance formation of the matrix arrays.

In a particular embodiment, a sequencing system includes a flow cell in which a sensory array is disposed, includes communication circuitry in electronic communication with the sensory array, and includes containers and fluid controls in fluidic communication with the flow cell. In an example, FIG. 13 illustrates an expanded and cross-sectional view of a flow cell 100 and illustrates a portion of a flow chamber 106. A reagent flow 108 flows across a surface of a well array 102, in which the reagent flow 108 flows over the open ends of wells of the well array 102. The well array 102 and a sensor array 105 together can form an integrated unit forming a lower wall (or floor) of flow cell 100. A reference electrode 104 can be fluidly coupled to flow chamber 106. Further, a flow cell cover 130 encapsulates flow chamber 106 to contain reagent flow 108 within a confined region.

FIG. 14 illustrates an expanded view of a well 201 and a sensor 214, as illustrated at 110 of FIG. 13. The volume, shape, aspect ratio (such as base width-to-well depth ratio), and other dimensional characteristics of the wells can be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the well interior by a material layer 216. In addition, a conductive layer (not illustrated) can be disposed over the sensor plate 220. In an example, the material layer 216 includes an ion sensitive material layer. The material layer 216 can be a ceramic layer, such as an oxide of zirconium, hafnium, tantalum, aluminum, or titanium, or a nitride of titanium. In an example, the material layer 216 can have a thickness in a range of 5 nm to 100 nm, such as a range of 10 nm to 70 nm, a range of 15 nm to 65 nm, or even a range of 20 nm to 50 nm.

While the material layer 216 is illustrated as extending beyond the bounds of the illustrated FET component, the material layer 216 can extend along the bottom of the well 201 and optionally along the walls of the well 201. The sensor 214 can be responsive to (and generate an output signal related to) the amount of a charge 224 present on material layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents can move in and out of the wells by a diffusion mechanism 240.

In an embodiment, reactions carried out in the well 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, multiple copies of the same analyte can be analyzed in the well 201 at the same time in order to increase the output signal generated. In an embodiment, multiple copies of an analyte can be attached to a solid phase support 212, either before or after deposition into the well 201. The solid phase support 212 can be a polymer matrix, such as a hydrophilic polymer matrix, for example, a hydrogel matrix or the like. For simplicity and ease of explanation, solid phase support 212 is also referred herein as a polymer matrix.

The well 201 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 201 can have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 201 can have a characteristic diameter of at least 0.01 micrometers.

While FIG. 14 illustrates a single-layer wall structure and a single-layer material layer 216, the system can include, one or more wall structure layers, one or more conductive layers or one or more material layers. For example, the wall structure can be formed of one or more layers, including an oxide of silicon or TEOS or including a nitride of silicon.

In a particular example illustrated in FIG. 15, a system 300 includes a well wall structure 302 defining an array of wells 304 disposed over or operatively coupled to sensor pads of a sensor array. The well wall structure 302 defines an upper surface 306. A lower surface 308 associated with the well is disposed over a sensor pad of the sensor array. The well wall structure 302 defines a sidewall 310 between the upper surface 306 and the lower surface 308. As described above, a material layer in contact with sensor pads of the sensor array can extend along the lower surface 308 of a well of the array of wells 304 or along at least a portion of the wall 310 defined by the well wall structure 302. The upper surface 306 can be free of the material layer. In particular, a polymer matrix can be disposed in the wells of the array of wells 304. The upper surface 306 can be substantially free of the polymer matrix. For example, the upper surface 306 can include an area that is free of the polymer matrix, such as at least 70% of the total area, at least 80% of the total area, at least 90% of the total area or approximately 100% of the total area.

While the wall surface of FIG. 14 is illustrated as extending substantially vertically and outwardly, the wall surface can extend in various directions and have various shapes. Substantially vertically denotes extending in a direction having a component that is normal to the surface defined by the sensor pad. For example, as illustrated in FIG. 16, a well wall 402 can extend vertically, being parallel to a normal component 412 of a surface defined by a sensor pad. In another example, the wall surface 404 extends substantially vertically, in an outward direction away from the sensor pad, providing a larger opening to the well than the area of the lower surface of the well. As illustrated in FIG. 16, the wall surface 404 extends in a direction having a vertical component parallel to the normal component 412 of the surface 414. In an alternative example, a wall surface 406 extends substantially vertically in an inward direction, providing an opening area that is smaller than an area of the lower surface of the well. The wall surface 406 extends in a direction having a component parallel to the normal component 412 of the surface 414.

While the surfaces 402, 404, or 406 are illustrated by straight lines, some semiconductor or CMOS manufacturing processes can result in structures having nonlinear shapes. In particular, wall surfaces, such as wall surface 408 and upper surfaces, such as upper surface 410, can be arcuate in shape or take various nonlinear forms. While the structures and devices illustrated herewith are depicted as having linear layers, surfaces, or shapes, actual layers, surfaces, or shapes resulting from semiconductor processing can differ to some degree, possibly including nonlinear and arcuate variations of the illustrated embodiment.

FIG. 17 includes an illustration of exemplary wells including ion sensitive material layers. For example, a well structure 502 can define an array of wells, such as exemplary wells 504, 506, or 508. The wells (504, 506, or 508) can be operatively coupled to an underlying sensor (not illustrated) or linked to such an underlying sensor. Exemplary well 504 includes an ion sensitive material layer 510 defining the bottom of the well 504 and extending into the structure 502. While not illustrated in FIG. 17, a conductive layer, such as a gate, for example, a floating gate of ion sensitive field effect transistor can reside below the ion sensitive material layer 510.

In another example, as illustrated by well 506, an ion sensitive material layer 512 can define the bottom of the well 506 without extending into the structure 502. In a further example, a well 508 can include an ion sensitive layer 514 that extends along at least a portion of a sidewall 516 of the well 508 defined by the structure 502. As above, the ion sensitive material layers 512 or 514 can reside over conductive layers or gates of underlying electronic devices.

Returning to FIG. 14, the matrix material 212 is conformal with the well structure. In particular, the matrix material can be cured in place to be conformal to the walls and bottom surface of the well. An upper surface through which the wells are defined can include an area that is substantially free of the matrix material, such as at least 70% of the total area, at least 80% of the total area, at least 90% of the total area or approximately 100% of the total area. Depending upon the nature of the well structure, the polymer matrix can be physically secured to the well wall structure. In another example, the polymer matrix can be chemically bound to the well wall structure. In particular, the polymer matrix can be covalently bound to the well wall structure. In another example, the polymer matrix can be bound by hydrogen bonding or ionic bonding to the well wall structure.

The polymer matrix can be formed from matrix precursors, such as a radically polymerizable monomer, such as a vinyl-based monomer. In particular, the monomer can include a hydrophilic monomer, such as an acrylamide, vinyl acetate, hydroxyalkylmethacrylate, variations or derivatives thereof, copolymers thereof, or any combination thereof. In a particular example, the hydrophilic monomer is an acrylamide, such as an acrylamide functionalized to include hydroxyl groups, amino groups, carboxyl groups, halogen groups, or a combination thereof. In an example, the hydrophilic monomer is an aminoalkyl acrylamide, an acrylamide functionalized with an amine terminated polypropylene glycol (D, illustrated below), an acrylopiperazine (C, illustrated below), or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide (A, illustrated below), N-(hydroxymethyl)acrylamide (B, illustrated below), or a combination thereof. In another example, the a comonomer can include a halogen modified acrylate or acrylamide, such as a N-(5-bromoacetamidylpentyl)acrylamide (BRAPA, E, illustrated below). In another example, a comonomer can include an oligonucleotide modified acrylate or acrylamide monomer. In a further example, a mixture of monomers, such as a mixture of hydroxyalky acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1. In another example, the amine functionalize acrylamide can be included in a ratio of hydroxyalkyl acrylamide:bromine functionalized acrylamide or acrylamide:bromine functionalized acrylamide in a range of 100:1 to 1:1, such as a range of 100:1 to 2:1, a range of 50:1 to 3:1, a range of 50:1 to 5:1 or even a range of 50:1 to 10:1.

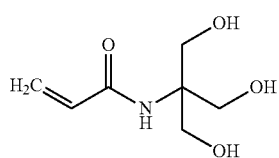

A

-continued

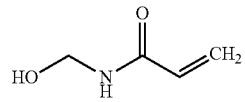

B

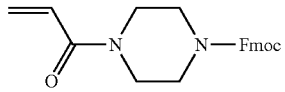

C

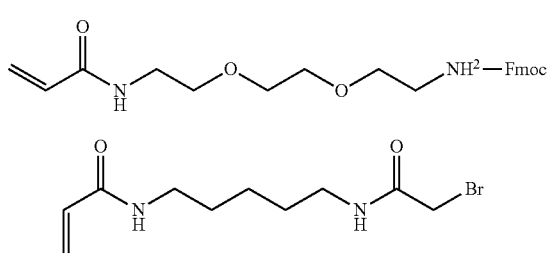

D

E

In a further example, an oligonucleotide functionalized acrylamide or acrylate monomer, such as an Acrydite™ monomer, can be included to incorporate oligonucleotides into the polymer matrix.

Another exemplary matrix precursor includes a crosslinker. In an example, the crosslinker is included in a mass ratio of monomer to crosslinker in a range of 15:1 to 1:2, such as a range of 10:1 to 1:1, a range of 6:1 to 1:1, or even a range of 4:1 to 1:1. In particular, the crosslinker can be a divinyl crosslinker. For example, a divinyl crosslinker can include a diacrylamide, such as N,N'-(ethane-1,2-diyl)bis(2-hydroxyl ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a protected derivative thereof, or a combination thereof.

In one example, polymer networks comprise polyacrylamide gels with total monomer percentages in the range of from 3-20 percent, and more preferably, in the range of from 5 to 10 percent. In one embodiment, crosslinker percentage of monomers is in the range of from 5 to 10 percent. In a particular embodiment, polymer networks comprise 10 percent total acrylamide of which 10 percent is bisacrylamide crosslinker.

Polymerization can be initiated by an initiator within the solution. For example, the initiator can be a water-based. In another example, the initiator can be a hydrophobic initiator, preferentially residing in a hydrophobic phase. An exemplary initiator includes ammonium persulfate or TEMED (tetramethylethylenediamine). TEMED can accelerate the rate of formation of free radicals from persulfate, in turn catalyzing polymerization. The persulfate free radicals, for example, convert acrylamide monomers to free radicals which react with unactivated monomers to begin the polymerization chain reaction. The elongating polymer chains can be randomly crosslinked, resulting in a gel with a characteristic porosity which depends on the polymerization conditions and monomer concentrations. Riboflavin (or riboflavin-5'-phosphate) can also be used as a source of free radicals, often in combination with TEMED and ammonium persulfate. In the presence of light and oxygen, riboflavin is converted to its leuco form, which is active in initiating polymerization, which is usually referred to as photochemical polymerization.

In another example, an azo initiator can be used to initiate polymerization. Exemplary water soluble azo initiators are illustrated in Table 1 and exemplary oil soluble azo initiators are illustrated in Table 2. In particular, the azo initiator can be azobisisobutyronitrile (AIBN).

TABLE I

Water Soluble Azo Initiator Compounds

| Structure | 10 hour half-life decomposition temperature |
|---|---|
| 4,4'-bis(4,5-dihydro-1H-imidazol-2-yl)-2,2'-azobis(2-methylpropane) · 2HCl | 44° C. |
| 4,4'-bis(4,5-dihydro-1H-imidazol-2-yl)-2,2'-azobis(2-methylpropane) · 2H$_2$SO$_4$ · 2H$_2$O | 47° C. |
| 2,2'-azobis(2-methylpropionamidine) · 2HCl | 56° C. |
| 2,2'-azobis[N-(2-carboxyethyl)-2-methylpropionamidine] · 4H$_2$O | 57° C. |
| 2,2'-azobis[2-(1-(2-hydroxyethyl)-4,5-dihydro-1H-imidazol-2-yl)propane] · 2HCl | 60° C. |
| 2,2'-azobis[2-(4,5-dihydro-1H-imidazol-2-yl)propane] | 61° C. |
| 2,2'-azobis[2-methyl-N-(pyrrolidin-1-yl)propionamidine] + 2HCl | 67° C. |
| 2,2'-azobis{2-methyl-N-[1,1-bis(hydroxymethyl)-2-hydroxyethyl]propionamide} | 80° C. |
| 2,2'-azobis[2-methyl-N-(2-hydroxyethyl)propionamide] | 87° C. |

TABLE II

Oil Soluble Azo Initiator Compounds

| Structure | 10 hour half-life decomposition temperature |
|---|---|
| (structure 1) | 30° C. |
| (structure 2) | 51° C. |
| (structure 3) | 66° C. |
| (structure 4) | 67° C. |
| (structure 5) | 88° C. |
| (structure 6) | 96° C. |
| (structure 7) | 104° C. |
| (structure 8) | 110° C. |
| (structure 9) | 111° C. |

In a further example, precursors to the polymer matrix can include surface reactive additives to enhance binding with surface. Exemplary additives include functionalize acrylic monomers or functionalized acrylamide monomers. For example, an acrylic monomer can be functionalized to bind with a surface material, such as a ceramic material forming the bottom or sidewall of a well. In an example, the additive can include an acryl-phosphonate, such as methacrylphosphonate. In another example, the additive can include dimethylacrylamide or polydimethylacrylamide. In a further example, the additive can include a polylysine modified with polymerizable groups, such as acrylate groups.

In another example, polymerization can be facilitated using an atom transfer radical polymerization (ATRP). The ATRP system can include an initiator, a transition metal ion, and a ligand. An exemplary transition metal ion complex includes a copper-based complex. An exemplary ligand includes 2,2'-bipyridine, 4,4'-di-5-nonyl-2,2'-bipyridine, 4,4',4"-tris(5-nonyl)-2,2':6',2"-terpyridine, N,N,N',N',N"-pentamethyldiethylenetriamine, 1,1,4,7,10,10-hexamethyl-triethylenetetramine, tris(2-dimethylaminoethyl)amine, N,N-bis(2-pyridylmethyl)octadecylamine, N,N,N',N'-tetra[(2-pyridyl)methyl]ethylenediamine, tris[(2-pyridyl)methyl]amine, tris(2-aminoethyl)amine, tris(2-bis(3-butoxy-3-oxopropyl)aminoethyl)amine, tris(2-bis(3-(2-ethylhexoxy)-3-oxopropyl)aminoethyl)amine, tris(2-bis(3-dodecoxy-3-oxopropyl)aminoethyl)amine, variations and derivatives thereof, or combinations thereof. An exemplary initiator includes 2-bromopropanitrile, ethyl 2-bromoisobutyrate, ethyl 2-bromopropionate, methyl 2-bromopropionate, 1-phenyl ethylbromide, tosyl chloride, 1-cyano-1-methyl-ethyldiethyldithiocarbamate, 2-(N,N-diethyldithiocarbamyl)-isobutyric acid ethyl ester, dimethyl 2,6-dibromo-heptanedioate, variations or derivatives thereof, or any combination thereof. Optionally, the BRAPA monomer can function as a branching agent in the presence of an ATRP system.

In an example, ATRP is initiated at a surface to directly bond the polymer to the surface. For example, acrylate monomers, acrylamide monomers, Acrydite™ monomers, succinimidyl acrylates, bis-acrylate or bis-acrylamide monomers, derivatives thereof, or combinations thereof can be applied in solution to the initiated surface in the presence of a transition metal ion/ligand complex.

In another, the ATRP system can be used to attach a polymer to a surface of the well using a modified phosphonate, sulfonate, silicate, or zirconate compounds. In particular, an amine or hydroxyl terminated alkyl phosphonate or an alkoxy derivative thereof can be applied to a surface and initiated using an initiator. The catalyst complex and monomers can be applied, extending the surface compound.

In an exemplary method, an aqueous solution including precursors to the polymer matrix can be applied into wells of the structure defining an array of wells. The aqueous solution in the wells can be isolated by providing an immiscible fluid over the wells and initiating polymerization of the polymer precursors within the solution within the wells.

Figure 18:
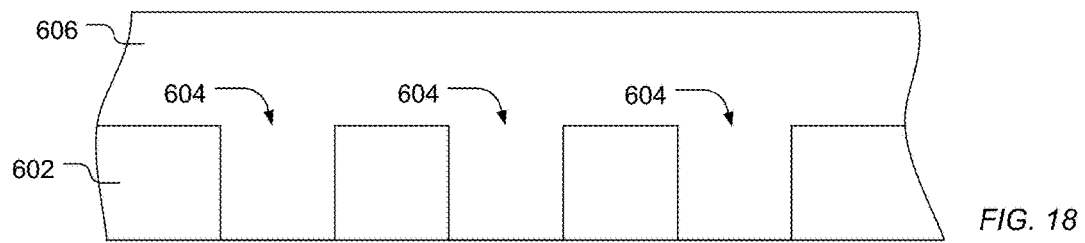

For example, FIG. 18 illustrates an exemplary well structure 602 defining wells 604. One or more sensors (not illustrated) can be operatively coupled or linked to the wells 604. For example, one or more sensors can include gate structures in electrical communication to at least the bottom surface of the wells 604. An aqueous solution 606 that includes polymer precursors, among other components, is provided over the wells and distributes the solution including the polymer precursors into the wells 604. Exemplary polymer precursors include monomers, crosslinkers, initiators, or surface reactive agents, among others, such as described above. Optionally, the wells 604 can be wet prior to deposition using a hydrophilic solution, such as a solution including water, alcohol, or mixtures thereof, or a solution including water and a surfactant. An exemplary alcohol includes isopropyl alcohol. In another example, the alcohol includes ethanol. While not illustrated, the bottom surface of the well and optionally the sidewall of the well can include an ion sensitive material. Such ion sensitive material can overlie conductive structure of an underlying electronic device, such as field effect transistor. One or more surfaces of the well can be treated with a surface reactive additive prior to applying a solution including polymer precursors.

Distributing the aqueous solutions including polymer precursors into the well 604 can be further enhanced by agitating the structure such as through spinning or vortexing. In another example, vibration, such as sonic or supersonic vibrations, can be used to improve distribution of the aqueous solution within the wells 604. In a further example, the wells can be degassed using a vacuum and the solutions applied while under a negative gauge pressure. In an example, the aqueous solution is distributed to wells at room temperature. In another example, the aqueous solution is distributed at a temperature below room temperature, particularly when an aqueous-based initiator is used. Alternatively, the aqueous solution is distributed at an elevated temperature.

Figure 19:
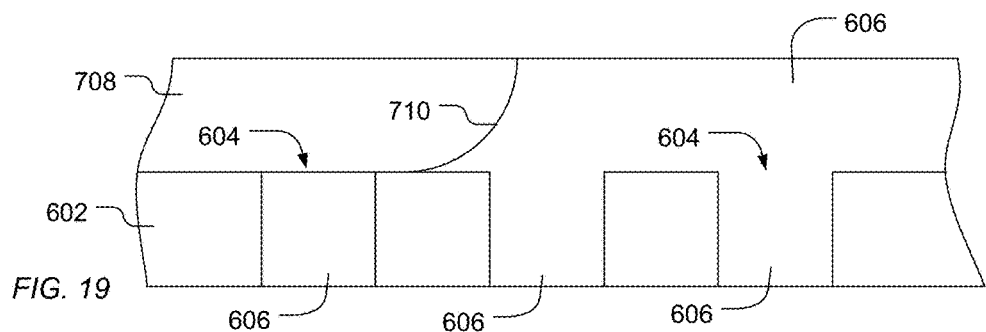
Figure 20:
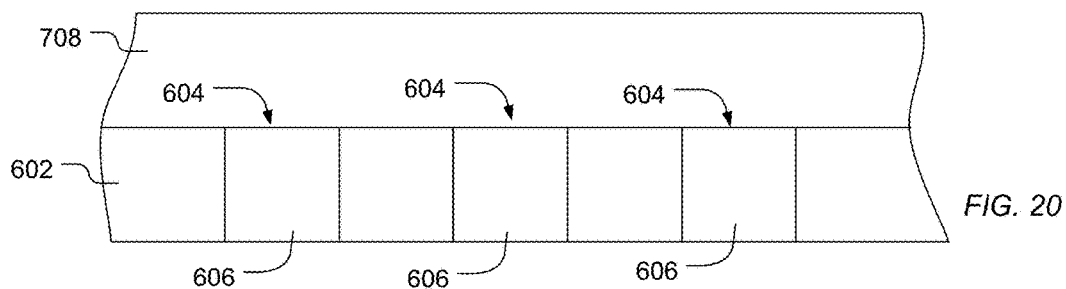

As illustrated in FIG. 19, an immiscible fluid 708 is applied over the well 604 pushing the aqueous solution 606 away from the top of the wells and isolating the aqueous solution 606 within the wells 604, as illustrated in FIG. 20. An exemplary immiscible fluid includes mineral oil, silicone oil (e.g., poly(dimethylsiloxane)), heptane, carbonate oils (e.g. diethylhexyl carbonate (Tegosoft DEC®), or combinations thereof.

Initiators can be applied within the aqueous solution 606. Alternatively, initiators can be provided within the immiscible fluid 708. Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour.

Figure 21:
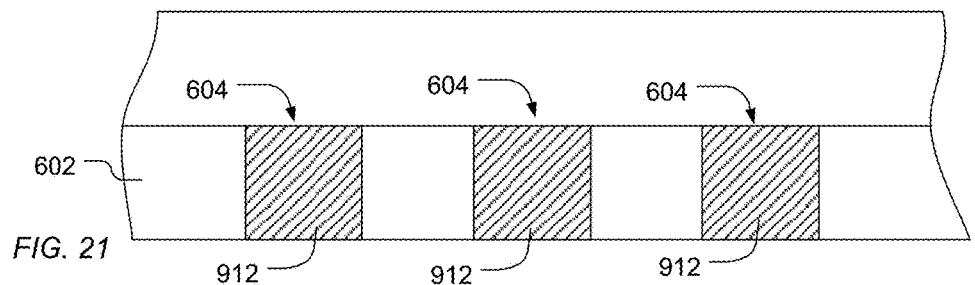

As a result of the polymerization, an array of polymer matrices 912 are formed within the wells 604 defined by the well structure 602, as illustrated in FIG. 21. Optionally, the array can be washed with NaOH (e.g., 1 N NaOH) to remove polymer from interstitial areas between wells.

In an alternative example, an emulsion including an aqueous solution of polymer precursors as a dispersed phase within an immiscible fluid can be used to deposit droplets of aqueous solution within wells. For example, as illustrated in FIG. 22, a well structure 1002 defines wells 1004. The wells can be operatively coupled or electrically linked to one or more sensors (not illustrated). As described above, the bottom surface and optionally side surfaces of the walls of the wells 1004 can be defined by ion sensitive material layers which can overlie conductive features of underlying electronic devices.

An emulsion 1006 can include dispersed aqueous droplets 1008 that include polymer precursors within a continuous immiscible fluid 1010. The droplets 1008 can settle into the wells 1004. In particular, the aqueous droplets 1008 have a density greater than the immiscible fluid 1010. An exemplary immiscible fluid includes mineral oil, silicone oil (e.g., poly(dimethylsiloxane)) heptanes, carbonate oils (e.g. diethylhexyl carbonate (Tegosoft DEC®), or combinations thereof. In a further example, distribution of the aqueous droplets into wells 1004 can be facilitated by spinning, vortexing, or sonicating the fluid or structures. Optionally, the wells 604 can be wet prior to deposition using a hydrophilic solution, such as a solution including water, alcohol, or mixtures thereof, or a solution including water and a surfactant. The temperature during distribution of the droplets into wells can be performed at room temperature. Alternatively, the distribution can be performed at an elevated temperature.

As illustrated in FIG. 23, the droplets coalesce within the wells 1004 to provide isolated solutions including polymer precursors 1112. Optionally, the emulsion 1006 can be replaced with an immiscible fluid, such as the immiscible fluid 1010 without droplets 1008 or a different immiscible fluid 1116. An exemplary immiscible fluid includes mineral oil, silicone oil (e.g., poly(dimethylsiloxane)) heptanes, carbonate oils (e.g. diethylhexyl carbonate (Tegosoft DEC®), or combinations thereof. Alternatively, the emulsion 1006 can remain in place during polymerization. As such, the solutions 1112 within the wells 1004 are isolated from the solution in other wells 1004. Polymerization can be initiated resulting in a polymer matrix 1214 within the wells 1004, as illustrated at FIG. 24. As above, polymerization can be initiated thermally. In another example, polymerization can be initiated using an oil phase initiator. Alternatively, polymerization can be initiated using an aqueous phase initiator. In particular, a second emulsion can be applied over the wells 1004. The second emulsion can include a dispersed aqueous phase including aqueous phase initiator.

Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour. Optionally, the array can be washed with NaOH (e.g., 1 N NaOH) to remove polymer from interstitial areas between wells.

In another example, an array of matrix material can be formed within wells of a well array using initiators secured to the surface of the well array. For example, as illustrated in FIG. 25, a structure 1302 can define wells 1304. A material layer 1306 can define a lower surface of the wells 1304. Anchoring compounds 1308, such as anchoring compounds useful in Atom Transfer Radical Polymerization (ATRP), can be secured to the material layer 1306 defining a bottom surface of the wells 1304. Alternatively, a sidewall material defined within the wells or layers of the structure 1302 expose within the wells 1304 can anchor compounds such as compounds useful in ATRP, as described above.

In such an example, a solution 1310 including polymer precursors such as monomers, crosslinkers, and optionally surface reactive additive, can be applied over the structure 1302 and within the wells 1304. The anchoring compounds 1308 can be initiated to facilitate polymerization extending from the anchoring compound, isolating the polymerization within the wells 1304 and securing the polymer to the well 1304. In an example, the anchoring compound has a surface reactive group and a distal radical-forming group. The surface reactive group can include a phosphonate, a silicate, a sulfonate, a zirconate, titanate or a combination thereof. The distal radical-forming group can include an amine or hydroxyl that can undergo transfer, for example, with a halogenated (e.g., bromilated) compound and subsequently form a free-radical for use in polymerizing the polymer precursors and anchoring the resulting polymer to a well surface. Typically, an ATRP system can be selected to terminate polymerization after a statistical average length or number of monomer additions. In such a manner, the amount polymerization within a well 1304 can be controlled. In a further example, other agents influencing chain extension or termination can be applied and added to the aqueous solution 1310.

In another example illustrated in FIG. 26, a structure 1402 can define wells 1404. The wells 1404 can include a material layer 1406 that extends along sidewalls 1410 of the structure 1402 and wells 1404. The initiator 1408 can be secured to the material layer 1406 along the bottom of the well 1404 and along the sidewalls 1410. A solution 1412 including polymer precursors, crosslinkers, and other agents can be applied over the structure 1402 and the wells 1404.

As illustrated in FIG. 27, polymer matrices 1512 are formed as a result of the initiated polymerization extending from surfaces within the wells 1304, such as surfaces defined by the material layer 1306.

Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour.

Once formed, the polymer matrices can be activated to facilitate conjugation with a target analyte, such as a polynucleotide. For example, functional groups on the polymer matrices can be enhanced to permit binding with target analytes or analyte receptors (e.g., oligonucleotide primers). In a particular example, functional groups of the hydrophilic polymer matrix can be modified with reagents capable of converting the hydrophilic polymer functional groups to reactive moieties that can undergo nucleophilic or electrophilic substitution. For example, hydroxyl groups on the polymer matrices can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate can further react with liberated chlorine to provide chlorinated functional groups that can be used in a process to conjugate the matrix. In another example, amine groups on the polymer matrices can be activated.

For example, target analyte or analyte receptors can bind to the hydrophilic polymer through nucleophilic substitution with the sulfonate group. In particular example, target analyte receptors terminated with a nucleophile, such as an amine or a thiol, can undergo nucleophilic substitution to replace the sulfonate groups in the polymer matrices. As a result of the activation, conjugated polymer matrices can be formed.

In another example, the sulfonated polymer matrices can be further reacted with mono- or multi-functional mono- or multi-nucleophilic reagents that can form an attachment to the matrix while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to oligonucleotides comprising nucleophilic groups.

In another example, a monomer containing the functional group can be added during the polymerization. The monomer can include, for example, an acrylamide containing a carboxylic acid, ester, halogen or other amine reactive group. The ester group can be hydrolyzed before the reaction with an amine oligo.

Other conjugation techniques include the use of monomers that comprise amines. The amine group is a nucleophilic group that can be further modified with amine reactive bi-functional bis-electrophilic reagents that yield a monofunctional electrophilic group subsequent to attachment to the polymer matrix. Such an electrophilic group can be reacted with oligonucleotides having a nucleophilic group, such as an amine or thiol, causing attachment of the oligonucleotide by reaction with the vacant electrophile.

If the polymer matrix is prepared from a combination of amino- and hydroxyl-acrylamides, the polymer matrix includes a combination of nucleophilic amino groups and neutral hydroxyl groups. The amino groups can be modified with di-functional bis-electrophilic moieties, such as a di-isocyanate or bis-NHS ester, resulting in a hydrophilic polymer matrix reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the matrix via sulfonate activation. For example, reaction of sulfonated matrices with thiobenzoic acid anion and hydrolysis of the consequent thiobenzoate incorporates a thiol into the matrix which can be subsequently reacted with a maleimide substituted biomolecule to yield a thio-succinimide linkage to the biomolecule.

Thiol can also be reacted with a bromo-acetyl group or bromo-amidyl group. In a particular example, when n-(5-bromoacetamidylpentyl)acrylamide (BRAPA) is included as a comonomer, oligonucleotides can be incorporated by forming a thiobenzamide-oligonucleotide compound, for example, as illustrated below, for reacting with bromo-acetyl groups on the polymer.

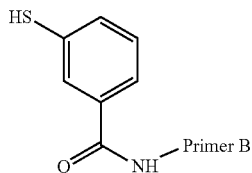

The thiobenzamide-oligonucleotide compound can be formed by reacting the following dithiobenzoate-NHS compound with an amine terminated oligonucleotide and activating the dithiobenzamide-oligonucleotide compound to form the above illustrated thiobenzamide-oligonucleotide compound.

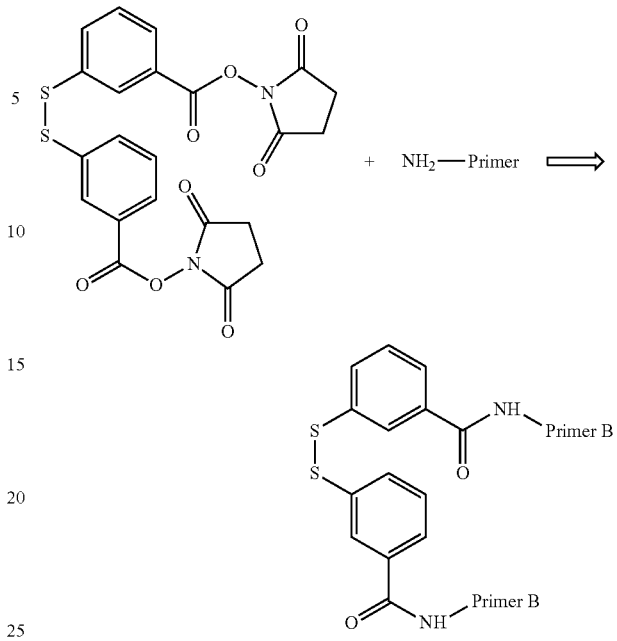

Alternatively, acrydite oligonucleotides can be used during the polymerization to incorporate oligonucleotides. An exemplary acrydite oligonucleotide can include an ion-exchanged oligonucleotide.

Covalent linkages of biomolecules onto refractory or polymeric substrates can be created using electrophilic moieties on the substrate coupled with nucleophilic moieties on the biomolecule or nucleophilic linkages on the substrate coupled with electrophilic linkages on the biomolecule. Because of the hydrophilic nature of most common biomolecules of interest, the solvent of choice for these couplings is water or water containing some water soluble organic solvent in order to disperse the biomolecule onto the substrate. In particular, polynucleotides are generally coupled to substrates in water systems because of their poly-anionic nature. Because water competes with the nucleophile for the electrophile by hydrolyzing the electrophile to an inactive moiety for conjugation, aqueous systems can result in low yields of coupled product, where the yield is based on the electrophilic portion of the couple. When high yields of electrophilic portion of the reaction couple are desired, high concentrations of the nucleophile drive the reaction and mitigate hydrolysis, resulting in inefficient use of the nucleophile. In the case of polynucleic acids, the metal counter ion of the phosphate can be replaced with a lipophilic counterion, in order to help solubilize the biomolecule in polar, non-reactive, non-aqueous solvents. These solvents can include amides or ureas such as formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof; carbonates such as dimethyl carbonate, propylene carbonate, or a combination thereof; ethers such as tetrahydrofuran; sulfoxides and sulfones such as dimethylsulfoxide, dimethylsulfone, or a combination thereof; hindered alcohols such as tert-butyl alcohol; or a combination thereof. Lipophilic cations can include tetraalkylammomiun or tetraarylammonium cations such as tetramethylamonium, tetraethylamonium, tetrapropylamonium, tetrabutylamonium, tetrapentylamonium, tetrahexylamonium, tetraheptylamonium, tetraoctylamonium, and alkyl and aryl mixtures thereof, tetraarylphosphonium cations such as tetraphenylphosphonium, tetraalkylarsonium or tetraarylarsonium such as tetraphenylarsonium, and trialkylsulfonium cations such as trimethylsulfonium, or a combination thereof. The conversion of polynucleic acids into organic solvent soluble materials by exchanging metal cations with lipophilic cations can be performed by a variety of standard cation exchange techniques.

In a particular embodiment, the polymer matrices are exposed to target polynucleotides having a segment complementary to oligonucleotides conjugated to the polymer matrices. The polynucleotides are subjected to amplification, such as through polymerase chain reaction (PCR) or recombinase polymerase amplification (RPA). For example, the target polynucleotides are provided in low concentrations such that a single polynucleotide is likely to reside within a single polymer matrix of the array of polymer matrices. The polymer matrix can be exposed to enzymes, nucleotides, salts or other components sufficient to facilitate duplication of the target polynucleotide.

In a particular embodiment, an enzyme such as a polymerase is present, bound to, or is in close proximity to the polymer matrix. A variety of nucleic acid polymerase can be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

In some embodiments, methods for distributing a single target polynucleotide into the reaction chamber and amplifying the single target polynucleotide comprise a nucleic acid amplification reaction. In some embodiments, any type of nucleic acid amplification reaction can be conducted including polymerase chain reaction (PCR) (U.S. Pat. Nos. 4,683,195 and 4,683,202 both granted to Mullis), ligase chain reaction (LCR) (Barany 1991 Proceedings National Academy of Science USA 88:189-193; Barnes 1994 Proceedings National Academy of Science USA91:2216-2220), helicase-dependent amplification (HDA) or isothermal self-sustained sequence reaction (Kwoh 1989 Proceedings National Academy of Science USA 86:1173-1177; WO 1988/10315; and U.S. Pat. Nos. 5,409,818, 5,399,491, and 5,194,370).

In some embodiments, the amplification reaction includes recombinase polymerase amplification (RPA). (See, e.g., U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, methods for distributing a single target polynucleotide into the reaction chamber and amplifying the single target polynucleotide comprise an isothermal amplification condition. In some embodiments, a nucleic acid amplification reaction can be conducted under isothermal conditions. In some embodiments isothermal amplification conditions comprise a nucleic acid amplification reaction subjected to a temperature variation which is constrained within a limited range during at least some portion of the amplification, including for example a temperature variation is within about 20° C., or about 10° C., or about 5° C., or about 1-5° C., or about 0.1-1° C., or less than about 0.1° C. In some embodiments, a nucleic acid amplification reaction can be conducted under isothermal or thermal-cycling conditions.

In some embodiments, an isothermal nucleic acid amplification reaction can be conducted for about 2, 5, 10, 15, 20, 30, 40, 50, 60 or 120 minutes.

In some embodiments, an isothermal nucleic acid amplification reaction can be conducted at about 15-25° C., or about 25-35° C., or about 35-40° C., or about 40-45° C., or about 45-50° C., or about 50-55° C., or about 55-60° C.

In some embodiments, nucleic acids that have been amplified according to the present teachings can be used in any nucleic acid sequencing workflow, including sequencing by oligonucleotide probe ligation and detection (e.g., SOLiD™ from Life Technologies, WO 2006/084131), probe-anchor ligation sequencing (e.g., Complete Genomics™ or Polonator™), sequencing-by-synthesis (e.g., Genetic Analyzer and HiSeg™, from Illumina), pyrophosphate sequencing (e.g., Genome Sequencer FLX from 454 Life Sciences), ion-sensitive sequencing (e.g., Personal Genome Machine (PGM™) and Ion Proton™ Sequencer, both from Ion Torrent Systems, Inc.), and single molecule sequencing platforms (e.g., HeliScope™ from Helicos™).

In some embodiments, nucleic acid that have been amplified according to the present teachings can be sequenced by any sequencing method, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrophosphate detection sequencing, capillary electrophoresis, gel electrophoresis, next-generation, massively parallel sequencing platforms, sequencing platforms that detect hydrogen ions or other sequencing by-products, and single molecule sequencing platforms. In some embodiments, a sequencing reaction can be conducted using at least one sequencing primer that can hybridize to any portion of the polynucleotide constructs, including a nucleic acid adaptor or a target polynucleotide.

In some embodiments, nucleic acid amplified according to the present teachings can be sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286(2006); Esfandyapour et al., U.S. Patent Publication No. 2008/01666727; and Sakurai et al., Anal. Chem. 64: 1996-1997 (1992).

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced can be captured in a microwell, and nucleotides can be flowed across the well, one at a time, under nucleotide incorporation conditions. The polymerase incorporates the appropriate nucleotide into the growing strand, and the hydrogen ion that is released can change the pH in the solution, which can be detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion Torrent PGM™ or Proton™ sequencer (Ion Torrent™ Systems, Life Technologies Corporation).

In some embodiments, target polynucleotides produced using the methods, systems and kits of the present teachings can be used as a substrate for a biological or chemical reaction that is detected and/or monitored by a sensor including a field-effect transistor (FET). In various embodiments the FET is a chemFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise 102, 103, 104, 105, 106, 107 or more FETs.

In some embodiments, one or more microfluidic structures can be fabricated above the FET sensor array to provide for containment and/or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there can be a 1:1 correspondence of FET sensors and reaction wells.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction can be performed in a solution or a reaction chamber that is in contact with, operatively coupled, or capacitively coupled to a FET such as a chemFET or an ISFET. The FET (or chemFET or ISFET) and/or reaction chamber can be an array of FETs or reaction chambers, respectively.

In some embodiments, a biological or chemical reaction can be carried out in a two-dimensional array of reaction chambers, wherein each reaction chamber can be coupled to a FET, and each reaction chamber is no greater than 10 μm$^3$ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^2$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 20100301398; U.S. Patent Publication No. 20100300895; U.S. Patent Publication No. 20100300559; U.S. Patent Publication No. 20100197507, U.S. Patent Publication No. 20100137143; U.S. Patent Publication No. 20090127589; and U.S. Patent Publication No. 20090026082, which are incorporated by reference in their entireties.

In one aspect, the disclosed methods, compositions, systems, apparatuses and kits can be used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion Torrent PGM™ or Proton™ sequencer (Ion Torrent™ Systems, Life Technologies Corporation).

In some embodiments, the disclosure relates generally to methods for sequencing nucleic acids that have been amplified by the teachings provided herein. In one exemplary embodiment, the disclosure relates generally to a method for obtaining sequence information from polynucleotides, comprising: (a) amplifying nucleic acids; and (b) performing template-dependent nucleic acid synthesis using at least one of the amplified nucleic acids produced during step (a) as a template. The amplifying can optionally be performed according to any of the amplification methods described herein.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, the disclosure relates generally to a method for sequencing a nucleic acid, comprising: (a) amplifying nucleic acids according to the methods disclosed herein; (b) disposing the amplified nucleic acids into a plurality of reaction chambers, wherein one or more of the reaction chambers are in contact with a field effect transistor (FET). Optionally, the method further includes contacting amplified nucleic acids which are disposed into one of the reaction chambers, with a polymerase thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET can be selected from the group consisting of: ion-sensitive FET (isFET) and chemically-sensitive FET (chemFET).

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

FIG. 28 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors as described herein. The flow cell 101 includes an inlet 102, an outlet 103, and a flow chamber 105 defining a flow path of reagents over the microwell array 107.

The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes an array of reaction regions as described herein, also referred to herein as microwells, which are operationally associated with corresponding chemical sensors in the sensor array. For example, each reaction region may be coupled to a chemical sensor suitable for detecting an analyte or reaction property of interest within that reaction region. The microwell array 107 may be integrated in the integrated circuit device 100, so that the microwell array 107 and the sensor array are part of a single device or chip.

The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array. The array controller 124 also provides a reference bias voltage to the reference electrode 108 to bias the reagents 114 flowing over the microwell array 107.

During an experiment, the array controller 124 collects and processes output signals from the chemical sensors of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 28.

The values of the output signals of the chemical sensors indicate physical and/or chemical parameters of one or more reactions taking place in the corresponding reaction regions in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

The user interface 128 may display information about the flow cell 101 and the output signals received from chemical sensors in the sensor array on the integrated circuit device 100. The user interface 128 may also display instrument settings and controls, and allow a user to enter or set instrument settings and controls.

In an exemplary embodiment, during the experiment the fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors indicating chemical reactions occurring in response to the delivery of the reagents 114.

During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

FIG. 29 illustrates cross-sectional and expanded views of a portion of the integrated circuit device 100 and flow cell 101. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed.

The chemical sensors of the sensor array 205 are responsive to (and generate output signals) chemical reactions within associated reaction regions in the microwell array 107 to detect an analyte or reaction property of interest. The chemical sensors of the sensor array 205 may for example be chemically sensitive field-effect transistors (chemFETs), such as ion-sensitive field effect transistors (ISFETs). Examples of chemical sensors and array configurations that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

FIG. 30 illustrates a cross-sectional view of two representative chemical sensors and their corresponding reaction regions according to an exemplary embodiment. In FIG. 30, two chemical sensors 350, 351 are shown, representing a small portion of a sensor array that can include millions of chemical sensors. In some embodiments, the sensor array can include at least 1 million chemical sensors and optionally at least 1 million corresponding reaction regions, at least 10 million chemical sensors and optionally at least 10 million corresponding reaction regions, at least 100 million chemical sensors and optionally at least 100 million corresponding reaction regions, at least 500 million chemical sensors and optionally at least 500 million corresponding reaction regions, or even at least 1 billion chemical sensors and optionally at least 1 billion corresponding reaction regions.

Chemical sensor 350 is coupled to corresponding reaction region 301, and chemical sensor 351 is coupled to corresponding reaction region 302. Chemical sensor 350 is representative of the chemical sensors in the sensor array. In the illustrated example, the chemical sensor 350 is an ion-sensitive field effect transistor. The chemical sensor 350 includes a floating gate structure 318 having a floating gate conductor (referred to herein as the sensor plate 320) separated from the reaction region 301 by sensing material 316. As shown in FIG. 30, the sensor plate 320 is the uppermost patterned layer of conductive material in the floating gate structure 318 underlying the reaction region 301.

In the illustrated example, the floating gate structure 318 includes multiple patterned layers of conductive material within layers of dielectric material 319. As described in more detail below, the upper surface of the sensing material 316 acts as the sensing surface 317 for the chemical sensor 350.

In the illustrated embodiment, the sensing material 316 is an ion-sensitive material, such that the presence of ions or other charged species in a solution in the reaction region 301 alters the surface potential of the sensing surface 317. The change in the surface potential is due to the protonation or deprotonation of surface charge groups at the sensing surface caused by the ions present in the solution. The sensing material 316 may be deposited using various techniques, or naturally formed during one or more of the manufacturing processes used to form the chemical sensor 350. In some embodiments, the sensing material 316 is a metal oxide, such as an oxide of silicon, tantalum, aluminum, lanthanum, titanium, zirconium, hafnium, tungsten, palladium, iridium, etc.

In some embodiments, the sensing material 316 is an oxide of the upper layer of conductive material of the sensor plate 320. For example, the upper layer of the sensor plate 320 may be titanium nitride, and the sensing material 316 may comprise titanium oxide or titanium oxynitride. More generally, the sensing material 316 may comprise one or more of a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas sensing materials comprising polyvinyl chloride containing valinomycin provide sensitivity to potassium ions. Materials sensitive to other ions such as sodium, silver, iron, bromine, iodine, calcium, and nitrate may also be used, depending upon the implementation.

The chemical sensor 350 also includes a source region 321 and a drain region 322 within a semiconductor substrate 354. The source region 321 and the drain region 322 comprise doped semiconductor material have a conductivity type different from the conductivity type of the substrate 354. For example, the source region 321 and the drain region 322 may comprise doped P-type semiconductor material, and the substrate may comprise doped N-type semiconductor material.

Channel region 323 separates the source region 321 and the drain region 322. The floating gate structure 318 overlies the channel region 323, and is separated from the substrate 354 by a gate dielectric 352. The gate dielectric 352 may be for example silicon dioxide. Alternatively, other dielectrics may be used for the gate dielectric 352.

As shown in FIG. 30, the reaction region 301 extends through a fill material 310 on the dielectric material 319. The fill material 310 may for example comprise one or more layers of dielectric material, such as silicon dioxide or silicon nitride.

The dimensions (e.g. the width and depth) of the reaction regions 301, 302, and their pitch (the center-to-center distance between adjacent reaction regions), can vary from implementation to implementation. In some embodiments, the reaction regions can have a characteristic diameter, defined as the square root of 4 times the plan view cross-sectional area (A) divided by Pi (e.g., sqrt(4*A/$\pi$), of not greater than 5 micrometers, such as not greater than 3.5 micrometers, not greater than 2.0 micrometers, not greater than 1.6 micrometers, not greater than 1.0 micrometers, not greater than 0.8 micrometers, not greater than 0.6 micrometers, not greater than 0.4 micrometers, not greater than 0.2 micrometers or even not greater than 0.1 micrometers.

In some embodiments, the pitch between adjacent reaction regions is not greater than 10 micrometers, not greater than 5 micrometers, not greater than 2 micrometers, not greater than 1 micrometer, or even not greater than 0.5 micrometers.

In the illustrated embodiment, the reaction regions 301, 302 are separated by a distance that that is equal to their width. Alternatively, the separation distance between adjacent reaction regions may be less than their width. For example, the separation distance may be a minimum feature size for the process (e.g. a lithographic process) used to form the reaction regions 301, 302. In such a case, the separation distance may be significantly less than the width of individual reaction regions.

The sensor plate 320, the sensing material 316 and the reaction region 301 may for example have circular cross-sections. Alternatively, these may be non-circular. For example, the cross-section may be square, rectangular, hexagonal, or irregularly shaped.

The device in FIG. 30 can also include additional elements such as array lines (e.g. word lines, bit lines, etc.) for accessing the chemical sensors, additional doped regions in the substrate 354, and other circuitry (e.g. access circuitry, bias circuitry etc.) used to operate the chemical sensors, depending upon the device and array configuration in which the chemical sensors described herein are implemented. In some embodiments, the device may for example be manufactured using techniques described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

In operation, reactants, wash solutions, and other reagents may move in and out of the reaction region 301 by a diffusion mechanism 340. The chemical sensor 350 is responsive to (and generates an output signal related to) the amount of a charge 324 present on the sensing material 316 opposite the sensor plate 320. Changes in the charge 324 cause changes in the voltage on the floating gate structure 318, which in turn changes in the threshold voltage of the transistor. This change in threshold voltage can be measured by measuring the current in the channel region 323 between the source region 321 and a drain region 322. As a result, the chemical sensor 350 can be used directly to provide a current-based output signal on an array line connected to the source region 321 or drain region 322, or indirectly with additional circuitry to provide a voltage-based output signal.

In an embodiment, reactions carried out in the reaction region 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, multiple copies of the same analyte may be analyzed in the reaction region 301 at the same time in order to increase the output signal generated. In an embodiment, multiple copies of an analyte may be attached to a solid phase support 312, either before or after deposition into the reaction region 301. The solid phase support 312 may be microparticles, nanoparticles, beads, solid or porous comprising gels, or the like. For simplicity and ease of explanation, solid phase support 312 is also referred herein as a particle. For a nucleic acid analyte, multiple, connected copies may be made by rolling circle amplification (RCA), exponential RCA, Recombinase Polymerase Amplification (RPA), Polymerase Chain Reaction amplification (PCR), emulsion PCR amplification, or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of nucleotide addition (which may be referred to herein as "nucleotide flows" from which nucleotide incorporations may result) and washing. The primer may be annealed to the sample or template so that the primer's 3' end can be extended by a polymerase whenever nucleotides complementary to the next base in the template are added.

Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a chemical sensor can be determined.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the templates, optionally bound to a polymerase, are distributed, deposited or positioned to different sites of the array. The site of the array include primers and the methods can include hybridizing different templates to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction can be exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing can be performed according to the user protocols supplied with the PGM™ or Proton™ sequencer. Example 3 provides one exemplary protocol for ion-based sequencing using the Ion Torrent PGM™ sequencer (Ion Torrent™ Systems, Life Technologies, CA).

In some embodiments, the disclosure relates generally to methods for sequencing a population of template polynucleotides, comprising: (a) generating a plurality of amplicons by clonally amplifying a plurality of template polynucleotides onto a plurality of surfaces, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal in nature. In some embodiments, a sufficient number of substantially monoclonal amplicons are produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the present teachings provide systems for nucleic acid amplification, comprising any combination of: beads attached with a plurality of a first primer, second primer, third primer, polynucleotides, recombinase, recombinase loading protein, single-stranded binding protein (SSB), polymerase, nucleotides, ATP, phosphocreatine, creatine kinase, hybridization solutions, and/or washing solutions. A system can include all or some of these components. In some embodiments, systems for nucleic acid amplification can further comprise any combination of: buffers and/or cations (e.g., divalent cations).

In some embodiments, the present teachings provide kits for nucleic acid amplification. In some embodiments, kits include any reagent that can be used for nucleic acid amplification. In some embodiments, kits include any combination of: beads attached with a plurality of a first primer, second primer, third primer, polynucleotides, recombinase, recombinase loading protein, single-stranded binding protein (SSB), polymerase, nucleotides, ATP, phosphocreatine, creatine kinase, hybridization solutions, washing solutions, buffers and/or cations (e.g., divalent cations). A kit can include all or some of these components.

In some embodiments, the disclosure relates generally to methods, compositions, systems useful for amplifying different nucleic acid templates in parallel in a plurality of compartmentalized reaction volumes, as opposed to amplification within a single continuous liquid phase. For example, the nucleic acid templates can be distributed or deposited into an array of reaction chambers, or an array of reaction volumes, such that at least two such chambers or volumes in the array each receive a single nucleic acid template. In some embodiments, a plurality of separate reaction volumes is formed. The reaction chambers (or reaction volumes) can optionally be sealed prior to amplification. In another embodiment, the reaction mixture can be compartmentalized or separated into a plurality of microreactors dispersed within a continuous phase of an emulsion. The compartmentalized or separate reaction volumes optionally do not mix or communicate, or are not capable of mixing or communicating, with each other. In some embodiments, at least some of the reaction chambers (or reaction volumes) include a recombinase, and optionally a polymerase. The polymerase can be a strand-displacing polymerase.

In some embodiments, the disclosure relates generally to compositions, systems, methods, apparatuses and kits for nucleic acid synthesis and/or amplification including emulsions. As used herein, the term "emulsion" includes any composition including a mixture of a first liquid and a second liquid, wherein the first and second liquids are substantially immiscible with each other. Typically, one of the liquids is hydrophilic while the other liquid is hydrophobic. Typically, the emulsion includes a dispersed phase and a continuous phase. For example, the first liquid can form a dispersed phase that is dispersed in the second liquid, which forms the continuous phase. The dispersed phase is optionally comprised predominantly of the first liquid. The continuous phase is optionally comprised predominantly of the second liquid. In various embodiments, the same two liquids can form different types of emulsions. For example, in a mixture including both oil and water can form, firstly, an oil-in-water emulsion, where the oil is the dispersed phase, and water is the dispersion medium. Secondly, they can form a water-in-oil emulsion, where water is the dispersed phase and oil is the external phase. Multiple emulsions are also possible, including a "water-in-oil-in-water" emulsion and an "oil-in-water-in-oil" emulsion. In some embodiments, the dispersed phase includes one or more microreactors in which nucleic acid templates can be individually amplified. One or more microreactors can form compartmentalized reaction volumes in which separate amplification reactions can occur. One example of a suitable vehicle for nucleic acid amplification includes a water-in-oil emulsion wherein the water-based phase includes several aqueous microreactors that are dispersed within an oil phase of an emulsion. In some embodiments, the emulsion can further include an emulsifier or surfactant. The emulsifier or surfactant can be useful in stabilizing the emulsion under nucleic acid synthesis conditions.

In some embodiments, the disclosure relates generally to a composition comprises an emulsion including a reaction mixture. The emulsion can include an aqueous phase. The aqueous phase can be dispersed in a continuous phase of the emulsion. The aqueous phase can include one or more microreactors. In some embodiments, the reaction mixture is contained in a plurality of liquid phase microreactors within a phase of an emulsion. Optionally, the reaction mixture includes a recombinase. Optionally, the reaction mixture includes a plurality of different polynucleotides. Optionally, the reaction mixture includes a plurality of supports. Optionally, the reaction mixture includes any combination of a recombinase, a plurality of different polynucleotides and/or a plurality of supports. Optionally, at least one of the supports can be attached to a substantially monoclonal nucleic acid population.

In some embodiments, the disclosure relates generally to a composition comprising a reaction mixture, the reaction mixture including (i) a plurality of supports, (ii) a plurality of different polynucleotides and (iii) a recombinase, the reaction mixture contained in a plurality of liquid phase microreactors in an emulsion.

In some embodiments, the disclosure relates generally to a composition comprising a reaction mixture, the reaction mixture including (i) a recombinase and (ii) a plurality of supports, at least one of the supports being attached to a substantially monoclonal nucleic acid population, wherein the reaction mixture is contained in a plurality of liquid phase microreactors in an emulsion.

Optionally, the emulsion includes a hydrophilic phase.

Optionally, the emulsion comprises a hydrophilic phase dispersed in a hydrophobic phase. For example, the emulsion can include a water-in-oil emulsion.

In some embodiments, the hydrophilic phase includes a plurality of microreactors.

Optionally, the reaction mixture is contained in a single reaction vessel.

Optionally, the sequences of the plurality of different polynucleotides can be the same or different.

Optionally, at least one of the plurality of supports is linked to a plurality of first primers (e.g., forward amplification primers).

Optionally, the reaction mixture further includes a plurality of a second primer (e.g., reverse amplification primers).

In some embodiments, at least one of the plurality of supports further includes a plurality of second primers.

In some embodiments, at least one of the plurality of supports includes a plurality of first and second primers.

In some embodiments, the first and second primers comprise the same sequences. In some embodiments, the first and second primers comprise different sequences.

In some embodiments, the support comprises a bead, particle, a planar surface, or an interior wall of a channel or tube.

In some embodiments, the reaction mixture further includes a polymerase and a plurality of nucleotides.

In some embodiments, the disclosure relates generally to a composition comprising an emulsion. Optionally, the emulsion comprises a hydrophilic phase and a hydrophobic phase. Optionally, the emulsion comprises a hydrophilic phase dispersed in a hydrophobic phase. Optionally, the hydrophilic phase can include any combination of a plurality of polynucleotide templates, a plurality of supports and/or a recombinase. Optionally, the hydrophilic phase can include a plurality of polynucleotide templates. Optionally, the hydrophilic phase can include a plurality of supports. Optionally, the hydrophilic phase can include a recombinase.

In some embodiments, a composition comprises an emulsion comprising a hydrophilic phase and a hydrophobic phase, wherein the hydrophilic phase includes a plurality of polynucleotide templates, a plurality of supports and a recombinase.

In some embodiments, the disclosure relates generally to a composition comprises an emulsion including a hydrophilic phase dispersed in a hydrophobic phase. Optionally, the hydrophilic phase includes a plurality of microreactors. Optionally, at least two microreactors of the plurality includes a different polynucleotide template. Optionally, the sequences of the different polynucleotide templates is the same or different. Optionally, a first microreactor includes a first polynucleotide template and a second microreactor includes a second polynucleotide template. Optionally, the first and the second polynucleotide templates comprise the same or different sequences. Optionally, at least two microreactors of the plurality includes a recombinase.

In some embodiments, a composition comprises an emulsion including a hydrophilic phase dispersed in a hydrophobic phase, wherein the hydrophilic phase including a plurality of microreactors, at least two microreactors of the plurality including a different polynucleotide template and a recombinase.

In some embodiments, the hydrophilic phase includes a plurality of aqueous microreactors, at least two of the microreactors each including a different polynucleotide template, a support, and a recombinase.

Optionally, a first microreactor includes a first polynucleotide template and a second microreactor includes a second polynucleotide template. Optionally, the first and the second polynucleotide templates comprise the same or different sequences.

Optionally, at least one of the plurality of supports is linked to a plurality of first primers (e.g., forward amplification primers).

Optionally, the reaction mixture further includes a plurality of a second primer (e.g., reverse amplification primers).

In some embodiments, at least one of the plurality of supports further includes a plurality of second primers.

In some embodiments, at least one of the plurality of supports includes a plurality of first and second primers.

In some embodiments, the first and second primers comprise the same sequences.

In some embodiments, the first and second primers comprise different sequences. In some embodiments, the hydrophilic phase further includes a polymerase.

In some embodiments, the polymerase comprises a strand displacing polymerase. In some embodiments, the hydrophilic phase includes nucleotides.

In some embodiments, the disclosure relates generally to methods (as well as associated compositions and systems) for nucleic acid synthesis, comprising: (a) forming a reaction mixture; and (b) subjecting the reaction mixture to amplification conditions. Optionally, the reaction mixture is contained within a hydrophilic phase of an emulsion. Optionally, the emulsion includes a hydrophilic phase and a hydrophobic phase. Optionally, the emulsion comprises a hydrophilic phase dispersed in a hydrophobic phase. Optionally, the reaction mixture contains any combination of a plurality of supports, a plurality of different polynucleotides and/or a recombinase. Optionally, the reaction mixture contains a plurality of supports. Optionally, the reaction mixture contains a plurality of different polynucleotides. Optionally, the sequences of the different polynucleotide templates is the same or different. Optionally, a first microreactor includes a first polynucleotide template and a second microreactor includes a second polynucleotide template. Optionally, the first and the second polynucleotide templates comprise the same or different sequences. Optionally, the reaction mixture contains a recombinase. Optionally, the amplification conditions include isothermal or thermo-cycling temperature conditions. Optionally, the method further includes forming at least two supports subjecting the emulsion to amplification conditions results in forming a plurality of supports, wherein at least two of the supports are each independently attached to a substantially monoclonal nucleic acid population.

In some embodiments, the disclosure relates generally to methods (as well as associated compositions and systems) for nucleic acid synthesis, comprising: (a) forming a reaction mixture containing a plurality of supports, a plurality of different polynucleotides and a recombinase, the reaction mixture contained within a hydrophilic phase of an emulsion; and (b) subjecting the emulsion including the reaction mixture to isothermal amplification conditions, thereby generating a plurality of supports and a substantially monoclonal nucleic acid population attached thereto.

In some embodiments, the emulsion includes a water-in-oil emulsion. In some embodiments, the liquid phase microreactors comprise a hydrophilic phase. In some embodiments, the emulsion comprises a hydrophilic phase dispersed in a hydrophobic phase. In some embodiments, the reaction mixture is formed in a single reaction vessel. Optionally, the sequences of the plurality of different polynucleotide templates is the same or different. Optionally, a first polynucleotide template includes a first sequence and a second polynucleotide template includes a second sequence Optionally, the first and the second polynucleotide template sequences are the same or different. Optionally, at least one of the plurality of supports is linked to a plurality of first primers (e.g., forward amplification primers). Optionally, the reaction mixture further includes a plurality of a second primer (e.g., reverse amplification primers). In some embodiments, at least one of the plurality of supports further includes a plurality of second primers. In some embodiments, at least one of the plurality of supports includes a plurality of first and second primers. In some embodiments, the first and second primers comprise the same sequences. In some embodiments, the first and second primers comprise different sequences. In some embodiments, the nucleic acid synthesis method further includes recovering from the reaction mixture at least some of the supports attached to substantially nucleic acid monoclonal populations. In some embodiments, the nucleic acid synthesis method further includes depositing onto a surface at least some of the supports attached to the substantially monoclonal nucleic acid populations. In some embodiments, the nucleic acid synthesis method further includes forming an array by depositing onto a surface at least some of the supports attached to the substantially monoclonal nucleic acid populations. In some embodiments, the nucleic acid synthesis method further includes sequencing at least one substantially monoclonal nucleic acid population attached to the support. In some embodiments, the support comprises a bead, particle, a planar surface, or an interior wall of a channel or tube. In some embodiments, the reaction mixture further includes a polymerase and a plurality of nucleotides. In some embodiments, the polymerase comprises a strand displacing polymerase.

In some embodiments, methods for nucleic acid synthesis comprise forming an emulsion. Optionally, the emulsion comprises a hydrophilic phase and a hydrophobic phase. Optionally, the emulsion comprises a hydrophilic phase dispersed in a hydrophobic phase. Optionally, the hydrophilic phase includes a plurality of microreactors. Optionally, at least two microreactors of the plurality include individual polynucleotide templates. Optionally, at least two microreactors of the plurality include a different polynucleotide template. Optionally, a first microreactor includes a first polynucleotide template, and a second microreactor includes a second polynucleotide template. Optionally, the first and the second polynucleotide templates have the same or different sequences. Optionally, at least two microreactors of the plurality including a recombinase.

In some embodiments, the disclosure relates generally to methods (as well as associated compositions and systems) for nucleic acid synthesis, comprising: forming an emulsion including a hydrophilic phase dispersed in a hydrophobic phase, the hydrophilic phase including a plurality of microreactors, at least two microreactors of the plurality including a different polynucleotide template and a recombinase.

In some embodiments, the emulsion includes a water-in-oil emulsion. In some embodiments, the hydrophilic phase further includes a polymerase. In some embodiments, the polymerase is a strand displacing polymerase. In some embodiments, the hydrophilic phase includes nucleotides. In some embodiments, the emulsion is formed in a single reaction vessel. Optionally, the sequences of the different polynucleotide templates are the same or different. Optionally, a first microreactor includes a first polynucleotide template and a second microreactor includes a second polynucleotide template. Optionally, the first and the second polynucleotide templates comprise the same or different sequences. In some embodiments, the at least two microreactors of the plurality include a plurality of supports. Optionally, at least one of the plurality of supports is linked to a plurality of first primers (e.g., forward amplification primers). Optionally, the reaction mixture further includes a plurality of a second primer (e.g., reverse amplification primers). In some embodiments, at least one of the plurality of supports further includes a plurality of second primers. In some embodiments, at least one of the plurality of supports includes a plurality of first and second primers. In some embodiments, the first and second primers comprise the same sequences. In some embodiments, the first and second primers comprise different sequences. In some embodiments, the hydrophilic phase includes a reaction mixture. In some embodiments, the reaction mixture comprises a plurality of polynucleotide templates, a plurality of supports and a recombinase. In some embodiments, methods for nucleic acid synthesis further comprise subjecting the emulsion (e.g., including the reaction mixture) to isothermal amplification conditions, thereby generating a plurality of substantially monoclonal nucleic acid populations. In some embodiments, the plurality of substantially monoclonal nucleic acid populations are attached to the plurality of supports. In some embodiments, the nucleic acid synthesis method further includes recovering from the reaction mixture at least some of the supports attached to substantially nucleic acid monoclonal populations. In some embodiments, the nucleic acid synthesis method further includes depositing onto a surface at least some of the supports attached to the substantially monoclonal nucleic acid populations. In some embodiments, the nucleic acid synthesis method further includes forming an array by depositing onto a surface at least some of the supports attached to the substantially monoclonal nucleic acid populations. In some embodiments, the nucleic acid synthesis method further includes sequencing at least one substantially monoclonal nucleic acid population attached to the support. In some embodiments, the support comprises a bead, particle, a planar surface, or an interior wall of a channel or tube. In some embodiments, the reaction mixture further includes a polymerase and a plurality of nucleotides. In some embodiments, the polymerase comprises a strand displacing polymerase.

The section headings used herein are for organizational purposes only and are not to be construed as limiting the described subject matter in any way.

All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control.

It will be appreciated that there is an implied "about" prior to the temperatures, concentrations, times, etc., discussed in the present teachings, such that slight and insubstantial deviations are within the scope of the present teachings herein.

Unless otherwise required by context, singular terms shall include pluralities and plural terms shall include the singular.

The use of "comprise", "comprises", "comprising", "contain", "contains", "containing", "include", "includes", and "including" are not intended to be limiting.

It is to be understood that both the foregoing general description and the following detailed description are exemplary and explanatory only and are not restrictive of the invention.

Unless otherwise defined, scientific and technical terms used in connection with the present teachings described herein shall have the meanings that are commonly understood by those of ordinary skill in the art. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with exemplary embodiments provided herein, the following terms, unless otherwise indicated, shall be understood to have the following meanings:

As used herein the term "amplification" and its variants includes any process for producing multiple copies or complements of at least some portion of a polynucleotide, said polynucleotide typically being referred to as a "template". The template polynucleotide can be single stranded or double stranded. Amplification of a given template can result in the generation of a population of polynucleotide amplification products, collectively referred to as an "amplicon". The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes primer annealing and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, 75, 100 or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis. Each cycle of nucleic acid synthesis optionally includes a single primer annealing step and a single extension step. In some embodiments, amplification includes isothermal amplification.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

As used herein, the term "support" and its variants include any solid or semisolid article on which reagents such as nucleic acids can be immobilized.

As used herein, the term "isothermal" and its variants, when used in reference to reference to any reaction conditions, process or method, includes conditions, processes and methods that are performed under substantially isothermal conditions. Substantially isothermal conditions include any conditions wherein the temperature is constrained within a limited range. In an exemplary embodiment, the temperature varies by no more than 20° C., typically by no more than 10° C., 5° C. or 2° C. Isothermal amplification includes any amplification reaction wherein at least two consecutive cycles of nucleic acid synthesis are performed under substantially isothermal conditions, and include amplification reactions wherein the temperature varies by no more than 20° C., 10° C., 5° C. or 2° C., over the duration of at least two consecutive cycles of nucleic acid synthesis, although the temperature may vary by greater than 20° C. during the remainder of the amplification process, including during other cycles of nucleic acid synthesis. Optionally, in an isothermal reaction (including isothermal amplification), the temperature is maintained at or around 50° C., 55° C., 60° C., 65° C., or 70° C. for at least about 10, 15, 20, 30, 45, 60 or 120 minutes. Optionally, any temperature variation is not more than 20° C., optionally within 10° C., for example within 5° C., or 2° C. during one or more amplification cycles (e.g., e.g., 1, 5, 10, 20, or all amplification cycles performed). In some embodiments, isothermal amplification can include thermocycling, where temperature variance is within isothermal ranges. In an example, the temperature variation is constrained between the denaturation step and another step such as annealing and/or extension. In an example, the difference between the denaturation temperature and the annealing or extension temperature is not more than 20° C., optionally within 10° C., for example within 5° C., or 2° C., for one or more cycles of amplification. The temperature is optionally constrained for at least 5, 10, 15, 20, 30, 35 or substantially all cycles of amplification.

As used herein, the term "sequencing" and its variants comprise obtaining sequence information from a nucleic acid strand, typically by determining the identity of at least some nucleotides (including their nucleobase components) within the nucleic acid molecule. While in some embodiments, "sequencing" a given region of a nucleic acid molecule includes identifying each and every nucleotide within the region that is sequenced, "sequencing" can also include methods whereby the identity of one or more nucleotides in is determined, while the identity of some nucleotides remains undetermined or incorrectly determined.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The term "complementary" and its variants, as used herein in reference to two or more polynucleotides, refer to polynucleotides including any nucleic acid sequences (e.g., portions of target nucleic acid molecules and primers) that can undergo cumulative base pairing at two or more individual corresponding positions in antiparallel orientation, as in a hybridized duplex. Optionally there can be "complete" or "total complementarity between a first and second nucleic acid sequence where each nucleotide in the first nucleic acid sequence can undergo a stabilizing base pairing interaction with a nucleotide in the corresponding antiparallel position on the second nucleic acid sequence (however, the term "complementary" by itself can include nucleic acid sequences that are not completely complementary over their entire length); "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90% or 95%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. "Noncomplementary" describes nucleic acid sequences in which less than 20% of the residues of one nucleic acid sequence are complementary to residues in the other nucleic acid sequence. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding between the nucleobases of nucleotides and/or polynucleotides at positions antiparallel to each other. The complementarity of other artificial base pairs can be based on other types of hydrogen bonding and/or hydrophobicity of bases and/or shape complementarity between bases.

The term "double stranded" and its variants, as used herein in reference to any polynucleotide or nucleic acid molecule, refer to any polynucleotide or nucleic acid molecule having one or more strands and including a region containing nucleotide residues that are base paired with nucleotide residues, for example as in a nucleic acid duplex. Optionally the double stranded polynucleotide (or nucleic acid molecule) can be "completely" or "totally" double stranded, such that each nucleotide residue in the polynucleotide (or nucleic acid molecule) is base paired with another corresponding nucleotide residue. In some embodiments, the double stranded polynucleotide includes one or more single stranded regions containing nucleotide residues that are not base paired with any other nucleotide residue. In some embodiments, at least 51%, 75%, 85%, 95%, 97% or 99%, of the nucleotide residues in the double stranded polynucleotide (or nucleic acid molecule) are base paired with other nucleotide residues. In some embodiments, a double stranded polynucleotide (or nucleic acid molecule) includes two strands that are not covalently linked to each other; alternatively, the double stranded polynucleotide (or nucleic acid molecule) includes a single strand that is base paired with itself over at least some portion of its length as in, for example, a hairpin oligonucleotide. A polynucleotide is said to be "substantially double stranded" when at least 85% of the nucleotide residues of the polynucleotide are base paired with corresponding nucleotide residues. Two nucleic acid sequences are said to be "double stranded" when the residues of one nucleic acid sequence are base paired with corresponding residues in the other nucleic acid sequence. In some embodiments, base pairing can occur according to some conventional pairing paradigm, such as the A-T/U and G-C base pairs formed through specific Watson-Crick type hydrogen bonding between the nucleobases of nucleotides and/or polynucleotides positions antiparallel to each other; in other embodiments, base pairing can occur through any other paradigm whereby base pairing proceeds according to established and predictable rules.

As used herein, the term "single stranded" and its variants, when used in reference to any polynucleotide or nucleic acid molecule, refer to any polynucleotide or nucleic acid molecule including a region containing nucleotide residues that are not base paired with any nucleotide residues. Optionally the single stranded polynucleotide (or nucleic acid molecule) can be "completely" or "totally" single stranded, such that each nucleotide residue in the polynucleotide (or nucleic acid molecule) is not base paired with any other nucleotide residue. In some embodiments, the single stranded polynucleotide includes one or more double stranded regions containing nucleotide residues that are base paired with nucleotide residue. In some embodiments, at least 51%, 75%, 85%, 95%, 97% or 99%, of the nucleotide residues in the single stranded polynucleotide (or nucleic acid molecule) are not base paired with other nucleotide residues. A polynucleotide is said to be "substantially single stranded" when at least 85% of the nucleotide residues of the polynucleotide are not base paired with nucleotide residues.

As used herein, the term "denature" and its variants, when used in reference to any double stranded polynucleotide molecule, or double stranded polynucleotide sequence, includes any process whereby the base pairing between nucleotides within opposing strands of the double stranded molecule, or double stranded sequence, is disrupted. Typically, denaturation includes rendering at least some portion or region of two strands of the double stranded polynucleotide molecule or sequence single stranded. In some embodiments, denaturation includes separation of at least some portion or region of two strands of the double stranded polynucleotide molecule or sequence from each other. Typically, the denatured region or portion is then capable of hybridizing to another polynucleotide molecule or sequence. Optionally there can be "complete" or "total" denaturation of a double stranded polynucleotide molecule or sequence. Complete denaturation conditions are for example conditions that would result in complete separation of a significant fraction (e.g., more than 10%, 20%, 30%, 40% or 50%) of a large plurality of strands from their extended and/or full-length complements. Typically, complete or total denaturation disrupts all of the base pairing between the nucleotides of the two strands with each other. Similarly a nucleic acid sample is optionally considered fully denatured when more than 80% or 90% of individual molecules of the sample lack any double-strandedness (or lack any hybridization to a complementary strand).

Alternatively, the double stranded polynucleotide molecule or sequence can be partially or incompletely denatured. A given nucleic acid molecule can be considered partially-denatured when a portion of at least one strand of the nucleic acid remains hybridized to a complementary strand, while another portion is in an unhybridized state (even if it is in the presence of a complementary sequence). The unhybridized portion is optionally at least 5, 7, 8, 10, 12, 15, 17, 20, or 50 nucleotides long. The hybridized portion is optionally at least 5, 7, 8, 10, 12, 15, 17, 20, or 50 nucleotides long. Partial denaturation includes situations where some but not all, of the nucleotides of one strand or sequence, are based paired with some nucleotides of the other strand or sequence within a double stranded polynucleotide. In some embodiments, at least 20% but less than 100%, of the nucleotide residues of one strand of the partially denatured polynucleotide (or sequence) are not base paired to nucleotide residues within the opposing strand. Under exemplary conditions at least 50% of nucleotide residues within the double stranded polynucleotide molecule (or double stranded polynucleotide sequence) are in single stranded (or unhybridized) from, but less than 20% or 10% of the residues are double stranded.

Optionally, a nucleic acid sample can be considered to be partially denatured when a substantial fraction of individual nucleic acid molecules of the sample (e.g., above 20%, 30%, 50%, or 70%) are in a partially denatured state. Optionally less than a substantial amount of individual nucleic acid molecules in the sample are fully denatured, e.g., not more than 5%, 10%, 20%, 30% or 50% of the nucleic acid molecules in the sample. Under exemplary conditions at least 50% of the nucleic acid molecules of the sample are partly denatured, but less than 20% or 10% are fully denatured. In other situations, at least 30% of the nucleic acid molecules of the sample are partly denatured, but less than 10% or 5% are fully denatured. Similarly, a nucleic acid sample can be considered to be non-denatured when a minority of individual nucleic acid molecules in the sample are partially or completely denatured.

In an embodiment, partially denaturing conditions are achieved by maintaining the duplexes as a suitable temperature range. For example, the nucleic acid is maintained at temperature sufficiently elevated to achieve some heat-denaturation (e.g., above 45° C., 50° C., 55° C., 60° C., 65° C., or 70° C.) but not high enough to achieve complete heat-denaturation (e.g., below 95° C. or 90° C. or 85° C. or 80° C. or 75° C.). In an embodiment the nucleic acid is partially denatured using substantially isothermal conditions.

Partial denaturation can also be achieved by other means, e.g., chemical means using chemical denaturants such as urea or formamide, with concentrations suitably adjusted, or using high or low pH (e.g., pH between 4-6 or 8-9). In an embodiment, partial denaturation and amplification is achieved using recombinase-polymerase amplification (RPA). Exemplary RPA methods are described herein.

In some embodiments, complete or partial denaturation is accomplished by treating the double stranded polynucleotide sequence to be denatured using appropriate denaturing agents. For example, the double stranded polynucleotide can be subjected to heat-denaturation (also referred to interchangeably as thermal denaturation) by raising the temperature to a point where the desired level of denaturation is accomplished. In some embodiments, complete thermal denaturation of a double stranded polynucleotide, the temperature can be adjusted to achieve complete separation of the two strands of the polynucleotide, such that at least 90% of the strands are in single stranded form across their entire length. In some embodiments, complete thermal denaturation of a polynucleotide molecule (or polynucleotide sequence) is accomplished by exposing the polynucleotide molecule (or sequence) to a temperature that is at least 5° C., 10° C., 15° C., 20° C., 25, 30° C., 50° C., or 100° C., above the calculated or predict melting temperature (Tm) of the polynucleotide molecule or sequence.

Alternatively, chemical denaturation can be accomplished by contacting the double stranded polynucleotide to be denatured with appropriate chemical denaturants, such as strong alkalis, strong acids, chaotropic agents, and the like and can include, for example, NaOH, urea, or guanidine-containing compounds. In some embodiments, partial or complete denaturation is achieved by exposure to chemical denaturants such as urea or formamide, with concentrations suitably adjusted, or using high or low pH (e.g., pH between 4-6 or 8-9). In an embodiment, partial denaturation and amplification is achieved using recombinase-polymerase amplification (RPA). Exemplary RPA methods are described herein.

The terms "melting temperature", "Tm" or "$T_m$" and their variants, when used in reference to a given polynucleotide (or a given target sequence within a polynucleotide) typically refers to a temperature at which 50% of the given polynucleotide (or given target sequence) exists in double-stranded form and 50% is single stranded, under a defined set of conditions. In some embodiments, the defined set of conditions can include a defined parameter indicating ionic strength and/or pH in an aqueous reaction condition. A defined condition can be modulated by altering the concentration of salts (e.g., sodium), temperature, pH, buffers, and/or formamide. Typically, the calculated thermal melting temperature can be at about 5-30° C. below the $T_m$, or about 5-25° C. below the $T_m$, or about 5-20° C. below the $T_m$, or about 5-15° C. below the $T_m$, or about 5-10° C. below the $T_m$. Methods for calculating a $T_m$ are well known and can be found in Sambrook (1989 in "Molecular Cloning: A Laboratory Manual", $2^{nd}$ edition, volumes 1-3; Wetmur 1966, J. Mol. Biol., 31:349-370; Wetmur 1991 Critical Reviews in Biochemistry and Molecular Biology, 26:227-259). Other sources for calculating a $T_m$ for hybridizing or denaturing nucleic acids include OligoAnalyze (from Integrated DNA Technologies) and Primer3 (distributed by the Whitehead Institute for Biomedical Research). In some embodiments, the term "melting temperature", "Tm" and "$T_m$" and their variants includes both the actual Tm of the given polynucleotide (or target sequence), as measured empirically using defined conditions, or the predicted or calculated Tm. In some embodiments, the Tm of a template can be predicted or calculated without using the sequence of the template, by assuming that the template includes a certain proportion of the four common nucleotides (A, C, G and T) and has a certain length (or, in the case of a population of templates, an average length). For example, it can be assumed that a population of templates, that migrates as a smear on a gel, includes 25% each of A, C. G or T, and has an average length of 200, 300, 400 base pairs.

The term "label" and its variants, as used herein with respect to a chemical moiety, includes any composition comprising an optically or non-optically detectable moiety, where the detectable moiety has been artificially added, linked or attached via chemical manipulation to second moiety that is unlabeled. Typically, addition of the label is performed by a user (or by an upstream provider) with the purpose of enhancing detectability of the second moiety. Optically or non-optically detectable components of a composition that already exist in the naturally occurring form of the composition (for example, hydrogen ions and amino acids present in a typical DNA molecule, an RNA molecule, or a nucleotide within a natural cell) are not labels for purposes of this disclosure. Some typical labels include fluorescent moieties and dyes.

A nucleic acid can be considered immobilized if it is attached to a support in a manner that is substantially stable, at least during conditions of choice (e.g., during the amplification reaction). The attachment can be by any mechanism, including but not limited to non-covalent bonding, ionic interactions, covalent linkage. If a first nucleic acid is hybridized to a second nucleic acid immobilized on a support, then the first nucleic acid can also be considered to be immobilized to the support during amplification, if amplification conditions are such that substantial amounts of the first and second nucleic acids are associated or connected with each other at any or all times during amplification. For example the first and second nucleic acids can be associated together by hybridization involving Watson-Crick base pairing or hydrogen bonding. In an example, the amplification conditions of choice allow at least 50%, 80%, 90%, 95% or 99% of the first nucleic acid to remain hybridized with the second nucleic acid, or vice versa. A nucleic acid can be considered unimmobilized or non-immobilized if it is not directly or indirectly attached to or associated with a support.

A medium can be considered flowable under conditions of choice if the medium is under those conditions at least temporarily a fluid medium that does not substantially or completely restrain or impede transfer or movement of an unimmobilized molecule. The unimmobilized molecule is not itself immobilized to a solid support or surface or associated with another immobilized molecule. In an embodiment, the unimmobilized molecule is a solute (e.g., a nucleic acid) through the flowable medium. Exemplary transfer or movement in the medium can be by means of diffusion, convection, turbulence, agitation, Brownian motion, advection, current flows, or other molecular movements within the liquid) from any first point in the continuous phase to any other point in fluid communication or in the same continuous phase. For example, in a flowable medium a significant amount of an unimmobilized nucleic acid is transferred from one immobilization site to another immobilization site that is within the same continuous phase of the flowable medium, or in fluid communication with the first immobilization site. Optionally, the rate of transfer or movement of the nucleic acid in the medium is comparable to the rate of transfer or movement of the nucleic acid in water. In some instances, the conditions of choice are conditions that the medium is subjected to during amplification. The conditions of choice may or may not allow the flowable medium to remain substantially motionless. The conditions may or may not subject the flowable medium to active mixing, agitation or shaking. The medium is optionally flowable at least temporarily during amplification. For example the medium is flowable under at least one preamplification and/or amplification condition of choice. Optionally, a flowable medium does not substantially prevent intermingling of different unimmobilized nucleic acids or transfer of an unimmobilized nucleic acid between different zones of a continuous phase of the flowable medium. The movement or transfer of nucleic acids for example can be caused by means of diffusion or convection. A medium is optionally considered nonflowable if unimmobilized nucleic acids upon amplification fail to spread or move between different immobilization sites or over the entire continuous phase. Generally, a flowable medium does not substantially confine unimmobilized nucleic acids (e.g., the templates or amplicons) within limited zones of the reaction volume or at fixed locations during the period of amplification. Optionally, a flowable medium can be rendered non-flowable by various means or by varying its conditions. Optionally, a medium is flowable if it is liquid or is not semisolid. A medium can be considered flowable if its fluidity is comparable to pure water. In other embodiments, a medium can be considered flowable if it a fluid that is substantially free of polymers, or if its viscosity coefficient is similar to that of pure water.

As will be appreciated by one of ordinary skill in the art, references to templates, initializing oligonucleotides, extension probes, primers, etc., can refer to populations or pools of nucleic acid molecules that are substantially identical within a relevant portion, rather than single molecules. For example, a "template" can refer to a plurality of substantially identical template molecules; a "probe" can refer to a plurality of substantially identical probe molecules, etc. In the case of probes that are degenerate at one or more positions, it will be appreciated that the sequence of the probe molecules that comprise a particular probe will differ at the degenerate positions, i.e., the sequences of the probe molecules that constitute a particular probe may be substantially identical only at the nondegenerate position(s). These terms within this application are intended to provide support for either a population or a molecule. Where it is intended to refer to a single nucleic acid molecule (i.e., one molecule), the terms "template molecule", "probe molecule", "primer molecule", etc., may be used instead. In certain instances the plural nature of a population of substantially identical nucleic acid molecules will be explicitly indicated.

"Template", "oligonucleotide", "probe", "primer", "template", "nucleic acid" and the like are intended to be interchangeable terms herein. These terms refer to polynucleotides, not necessarily limited to any length or function. The same nucleic acid can be regarded as a "template", "probe" or "primer" depending on the context, and can switch between these roles with time. A "polynucleotide," also called a "nucleic acid," is a linear polymer of two or more nucleotides joined by covalent internucleosidic linkages, or variant or functional fragments thereof. In naturally occurring examples of these, the internucleoside linkage is typically a phosphodiester bond. However, other examples optionally comprise other internucleoside linkages, such as phosphorothiolate linkages and may or may not comprise a phosphate group. Polynucleotides include double- and single-stranded DNA, as well as double- and single-stranded RNA, DNA:RNA hybrids, peptide-nucleic acids (PNAs) and hybrids between PNAs and DNA or RNA, and also include known types of modifications. Polynucleotides can optionally be attached to one or more non-nucleotide moieties such as labels and other small molecules, large molecules such proteins, lipids, sugars, and solid or semi-solid supports, for example through either the 5' or 3' end. Labels include any moiety that is detectable using a detection method of choice, and thus renders the attached nucleotide or polynucleotide similarly detectable using a detection method of choice. Optionally, the label emits electromagnetic radiation that is optically detectable or visible. In some cases, the nucleotide or polynucleotide is not attached to a label, and the presence of the nucleotide or polynucleotide is directly detected. A "nucleotide" refers to a nucleotide, nucleoside or analog thereof. Optionally, the nucleotide is an N- or C-glycoside of a purine or pyrimidine base. (e.g., deoxyribonucleoside containing 2-deoxy-D-ribose or ribonucleoside containing D-ribose). Examples of other analogs include, without limitation, phosphorothioates, phosphoramidates, methyl phosphonates, chiral-methyl phosphonates, 2-O-methyl ribonucleotides. Referring to a nucleic acid by any one of these terms should not be taken as implying that the nucleic acid has any particular activity, function or properties. For example, the word "template" does not indicate that the "template" is being copied by a polymerase or that the template is not capable of acting as a "primer" or a "probe".

It will be appreciated that in certain instances nucleic acid reagents involved in amplification such as a template, probe, primer, etc., may be a portion of a larger nucleic acid molecule that also contains another portion that does not serve the same function. Optionally, this other portion does not serve any template, probe, or primer function. In some instances, a nucleic acid that substantially hybridizes to an optionally-immobilized primer (e.g., on an immobilization site) is considered to be the "template". Any one or more nucleic acid reagents that are involved in template walking (template, immobilized strands, immobilized or unimmobilized primer, etc.) may be generated before or during amplification from other nucleic acids. The nucleic acid reagent is optionally generated from (and need not be identical to) an input nucleic acid by making one or more modifications to the nucleic acid that was initially introduced into the template walking medium. An input nucleic acid can for example be subjected to restriction digestion, ligation, one or more amplification cycles, denaturation, mutation, etc, to generate a nucleic acid that serves as the template, primer, etc, during amplification or further amplification. For example, a double-stranded input nucleic acid can be denatured to generate a first single-stranded nucleic acid which optionally is used to generate a second complementary strand. If so desired, the first single-stranded nucleic acid can be considered the "template" for our purposes herein. Alternatively, the second complementary strand generated from the first single-stranded nucleic acid can be considered the "template" for our purposes herein. In another example, a template is derived from an input nucleic acid and is not necessarily identical to the input nucleic acid. For example, the template can comprise additional sequence not present an input nucleic acid. In an embodiment the template can be an amplicon generated from an input nucleic acid using one or more primers with a 5' overhang that is not complementary to the input nucleic acid.

The term "hybridize" and its variants, as used herein in reference to two or more polynucleotides, refer to any process whereby any one or more nucleic acid sequences (each sequence comprising a stretch of contiguous nucleotide residues) within said polynucleotides undergo base pairing at two or more individual corresponding positions, for example as in a hybridized nucleic acid duplex. Optionally there can be "complete" or "total" hybridization between a first and second nucleic acid sequence, where each nucleotide residue in the first nucleic acid sequence can undergo a base pairing interaction with a corresponding nucleotide in the antiparallel position on the second nucleic acid sequence. In some embodiments, hybridization can include base pairing between two or more nucleic acid sequences that are not completely complementary, or are not base paired, over their entire length. For example, "partial" hybridization occurs when two nucleic acid sequences undergo base pairing, where at least 20% but less than 100%, of the residues of one nucleic acid sequence are base paired to residues in the other nucleic acid sequence. In some embodiments, hybridization includes base pairing between two nucleic acid sequences, where at least 50%, but less than 100%, of the residues of one nucleic acid sequence are base paired with corresponding residues in the other nucleic acid sequence. In some embodiments, at least 70%, 80%, 90% or 95%, but less than 100%, of the residues of one nucleic acid sequence are base paired with corresponding residues in the other nucleic acid sequence. Two nucleic acid sequences are said to be "substantially hybridized" when at least 85% of the residues of one nucleic acid sequence are base paired with corresponding residues in the other nucleic acid sequence. In situations where one nucleic acid molecule is substantially longer than the other (or where the two nucleic acid molecule include both substantially complementary and substantially non-complementary regions), the two nucleic acid molecules can be described as "hybridized" even when portions of either or both nucleic acid molecule can remain unhybridized. "Unhybridized" describes nucleic acid sequences in which less than 20% of the residues of one nucleic acid sequence are base paired to residues in the other nucleic acid sequence. In some embodiments, base pairing can occur according to some conventional pairing paradigm, such as the A-T/U and G-C base pairs formed through specific Watson-Crick type hydrogen bonding between the nucleobases of nucleotides and/or polynucleotides positions antiparallel to each other; in other embodiments, base pairing can occur through any other paradigm whereby base pairing proceeds according to established and predictable rules.

Hybridization of two or more polynucleotides can occur whenever said two or more polynucleotides come into contact under suitable hybridizing conditions. Hybridizing conditions include any conditions that are suitable for nucleic acid hybridization; methods of performing hybridization and suitable conditions for hybridization are well known in the art. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "$T_m$"; parameters such as salts, buffers, pH, temperature, GC % content of the polynucleotide and primers, and/or time. Typically, hybridization is favored in lower temperatures and/or increased salt concentrations, as well as reduced concentrations of organic solvents. High-stringency hybridization conditions will typically require a higher degree of complementary between two target sequences for hybridization to occur, whereas low-stringency hybridization conditions will favor hybridization even when the two polynucleotides to be hybridized exhibit lower levels of complementarity. The hybridization conditions can be applied during a hybridization step, or an optional and successive wash step, or both the hybridization and optional wash steps.

Examples of high-stringency hybridization conditions include any one or more of the following: salt concentrations (e.g., NaCl) of from about 0.0165 to about 0.0330; temperatures of from about 5° C. to about 10° C. below the melting point ($T_m$) of the target sequences (or polynucleotides) to be hybridized; and/or formamide concentrations of about 50% or higher. Typically, high-stringency hybridization conditions permit binding between sequences having high homology, e.g., ≥95% identity or complementarity. In one exemplary embodiment of high-stringency hybridization conditions, hybridization is performed at about 42° C. in a hybridization solution containing 25 mM $KPO_4$ (pH 7.4), 5×SSC, 5×Denhardt's solution, 50 μg/mL denatured, sonicated salmon sperm DNA, 50% formamide, 10% Dextran sulfate, and 1-15 ng/mL double stranded polynucleotide (or double stranded target sequence), while the washes are performed at about 65° C. with a wash solution containing 0.2×SSC and 0.1% sodium dodecyl sulfate.

Examples of medium-stringency hybridization conditions can include any one or more of the following: salt concentrations (e.g., NaCl) of from about 0.165 to about 0.330; temperatures of from about 20° C. to about 29° C. below the melting point ($T_m$) of the target sequences to be hybridized; and/or formamide concentrations of about 35% or lower. Typically, such medium-stringency conditions permit binding between sequences having high or moderate homology, e.g., ≥80% identity or complementarity. In one exemplary embodiment of medium stringency hybridization conditions, hybridization is performed at about 42° C. in a hybridization solution containing 25 mM $KPO_4$ (pH 7.4), 5×SSC, 5× Denhart's solution, 50 μg/mL denatured, sonicated salmon sperm DNA, 50% formamide, 10% Dextran sulfate, and 1-15 ng/mL double stranded polynucleotide (or double stranded target sequence), while the washes are performed at about 50° C. with a wash solution containing 2×SSC and 0.1% sodium dodecyl sulfate.

Examples of low-stringency hybridization conditions include any one or more of the following: salt concentrations (e.g., NaCl) of from about 0.330 to about 0.825; temperatures of from about 40° C. to about 48° C. below the melting point ($T_m$) of the target sequences to be hybridized; and/or formamide concentrations of about 25% or lower. Typically, such low-stringency conditions permit binding between sequences having low homology, e.g., ≥50% identity or complementarity.

Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher.

In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer.

In some embodiments, hybridization or wash conditions can be conducted at a pH range of about 5-10, or about pH 6-9, or about pH 6.5-8, or about pH 6.5-7.

In some embodiments, the term "monoclonal" and its variants is used to describe a population of polynucleotides where a substantial portion of the members of the population (e.g., at least about 50%, typically at least 75%, 80%, 85%, 90%, 95%, or 99%) share at least 80% identity at the nucleotide sequence level. Typically, at least about 90% of the population, typically at least about 95%, more typically at least about 99%, 99.5% or 99.9%) are generated via amplification or template-dependent replication of a particular polynucleotide sequence, which is present amongst a substantial portion of members of the monoclonal polynucleotide population. All members of a monoclonal population need not be completely identical or complementary to each other. For example, different portions of a polynucleotide template can become amplified or replicated to produce the members of the resulting monoclonal population; similarly, a certain number of "errors" and/or incomplete extensions may occur during amplification of the original template, thereby generating a monoclonal population whose individual members can exhibit sequence variability amongst themselves. In some embodiments, at least 50% of the members of the monoclonal population are at least 80% identical to a reference nucleic acid sequence (i.e., a nucleic acid of defined sequence used as a basis for a sequence comparison). In some embodiments, at least 60%, at least 70%, at least 80%, at least 90%, at least 95%, at least 99%, or more of the members of a population include a sequence that is at least 80%, 85%, 90%, 95%, 97% or 99% identical (or complementary) to the reference nucleic acid sequence. In some embodiments, a low or insubstantial level of mixing of non-homologous polynucleotides may occur during nucleic acid amplification reactions described herein, and thus a substantially monoclonal population may contain a minority of diverse polynucleotides (e.g., less than 30%, less than 20%, less than 10%, less than 5%, less than 1%, less than 0.5%, less than 0.1%, or less than 0.001%, of diverse polynucleotides). As used herein, the phrase "substantially monoclonal" and its variants, when used in reference to one or more polynucleotide populations, refer to one or more polynucleotide populations comprised of polynucleotides that are at least 80% identical to the original single template used as a basis for clonal amplification to produce the substantially monoclonal population.

In some embodiments, at least 80% of the members of the amplicon, typically at least 90%, more typically at least 95%, even more typically at least 99%, of the members of the amplicon will share greater than 90% identity, typically greater than 95% identity, more typically greater than 97%, and even more typically greater than 99% identity with the polynucleotide template. Alternatively, the members of the amplicon can be greater than 90% complementary, typically greater than 95% complementary, more typically greater than 97% complementary, even more typically greater than 99% complementary, to the original template. In some embodiments, members of a substantially monoclonal nucleic acid population can hybridize to each other under high stringency hybridization conditions.

In some embodiments, an amplicon is referred to as "monoclonal" or "substantially monoclonal" if it includes sufficiently few polyclonal contaminants to produce a detectable signal in any method of nucleic acid analysis that is influenced by the sequence of the template. For example, a "monoclonal" population of polynucleotides can include any population that produces a signal (e.g., a sequencing signal, a nucleotide incorporation signal and the like) that can be detected using a particular sequencing system. Optionally, the signal can subsequently be analyzed to correctly determine the sequence and/or base identity of any one or more nucleotides present within any polynucleotide of the population. Examples of suitable sequencing systems for detection and/or analysis of such signals include the Ion Torrent sequencing systems, such as the Ion Torrent PGM™ sequence systems, including the 314, 316 and 318 systems, and the Ion Torrent Proton™ sequencing systems, including Proton I, Proton II and Proton III (Life Technologies, Carlsbad, Calif.). In some embodiments, the monoclonal amplicon permits the accurate sequencing of at least 5 contiguous nucleotide residues on an Ion Torrent sequencing system.

As used herein, the term "clonal amplification" and its variants refer to any process whereby a substantially monoclonal polynucleotide population is produced via amplification of a polynucleotide template. In some embodiments of clonal amplification, two or more polynucleotide templates are amplified to produce at least two substantially monoclonal polynucleotide populations.

As used herein, the term "adaptor" includes polynucleotides or oligonucleotides comprising DNA, RNA, chimeric RNA/DNA molecules, or analogs thereof and typically refers to an added or extraneous sequence that is linked or attached to the target polynucleotide of interest (e.g., the template) during the course of manipulation. Ligation of the adapter to the template can optionally occur prior to or after template amplification. In some embodiments, the adapter can include a primer binding sequence that is substantially identical, or substantially complementary, to a sequence within a corresponding primer. In some embodiments, a first adapter including a first primer binding site is ligated to one end of a linear double stranded template, while a second adapter including a second primer binding site is ligated to the other end.

As used herein, the term "binding partners" includes two molecules, or portions thereof, which have a specific binding affinity for one another and typically will bind to each other in preference to binding to other molecules. Typically but not necessarily some or all of the structure of one member of a specific binding pair is complementary to some or all of the structure possessed by the other member, with the two members being able to bind together specifically by way of a bond between the complementary structures, optionally by virtue of multiple noncovalent attractions.

In some embodiments, molecules that function as binding partners include: biotin (and its derivatives) and their binding partner avidin moieties, streptavidin moieties (and their derivatives); His-tags which bind with nickel, cobalt or copper; cysteine, histidine, or histidine patch which bind Ni-NTA; maltose which binds with maltose binding protein (MBP); lectin-carbohydrate binding partners; calcium-calcium binding protein (CBP); acetylcholine and receptor-acetylcholine; protein A and binding partner anti-FLAG antibody; GST and binding partner glutathione; uracil DNA glycosylase (UDG) and ugi (uracil-DNA glycosylase inhibitor) protein; antigen or epitope tags which bind to antibody or antibody fragments, particularly antigens such as digoxigenin, fluorescein, dinitrophenol or bromodeoxyuridine and their respective antibodies; mouse immunoglobulin and goat anti-mouse immunoglobulin; IgG bound and protein A; receptor-receptor agonist or receptor antagonist; enzyme-enzyme cofactors; enzyme-enzyme inhibitors; and thyroxine-cortisol. Another binding partner for biotin can be a biotin-binding protein from chicken (Hytonen, et al., BMC Structural Biology 7:8).

An avidin moiety can include an avidin protein, as well as any derivatives, analogs and other non-native forms of avidin that can bind to biotin moieties. Other forms of avidin moieties include native and recombinant avidin and streptavidin as well as derivatized molecules, e.g. nonglycosylated avidins, N-acyl avidins and truncated streptavidins. For example, avidin moiety includes deglycosylated forms of avidin, bacterial streptavidins produced by *Streptomyces* (e.g., *Streptomyces avidinii*), truncated streptavidins, recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin™, Captavidin™, Neutravidin™ and Neutralite Avidin™.

EXAMPLES

Embodiments of the present teachings can be further understood in light of the following examples, which should not be construed as limiting the scope of the present teachings in any way.

Example 1

A nucleic acid amplification reaction was conducted in single reaction vessel in a single continuous liquid phase in a total reaction volume of ~220 µL.

About 420 million beads were washed with water ×1 time (vortex/spin) then washed in buffer ×1 time (vortex/spin) in a 1.5 mL tube (tube 1).

The recombinase source was from a TwistAmp™ Basic kit (from TwistDx, Cambridge, Great Britain). Dehydrated pellets in the kit contain usvX recombinase, usvY recombinase loading protein, gp32 protein, Bsu DNA polymerase, dNTPs, ATP, phosphocreatine and creatine kinase. Four pellets from a TwistAmp™ Basic kit were rehydrated in 120 µL of Rehydration buffer supplied from the kit (tube 2). The recombinase solution was vortexed and spun, then iced. Two heat blocks were prepared, one set at about 68-70° C., and one at 40° C.

The supernatant was removed from the bead pellet (tube 1) leaving about ~20 µL of liquid at the bottom.

A reverse primer (2 µL of a 100 µM stock) was added to the bead tube (tube 1), then vortexed and spun. The reverse primer sequence: 5'-ATCCCTGCGTGTCTCCGAC-3 (SEQ ID NO:1).

A biotinylated reverse primer (2 µL of a 10 µM stock) was added to the bead tube (tube 1), then vortexed and spun. The biotinylated reverse primer sequence: 5'Bio-ATCCCT-GCGTGTCTCCGAC-3'(SEQ ID NO:2).

One µL of polynucleotide library (at various concentrations) was added to the bead tube (tube 1), and vortexed/spun, and placed on ice. The library concentration varied depending on the desired DNA-to-bead ratio of 1:50, 1:75, 1:200.

The rehydrated recombinase mix (tube 2, reconstituted in 120 µL rehydration buffer) was added to the bead tube (tube 1), and vortexed, spun; and placed on ice.

65 µL of an exemplary sieving agent of the disclosure was added to the bead tube, vortexed, and spun, and put on ice.

11 µL of iced 280 mM Mg-acetate was added to the bead tube (in the middle), then vortexed 3 seconds at a maximum setting and put back on ice for 10 seconds, and incubated at 40° C. for 20 minutes on the heat block.

The reaction was heat-killed at 68° C.-70° C. for 10 minutes in the heat block.

The reaction tube was topped off with TE buffer, vortexed and spun at a maximum setting (~20 KG) for 3 minutes, the solution was removed from the beads, leaving ~100 µL. The wash step was repeated two times.

The beads were washed once with recovery solution.

The reaction tube was topped off with wash buffer, vortexed and spun at a maximum setting (~20 KG) for 3 minutes, the solution was removed from the beads, leaving ~100 µL. The wash step was repeated two times.

After the last spin, bring the solution down to 100 µL (wash solution).

The beads were enriched by binding the biotinylated polynucleotides with paramagnetic beads conjugated with streptavidin (MyOne™ Bead from Dynabeads).

The enriched beads were loaded into an Ion Torrent ion-sensitive chip and a standard sequencing reaction was conducted. A significant portion of the enriched beads were determined to include a substantially monoclonal population of amplified polynucleotides, as evidenced by the observation of detectable sequencing signals on the Ion Torrent PGM™ sequencer from such beads. The sequencing signals were analyzed to determine a sequence present within the amplicon of each such bead.

Example 2

About 240 million beads (attached with forward primers) were washed once in annealing buffer (from Ion Sequencing kit, e.g., PN 4482006) in a 2 mL tube. The supernatant was removed (except ~50 µL) and discarded. The beads were resuspended in 100 µL annealing buffer.

Barcoded DNA libraries having either 300 bp or 400 bp insert (about 120-240 million copies) was pre-hybridized with the washed beads. The library included an insert sequence joined at one end to an adaptor that hybridizes to a forward primer and joined at the other end to an adaptor that hybridizes to a reverse primer. The template/bead ratios tested included 1:1, 0.75:1, and 0.5:1. The final volume was adjusted to 200 µL with annealing buffer. The tube was mixed by vortexing and spun. The tube was incubated at 95-100° C. for 3 minutes, and at 37° C. for 5 minutes. One mL of annealing buffer was added, the tube was vortexed and spun at more than 16,000×G for 3.5 minutes, and the supernatant was discarded. One mL of 10 mM potassium-acetate was added, the tube was vortexed and spun at more than 16,000×G for 3.5 minutes, and the supernatant was discarded. The potassium-acetate wash was repeated once. The beads were resuspended in 480 µL of potassium acetate (tube 1).

The recombinase source was from a TwistAmp™ Basic kit (from TwistDx, Cambridge, Great Britain). See Example 1 above for a list of components in the dehydrated pellets from the Basic kit. In a 15 mL tube (tube 2), 96 pellets from a TwistAmp™ Basic kit were rehydrated in 2.88 mL of Rehydration buffer supplied from the kit.

48 µL of 100 µM reverse primers (non-immobilized primers) were added to the washed/pre-hybridized beads (tube 1). 48 µL of 10 µM biotinylated reverse primers (non-immobilized primers) were added to the washed/pre-hybridized beads, and the tube was vortexed (tube 1). The contents of tube 1 (containing the library, beads and reverse primers) was added to tube 2 (containing rehydrated pellets), and tube 2 was vortexed for 5 seconds and placed on ice. 144 µL of T4 gp32 protein (15 µg/µL) was added, and vortexed and returned to ice. 1.56 mL of an exemplary sieving agent of the disclosure was added, the tube was vortexed and returned to ice. After the reaction remained on ice for more than 5 minutes, 264 µL of magnesium acetate was added, the tube was vortexed three times for 3 seconds each. 50 µL samples were aliquoted into an ice-chilled 96-well plate. The 96-well plate was incubated at 40° C. for 25 minutes on a thermo-cycler (the temperature was sustained at 40° C.).

To stop the reaction, 150 µL of 100 mM EDTA was added to each well. All the reactions were pooled and centrifuged at more than 16,000×G for 3.5 minutes. The supernatant was discarded. 1 mL of Tris/1% SDS was added, and the tube was vortexed. The beads were washed twice in 1 mL OneTouch wash solution. The beads were resuspended in 100 µL.

Beads templated with copies of the library were enriched by binding with paramagnetic streptavidin beads (MyOne™ beads from Dynabeads). The enriched beads were loaded into an Ion Torrent PGM ion-sensitive chip.

A standard sequencing reaction was conducted according to manufacturer's instructions in an Ion PGM™ Sequencing 400 Kit (User Guide PN4474246B). A significant portion of the enriched beads that were loaded onto the chip were determined to include substantially monoclonal populations of amplified polynucleotides, as evidenced by the observation of detectable sequencing signals on the Ion Torrent PGM™ sequencer from these beads. The sequencing signals were analyzed by Torrent Suite Software to determine the sequence present within the amplicon of these beads.

Figure 9:
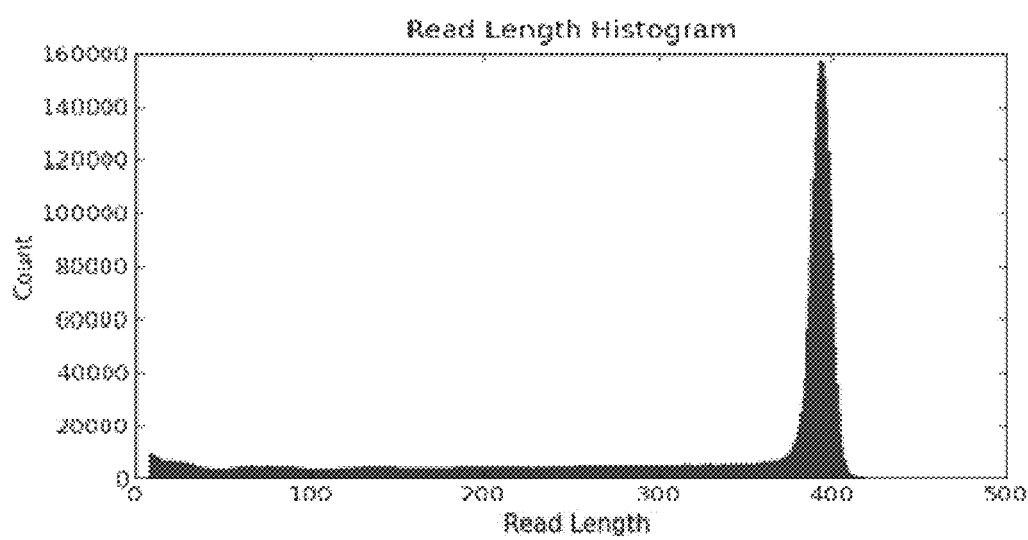
FIG. 9 depicts an exemplary read length histogram from an Ion Torrent™ PGM sequencing run of polynucleotide templates amplified using a recombinase-mediated amplification reaction.

The sequencing data yielded 305 bp mean read length (FIG. 9), and the aligned quality measurements were 1.16 G (AQ17) and 1.07 G (AQ20).

Example 3

About 250 million beads (attached with forward primers) were washed once in 1.5 mL of annealing buffer (from Ion Sequencing kit, e.g., PN 4482006), vortexed, and spun at 15,000×G for 6 minutes. The supernatant was discarded leaving about 50 µL in the tube.

A library having 140 bp insert (about 50 million copies) was pre-hybridized with the washed beads. The library included an insert sequence joined at one end to an adaptor that hybridizes to a forward primer and joined at the other end to an adaptor that hybridizes to a reverse primer. The library (0.81 µL of a 62 M stock) and 0.1 mL Annealing buffer was added to the washed beads and mixed by pipetting up and down. The bead/template ratio was about 5:1. The tube was incubated at 92-95° C. for 7 minutes, and at 37° C. for 10 minutes. One mL of annealing buffer was added, the tube was vortexed and spun at more than 15,000×G for 6 minutes, and the supernatant was discarded. One mL of 10 mM potassium-acetate was added, the tube was vortexed and spun at more than 15,000×G for 6 minutes, and the supernatant was discarded. The potassium-acetate wash was repeated once and the tube placed on ice. About 60 µL of liquid remained in the tube (tube 1).

The recombinase source was from a TwistAmp™ Basic kit (from TwistDx, Cambridge, Great Britain). See Example 1 above for a list of components in the dehydrated pellets from the Basic kit. 8 pellets from a TwistAmp™ Basic kit were rehydrated in about 240 µL of Rehydration buffer supplied from the kit. The pellets and rehydration buffer were vortexed, spun and iced.

4 µL of 100 µM reverse primers (non-immobilized primers) and 1 µL of 10 µM biotinylated reverse primers (non-immobilized primers) were added to the washed/pre-hybridized beads (tube 1), and the tube was vortexed and spun (tube 1). The contents of tube 1 (containing the library, beads and reverse primers) was added to tube 2 (containing rehydrated pellets), and tube 2 was vortexed and placed on ice. 130 µL of an exemplary sieving agent of the disclosure was added, the tube was vortexed and returned to ice. 24 µL of ice cold 280 mM magnesium acetate was added, the tube was vortexed and spun. The total reaction volume was about 332 µL. The tube was incubated at 40° C. for 60 minutes.

1 ml of 100 mM EDTA was added to stop the reaction. The tube was vortexed and spun at 15,000×G for 6 minutes. The supernatant was discarded leaving about 20 µL in the tube. The EDTA stop reaction step, vortexing and spinning steps were repeated. 1 mL of Tris/1% SDS was added, and the tube was vortexed and spun at 15,000×G for 6 minutes. The supernatant was discarded leaving about 50 µL in the tube. The beads were washed in 1 mL OneTouch wash solution by vortexing and spinning, leaving about 100 µL in the tube. All reactions were pooled and spun at 15,000×G for 6 minutes, the supernatant was discarded, leaving about 100 µL in the tube.

Beads templated with copies of the library were enriched by binding with paramagnetic streptavidin beads (MyOne™ beads from Dynabeads). The enriched beads were loaded into an Ion Torrent Proton I™ ion-sensitive chip.

A standard sequencing reaction was conducted according to manufacturer's instructions in an Ion PI™ Sequencing 200 Kit (User Guide PN MAN0007491). A significant portion of the enriched beads that were loaded onto the chip were determined to include substantially monoclonal populations of amplified polynucleotides, as evidenced by the observation of detectable sequencing signals on the Ion Torrent Proton™ sequencer from these beads. The sequencing signals were analyzed by Torrent Suite Software to determine the sequence present within the amplicon of these beads.

Figure 10:
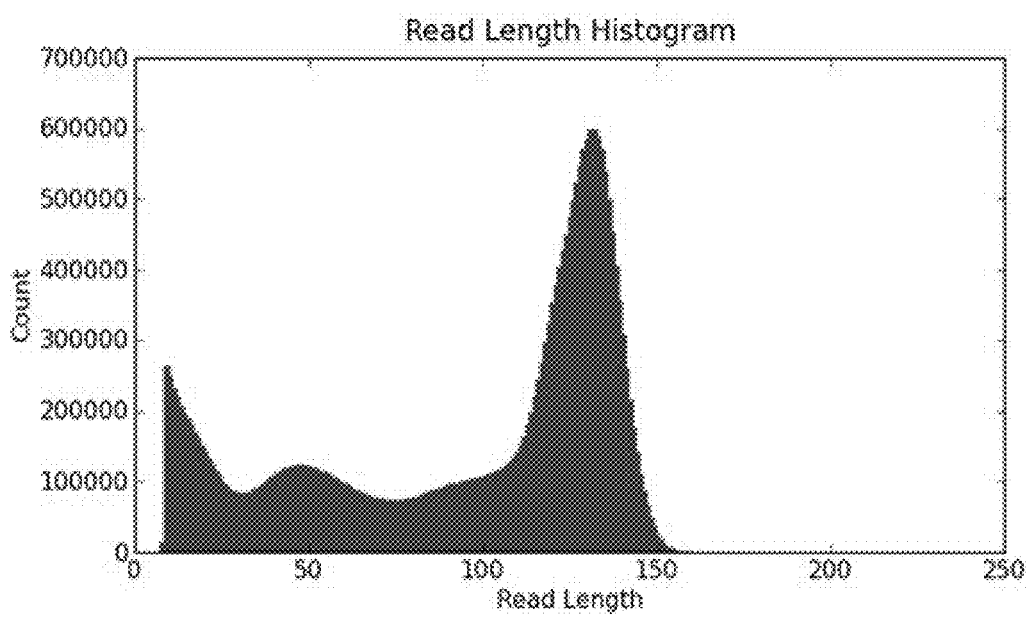
FIG. 10 depicts an exemplary read length histogram from an Ion Torrent™ Proton sequencing run of polynucleotide templates amplified using a recombinase-mediated amplification reaction.
Figure 11:
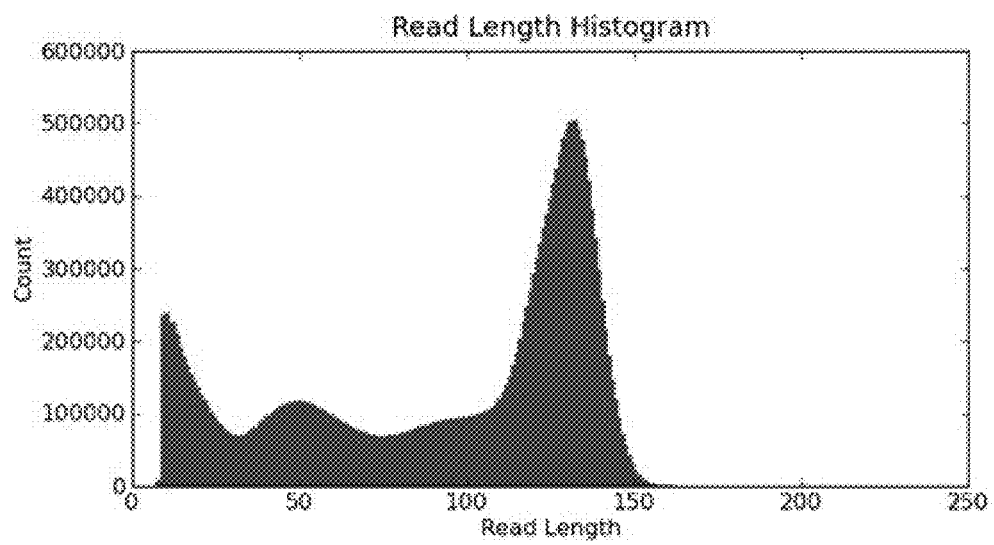
FIG. 11 depicts an exemplary read length histogram from an Ion Torrent™ Proton sequencing run of polynucleotide templates amplified using a recombinase-mediated amplification reaction.

Two sequencing runs were performed. The sequencing data yielded 96 bp mean read length for the first run (FIG. 10) and 94 bp read length for the second run (FIG. 11). The aligned quality measurements were 1.76 G (AQ17) and 1.43 G (AQ20) for the first run, and 1.48 G (AQ17) and 1.17 G (AQ20) for the second run.

Example 4

20 µL of beads (attached with forward primers) (103 million/µL) was mixed with 440 µL of 10 mM potassium acetate and 3 µL of 1 M Tris (pH 8). The beads were mixed by vortexing and spun down.

16 µL of a library having 200 bp insert (about 199 million copies) was denatured by mixing with 2 µL of NaOH, vortexed and spun, and allowed to sit for 1 minute. The reaction was neutralized by adding 440 µL of 10 mM potassium acetate and 3 µL of 1M Tris pH 8. The library included an insert sequence joined at one end to an adaptor that hybridizes to a forward primer and joined at the other end to an adaptor that hybridizes to a reverse primer.

The beads were added to the denatured library. The bead/template ratio was about 10:1 (200 billion beads:200 million library). The tube was vortexed, and allowed to sit at room temperature for 5 minutes (tube 1).

The recombinase source was from a TwistAmp™ Basic kit (from TwistDx, Cambridge, Great Britain). See Example 1 above for a list of components in the dehydrated pellets from the Basic kit. In a 15 mL tube (tube 2), 96 pellets from a TwistAmp™ Basic kit were rehydrated in 3 mL of Rehydration buffer supplied from the kit (tube 2).

24 µL of 100 µM reverse primers (non-immobilized primers) and 2 µL of 100 µM biotinylated reverse primers (non-immobilized primers) were added to the washed/pre-hybridized beads, and the tube was vortexed (tube 1) and iced. 1.6 mL of an exemplary sieving agent of the disclosure was added to tube 2, the tube was vortexed 5 seconds, rotated/spin by hand for 10 seconds, vortexed for 5 seconds, and placed on ice. 260 µL of 280 mM magnesium acetate was added to tube 2, the tube was vortexed 5 seconds and rotated/spin by hand for 10 seconds (vortex and rotate/spin three times), placed on ice. 50 µL samples were aliquoted into an ice-chilled 96-well plate. The 96-well plate was incubated at 40° C. for 60 minutes.

100 µL of 200 mM EDTA was added to each well to stop the reaction. All the reactions were pooled and centrifuged at maximum speed for 7 minutes. The supernatant was discarded. The pellets were resuspended in 1 mL Recovery buffer with 1% SDS, vortexed for 30 seconds, and spun at maximum speed for 6 minutes. After every spin, the tubes were reduced by half by pooling the contents of two tubes. The pellets were resuspended in 1 mL Recovery buffer with 1% SDS, vortexed for 30 seconds, and spun at 1550 rpm for 7 minutes.

Beads templated with copies of the library were enriched by binding with paramagnetic streptavidin beads (MyOne™ beads from Dynabeads). During the enriching step, ES-wash buffer was replaced with Recovery buffer with 0.1% SDS. The beads were finally resuspended in 1 mL water and reduced to 100 µL. The enriched beads were loaded into an Ion Torrent Proton I™ ion-sensitive chip.

A standard sequencing reaction was conducted according to manufacturer's instructions in an Ion PI™ Sequencing 200 Kit (User Guide PN MAN0007491). A significant portion of the enriched beads that were loaded onto the chip were determined to include substantially monoclonal populations of amplified polynucleotides, as evidenced by the observation of detectable sequencing signals on the Ion Torrent Proton™ sequencer from these beads. The sequencing signals were analyzed by Torrent Suite Software to determine the sequence present within the amplicon of these beads.

Figure 12:
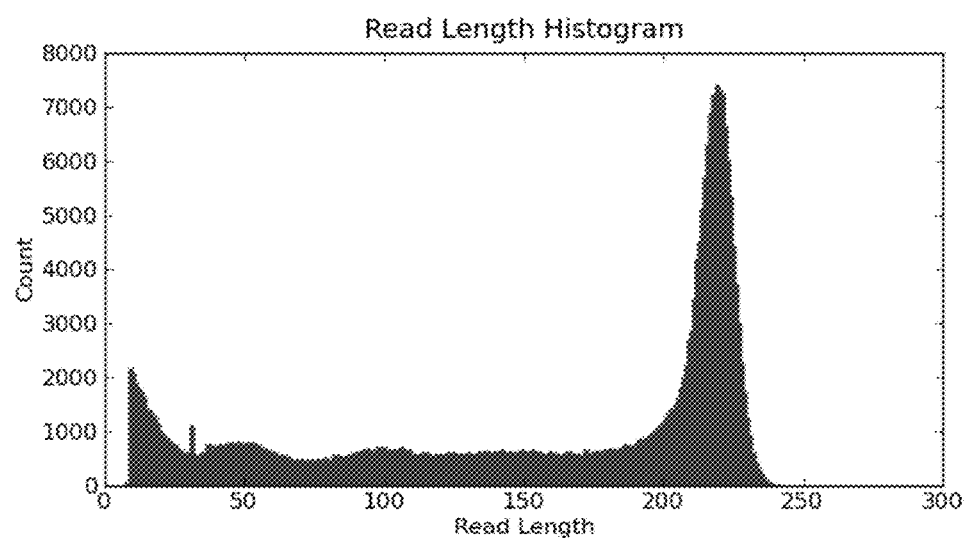
FIG. 12 depicts an exemplary read length histogram from an Ion Torrent™ Proton sequencing run of polynucleotide templates amplified using a recombinase-mediated amplification reaction.

The sequencing data yielded 144 bp mean read length (FIG. 12), and the aligned quality measurements was 4 G (AQ17).

Example 5

375 million beads (attached with forward primers) were washed in dH$_2$O by vortexing and spinning. The supernatant was removed (except ~50 µL). A DNA library (about 75 million molecules) was added to the washed beads. About 4 µL of reverse primer (non-biotinylated) and 0.4 µL of biotinylated reverse primer was added to the beads. About 0.8 µL of a fusion forward primer was added to the beads. Forty µL of magnesium acetate was added to the beads (final concentration 14 mM). dH$_2$O was added to the beads to a final total volume of 320 µL.

The recombinase source was from a TwistAmp™ Basic kit (from TwistDx, Cambridge, Great Britain). See Example 1 above for a list of components in the dehydrated pellets from the Basic kit. In a separate tube, 16 pellets from a TwistAmp™ Basic kit were rehydrated in 488 µL of Rehydration buffer supplied from the kit. For 400 bp libraries, 0.25 mg/ml of T4 gp32 protein (0.2 mg final concentration)

was added, or for 600 bp libraries, 0.5 mg/ml of T4 gp32 protein (0.4 mg final concentration) was added. The tube was vortexed to mix and spun.

The contents of the bead mixture was added to the recombinase tube, vortexed and spun. The bead/recombinase mixture was transferred to a tube with chilled oil and assembled on a 10 micron Sterlitech filter on an Ion Torrent OneTouch™ apparatus. Emulsions were generated and broken according to manufacture's instructions.

Beads templated with copies of the library were enriched (or the enriching step was omitted) by binding with paramagnetic streptavidin beads (MyOne™ beads from Dynabeads). The enriched beads were loaded into an Ion Torrent ion-sensitive chip and a standard sequencing reaction was conducted. A significant portion of the enriched beads were determined to include a substantially monoclonal population of amplified polynucleotides, as evidenced by the observation of detectable sequencing signals on the Ion Torrent PGM™ sequencer from such beads. The sequencing signals were analyzed to determine a sequence present within the amplicon of such beads.

Example 6

About 120 million beads (attached with forward primers) was washed once with annealing buffer. The supernatant was removed (except ~50 µL). The washed beads were resuspended in 100 µL of annealing buffer. About 60 million molecules of DNA library was added to the beads. The final volume was adjusted to 200 µL with annealing buffer. The beads and library were mixed by vortexing and spinning. The bead/library mix was heated to 95-100° C. for 3 minutes, then incubated at 37° C. for 5 minutes.

One mL of 10 mM potassium acetate was added to the bead/library mix, then vortexed and spun. The supernatant was discarded. The potassium acetate wash was repeated once. The bead/DNA was resuspended in 120 µL potassium acetate.

The recombinase source was from a TwistAmp™ Basic kit (from TwistDx, Cambridge, Great Britain). See Example 1 above for a list of components in the dehydrated pellets from the Basic kit. In a separate tube, 24 pellets from a TwistAmp™ Basic kit were rehydrated in 720 µL of Rehydration buffer supplied from the kit. An additional 54 µL of dNTP mix (containing 10 mM each dNTP) was added to the TwistAmp™ mix.

In a third tube, 3 µL of streptavidin (500 µM) was mixed with 12 µL biotinylated reverse primers (100 µM), then transferred to the bead/library tube. Recombinase mix was added to the bead/library tube, then vortexed to mix, and iced. 27 µL of T4 gp 32 protein (15/µg/µL) was added to the bead/library tube, then vortexed to mix. 390 µL of an exemplary sieving agent was added to the bead/library tube, the tube was inverted and vortexed to mix, and iced for at least 5 minutes. 80 µL of magnesium acetate was added to the bead/library tube, and the tube was vortexed, spun, and iced for at least 10 seconds. The bead/library tube was incubated at 40° C. for 40 minutes. The reaction was stopped by adding 500 µL EDTA (250 mM). The tube was spun at greater than 18,000×G for 3 minutes. The supernatant was discarded, the pellet was resuspended in 1 mL TE with 1% SDS. The pellet resuspended by pipetting up and down, and washed by adding 2 mL Ion Torrent OneTouch™ wash solution. The wash step was repeated once. The pellet was resuspended in 300 µL of melt-off solution, and incubated with rocking for 5 minutes.

Beads templated with copies of the library were enriched (or the enriching step was omitted) by binding with paramagnetic streptavidin beads (MyOne™ beads from Dynabeads). The enriched beads were loaded into an Ion Torrent ion-sensitive chip and a standard sequencing reaction was conducted. A significant portion of the enriched beads were determined to include a substantially monoclonal population of amplified polynucleotides, as evidenced by the observation of detectable sequencing signals on the Ion Torrent PGM™ sequencer from such beads. The sequencing signals were analyzed to determine a sequence present within the amplicon of such beads.

Example 7

Nucleic acid amplification was conducted on an Ion sequencing chip. First a template walking amplification reaction was performed on the chip followed by a recombinase-mediated amplification reaction.

An Ion Torrent PGM™ sequencing chip was prepared to contain low $T_M$ single-stranded primers attached at their 5' ends to the floor of the wells. The immobilized primers contained a polyA(30) sequence.

The double-stranded DNA template included a single-stranded terminal overhang sequence having a polyT(30) sequence.

Ion Torrent PGM™ sequencing chips were treated with a polymer to produce a matrix at the bottom of the wells. Capture primers were attached to the matrix.

The Ion Torrent PGM™ sequencing chip was pre-washed once with a TE-containing buffer, and vacuumed dry.

Forty microliters of a solution was mixed and loaded onto the chip. The final concentration of the solution contained: 1× Isothermal buffer from New England Biolabs, 1.6 mM $MgSO_4$, 3 mM dNTPs, 1 U/uL Bst polymerase (e.g., from New England Biolabs), 0.1 nM template, and nuclease-free water to 40 uL volume. The chip was centrifuged for 5 minutes and incubated at 37° C. for 30 minutes. The chip was vacuumed dry.

Template walking amplification: Forty microliters of a template walking solution was loaded onto the chip. The final concentration of the template walking solution contained: 1× Isothermal buffer from New England Biolabs, 3.6 mM $MgSO_4$, 5 mM dNTPs, 2 uM soluble single-stranded primer, 6 U/uL Bst polymerase (from New England Biolabs), and nuclease-free water to 40 uL volume. The chip was centrifuged, and incubated at 60° C. for 30 minutes. The chip was washed once with 1×TE-containing buffer and vacuumed dry.

Recombinase-mediated amplification: The recombinase source for this example was from a TwistAmp™ Basic kit (from TwistDx, Cambridge, Great Britain). See Example 1 above for a list of components in the dehydrated pellets from the Basic kit. Fifty microliters of an amplification reaction mixture (containing recombinase) was loaded onto the chip. The amplification reaction mixture contained: one pellet from a TwistAmp™ Basic kit (from TwistDx, Cambridge, Great Britain), 30 uL rehydration buffer from the TwistAmp™ Basic kit, 2 uM of a soluble primer that hybridizes with one adaptor of the DNA template, and nuclease-free water to 50 uL total volume. The chip was centrifuged for 2 minutes. Two microliters of magnesium acetate (280 mM stock) was added to the chip. The chip was centrifuged for 2 minutes, then incubated at 40° C. for 1 hour.

The chip was washed sequentially with 0.5 M EDTA (pH 8), TE-containing buffer, 1% SDS, and washed 2× with wash solution.

A majority of the wells were determined to include substantially monoclonal populations of amplified polynucleotides using a color-coded alignment map of the chip.

A standard sequencing reaction was conducted according to manufacturer's instructions in an Ion PI™ Sequencing 200 Kit (User Guide PN MAN0007491). The sequencing signals were analyzed by Torrent Suite Software to determine the sequence present within the amplicon of these beads. The sequencing data yielded 151 bp mean read length.

Example 8

Nucleic acid amplification was performed directly on an Ion Torrent PGM™ sequencing chip in the presence of recombinase, under isothermal conditions. A polymerized hydrogel was deposited in the wells of a PGM™ chip.

The recombinase source for this example was from a TwistAmp™ Basic kit (from TwistDx, Cambridge, Great Britain). See Example 1 above for a list of components in the dehydrated pellets from the Basic kit.

A polynucleotide template was denatured using a heat denaturation method or the recombinase method (described below), then proceeded to the nucleic amplification step.

(A) Heat denaturation method: a polynucleotide template library was diluted into a final volume of 60 μL in annealing buffer. The dilution targeted depositing about five copies of the template per well of an Ion Torrent Proton™ sequencing chip (about 600-650 million wells). The chip was washed once with annealing buffer, and set on a thermocycler set at 40° C. An aliquot of 100 μL of 1:1 annealing buffer-to-water ratio was mixed and pre-heated at 95° C. The template library was denatured by deposition onto the chip and incubating at 95° C. for 2 minutes. The buffer/water mixture (pre-heated to 95° C.) was pipette into the flowcell. The chip was transferred to the 40° C. thermocycler and incubated for 5 minutes. The chip was transferred to the bench top (approximately 25° C.). The chip was washed with 100 μL of annealing buffer. The chip was placed on a 4° C. thermocycler. The following are optional steps: 1 pellet from a TwistAmp™ Basic kit was rehydrated in 20 μL of water and 30 μL of Rehydration buffer supplied from the kit. The pellet mix was vortexed vigorously to dissolve the pellet. 50 μL of the pellet mix was loaded onto the chip. The chip was incubated at room temperature for at least one minute to allow the recombinase to bind the primers pre-loaded into the wells of the chip.

(B) Recombinase denaturation method: an Ion Torrent Proton™ sequencing chip (about 600-650 million wells) was washed with 150 μL of an annealing/water mix (1:1 ratio of annealing buffer and water). The chip was set on a 40° C. thermocycler. 2 pellets from a TwistAmp™ Basic kit was rehydrated in 60 μL of Rehydration buffer supplied from the kit. A polynucleotide template library was diluted into a final volume of 50 μL in annealing buffer. The dilution targeted depositing about five copies of the template per well of an Ion Torrent Proton™ sequencing chip. The total volume of the diluted template was added to the rehydrated pellet mix. The volume was adjusted to 100 μL with water. The pellet/template was vortexed to mix and spun. The pellet/template mix was loaded onto the Ion Torrent Proton™ sequencing chip (set on the 40° C. thermocycler) and incubated for 20 minutes. The chip was removed from the thermocycler and set at room temperature.

Nucleic acid amplification was performed as follows: All reagents were kept on ice. One pellet from a TwistAmp™ Basic kit were rehydrated in 30 μL of Rehydration buffer supplied from the kit, 16 μL of nuclease-free water, and 1 μL of 100 μM reverse amplification primer. The pellet was dissolved by vortexing and spinning Immediately prior to loading onto the chip, 3 μL of 280 μM of magnesium acetate was added to the pellet mix. The entire pellet mix was loaded onto the chip and incubated at 40° C. for 1 hour.

The amplification reaction was stopped by washing the chip with 0.1 M EDTA (pH 8). The chip was washed with a chip wash solution. The chip was washed with 1% SDS. The chip was washed twice with TEX wash solution.

The chip was prepared for sequencing: The chip was washed with melt off solution. The chip was washed three times with annealing buffer and placed on a 40° C. thermocycler. In a separate tube the sequencing primers were prepared: 80 μL of 50% annealing buffer was mixed with 50% sequencing primer, then preheated to 95° C. A 1:1 mixture of annealing buffer and water was prepared and pre-heated to 95° C. The chip was washed with pre-heated anneling/water buffer. The chip was loaded with 80 μL of the pre-heated primer mix. The chip was incubated for 5 minutes at 40° C. The chip was washed once with the annealing/water buffer. In a separate tube, 6 μL of sequencing polymerase was mixed with 57 μL of annealing/water mixture, and loaded onto the chip.

A standard sequencing reaction was conducted according to manufacturer's instructions.

What is claimed:

1. A method for amplifying a plurality of nucleic acid templates, comprising:
   a) providing a plurality of forward primers immobilized on a support, wherein the plurality of forward primers includes a first forward primer and a second forward primer, and wherein the plurality of forward primers have substantially identical sequences;
   b) providing a nucleic acid reverse strand from the plurality of nucleic acid templates, having a forward primer-binding sequence that can hybridize to any one of the plurality of forward primers;
   c) hybridizing the first forward primer to the forward primer-binding sequence on the nucleic acid reverse strand;
   d) generating an extended forward strand that is substantially complementary to the nucleic acid reverse strand and is hybridized thereto, by primer extension of the first forward primer using the reverse strand as a template, wherein the first forward primer becomes incorporated into the extended forward strand;
   e) denaturing at least a portion of the extended forward strand comprising the incorporated first forward primer and the forward primer-binding sequence on the nucleic acid reverse strand and hybridizing the second forward primer to the forward primer-binding sequence on the nucleic acid reverse strand;
   f) generating another extended forward strand that is substantially complementary to the reverse strand and is hybridized thereto, by primer extension of the second forward primer using the reverse strand as a template, wherein the second forward primer becomes incorporated into the extended forward strand; and
   g) amplifying the plurality of nucleic acid templates simultaneously in a single continuous liquid phase without first compartmentalizing, by performing one or more amplification cycles comprising steps (e)-(f) under isothermal conditions to form clonal or substantially clonal nucleic acid populations, wherein the incorporated second forward primer of step (e) of an amplification cycle acts as the incorporated first forward primer of step (e) of a subsequent amplification cycle and the second forward primer of step (e) in the subsequent amplification cycle is a new second forward primer that has not undergone primer extension; and wherein the amplifying is carried out using a recombinase and a polymerase.

2. The method of claim 1, wherein the support comprises only primers having sequences that are identical or substantially identical to the plurality of forward primers.

3. The method of claim 1, further comprising generating an extended third forward strand that is a full-length complement of the reverse strand and is hybridized thereto, by primer extension of the third forward primer using the reverse strand as a template.

4. The method of claim 1, further comprising:
   as part of step e), hybridizing a reverse primer to a reverse primer-binding sequence on the extended forward strand, by denaturing the reverse primer-binding sequence on the extended forward strand from the nucleic acid reverse strand, wherein the reverse primer is a soluble primer; and
   as part of step f) extending the reverse primer using the first forward strand as a template to generate an extended reverse strand that is a full-length complement of the forward strand and hybridized thereto.

5. The method of claim 1, wherein the individual substantially clonal nucleic acid populations are immobilized within or on a different support from other substantially clonal nucleic acid populations.

6. The method of claim 1, further comprising subjecting the extended forward strands to a sequencing reaction.

7. The method of claim 1, wherein during step (e) a portion of the nucleic acid reverse strand remains hybridized to the extended first forward strand.

8. The method of claim 1, wherein the extended forward strand and the nucleic acid reverse strand are not subjected to extreme denaturing conditions during step e).

9. The method of claim 8, wherein the extended forward strand and the nucleic acid reverse strand are not contacted with chemical denaturants during step e).

* * * * *

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: synthetic reverse primer

<400> SEQUENCE: 1
atccctgcgt gtctccgac                                              19

<210> SEQ ID NO 2
<211> LENGTH: 19
<212> TYPE: DNA
<213> ORGANISM: Artificial Sequence
<220> FEATURE:

```
<223> OTHER INFORMATION: synthetic reverse primer
<220> FEATURE:
<221> NAME/KEY: misc_feature
<222> LOCATION: (1)...(19)
<223> OTHER INFORMATION: biotinylation

<400> SEQUENCE: 2
atccctgcgt gtctccgac                                              19
```